US011479797B2

(12) United States Patent
Gray et al.

(10) Patent No.: US 11,479,797 B2
(45) Date of Patent: Oct. 25, 2022

(54) COMPOSITIONS AND METHODS FOR THE PRODUCTION OF COMPOUNDS

(71) Applicant: Ginkgo Bioworks, Inc., Boston, MA (US)

(72) Inventors: Daniel C. Gray, Medford, MA (US); Brian R. Bowman, New Rochelle, NY (US); Gregory L. Verdine, Boston, MA (US); Mathew Edward Sowa, Watertown, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 16/345,445

(22) PCT Filed: Oct. 27, 2017

(86) PCT No.: PCT/US2017/058805
§ 371 (c)(1),
(2) Date: Apr. 26, 2019

(87) PCT Pub. No.: WO2018/081592
PCT Pub. Date: May 3, 2018

(65) Prior Publication Data
US 2019/0249213 A1    Aug. 15, 2019

Related U.S. Application Data

(60) Provisional application No. 62/414,435, filed on Oct. 28, 2016.

(51) Int. Cl.
| C12P 19/62 | (2006.01) |
| C12N 15/52 | (2006.01) |
| C12N 9/10 | (2006.01) |
| C12N 15/74 | (2006.01) |
| C40B 40/02 | (2006.01) |

(52) U.S. Cl.
CPC ........... *C12P 19/62* (2013.01); *C12N 9/1029* (2013.01); *C12N 15/52* (2013.01); *C12N 15/74* (2013.01); *C40B 40/02* (2013.01); *C07K 2319/00* (2013.01)

(58) Field of Classification Search
None
See application file for complete search history.

(56) References Cited

U.S. PATENT DOCUMENTS

| 6,183,965 B1 | 2/2001 | Verdine et al. |
| 6,372,712 B1 | 4/2002 | Briesewitz et al. |
| 6,686,454 B1 | 2/2004 | Yatscoff et al. |
| 6,713,607 B2 | 3/2004 | Caggiano et al. |
| 7,220,552 B1 | 5/2007 | Crabtree et al. |
| 7,396,660 B2 | 7/2008 | Huang et al. |
| 7,851,183 B2 * | 12/2010 | Zotchev ............... C12N 15/52 435/72 |
| 8,664,186 B2 | 3/2014 | Aigle et al. |
| 9,250,237 B2 | 2/2016 | Liu et al. |
| 9,428,845 B1 | 8/2016 | Verdine et al. |
| 10,203,323 B2 | 2/2019 | Verdine et al. |
| 2002/0110874 A1 | 8/2002 | Khosla et al. |
| 2002/0147133 A1 | 10/2002 | Briesewitz et al. |
| 2003/0153053 A1 | 8/2003 | Reid |
| 2003/0175901 A1 | 9/2003 | Reeves et al. |
| 2004/0087496 A1 | 5/2004 | Kim et al. |
| 2005/0233431 A1 | 10/2005 | Ashley et al. |
| 2007/0203168 A1 | 8/2007 | Zhao |
| 2011/0117606 A1 | 5/2011 | Jorgensen et al. |
| 2012/0142622 A1 | 6/2012 | Aigle et al. |
| 2012/0208720 A1 | 8/2012 | Kashiwagi et al. |
| 2012/0270800 A1 | 10/2012 | Verdine et al. |
| 2013/0072439 A1 | 3/2013 | Nash et al. |
| 2014/0073581 A1 | 3/2014 | Liu et al. |
| 2015/0250896 A1 | 9/2015 | Zhao |
| 2015/0307855 A1 | 10/2015 | Yuzawa et al. |
| 2016/0341719 A1 | 11/2016 | Verdine et al. |

FOREIGN PATENT DOCUMENTS

| EP | 0393934 A1 | 10/1990 |
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/020216 A1 | 7/1996 |
| WO | WO-98/01546 A2 | 1/1998 |
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |
| WO | WO-01/36612 A1 | 5/2001 |

(Continued)

OTHER PUBLICATIONS

Yuzawa et al. "Bio-based production of fuels and industrial chemicals by repurposing antibiotic-producing type I modular polyketide synthases: opportunities and challenges", The Journal of Antibiotics 70: 378-385 (Year: 2017).*
Kushnir et al., "Minimally Invasive Mutagenesis Gives Rise to a Biosynthetic Polyketide Library", Agnew. Chem. Int. Ed. 51: 10664-10669 (2012). (Year: 2012).*
"SMART™ Drugs: Engineering Nature's Solution to the Undruggable Target Challenge," WarpDrive Bio, 2016, available www.warpdrivebio.com/docs/Warp%20Drive%20Bio_SMART%20Drugs%20Platform_2016.pdf> (31 pages).
"*Streptomyces iranensis* regulatory protein LuxR," EBI Database Accession No. CDR13506 (2014) (2 pages).
"*Streptomyces rapamycinicus* NRRL 5491 hypothetical protein," EBI Database Accession No. AGP59507 (2014) (2 pages).
"Substructure Search Report on Specifically Substituted Macrocycles—Substances Only", prepared by Science IP, dated Dec. 17, 2014 (6177 pages).

(Continued)

*Primary Examiner* — Anand U Desai
(74) *Attorney, Agent, or Firm* — Clark & Elbing LLP

(57) ABSTRACT

The present disclosure provides proteins, nucleic acids, vectors, and host molecules useful for the production of compounds of interest, and methods for their use.

15 Claims, 17 Drawing Sheets

Specification includes a Sequence Listing.

(56) References Cited

FOREIGN PATENT DOCUMENTS

| | | |
|---|---|---|
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/174489 A2 | 12/2012 |
| WO | WO-2014/009774 A1 | 1/2014 |
| WO | WO-2014/187959 A2 | 11/2014 |
| WO | WO-2015/132784 A1 | 9/2015 |
| WO | WO-2018/081592 A2 | 5/2018 |

OTHER PUBLICATIONS

Allain et al., "Cyclophilin B mediates cyclosporin A incorporation in human blood T-lymphocytes through the specific binding of complexed drug to the cell surface," Biochem J. 317 (Pt 2):565-70 (1996).
Andrei et al., "Stabilization of protein-protein interactions in drug discovery," Expert Opin Drug Discov. 12(9):925-40 (2017) (17 pages).
Antunes et al., "A mutational analysis defines Vibrio fischeri LuxR binding sites," J Bacteriol. 190(13):4392-7 (2008).
Archibald et al., "Discovery and Evaluation of Potent, Cysteine-based alpha4beta1 Integrin Antagonists," Bioorg Med Chem Lett. 10(9):993-995 (2000).
Banaszynski et al., "Characterization of the FKBP.rapamycin.FRB ternary complex," J Am Chem Soc. 127(13):4715-21 (2005).
Baranasic et al., "Draft Genome Sequence of *Streptomyces rapamycinicus* Strain NRRL 5491, the Producer of the Immunosuppressant Rapamycin," Genome Announc. 1(4):e000581-13 (2013) (2 pages).
Bayle et al., "Rapamycin analogs with differential binding specificity permit orthogonal control of protein activity," Chem Biol. 13(1):99-107 (2006).
Bender et al., "Periodate Oxidation of alpha-Keto gamma-Lactams. Enol Oxidation and beta-Lactam Formation. Mechanism of Periodate Hydrozylation Reactions," J Org Chem. 43(17):3354-3362 (1978).
Benjamin et al., "Rapamycin passes the torch: a new generation of mTOR inhibitors," Nat Rev Drug Discov. 10(11):868-80 (2011).
Bhuyan et al., "Antioxidant activity of peptide-based angiotensin converting enzyme inhibitors," Org. Biomol. Chem. 10(11):2237-47 (2012).
Blodgett et al., "Unusual transformations in the biosynthesis of the antibiotic phosphinothricin tripeptide," Nat Chem Biol. 3(8):480-5 (2007).
Briesewitz et al., "Affinity modulation of small-molecule ligands by borrowing endogenous protein surfaces," Proc Natl Acad Sci U.S.A. 96(5):1953-8 (1999).
Bruce, "In vivo protein complex topologies: sights through a cross-linking lens," Proteomics. 12(10):1565-75 (2012).
Burgess et al., "Controlled translocation of palladium(II) within a 22 ring atom macrocyclic ligand," Dalton Trans. 43(45):17006-16 (2014).
Chaurasia et al., "Molecular insights into the stabilization of protein-protein interactions with small molecule: The FKBP12-rapamycin-FRB case study," Chem Phys Lett. 587:68-74 (2013).
Che et al., "Inducing protein-protein interactions with molecular glues," Bioorganic & Medicinal Chemistry Letters (2018).
Chevalier et al., "Straightforward synthesis of bioconjugatable azo dyes. Part 1: Black Hole Quencher-1 (BHQ-1) scaffold," Tetrahedron Lett. 55(50):6759-63 (2014).
Findlay et al., "The structure of demethoxyrapamycin," Can J Chem. 60:2046-7 (1982).
Guerra et al., "LAL regulators SCO0877 and SCO7173 as pleiotropic modulators of phosphate starvation response and actinorhodin biosynthesis in *Streptomyces coelicolor*," PLoS One. 7(2):e31475 (2012) (11 pages).

He et al., "The LuxR family members GdmRI and GdmRII are positive regulators of geldanamycin biosynthesis in *Streptomyces hygroscopicus* 17997," Arch Microbiol. 189(5):501-10 (2008).
Horn et al., "Draft Genome Sequence of *Streptomyces iranensis*," Genome Announc. 2(4):e00616-14 (2014) (2 Pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in *Streptomyces roseosporus*" J Bacteriol. 179(1):180-6 (1997).
Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).
Huang et al., "Enhanced rapamycin production in *Streptomyces hygroscopicus* by integrative expression of aveR, a LAL family transcriptional regulator," World J Microbiol Biotechnol. 27:2103-9 (2011).
Hubler et al., "Synthetic routes to NEtXaa4-cyclosporin A derivatives as potential anti-HIV I drugs," Tetrahedron Lett. 41:7193-6 (2000).
International Search Report and Written Opinion for International Application No. PCT/US17/58805, dated Aug. 27, 2018 (16 pages).
Ishizawa et al., "TRAP display: a high-speed selection method for the generation of functional polypeptides," J Am Chem. 135(14):5433-40 (2013).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Kendrew et al., "Recombinant strains for the enhanced production of bioengineered rapalogs," Metab Eng. 15:167-73 (2013).
Kuhn et al., "Synthesis of Functional Ras Lipoproteins and Fluorescent Derivatives," J Am Chem Soc. 123(6):1023-35 (2001).
Kuramochi et al., "Identification of Small Molecule Binding Molecules by Affinity Purification Using a Specific Ligand Immobilized on PEGA Resin," Bioconjug. Chem. 19(12):2417-26 (2008).
Laureti et al., "Identification of a bioactive 51-membered macrolide complex by activation of a silent polyketide synthase in *Streptomyces ambofaciens*," Proc Natl Acad Sci USA. 108(15):6258-63 (2011).
Laureti et al., Supporting Material for "Identification of a bioactive 51-membered macrolide complex by activation of a silent polyketide synthase in *Streptomyces ambofaciens*," Proc Natl Acad Sci U.S.A. 108(15):6258-63 (2011), accessed via <https://www.pnas.org/content/suppl/2011/03/24/1019077108.DCSupplemental> (41 pages).
Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).
Mo et al., "Interspecies Complementation of the LuxR Family Pathway-Specific Regulator Involved in Macrolide Biosynthesis," J Microbiol Biotechnol. 26(1):66-71 (2016).
Ochi et al., "New strategies for drug discovery: activation of silent or weakly expressed microbial gene clusters," Appl Microbiol Biotechnol. 97(1):87-98 (2013).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science 291(5509):1790-2 (2001).

(56) References Cited

OTHER PUBLICATIONS

Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).
Ranganathan et al., "Knowledge-based design of bimodular and trimodular polyketide synthases based on domain and module swaps: a route to simple statin analogues," Chem Biol. 6(10):731-41 (1999).
Revill et al., "Genetically engineered analogs of ascomycin for nerve regeneration," J Pharmacol Exp Ther. 302(3):1278-85 (2002).
Ruan et al., "Binding of rapamycin analogs to calcium channels and FKBP52 contributes to their neuroprotective activities," Proc Natl Acad Sci U.S.A. 105(1):33-8 (2008).
Schwecke et al., "The biosynthetic gene cluster for the polyketide immunosuppressant rapamycin," Proc Natl Acad Sci USA. 92(17):7839-43 (1995).
Sieber et al., "Novel inhibitors of the calcineurin/NFATc hub—alternatives to CsA and FK506?," Cell Commun Signal. 7:25 (2009) (19 pages).
Smulik et al., "Synthesis of cyclosporin A-derived affinity reagents by olefin metathesis," Org Lett. 4(12):2051-4 (2002).
STN record of WO 2014/009774, available online Jan. 16, 2014 (4 pages).
STN record of WO 98/12217, available online Mar. 26, 1998 (6 pages).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Takakusagi et al., "Efficient one-cycle affinity selection of binding proteins or peptides specific for a small-molecule using a T7 phage display pool," Bioorg. Med. Chem. 16(22):9837-46 (2008).
UniProtKB Accession No. A0A061A6I8, Sep. 3, 2014, available www.uniprot.org/uniprot/A0A061A6I8>, (12 pages).
UniProtKB Accession No. Q54296, Nov. 1, 1996, available www.uniprot.org/uniprot/Q54296>, (12 pages).
UniProtKB Accession No. Q54297, Nov. 1, 1996, available www.uniprot.org/uniprot/Q54297.txt>, (3 pages).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22:816-28 (1983).
Wang et al., "Thermodynamic analysis of cyclosporin a binding to cyclophilin a in a lung tumor tissue lysate," Anal Chem. 76(15):4343-8 (2004).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Wu et al., "Synthesis of Ketone Analogues of Prolyl and Pipecolyl Ester FKBP12 Ligands," J Med Chem. 45(16):3558-3568 (2002).
Ding et al. "Insights into Bacterial 6-Methylsalicylic Acid Synthase and Its Engineering to Orsellinic Acid Synthase for Spirotetronate Generation," Chem Biol. 17(5):495-503 (2010).
Garg et al. "Elucidation of the Cryptic Epimerase Activity of Redox-Inactive Ketoreductase Domains from Modular Polyketide Synthases by Tandem Equilibrium Isotope Exchange," J. Am. Chem. Soc. 136(29):10190-10193 (2014).
Murphy et al. "Isolation and characterisation of amphotericin B analogues and truncated polyketide intermediates produced by genetic engineering of *Streptomyces nodosus*," Org Biomol Chem. 8(16):3758-70 (2010).
Partial Supplementary European Search Report for European Patent Application No. 17865512.2, dated May 7, 2020 (20 pages).
Power et al. "Engineered Synthesis of 7-Oxo- and 15-Deoxy-15-Oxo-Amphotericins: Insights into Structure-Activity Relationships in Polyene Antibiotics," Chem Biol. 15:78-86 (2008).
Reid et al. "A model of structure and catalysis of ketoreductase domains in modular polyketide synthases," Biochemistry. 42(1):72-79 (2003).
Tang et al. "Generation of New Epothilones by Genetic Engineering of a Polyketide Synthase in Myxococcus xanthus," J Antibiot (Tokyo). 58(3):178-184 (2005).
Weissman, "Genetic engineering of modular PKSs: from combinatorial biosynthesis to synthetic biology," Nat Prod Rep. 33(2):203-230 (2016).
"SMART™ Drugs: Engineering Nature's Solution to the Undruggable Target Challenge," WarpDrive Bio, 2016 (31 pages).
Chica et al., "Semi-rational approaches to engineering enzyme activity: combining the benefits of directed evolution and rational design," Curr Opin Biotechnol. 16(4):378-84 (2005).
Hong et al., "Evidence for an iterative module in chain elongation on the azalomycin polyketide synthase," Beilstein J Org Chem. 12:2164-2172 (2016).
Singh et al., "Protein Engineering Approaches in the Post-Genomic Era," Curr Protein Pept Sci. 19(1):5-15 (2018).
UniProtKB Accession No. A0A061A6I8, Sep. 3, 2014 (12 pages).
UniProtKB Accession No. Q54296, "Polyketide synthase," retrieved May 29, 2020 (12 pages).
UniProtKB Accession No. Q54296, Nov. 1, 1996 (12 pages).
UniProtKB Accession No. Q54297, Nov. 1, 1996 (3 pages).
Weissman et al., "Combinatorial biosynthesis of reduced polyketides," Nat Rev Microbiol. 3(12):925-36 (2005).
Jones et al., "Phage p1-derived artificial chromosomes facilitate heterologous expression of the FK506 gene cluster," PLoS One. 8(7):e69319 (2013) (9 pages).
NCBI Reference Sequence WP_053141444.1, retrieved Apr. 22, 2021 (1 page).
Keatinge-Clay et al., "The Structure of a Ketoreductase Determines the Organization of the Beta-Carbon Processing Enzymes of Modular Polyketide Synthases," Structure. 14(4):737-748 (2006).
NCBI Reference Sequence: WP_044578204.1 (2015) (2 pages).

* cited by examiner

FIG. 4B

COMPOSITIONS AND METHODS FOR THE PRODUCTION OF COMPOUNDS

BACKGROUND

Polyketide natural products are produced biosynthetically by polyketide synthases (PKSs), e.g., type I polyketide synthases, in conjunction with other tailoring enzymes. Polyketide synthases (PKSs) are a family of large, multidomain proteins whose catalytic functions are organized into modules to produce polyketides. The basic functional unit of polyketide synthase clusters is the module, which encodes a 2-carbon extender unit, e.g., derived from malonyl-CoA. The modules generally present in a polyketide synthase include i) a loading module; ii) extending modules; and iii) releasing modules. Within the module, the minimal domain architecture required for polyketide chain extension and elongation includes the ketosynthase (KS), acyl-transferase (AT) and the ACP (acyl-carrier protein) domains, and the specific chemistry of each module is encoded by the AT domain and by the presence of the β-ketone processing domains: ketoreductase (KR), dehydratase (DH), and enoylreductase (ER) domains. Polyketide synthase biosynthesis proceeds by two key mechanisms: polyketide chain elongation with a polyketide synthase extending module and translocation of the polyketide intermediate between modules. Productive chain elongation depends on the concerted function of the numerous catalytic domains both within and between modules.

Combinatorial biosynthesis is a general strategy that has been employed to engineer polyketide synthase (PKS) gene clusters to produce novel drug candidates (Weissman and Leadlay, Nature Reviews Microbiology, 2005). To date, these strategies have relied on engineering PKS domain deletions and/or domain swaps within a module or by swapping an entire module from another cluster to produce a chimeric cluster. The problem with this approach is that protein engineering of the polyketide megasynthases via wholesale domain replacement, insertion, or deletion can perturb the "assembly line" architecture of the PKS, thus drastically reducing the amount of polyketide synthesized.

SUMMARY OF THE INVENTION

The present disclosure provides compositions and methods useful to facilitate combinatorial biosynthesis of polyketides without a significant loss of compound production by mimicking and accelerating the mechanism by which domain activity is turned "on" or "off" by evolution (FIG. 1).

More specifically, the disclosure provides composition and methods for domain-level PKS engineering by utilizing short protein sequences in β-ketone processing domains that control enzymatic activity, i.e., ketoreductase (KR), dehydratase (DH), and enoylreductase (ER) domains (FIGS. 2A and 2B). The putative dead domain sequences are grafted onto live domains to inactivate domain activity and alter the chemical structure of the polyketide encoded by the cluster. Heterologous expression of the modified clusters in *Streptomyces* expression hosts then may be used to produce the novel compounds. The approach may further be utilized by performing multiple domain-level engineering operations into one cluster to generate a combinatorial library of engineered molecules.

Accordingly, in one aspect, the disclosure provides an engineered polyketide synthase, wherein the polyketide synthase includes one or more modified domains having altered enzymatic activity relative to a reference polyketide synthase including unmodified domains, wherein the engineered polyketide synthase is capable of producing a polyketide when expressed under conditions suitable to allow expression of a compound by the engineered polyketide synthase.

In some embodiments, the engineered polyketide synthase includes two or more modified domains having altered enzymatic activity.

In some embodiments, at least one modified domain has decreased enzymatic activity (e.g., at least one modified domain is functionally inactive).

In some embodiments, the modified domain is a β-ketone processing domain (e.g., a ketoreductase, a dehydratase, or an enoylreductase).

In another aspect, the disclosure provides a polyketide synthase including:
(a) a first domain including a conserved region of a domain of a first polyketide synthase; and
(b) a second domain including a conserved region of a domain of a second polyketide synthase.

In some embodiments, at least one of the first domain and the second domain is a β-ketone processing domain (e.g., a ketoreductase, a dehydratase, or an enoylreductase). In some embodiments, the first domain and the second domain are both β-ketone processing domains.

In some embodiments, at least one of the first domain and the second domain is a functionally inactive domain. In some embodiments, both of the first domain and the second domain are functionally inactive domains.

In some embodiments, the polyketide synthase includes (c) a conserved region of a domain (e.g., a functionally inactive domain) of a third polyketide synthase or the conserved region of a second domain of the second polyketide synthase.

In some embodiments, the polyketide synthase includes (d) a conserved region of a domain (e.g., a functionally inactive domain) of a fourth polyketide synthase, the conserved region of a second domain of the third polyketide synthase, or the conserved region of a third domain of the second polyketide synthase.

In some embodiments, the functionally inactive domain includes the amino acid sequence of the conserved region of any one of SEQ ID NO: 1-9.

In some embodiments of any of the foregoing polyketide synthases, the β-ketone processing domain includes a portion having at least 90% sequence identity to the conserved region of any one of SEQ ID NO:1-9.

SEQ ID NO: 1

DPDGTVLITGGSGVRAGALARHLVTERGVRHLLLLSRTTADEELLNELGELGARVDTAICDVSDRARLAQ

VLAGVSPEHPLTAVIHTAGALDDDVVESLTAQRLDTVLRPKADGAWHLHELTRDTDLAAFVMYSSAAGV

MGNPGQGNFAAATAFLDALAEQRRAEGLPALALAWGSSEETGGLTGLRAISAEHGMRLFDSASHRREPL

-continued

LVAASMDPVLAAEVPALLRSLRRPIARRAASADGVQWLAGLAPEERAKALLKVVCDTAATVLGHADARTI

PLTGAFKDLGVDSLTAVELRNSLTKATGLRLPATLVFDYPTPTALAVRL

SEQ ID NO: 2
DPDGTILITGGSGVLAGILARHLAAEHGARHLLLLSRTAPDEALIKELAELGARVETAACDVSDRAGLARVL

AGVSPEHPLTAVIHTAGALDDGVVESLTTQQLDTVLRPKADGAWHLHELTRDADLAAFVVYSSAAAVLGN

EGQGNYAAANAFLDALAEQRRTQGLPALALAWGPWEYTGDLTAQLTGTDQDRIRCSGMRTITAEDGMR

LFDTASHHGEPLLVPAVLDPTRDGEVPALLRSLRRPIARRAASADGGVQWLAALAPAEREKALLKLVCDS

AAMVLGHADARSIPAAGAFKDLGVDSLMAVELRNGLVKATGLRLPATLVFDYPTPTVLAARL

SEQ ID NO: 3
DPDGTVLITGERAGAVARRMAERGVRHLLLASGRVPDELMDLDTSVEVAVCDVSDRAALAGVLAGLPSL

TGVIQTAGEDVLPVLAGAITPTRDGEIPASLRLLRRPLVRRRVSAAGDSSLAALPPAERERALLKVVRDSA

AVVLGHADGRTVPATAAFKDLGLDSLTAVELRNSLRKATGLQLPATLVFDYPSPVALAARLG

SEQ ID NO: 4
HPFLGAALPAPDGDSLTLTGRITLDAHPWLADHIIRDTLILPGAAFAECVLRAGREVGCDLLEELVIEAPLVL

PATGGVAVRIAVGEPDDAGRRTFDLYARPDAAPGWNRHAGGTLKPGDALPATEAATETVAWPPADAEP

VDVDDLYDRLAAAGYAYGPAFQSVHAAWRTPDAIWAEVVLDGEPAGFGLHPALLDGALQLSALAATGGD

VAQLPFAWHDVRLPGHGADRLRVRL

SEQ ID NO: 5
HPLLGAIVAVPQSGGVAMTSRLSPRNHPWLAEHTLGGVPTVPTSVLVELAVRAGDEVGCGVVEELTVDA

PLLLPERGGVRVQVIVGATDANGQRGLDIFSAPEDTGQEAWTRHATGTLAPGGDIAADVDLSAWPPANA

QPVDVTDGYDLLERAGYGYGPAFQGVRAIWRRGEELFAEVALEPELTDTAARFGLHPALLDAAWHPELR

DEVAETSPDGRRWWSQPSRWAGLRLHTAGATVLRVRLAPVDADSMSLQAADETGDPVLTVDSLS

SEQ ID NO: 6
HPLLGAGMPIAGTGAVLFGTEVAHPWFDGHETLPAAAFAEIAVRAAAEVGSPVVGELHVELLPRIPADGR

LRLQTWVDGPDPTGVRRFTVHARPDPTAAWLRVASGVLTGAEAPVPAFAGGEPLHIADGTPAGFLLHPD

ATPAADWFGLVAHGSGARQQHVYQAGEGLCVTDDAGRPIVTAARVR

SEQ ID NO: 7
HPLLGWGVPVAEAGGRLYTGRVARQDGPVLSVAAFVEMAFAAAGGRPIRELSVDALLYIPDDGTAELQT

WVSEHRLTIHARYRDTEPWTRLATAALDTTAPATTHTPHPGLITTALTLTGDEAPAIWHDLTLHTSNATEL

HTHITPGDDGTLTITATDTTGQPVLTAHTAT

SEQ ID NO: 8
RLSALASLGEPQIVVRDDTPLVARLAREKSPALTIPGERAWVLEPDHSGVLQELALVAADTDVRPLRPGE

VRIEVRAAGLNFRDVLVALGTDLGDGVFGAEGAGVVLETGSDVRDLRPGDRVFGLLEGGHGSIAIADRR

MLAVIPEGWSFATAASVPEVFVIAYYGLVDLAGLRAGESVLIHAATGGVGMAATQIARHLGAQVYATAGV

GKQHILRDAGLGDDRIADSRTTDFREAFRDSTQGRGVDVVLNSLKGDFVDASLDLLADGGRFLELGQTDI

RDAGEIAAERPGTTYHSFTRMNAGPDRLREIIAELLALFEQGVLRPSPVHTWDIRHAREAFSWMSGGRHT

GKMVLTMPQRIDPGGTVLIAGDSEALARIAARHLGVRHLLLDRGVADAAPDAVVCDVSDHDALERVLADL

SPEHPLTAVIHTGGAAVTDEIRRLHDLTESLDLTDFVVFSQDAPAAVEAFARSRRAHGLPVRTIAWGIPEA

DPVVADEHLLGRALASAEQAQIVARVNTAGLRALTAANALPTLLRNLIRAEPEETGQSAWPHRFEAAGAD

REEALLDLIRANVVDILSLPTADRYAPDRTFREMGIDSLTAVGLRNSLAKATGLPLPTTMVFDYPTPAVLTA

RMREL

SEQ ID NO: 9
RLSTLVALGEPQIALRDSTPLVPRLAPESSTALTTPAARAWVLEPARSGTLRELSLVAADTDARPLRPGEV

RVDVRAAGLNFRDVLIALGTYPGDGVMGGEAAGVVLEVGPEVNDLSVGDRVFGLVTDGFGPVTITDRRL

LAAMPQDWSFTTAASAAMAFATAHYGLVELAGLKAGESVLIHAATGGVGMAATQIANHLGAHIYATASSG

-continued

```
KQHLLRAAGIDDDRIANSRTTGFRDAFLDSTGGRGVDVVLNSLSGEFVDSSLDLLAHGGRFIEMSTDIRDA

GRIAAERPGTTYQAFHLVDADPDRLREILTELLALFDQGILDPLPVQAWDIRQAREAFSWMSRARHTGKL

VLTIPQHIDPDGTVLITGGSGGLAGVVARHLVADKGARRLLLLSCDTLDATLAAELTESGARVDTAVCDVS

DRAALAQVLAGVSPEHPLTAIVHAGGAAVADESRQLHHLTKNRDLAAFVVFSQDAPAATEAFAGIRQAEG

LPVTTIAWGIPEAEPVVVGQHLLDRAMASADRAHVAARVNTAGLRALAAANALPPVLKNLVGAETDGTGH

QDWSRRFMVAEAARQQELLDLIRTTVMEILSLPTTARYFPDRTFRENGIDSLTAVELVNSLAKTTGLRLSA

TMVFDYPTPTALAGRMREL
```

In some embodiments of any of the foregoing polyketide synthases, the β-ketone processing domain is a ketoreductase, wherein the ketoreductase (a) includes an amino acid other than tyrosine at the position corresponding to the tyrosine in the conserved YAAAN (SEQ ID NO: 97) catalytic motif and does not include the conserved αFG helix in SEQ ID NO:1; (b) includes a glutamic acid residue at the position corresponding to alanine 6632 of S9-pksA ORF (the change in S9) in SEQ ID NO: 2; or (c) does not include the amino acids corresponding to amino acids 3386 to 3516 of WT S12-pksB ORF of SEQ ID NO: 3.

In some embodiments of any of the foregoing polyketide synthases, the β-ketone processing domain is a dehydratase, wherein the dehydratase includes (a) an aspartic acid at the position corresponding to the glycine at position 4288 in pksB of S679-pksB ORF in the conserved HXXXGXXXXP (SEQ ID NO: 98) motif of SEQ ID NO: 4; (b) a substitution in the conserved LPFXW (SEQ ID NO: 99) motif at the position corresponding to position 3066 to 3070 in S12-pksB ORF in SEQ ID NO: 5; (c) a deletion between Pro 6844 and Trp 6874 of S679-pksA ORF of SEQ ID NO: 6; or (d) a substitution or deletion at the positions corresponding to A, B, C, and D of SEQ ID NO: 7.

In some embodiments of any of the foregoing polyketide synthases, the β-ketone processing domain is an enoylreductase, wherein the enoylreductase does not include a lysine at the position corresponding to position 1546 of S12-pksB ORF in SEQ ID NO: 8 and/or the aspartic acid at the position corresponding to position 1568 of S12-pksB in SEQ ID NO: 8 or 9.

In another aspect, the disclosure provides a chimeric polyketide synthase, wherein at least one domain of the polyketide synthase has been modified as compared to a polyketide synthase having the sequence of SEQ ID NO: 10 or 11, wherein the modification results in altered enzymatic activity.

SEQ ID NO: 10
```
MSREEFIQPIHDLLRVNAERLGDKIAYADSRRELTHAELRTRTGRIAGHLVDLAVERGDRVAILLGNRVETI

ESYLAIARAGAIAVPLNPDATGAEVAHFLADSGAVLVITDSAHLDDVRRAAAAVTVVLVDEGPLPAGTRSF

AELATAEPPTPARDDLGLDEAAWMLYTSGTTGTPKGVVSTQGSGLWSAANCDVPAWELTENDVLLWPA

PLFHSLAHHLCLLATTAVGATARIMSGFVAGEVLHELEEHACTVLVGVPTMYHYLLGAVGEAGPRLPSLK

MGLVAGAVSPPALIEGFERVFGVPLLDTYGCTETTGSLTVNRLSGPRMPGSCGQAVPGISLRFVDPHTG

AEVAEGEEGELWASGPSLMIGYHGRPDATREVLSDGWYRTGDLARRSETGHVTITGRVKELIIRGGENIH

PRDIEAVALELPGVRDAAAAGKQHPVLGEIPALYLVPDADGVDAEAVLAACREKLSYFKVPEEIYRVDAIP

RTLSGKVKRAALTEAPAELLSAASGNGSLYRLEWVPAETPPAGTGGPVAVHVTRRAVATGPADLPDQEQ

AATWDALRGEQTGPGGPVLIDLDGADIDDARLSALASLGEPQIVVRDDTPLVARLAREKSPALTIPGERA

WVLEPDHSGVLQELALVAADTDVRPLRPGEVRIEVRAAGLNFRDVLVALGTDLGDGVFGAEGAGVVLET

GSDVRDLRPGDRVFGLLEGGHGSIAIADRRMLAVIPEGWSFATAASVPEVFVIAYYGLVDLAGLRAGESV

LIHAATGGVGMAATQIARHLGAQVYATAGVGKQHILRDAGLGDDRIADSRTTDFREAFRDSTQGRGVDV

VLNSLKGDFVDASLDLLADGGRFLELGQTDIRDAGEIAAERPGTTYHSFTRMNAGPDRLREIIAELLALFE

QGVLRPSPVHTWDIRHAREAFSWMSGGRHTGKMVLTMPQRIDPGGTVLIAGDSEALARIAARHLGVRHL

LLDRGVADAAPDAVVCDVSDHDALERVLADLSPEHPLTAVIHTGGAAVTDEIRRLHDLTESLDLTDFVVFS

QDAPAAVEAFARSRRAHGLPVRTIAWGIPEADPVVADEHLLGRALASAEQAQIVARVNTAGLRALTAANA

LPTLLRNLIRAEPEETGQSAWPHRFEAAGADREEALLDLIRANVVDILSLPTADRYAPDRTFREMGIDSLTA

VGLRNSLAKATGLPLPTTMVFDYPTPAVLTARMRELLAGESPAPARTAARAVAQDEPLAIVGMACRLPGG

VSSPDDLWRLVAAGTDAISEFPADRGWDVDNLYDPDPDAPGKTYTVLGGFLDGVAGFDASFFGISPREA

LAMDPQQRLMLEVSWEAFEHAGIPPRSVRGSDAGVFMGAFPSGYDAGLEEFGMTGDAVSVLSGRVSYF
```

```
FGLEGPAITVDTACSSSLVALHQASSALRQGECSLALVGGVTVLATPQTFVEFSRQRGLALDGRSKAFAD
AADGAGWAEGVGVLVVERLSDARAKGHQIWGVIRGSAVNQDGASNGLSAPNGPSQQRVIRQALANAGL
APHEVDVVEAHGTGTTLGDPIEAQAVIATYGQDREQPLLLGSLKSNVGHTQAAAGVSGVIKMVMALQHD
TVPATLHVDAPSRHVDWTAGAVELVTENRPWPETGRVRRAGVSSFGISGTNAHVILESAPEQPVSPPEA
VAPVVASDRVPLVISAKTPAALAEMENRLRAYLAAAPGADPRAVASTLATARSVFEHRAVLLGENTITGTV
AGADPRVVFVFPGQGWQQLGMGRALRESSPVFAARMAECAAALSEFVDWDLFTMLDDPAVIDRIDVLQ
PACWAVMMSLAAVWQAAGVRPDAVIGHSQGEIAAACVAGALSLRDAARIVALRSQLLAREMVGHGVMA
AVALPADDIPLVDGVWIGACNGPSSTVISGTPEAVEVVVAACEERGARVRRITAAVASHSPLGEKIRTELL
GISASIPSRTPVVPWLSTADGIWIEAPLDPAYWWRNLREPVGFGPAVDLLQARGENVFLEMSASPVLLPA
MNDAVTVATLRRDDGTPDRMLTALAEAHAHGVIVDWPRVFGSTTRVLDLPTYAFEHQRYWAVSADRPS
DAGHPMVETVVPLPASGGVALTGRVSLATHAWLADHAVRGTALLPGTAFVELVTRAATEVDCPVIDELVI
EAPLPLTQTGAVQLSTTVGEADESGRRPVTVFSQADGTDAWTRHVTATIGRAASLPDPVAWPPAQAEPV
DVTGFYDELAAAGYEYGPAFQGLRAAWSDGDTVYAEVVLAEEQAHEVDRYAVHPALLDAALQAGMVNT
AGTGQGVRLPFSWNGIQVHSTGATTLRVAATPLADGWSVRAAADNGRPVATIGSLVTRPVTTDMLGSTT
DDLFAVVWTEITAPEPGDPSDVGVFTALPEAGGDPLTQTRALTAQVLQTVQQWLAGEDRPLVVRTGTDL
ASAAVSGLVRSAQSEHPGRLILVESDDELTPEQLAGTAGLDEPRIRIDGGHYEVPRLAREDASLTVPEDR
AWLLELPGSGTLRDLRVIPTDTAERPLRWGEVRVGVRAGGLNFRDVVVALGMVTDPRPAGGEAAGVVL
ETGPGVEDLSPGDRVFGILDGGFGSVAIADRRLLAVIPDGWSFTTAASIPVVFATAYYGLVDLAGLRAGES
VLIHAATGGVGMAATQIARHLGAEIYGTAGIAKQHVLRDAGLGDDRIADSRTTGFRETFRDSTQGRGVDV
VLNSLSGDFVDASLDVLAEGGRFIEMGKTDIRDAEQITHATYRAFDLMDAGPDRVREIIAELLGLFEQGVL
RPLPVQAWDIRQARDAFTWMSRARHIGKIVLTIPQQLDPDGTVLISGGSGVLAGILARHLVAERGVRHLLL
VSRSAPSEALISELTALGAQVETVACDVSDRVALEQVLDGVPLTAVFHTAAALDDGVVESLTPQRVDTVL
RPKADAAWYLHELTRDADLAAFVMYSSVAGIMGAAGQGNYAAANAFLDALAAHRRREGLPALSLAWGL
WEDASGLSAGLTETDHDRIRRGGLEAIAAEHGMRLFDTATRQGEPVLLASPLNLTRQGEVPALLRTLHRP
VARRAATANGRPADLTPEALLKLVCGRAAAVLGHVDADAVPVAVAFRDLGVDSLTAVELRNSLAKATGLR
LPATLVFDYPTPTVLAGRLGELLAGGTAPVRAAVVRRAAASDEPLAIVGMACRLPGGVLSPEDLWRLVES
GGDAISGFPVDRGWDVENLFDPDPDAAGRTYAVRGGFLDGAAGFDASFFGISPREAQAMDPQQRLVLE
VSWEAFERAGIEPGSVRGSDTGVFMGAYPGGYGVGTDLGGFGMTSVAVSVLAGRVSYFFGLEGPAMT
VDTACSSSLVALHQAGSALRQGECSLALVGGVTVMPTPQTFVEFSRQRGLAADGRCKAFADAADGTGF
SEGVGVLLVERLSDAQARGHNILAVVRGSAVNQDGASNGLTAPNGPSQQRVIRQALANAGLAGAEVDVV
EAHGTGTTLGDPIEAQAVIATYGQDRDQPVLLGSLKSNLGHTQAAAGVSGVIKMVMALRHDTVPATLHID
EPSRHIDWTAGAVELVTENQSWPETGRARRAAVSSFGISGTNAHVILESAPAQPVPLVDTPVSAVTAGVV
PLPISARTVPALADLEDRLRAYLTTTPETDLPAVASTLAVTRSVFEHRAVLLGEETVTGIAVSDPRVVFVFS
GQGSQRVGMGEELAAAFPLFARLHRQVWDLLDVPDLEVDDTGYVQPALFALQVALFGLLESWGVRPEA
VIGHSVGEVAAGYVAGVWSLEDACTLVSARARLMQALPAGGAMVAVPVSEERARAVLVDGVEIAAVNGP
ASVVLSGDESAVLRVAEGLGRWTRLSASHAFHSVRMEPMLEEFRQVASELTYREPRIVMAAGEQVTTPE
YWVRQVRDTVRFGDQVAAFGDAVFLEIGPDRTLSRLIDGIPTLHGDDEQHAVVAALAELHVQGVPIDWSS
ILGANPARVLDLPTYAFQHERYWMVSTGRVGGEGHPLLGWGVPVAEAGGRLYTGRVARQDGPVLSVAA
FVEMAFAAAGGRPIRELSVDALLYIPDDGTAELQTWVSEHRLTIHARYRDTEPWTRLATAALDTTAPATTH
TPHPGLITTALTLTGDEAPAIWHDLTLHTSNATELHTHITPGDDGTLTITATDTTGQPVLTAHTATPTTIPVH
```

-continued

```
TPTTPADDLLTLTWTQIPTPGPGDPTDIAVCTALPDPDGDPLAQTRTLTAQVLQSIQTTLTGEDRPLVVHT

GTGLASAAVSGLVRSAQSEHPDRFILVESDDSLPQAQLAAVAGLDEPWLRITGSCYEVPRLTKTTTATAT

AVSEPVWNPDGTVLITGGSGALAGILARHLVTERGVRHLLLISRSTPSTTLTDELRELGAHVDVAACDVSD

RDALARVLDGVDLTAVFHTAGALDDGVVESLTPQRLDTVLTPKADGAWHLHELTRDRDLTAFVMYSSAA

GVMGAAGQGNYAAANAFLDALAEHRHADGLPALSLAWGMWDDTDGMTASLSGTDHRRIRRSGQRAIT

AEHGMRLLDKASGRSEPVLVATAMNPIPDTDLPALLRSLYPKTARKSQPIQELSPEALLKIVRDSAALMLG

HPNTDAIAATTAFRDLGVDSLIAVELRNSLAKATGLRLPATLVFDYPTPTVLAGRLGELLAGVTPQRHATV

RTGTASDEPLAIVGMACRLPGGVSSPEDLWRLVESGTDAITDFPTDRGWDTDDLFDPDPDTAGKTYTVH

GGFLDDVAGFDASFFGISPREAQAMDPQQRLVLEAAWEAFERAGIEPGSVRGSDTGVFMGAYPGGYGI

GADLGGFGATAGAGSVLSGRLSYFFGLEGPAMTVDTACSSSLVALHQAGSALRQGECSLALVGGVTVIA

NPQIFVEFSRQRGLAADGRCKAFADSADGTGWSEGVGVLLVERLSDAQARGHNILAVVRGSAVNQDGA

SNGLTAPNGPSQQRVIRQALANAGLAGAEVDVVEAHGTGTTLGDPIEAQAVIATYGQDRDQSVLLGSLKS

NLGHTQAAAGVSGVIKMVMALQNGVVPRTLHADQPSRHIDWTAGAVELVTENQPWPELDRPRRAAVSA

FGVSGTNAHVILESAPDQPVPLVDTPVSAVTAGVVPLPISARTVPALADLEDQLRAYLTTAPETDLPAVAS

TLATTRSVFEHRAVLLGEDTVTGTAIPDPRIVFVFSGQGSQRAGMGEELAAAFPLFARLHRQVWDLLDVP

DLDVDDTGYVQPALFALQVALFGLLESWGVRPRAVIGHSVGEVAAGYVAGVWSLEDACALVSARARLM

QALPAGGAMVAVPVSEERARAVLVDGVEIAAVNGPASVVLSGDEAAVLRVAEGLGRWTRLSASHAFHSV

RMEPMLEEFRQVVSRLTYREPRIVMAAGEQVTTPEYWVRQVRETVRFGDQVAAFGDAVFLEIGPDRTLS

RLIDGIAMLDGDDEVRAAVAALAMMHVQGVGVDWPAILGTTTGRVLDLPTYAFQHERYWMANADEGHP

LLGKVEHPLLGSVMALPNSDGVVLTGRISLATHAWLADHVVRGTVLLPGTGFVEMVARAAAEVGCGVIDE

LLIEAPLLLPEHGGVHLSVSVGEADGAGRRPVTVFAQADDAEVWVRQVTATISPAGPAVSLPELEVWPPV

QAEPVDVSTFYERLARADWQWGPAFQGLRAAWRDGDTIYAEIVLADEEAREADQFLVHPALLDAALQTS

VLKTPDDLRLPFSWNQIEFHATGAAILRVAVTPVADRWIVHAADSTGRPVATIGALVSRPVTAETLGSNTD

DLFALTWTEIPTPGPGDPADVAVCTALPEPDSDPLTQTRTLTAQVLQSIQTSLTGEDRPLVVHTGTGLASA

AVSGLVRSAQSEHPDRFILVECDDETLTPDQLAATAGLDEPWLRITGGHYEVPRLTKTTTAAATTVSEPV

WDPDGTVLITGGSGALAGILARHLVTERSVRHLLLISRSTPSTTLINELRELGAHIETAACDVSDRDALARV

LDGVDLTAVFHTAGALDDGVVESLTPQRLDTVLMPKADAAWHLHELTRDRDLAAFVMYSSAAGVMGAA

GQGNYAAANAFLDALAEHRRADGLPALSLAWGMWDDADGMTASLSGTDHRRIRRSGQRAITAEHGMRL

LDKASGRSEPVLVATAMNPAGEGEVPALLRTLHRPVARRAATTNGRPADLTPEALLKVVRDSAAVVLGH

ASADTVPAATAFQELGLDSLIAVELRNSLAKATGLRLPATMVFDYPTPAALAGRLGELLAGETTPATAAVV

RRATASDEPLAIVGMACRLPGGVSSPEDLWRLVESGFDAITGFPTDRGWDVDNLYDPDPDAPGKSTTLH

GGFLDDVAGFDASFFGISPREAVAMDPQQRLAMEVSWEAFERAGIEPGSVRGSDTGVFMGAYPGGYGI

GAELGGFMLTGRAGSVLAGRVSYFFGLEGPAMTVDTACSSSLVALHQAAYALRQGECSLALVGGVTVM

PTPVMFVEFSQQQNLADDGRCKAFADSADGTGWSEGVGVLLVERLSDAQARGHNILAVVRGSAVNQD

GASNGLTAPNGPSQQRVIRSALTSAGLTTADVDVVEAHGTGTTLGDPIEAQAVLATYGQDRDQPVLLGSL

KSNLGHTQAAAGVSGVIKMVMALQNGVVPRTLHVEEPSRHVDWTAGAVELVTENQSWPETGRARRAAV

SSFGFSGTNAHVILESAPAQPVPPMDTPAPAVTTGVVPLPISAKSLPALADLEDQLRAYLTATPETDLPAV

ASTLAMTRSVFEHRAVLLGEETVTGTAIPDPRIVFVFSGQGSQRVGMGEELAAAFPLFARLHRQVWDLLD

VPDLDVDDTGYVQPALFALQVALFGLLESWGVRPRAVIGHSVGEVAAGYVAGVWSLEDACALVSARARL

MQALPAGGAMVAVPVSEERARVALVDGVEIAAVNGPASVVLSGDEAAVLQIAEGLGRWTRLSASHAFHS

VRMEPMLEEFGQVASELTYQEPRIVMAAGEQVTTPEYWVRQVRDTVRFGDQVAAFGDAVFLEIGPDRTL
```

-continued

```
SRLIDGIAMLDGDDEVRAAVAALAELHVQGVPIDWPAVLGTTTGRVLDLPTYAFQHQRYWAASTDRPAG

DGHPLLDTVVALPGADGVVLTGRISLATHAWLADHAVRGTVLLPGTGFVEMVARAAAEVGCAVVDELVIE

APLLLPASGGVQLSVSVGEADDAGHRPVTVHSQADETEAWVRHVTATISPSGPIVSPPEFEVWPPAQAE

PVEVARFYDELAAAGYEYGAAFQGLRAAWRAGETIYAEVVLAEDQTLEAARFTVHPALLDAALQANILNA

SGDLRLPFSWGQVQFHTTGAATLRVAVTPVADGWTIQATDDAGRPVATVGSVVARPVAGLGATAEDLFA

LTWNEIPAPGQGGRTVGRFEDLADDGPVPELVVFTALPDVDADPLVRTRALTARVLEAIQRWLGEPRFA

DSTLVVRTGTDLASAAVSGLVRSAQSEHPDRFILVEGDSSPVEIGLDEPWLRVDGGRYEVPRLIRLSAEP

VQEAAWNPDGMVLITGGTGALAGILARHLVAENKARRLLLVSRSVPDDALISELTELGAEVGTAVCDVSD

RAALARVLAGVPSLTAVIHTAGVLDDGVMESLTPQRLDTVLRAKADGAWHLHELTRDRDLAAFVMYSSA

AGLMGSPGQGNYAAANAFLDALAVERRAEGLPALSLAWGFWEETTGLTANLTGADRDRIRRGGLQTITA

ERGMRMFDTATQHGEPVLLAAPISPVRDGEVPALLRSLHRRGTRRGTTADASAQWLAGLAPEEREGALI

KVVRDTAAVVLGHADAGTIPVTAAFKDLGLDSLTAVELRNSLAKSTGLRLPATMVFDYPTPASLAARLDDL

MNPRVSSTALLAELDRIEGMFDSVTFDEKQASLVKDRLSAALGKWQQISRSADVATVALANADAGEILDFI

DREFGNPTI

SEQ ID NO: 11
MPDHDKLVEYLRWATAELHTTRAKLQAATEAGTQPLAIVGMACRLPGGVSSPEDLWRLVESGTDAISGF

PVDRGWDVDGLYDPDPDVPGKSYTVEGGFLDAVTGFDAPFFGISPREALAMDPQQRLVLEASWEAFER

AGIEPGSVRGSDTGVFMGAFPGGYGTGADLGGFGMTGGAASVLSGRVSYFFGLEGPAMTVDTVCSSSL

VALHQAGYALRHGECSLALVGGVTVMSTPQTFVEFSRQRGLAADGRCKAFADNADGTGWSEGVGVLLV

ERLSDAQARGHNILAVVRGSAVNQDGASNGLTAPNGPSQQRVIRQALANAGLTGADVDVVEAHGTGTTL

GDPIEAQAVIATYGRDRDQPVLLGSLKSNLGHTQAAAGVSGVIKMVMALQNGVVPRTLHIEEPSRHVDWT

AGAVQLVTENRPWPELGRARRAAVSSFGLSGTNAHVILESAPDQPPAPTTDTPVSAVTAGVVPLPISAKT

VPALADLEDRLRTYLTTTPDTDLPAVASTLATTRSLFEHRAVLLGEDTVTGTAIPDPRVVFVFPGQGWQW

QGMGSALLTSSTVFAERMAECAAALSEFVDWDLLTVLDDPSVVDRVDVVQPACWAVMISLAAVWQAAGI

HPDIVLGHSQGEIAAACLAGAISLPDAARIVAQRSQLIAHQLTGHGAMASISLPADDIPTTDKVWIAAHNGT

STVIAGDPQAVEAVLATCETRGARVRKINVDYASHTPHVEQIRTELLDITTGIEAHTPAVPWLSTTDNTWID

QPLDPTYWYRNLREPVRFGPAIDLLQTQDNNLFIEISASPVLLQTMDNAATVATLRRDEDTTQRLLTAFAE

AHVHGATIDWPTVLDTTTTPVLDLPTYPFQRQRYWATSNGRSTGQGHPLLETVVALPGTDGVALTGRISL

ATHPWLTDHTVRGTVLLPGTAFVELVTRAATEVNCQIIDELIIEAPLPLPQTDGVQLSVTVGEADEAGHRP

VTVYSQTDESDDWIQHVTATIGPGASLPETAAWPPAHAEPVNVTGLYDNLAAAGYEYGPAFQGLQAAW

RAGDTVYAEVTLAEEQAQETARFTMHPALLDAALHTIALHDTGDLHLPFSWTRVQFHGTGAATLRVAVTP

AADGWNIRATDDTGRAVATIGSLVTRPMAAETTDDLLALTWTEIPAPEPVDPTDVVVFTALPDTVEDVPA

QTRALTTRVLHTIQEWLADDDRTLIVRTGTDLASAAVSGLVRSAQSEHPGRFILVESADEALTQEQLAATA

GLDEPRLRITGGRYEVPRLTREDTALAVPTDRAWLLEQPRSGSLEDLALLPTDAAERPLQAGEVRIGVRA

AGMNFRDVVVALGMVTDTRLAGGEAAGVVLEVGTDVNDFRPGDRVFGILEGGFGSVAICDHRTLAVIPD

GWSFTTAASVPIAFATAYYGLVDLAGLRAGESVLIHAATGGVGIAATQIARHLGAEIYGTASVGKQHVLRD

AGLADDRIADSRTTDFRDTFRDGTQGRGVDVVLNSLRGEFIDASLDLLVDGGRFIEMGKTDIRDAAQIPDA

TYHAFDLMDAGHDRLREIMTELLALFEQGVLHPMPVHAFDIRQAREAFSWMSRARHIGKLVLTIPQPIDPD

GTVLITGGSGVLAGIVARYLVTENRARHLLLLSRSAPSASLIDELTALGAHVDVAACDVADRAALAEILDGV

DLTAVIHTAGALDDGVVESLTPQRLDTVLTPKADGAWHLHELTRDRDLAAFIVYSSAAGVLGAAGQGNYA

AANAFLDALAVHRRLEGLPGLSLAWGLWEDASGLTADLTDADRDRIRRSGQRAITAAYGMRMLDAATRQ
```

-continued

SEAILLAAPISPIQDGDVPAILRSLHRRVGRRASVAHGHPADLTPEALLKVVRDSAAMVLGHTNADTVPTA

TAFQELGLDSLTAVELRNSLTKATGLRLPATMAFDYPTPDALAARLGELLAGEAAPKAAAAVRRATASDE

PLAIVGMACRLPGGVSSPEDLWRLVESGTDAITDFPTDRGWDTDTLFDPDPDTPGKTYTVHGGFLNDVA

GFDAPFFGISPREAVAMDPQQRLVLESSWEAFERAGIQPDSIRGSDTGVFMGAYPDGYGIGADLAGFGV

TAGAGSVLSGRVSYFFGLEGPAMTVDTACSSSLVALHQAAYALRQGECSLALVGGVTVMPSPRTFIEFS

RQRGLAADGRSKAFADAADGTGFSEGVGVLLVERLSDAQAKGHNILALVRSSAVNQDGASNGLTAPNG

PSQQRVIQSALAGAGLTSADVDVVEAHGTGTTLGDPIEAQAVLATYGQDRDQPVLLGSLKSNLGHTQAA

AGVSGVIKMVMALQHNTVPATLHVDAPSRHVDWTAGAVRLATENQPWPETNRPRRAGVSSFGVSGTNA

HVILEQAPAASPVEPVDTTDVVIPLVVSARSSGSLSDQADRLAALVGSPDAPALTSLADALLTRRTVFSQR

AVVVAGSHEQAAAGLRALASGDSHPALVTGAAGPARGVVLVFPGQGSQWAGMGAELLDTSPVFAARIA

ECAEALRPWVDWSLDEVLRGDASADVLGRVDVVQPASFAVMVGLAAVWESAGVRPDAVLGHSQGEIAA

AYVAGALSLTDAAKIVAVRSRLIAARLAGRGGMASVALAPDEAAAKLGRTELAAVNGPASVVIAGDAEALD

ETLAMLEGEAVRVRRVAVDYASHTPHVEELEQSMAEALADVRSRQPRVGFLSTVTGDWVTEAGALDGG

YWYRNLRQPVRFGPAVASLAEAGYTVFVEASAHPVLVQPVAETLDRTDAVVTGTLRRQDGGLPRLLTSM

AELFVGGVPVNWPVLLPAGAVRGWVDLPTYAFDHQRYWLENRVATDAAALGLAGADHPLLGAIVAVPQ

SGGVAMTSRLSPRNHPWLAEHTLGGVPTVPTSVLVELAVRAGDEVGCGVVEELTVDAPLLLPERGGVRV

QVIVGATDANGQRGLDIFSAPEDTGQEAWTRHATGTLAPGGDIAADVDLSAWPPANAQPVDVTDGYDLL

ERAGYGYGPAFQGVRAIWRRGEELFAEVALEPELTDTAARFGLHPALLDAAWHPELRDEVAETSPDGRR

WWSQPSRWAGLRLHTAGATVLRVRLAPVDADSMSLQAADETGDPVLTVDSLSLCAVSADQLTTAESSD

DALFRLEWTPLSKAPTAARSWVPVETGADVAALDGQAVVDAVMLEAAGTGDALELTCRVLEVVQAWLTL

PGWDESRLVVVTRGAVGAVGDPAGSAVWGLVRAAQAENPDRIALLDLDGGRPVEPLLAESEPQLAIRGA

EALVPRLIRAAAATDAPALFDESQTVLITGGTGSLGGLLARHLVGRYGLRRLVLVSRRGPDAPGAYELAAE

LAAHGAEAALVACDLTDRDAVARLLTEHHPTAVVHAAGVSDDGVIGTLTSDRLAYVFGPKATAARHLDEL

TRELLPDLAAFVTYSSISAVFLGAGSGGYAAANAYLDGLMARRHAEGLPGLSLAWGLWDQEADGGGMA

AGLQDITRNRMRRGGVLSFTPAEGMALFDAAMATDEALVVPVRLDLPALRAEAVAEGRSAPVLLRGLV

RPGRRLARTVSGGTGVLADLTPEALLKLVRGRAAAVLGHVDADAVPVAAAFKDLGVDSLTAVELRNSLAK

ATGLRLPATLVFDYPTPTVLAGRLGELLAGGTAPVRAAVVRRAAASDEPLAIVGMACRLPGGVLSPEDLW

RLVESGGDAISGFPVDRGWDVENLFDPDPDAAGRTYAVRGGFLDGAAGFDASFFGISPREAQAMDPQQ

RLVLEVSWEAFERAGIEPGSVRGSDTGVFMGAYPGGYGMGTDLGGFGMTSVAVSVLAGRVSYFFGLEG

PAMTVDTACSSSLVALHQAGSALRQGECSLALVGGVTVMPTPQTFVEFSRQRGLAADGRCKAFADAAD

GTGFSEGVGVLLVERLSDAQARGHNILAVVRGSAVNQDGASNGLTAPNGPAQQRVIQSALAGAGLASAD

VDVVEAHGTGTTLGDPIEAQAVIATYGQDRDQPVLLGSLKSNLGHTQAAAGVSGVIKMVMALQNGVVPR

TLHIDEPSRHIDWTAGAVELVTENQSWPETGRARRAAVSSFGISGTNAHVILESAPAQPVPLVDTPVSDV

TAGVVPLPISARTVPALADLEDQLRAYLTTAPETDLPAVASTLAMTRSVFEHRAVLLGEETVTGIAVSDPR

VVFVFSGQGSQRVGMGEELAAAFPLFARLHRQVWDLLDVPDLEVDDTGYVQPALFALQVALFGLLESW

GVRPRAVIGHSVGEVAAGYVAGVWSLEDACTLVSARARLMQALPAGGAMVAVPVSEERARAVLVDGVEI

AAVNGPASVVLSGDESAVLRVAEGLGRWTRLSASHAFHSVRMEPMLEEFRQVASELTYREPRIVMAAGE

QVTTPEYWVRQVRDTVRFGDQVAAFGDAVFLEIGPDRTLSRLIDGIAMLDGDDEVRAAVAALAMMHVQG

VGVDWPAVLGTTTGRVLDLPTYAFQHERYWMVSTGRPGGEGHPLLGWGVPVAEADGRLYTGRVARQD

GPVLPVAAFVEMAFAAAGGRPIRELSVDALLYIPDDGTAELQTWVSEHRLTIHARYRDTEPWTRLATATLD

-continued

```
TTEPATTHTPHPGLITTALTLTGDEAPAIWHDLTLHTSNATELHTHITPGDDGTLTITATDATGQPVLTAHAA

TPTTIPVHTPTTPADDLLTLTWTQIPTPGPGDGADIAVCTALPDPDSDPLAQTRTLTAQVLHSIQASLTGED

RPLVVHTGTGLASAAVSGLVRSAQSEHPDRFILVESDETLTPDQLAAVAGLDEPWLRITDGRYEVPRLTK

TTTTATATAVSEPVWDPDGTVLITGGSGALAGILARHLVTERGVRHLLLVSRSTPSTTLIDELRELGAHVDV

AACDVSDRAALARVLDGVDLTAVFHTAGALDDGVVESLTPQRVDAVLRPKADGAWHLHELTRDRDLTAF

VMYSSAAGVMGAAGQGNYAAANAFLDALAEHRRADGLPALSLAWGMWDDADGMTASLSGTDHRRIRR

SGQRAITAEHGMRLLDKASGRSEPVLATAMNPIPDTDLPALLRSLYPKTARKSQPIQELSPEALLKIVRDS

AAMVLGHANADTVPTATALQELGLDSLTAVELRNSLTKATGLRLPATMAFDYPTPAALAGRLGELLAGDT

TPATAAVVRRATASDEPLAIVGMACRLPGGVSTPEDLWRLVESGTDAITDFPTDRGWDTDDLFDPDPDT

PGKTYTVHGGFLDDVAGFDASFFGISPREALAMDSQQRLVLEAAWEAFERAGIEPGSVRGSDTGVFMGA

YPDGYGIGADLGGFGATAGAGSVLSGRLSYFFGLEGPAMTVDTACSSSLVALHQAGSALRQGECSLALV

GGVTVIANPQIFVEFSRQRGLAADGRCKAFADNADGTGFSEGVGVLLVERLSDAQAKGHNILALVRSSAV

NQDGASNGLTAPNGPSQQRVIRQALANAGLTGAEVDVVEAHGTGTTLGDPIEAQAVLATYGQDRDQPVL

LGSLKSNLGHTQAAAGVSGVIKMVMALRHDTVPATLHIDEPSRHIDWTAGAVELVTENQPWPVLGRPRR

AAVSAFGVSGTNAHVILESAPDQPPAPATDTPAPAATAGVVPLPISAKTVPALADLEDRLRTYLTTTPETDL

PAVASTLATTRSLFEHRAVLLGEDTVTGTTIPDPRIVFVFPGQGWQWQGMGSALLTSSTVFAERMAECA

AALSEFVDWDLLTVLDDPSIVDRVDVVQPACWAVMISLAAVWQAAGIHPDIVLGHSQGEIAAACLAGAISL

PDAARIVAQRSQLIAHQLTGHGAMASISLPADDIPTTDKVWIAAHNGTSTVIAGDPQALDTVLATCETHGA

RVRKINVDYASHTPHVEQIRTELLDITTDIEAHTPTVPWLSTTDNTWIDQPLDPTYWYRNLREPVRFGPAID

LLQTQDNNLFIEISASPVLLQTMDNATTVATLRRDEDTTQRLLTAFAEAHVHGATIDWPTVLDTTTTPVLDL

PTYPFQRQRYWATSNGRPTSQGHPLLETVVALPGTHGVALTGRISLATHPWLTDHTVRGTVLLPGTAFV

ELVTHAATEVNCQVIDELIIEAPLPLPQNGGVQLSVTVGEADEAGHRPVTVYSQTDESDDWVQHVTATIAP

GVSSSESAAWPPAQAEPVNVTGLYDNLAAAGYEYGPAFQGLQTAWRDGSTVYAEVTLAEEQAQETARF

TMHPALLDAALHTIALHDTADLQLPFSWRQVQFHGSGAATLRVAVTPAADGWNIRATDDTGQTVATIGSL

VTRPMAAETTNDLLALTWTEIPAPEPVDPADVVVFTALPEPGSDPLAQTRALTTRVLHTIQEWLADDDRTL

IVRTGTDLASAAVSGLVRSAQSEHPGRFILVESDDETLTHEQLAATAGLDEPRLRITDGRYEVPRLTREDT

ALAVPEGGAWMLDQPSRSGTLQDLRLVPTDAAERPLRPGEVRVGVRAAGLNFRDVAVALGMVTDTRLI

GGEGAGVVLEAGPGVEDLRPGDRVFGLLEGGFGPVAVADRRALALIPDGWSFTTAASVPIAFATAYYGLL

DLAGLRAGESVLIHAATGGVGMAATQIARHLGADVYATASTGKQHVLRDAGLSDDRIADSRTTGFRETFR

DSTDGRGVDVVLNSLKGDFVDASLDLLVDGGRFIEMGKTDIRDAAQIPDATYRAFDLMDAGPERLREIITE

LLALFEQGVLRPLPVHAFDIRQARDAFGWMSRARHIGKLVLTIPQPIDPDGTVLITGGSGVLAGIVARHLVI

AEGLRNLLLLSRSAPSEALIGELTALGAQVETAACDIADRAALARVLDGVPLTAVIHTAGALDDGVVESLDP

QRLDSVLTPKADGAWHLHELTRDRDLAAFIMYSSAAGVLGAAGQGNYAAANAFVDALAVHRRFMGLPAL

SLAWGLWDDTSALTAGLTDSDHDRIRRSGARTITAEHGMRMFDAATRQSEAVLLAAPMGPIRGEDVPAL

LRGLATVRQPRTRAKRDMGPERLRDRLNGRTSVEQHRIMVELVLAHATSVLGHESPDAIAPDRAFKDLG

MDSLTAIELRNHLVAETGVRLPATTAFDHPTADDLAKRLLAEVGLTPAPQRTEADIREEVVVREPAGDDS

WTSEPIAIVSMSCRAPGGVDSPESLWRLVESGTDAITDFPGDRGWDVAGLYSPDPDTGYKTYCVQGGFL

DAAADFDAAFFGISPREALGMDPQQRLLLETSWEAIERARIDPRSLRGRNVGVYVGGAAQGYGVGAIDQ

QRDNVITGSSISLLSGRLSYALGLEGPGVTVDTACSSSLVALHLACQALRQRECSMALVSGVSVIPTPDVF

VEFSRQRGLAADGRCKSFSASADGTIWAEGVGVLVLERLSEATRLGHRVLAVVRGSAVNSDGASNGLTA

PNGVSQQRVIRQALTGAGLTAADVDVVEAHGTGTKLGDPIEAEAILATYGQDRSTPVCLGSLKSNIGHAM
```

-continued

```
AASGVLAVIKMVEAMRHGLIPRTLHVEEPSPHVDWASGDVALLTENQPWPDDAKLRRAGVSSFGLSGTN

AHVVLEQYRAPAAPDITTTEHEPLAWTLSARDPKALREQAGRLHAALTESPQWRPLDIGYSLATTRSNFA

HRAVAVGSDREDLLRALSKLADGSAWPALVTATAKDRRVAYLFDGQGSQRPDMGSGLYERFPAFARAW

DRISAEFGKHLDHSLTDVYLGRGDAATADLVDDTLYAQAGLFTMEIALFELLAEWGVRPDFVSGHSIGETA

AAYAAGVLSLEDVTTLIVARGRALRQVPPGAMVALRAGEDEAREFLGRTGAALDLAAVNSPTSVVVSGAS

EAVAGFRARWTESGREARTLNVRHAFHSRHVEAVLGEFREVLESLTFRTPALPVVSTVTGRLIEPTELST

SEYWLRQVRQTVRFHDAVRELSGQGVGTFVEIGPSGALASAGLECLGDEASFHAVQRPGSPGDVCLMT

AVAELHAGGTTVDWATVLAGGRATDLPVYPFQHGSYWLAPVTRAADGAPSAGVPAPGEYARPSAPEEP

RTMLELVRLEAAIALSITDPGLIADDSSFLDLGFDSISALRLSNRLAAVTGLDLPPSLLFDHPTPAELAARLD

ELSAADLDGAGVYALLEEIDELDDEDLDMTEEEQTAISELLTKLSAKWSR
```

In another aspect, the disclosure provides, a chimeric polyketide synthase, wherein at least one ketoreductase domain (a) includes an amino acid other than tyrosine at the position corresponding to the tyrosine in the conserved YAAAN catalytic motif and does not include the conserved αFG helix in SEQ ID NO: 1; (b) includes a glutamic acid residue at the position corresponding to alanine 6632 of S9-pksA ORF in SEQ ID NO: 2; or (c) does not include the amino acids corresponding to amino acids 3386 to 3516 of WT S12-pksB ORF of SEQ ID NO: 3.

In another aspect, the disclosure provides a chimeric polyketide synthase, wherein at least one dehydratase domain (a) an aspartic acid at the position corresponding to the glycine at position 4288 in pksB of S679-pksB ORF in the conserved HXXXGXXXXP motif of SEQ ID NO: 4; (b) includes a substitution in the conserved LPFXW motif at the position corresponding to position 3066 to 3070 in S12-pksB ORF in SEQ ID NO: 5; (c) includes a deletion corresponding to positions between Pro 6844 and Trp 6874 of S679-pksA ORF of SEQ ID NO: 6; or (d) includes a substitution or deletion at the positions corresponding to A, B, C, and D of SEQ ID NO: 7.

In another aspect, the disclosure provides a chimeric polyketide synthase, wherein at least one enoylreductase domain does not include a lysine at the position corresponding to position 1546 of S12-pksB ORF in SEQ ID NO: 8 and/or the aspartic acid at the position corresponding to position 1568 of S12-pksB in SEQ ID NO: 8 or 9.

In another aspect, the disclosure provides a chimeric polyketide synthase including a domain having at least 80% sequence identity to the amino acid sequence of (a) SEQ ID NO: 12, 13, or 14; (b) SEQ ID NO: 15, 16, or 17; (c) SEQ ID NO: 18, 19, or 20; (d) SEQ ID NO: 21, 22, or 23; (e) SEQ ID NO: 24, 25, 26, or 27; (f) SEQ ID NO: 28, 29, 30, or 31; (g) SEQ ID NO: 32, 33, 34, or 35; or (h) SEQ ID NO: 36 or 37.

```
SEQ ID NO: 12:
CGCGACCGGGACTTGGCCGCGTTCGTCATGTACTCCTCCGCGGCCGGTGTGATGGGTGCTGAGGG

CCAGGGCAACTACGCGGCGGCCAACGCGTTCCTCGATGCCCTGGCCGAGCACCGCCGC

SEQ ID NO: 13:
TCATGTACTCCTCCGCGGCCGGTGTGATGGGTGCTGCGGGCCAGGGCAACTTCGCGGCGGCCAAC

GCGTTCCTCGATGCCCTGGCCGAGCACCGCCGCGCTGACGGCTTGCCCGCACTCTCCCTGGCATG

GGGTATGTGGGACGACGCAGACGGTATGAGCGGTCAGCGGGCCATCACCGCCGAACACGGGAT

SEQ ID NO: 14:
GGCGTCGACCTGACCGCGGTGTTCCACACCGCCGGAGCCCTGGACGACGGTGTCGTGGAACTGGT

CGCCACCGCAATGAACCCGGCGGGGGAGGGTGAAGTCCCCGCGCTGCTGCGTACG

SEQ ID NO: 15:
CGCGACCGGGATCTGGCGGCGTTCGTCATGTACTCCTCCGCCGCGGGCCTCATGGGCAGCGAGGG

ACAGGGCAACTACGCGGCAGCCAACGCCTTCCTGGACGCGCTCGCGGTAGAGCGTCGT

SEQ ID NO: 16:
TCATGTACTCCTCCGCCGCGGGCCTCATGGGCAGCCCCGGACAGGGCAACTTCGCGGCAGCCAAC

GCCTTCCTGGACGCGCTCGCGGTAGAGCGTCGTGCGGAGGGTTTGCCCGCGCTCTCGCTGGCGTG

GGGTTTCTGGGAGGAAACGACCGGCCTGGGGGGATTGCAGACCATCACCGCCGAGCGCGGCAT

SEQ ID NO: 17:
GTGCCGTCCCTGACGGCGGTGATCCACACCGCGGGAGTCCTCGACGACGGGGTGATGGAATTGCT

TGCCGCACCGATGGCCCCGGTCCGGGACGGCGAGGTTCCCGCCCTGCTGCGGTCG
```

-continued

SEQ ID NO: 18:
GCGGCGGTGTACGGCCAGAGCGTCCAGGAACGCGTTGGCCGCAGCGTAGTTACCTTGTCCCTCAG

CGCCCAGGACGCCGGCGGCGGACGAGTACACGATGAATGCGGCCAAGTCCCTGTCGCG

SEQ ID NO: 19:
ATCCCGTACGCGGCGCTGATGGCACGCTGGCCGCTCAGGCCGCTCGCGTCCTCCCACAGTCCCCA

GGCCAGGGACAAACCAGGCAAACCCTCAAGGCGGCGGTGTACGGCCAGAGCGTCCAGGAACGCGT

TGGCCGCAGCGAAGTTACCTTGTCCGGCAGCGCCCAGGACGCCGGCGGCGGACGAGTACACGA

SEQ ID NO: 20:
TGACCGCAGGATCGCGGGACGTCCCCGTCCTGGATCGGGCTGATCGGCGCGGCGAGCAGTTCCA

CGACACCGTCGTCGAGGGCGCCGGCGGTGTGGATCACCGCGGTCAGGTCGACGCC

SEQ ID NO: 21:
GTGCCGCCTGGCCATCAGGCCGTCGAGGTAGGCGTTCGCGGCCGCGTAACCGCCGGAGCCCTCG

CCCAGGAACACCGCGGAGATGGAGGAGTAGGTGACGAACGCCGCCAGGTCGGGGAGCAA

SEQ ID NO: 22:
ATGCCCTCGGCCGGGGTGAACGACAGCACGCCGCCCATGCCGCCACCGTCGGCTTCCTGGTCCCA

CAGGCCCCACGCCAGGGACAGGCCGGGCAGCCCTTCGGCGTGCCGCCTGGCCATCAGGCCGTCG

AGGTAGGCGTTCGCGGCCGCGAAACCGCCGGAGCCCGCGCCCAGGAACACCGCGGAGATGGAGG

SEQ ID NO: 23:
GAGCACCACCCGACCGCGGTCGTGCATGCGGCTGGCGTGTCCGACGACGGCGTGATCGGCGTGG

TGCCGGTCCGGCTCGACCTGCCCGCCCTCCGCGCCGAAGCGGTCGCCGAGGGCCGC

SEQ ID NO: 24:
GAGGCGCGGGAAGCAGACCAGTTCCTGGTGCACCCCGCCCTGCTGGACGCGGCCTGGCATCCGG

AGCTGCGCGACGAAGTGGCCGAGACGAGCCCGGACGGCCGGCGCTGGTGGTCGCAACCGTCGCG

ATGGAACCAGATCGAGTTCCACGCGACCGGCGCGGCGATACTGCGCGTC

SEQ ID NO: 25:
GAGGCGCGGGAAGCAGACCAGTTCCTGGTGCACCCCGCCCTGCTGACCACCGCCCTCACCCTCAC

CGGCGACGAGGCACCCGCCATCTGGAACCAGATCGAGTTCCACGCGACCGGCGCGGCGATACTGC

GCGTC

SEQ ID NO: 26:
GTCACGGCCACGATCAGCCCCGCCGGCCCTGCCGTCTCGCTGCCGGCCTTCGCGGGTGGCGAACC

CCTGCACATCGCGGACGGCACCCCGGCCGGCTTCCTCCTGCATCCGGACGCGACACCGGCCGCCG

ACTGGAACCAGATCGAGTTCCACGCGACCGGCGCGGCGATACTGCGC

SEQ ID NO: 27:
CTCGGTTCGGTGATGGCGTTGCCGAACTCGGACGGTGTGGTGCTGACCGGCAGGATCTCGCGTCA

GGACGGTCCGGTTCTGTCCGTTGCGGCTTTCGTTGAAATGGCGTTCGCGGCTGCTGGTGGTCGCCC

GATCCGTGAACTGTCTGTTGACGCGCTGCTGTACATCCCGGACGACGGCACCGCGGAACTGCAGAC

CTGGGTCTCTGAACACCGTCTGACCATCCACGCACGTTACCGTGACACCGAACCGTGGACCCGTCT

GGCGACCGCCGCTCTGGACACCACCGCGCCTGCGACGACCCACACCCCGCACCCTGGTCTGATCA

CCACGGCGCTGACCCTGACCGGTGACGAAGCACCGGCGATCTGGAACCAGATCGAGTTCCACGCG

ACCGGCGCGGCGATACTGCGCGTCGCGGTGACACCGGTG

SEQ ID NO: 28:
CAGACGCTGGAGGCGGCCCGGTTTACGGTGCATCCCGCGCTGCTGGACGCGGCCTGGCATCCGGA

GCTGCGCGACGAAGTGGCCGAGACGAGCCCGGACGGCCGGCGCTGGTGGTCGCAACCGTCGCGA

TGGGGTCAGGTTCAGTTCCATACGACCGGCGCGGCGACGCTGCGGGTC

-continued

SEQ ID NO: 29:
CAGACGCTGGAGGCGGCCCGGTTTACGGTGCATCCCGCGCTGCTGACCACCGCCCTCACCCTCAC

CGGCGACGAGGCACCCGCCATCTGGGGTCAGGTTCAGTTCCATACGACCGGCGCGGCGACGCTGC

GGGTC

SEQ ID NO: 30
GTCACGGCCACGATCAGCCCGTCCGGTCCGATCGTCTCGCCGCCGGCCTTCGCGGGTGGCGAACC

CCTGCACATCGCGGACGGCACCCCGGCCGGCTTCCTCCTGCATCCGGACGCGACACCGGCCGCCG

ACTGGGGTCAGGTTCAGTTCCATACGACCGGCGCGGCGACGCTGCGG

SEQ ID NO: 31:
CTGGACACCGTCGTGGCGTTGCCGGGCGCGGACGGTGTGGTGCTGACCGGCAGGATCTCGCGTCA

GGACGGTCCGGTTCTGTCCGTTGCGGCTTTCGTTGAAATGGCGTTCGCGGCTGCTGGTGGTCGCCC

GATCCGTGAACTGTCTGTTGACGCGCTGCTGTACATCCCGGACGACGGCACCGCGGAACTGCAGAC

CTGGGTCTCTGAACACCGTCTGACCATCCACGCACGTTACCGTGACACCGAACCGTGGACCCGTCT

GGCGACCGCCGCTCTGGACACCACCGCGCCTGCGACGACCCACACCCCGCACCCTGGTCTGATCA

CCACGGCGCTGACCCTGACCGGTGACGAAGCACCGGCGATCTGGGGTCAGGTTCAGTTCCATACG

ACCGGCGCGGCGACGCTGCGGGTCGCGGTGACGCCGGTG

SEQ ID NO: 32:
CGACCCGTAGCGTCGCCGCGCCGGTACCGTGGAACTGCACCCGAGCCATCGCGACGGTTGCGACC

ACCAGCGCCGGCCGTCCGGGCTCGTCTCGGCCACTTCGTCGCGCAGCTCCGGATGCCAGGCCGC

GTCGAGCAGGGCGGGATGCATGGTGAAGCGGGCCGTTTCCTGGGCCTG

SEQ ID NO: 33:
CGACCCGTAGCGTCGCCGCGCCGGTACCGTGGAACTGCACCCGAGCCAGATGGCGGGTGCCTCGT

CGCCGGTGAGGGTGAGGGCGGTGGTGAGCAGGGCGGGATGCATGGTGAAGCGGGCCGTTTCCTG

GGCCTG

SEQ ID NO: 34:
CCGTAGCGTCGCCGCGCCGGTACCGTGGAACTGCACCCGAGTCCAGTCGGCGGCCGGTGTCGCGT

CCGGATGCAGGAGGAAGCCGGCCGGGGTGCCGTCCGCGATGTGCAGGGGTTCGCCACCCGCGAA

GGCCGGCAGTGACGCGCCGGGACCGATGGTGGCGGTGACGTGCTGGAT

SEQ ID NO: 35:
CTGGAAACCGTCGTGGCACTGCCCGGCACCGACGGGGTGGCACTGACCGGCCGAATCTCACGTCA

GGACGGTCCGGTTCTGTCCGTTGCGGCTTTCGTTGAAATGGCGTTCGCGGCTGCTGGTGGTCGCCC

GATCCGTGAACTGTCTGTTGACGCGCTGCTGTACATCCCGGACGACGGCACCGCGGAACTGCAGAC

CTGGGTCTCTGAACACCGTCTGACCATCCACGCACGTTACCGTGACACCGAACCGTGGACCCGTCT

GGCGACCGCCGCTCTGGACACCACCGCGCCTGCGACGACCCACACCCCGCACCCTGGTCTGATCA

CCACGGCGCTGACCCTGACCGGTGACGAAGCACCGGCGATCTGGACTCGGGTGCAGTTCCACGGT

ACCGGCGCGGCGACGCTACGGGTCGCGGTGACCCCGGCG

In some embodiments, at least one enoyl reductase domain of a polyketide synthase of the invention is encoded by a nucleic acid having at least 70% (e.g., at least 75%, at least 80%, at least 85%, at least 90%, at least 95%, at least 99%) sequence identity to any one of SEQ ID Nos: 35-36.

SEQ ID NO: 36:
GAACAGGGCGAGCAACTCGGTCATGATCTCGCGGAGCCGGTCGTGGCCGGCATCCATCAGGGTGA

AGGCATGGTAGGTGGCATCCGGGATCTGAGCGGCGTCGCGGATGTCGGTCTGGCCCATCTCGATG

AACCGGCCGCCGTCGACCAGCAGGTCGAGGGAGGCGTCGATGAACTC

SEQ ID NO: 37:
GAACAGGGCGAGCAACTCGGTCATGATCTCGCGGAGCCGGTCGTGGCCGGCATCCATCAGGTGGA

AGGCATGGTAGGTGGCATCCGGGATCTGAGCGGCGTCGCGGATGTCGGTGCCCATCTCGATGAAC

CGGCCGCCGTCGACCAGCAGGTCGAGGGAGGCGTCGATGAACTC

In another aspect, the disclosure provides a nucleic acid encoding any of the foregoing polyketide synthases.

In some embodiments of the invention, the nucleic acid further encodes an LAL, wherein the LAL includes a portion having at least 70% (e.g., at least 75%, at least 80%, at least 85%, at least 90%, at least 95%, at least 99%) sequence identity to the amino acid sequence of SEQ ID NO: 38. In some embodiments, the LAL includes a portion having the sequence of SEQ ID NO: 38. In some embodiments, the LAL has the sequence of SEQ ID NO: 38. In some embodiments, the nucleic acid lacks a TTA regulatory codon in at least one open reading frame.

In some embodiments, the expression vector includes any of the foregoing nucleic acids. In some embodiments, the expression vector is an artificial chromosome (e.g., a bacterial artificial chromosome).

In another aspect, the disclosure provides a host cell including any of the foregoing vectors or polyketide synthases. In some embodiments, the polyketide synthase is heterologous to the host cell.

In some embodiments of the invention, the host cell (e.g., a host cell naturally lacking an LAL and/or an LAL binding site) is engineered to express a recombinant LAL (e.g., a heterologous LAL). In some embodiments, the LAL is

SEQ ID NO 38:
MPAVESYELDARDDELRRLEEAVGQAGNGRGVVVTITGPIACGKTELLDAAAAKSDAITL

RAVCSEEERALPYALIGQLIDNPAVASQLPDPVSMALPGEHLSPEAENRLRGDLTRTLLALAAERPVLIGID

DMHHADTASLNCLLHLARRVGPARIAMVLTELRRLTPAHSQFHAELLSLGHHREIALRPLGPKHIAELARA

GLGPDVDEDVLTGLYRATGGNLNLGHGLIKDVREAWATGGTGINAGRAYRLAYLGSLYRCGPVPLRVAR

VAAVLGQSANTTLVRWISGLNADAVGEATEILTEGGLLHDLRFPHPAARSVVLNDLSARERRRLHRSALE

VLDDVPVEVVAHHQAGAGFIHGPKAAEIFAKAGQELHVRGELDAASDYLQLAHHASDDAVTRAALRVEAV

AIERRRNPLASSRHLDELTVAARAGLLSLEHAALMIRWLALGGRSGEAAEVLAAQRPRAVTDQDRAHLRA

AEVSLALVSPGASGVSPGASGPDRRPRPLPPDELANLPKAARLCAIADNAVISALHGRPELASAEAENVL

KQADSAADGATALSALTALLYAENTDTAQLWADKLVSETGASNEEEGAGYAGPRAETALRRGDLAAAVE

AGSAILDHRRGSLLGITAALPLSSAVAAAIRLGETERAEKWLAEPLPEAIRDSLFGLHLLSARGQYCLATGR

HESAYTAFRTCGERMRNWGVDVPGLSLWRVDAAEALLHGRDRDEGRRLIDEQLTHAMGPRSRALTLRV

QAAYSPQAQRVDLLEEAADLLLSCNDQYERARVLADLSEAFSALRHHSRARGLLRQARHLAAQCGATPL

LRRLGAKPGGPGWLEESGLPQRIKSLTDAERRVASLAAGGQTNRVIADQLFVTASTVEQHLTNVFRKLGV

KGRQHLPAELANAE.

In some embodiments, the nucleic acid further includes an LAL binding site, e.g., an LAL binding site having at least 80% (e.g., at least 85%, at least 90%, at least 95%, at least 99%) identity to the sequence of SEQ ID NO: 39 (CTAGGGGGTTGC). In some embodiments, the LAL binding site includes the sequence of SEQ ID NO: 39. In some embodiments, the LAL binding site has the sequence of SEQ ID NO: 39. In some embodiments, the LAL binding site includes the sequence SEQ ID NO: 40 (GGGGGT).

In some embodiments, the nucleic acid further includes an open reading frame positioned such that binding of the LAL to the LAL binding site promotes expression of the open reading frame. In some embodiments, the open reading frame encodes a compound-producing protein (e.g., a polyketide synthase).

In some embodiments, the nucleic acid further encodes a nonribosomal peptide synthase. In some embodiments, the nucleic acid further encodes a first P450 enzyme. In some embodiments, the nucleic acid further encodes a second P450 enzyme.

constitutively active. In some embodiments, the host cell is engineered by insertion of a LAL binding site in a nucleic acid. In some embodiments, the binding of the recombinant LAL to the LAL binding site promotes transcription of the nucleic acid (e.g., a nucleic acid encoding a compound-producing protein such as a polyketide synthase). In some embodiments, the LAL binding site is heterologous to the LAL. In some embodiments, the LAL binding site is endogenous to the LAL. In some embodiments, the LAL binding site includes the sequence GGGGGT (SEQ ID NO: 40).

In some embodiments, the host cell includes a nucleic acid including a heterologous LAL binding site operably linked to an open reading frame such that binding of an LAL to the heterologous LAL binding site promotes expression of the open reading frame. In some embodiments, the heterologous LAL binding site is a synthetic LAL binding site. In some embodiments, the heterologous LAL binding site promotes greater expression than the endogenous LAL binding site operably linked to the open reading frame. In some embodiments, the heterologous LAL binding site includes at least 8 contiguous nucleotides of $C_1$-$T_2$-$A_3$-$G_4$-$G_5$-$G_6$-$G_7$-$G_8$-$T_9$-$T_{10}$-$G_{11}$-$C_{12}$ (SEQ ID NO: 39), wherein none or up to six nucleotides other than any three nucleotides of $G_4$, $G_5$, $G_6$, $G_7$, $G_8$, $T_9$, and $T_{10}$ (e.g., $G_4$, $G_7$, and $T_9$; $G_5$, Ga, and $T_{10}$; or $G_6$, $G_7$, and $G_8$) are replaced by any other nucleotide.

In some embodiments, the recombinant LAL includes a portion having at least 70% (e.g., at least 75%, at least 80%, at least 85%, at least 90%, at least 95%, or at least 99%) sequence identity to the sequence of SEQ ID NO: 38. In some embodiments, the recombinant LAL includes a portion having the sequence of SEQ ID NO: 38. In some embodiments, the recombinant LAL has the amino acid sequence of SEQ ID NO: 38.

In some embodiments, the host cell is a bacterium (e.g., an actinobacterium such as *Streptomyces ambofaciens*, *Streptomyces hygroscopicus*, or *Streptomyces malayensis*). In some embodiments, the actinobaceterium is S1391, S1496, or S2441.

In some embodiments, the host cell has been modified to enhance expression of a compound-producing protein (e.g., a polyketide synthase). For example, in some embodiments, the host cell has been modified to enhance expression of a compound-producing protein (e.g., a polyketide synthase) by (i) deletion of an endogenous gene cluster which expresses a compound-producing protein (e.g., a polyketide synthase); (ii) insertion of a heterologous gene cluster which expresses a compound-producing protein (e.g., a polyketide synthase); (iii) exposure of the host cell to an antibiotic challenge; and/or (iv) introduction of a heterologous promoter that results in at least a two-fold increase in expression of a compound compared to the homologous promoter. An additional method to enhance the expression of polyketides is to optimize media conditions for growth. This includes the specific chemical and nutrient composition of the media, whether the fermentation is conducted in liquid or solid media, the time course of the fermentation, and the volume/scale of the fermentation run.

In another aspect, the disclosure provides a method of producing a polyketide, the method including the step of culturing any of the foregoing host cells under suitable conditions.

In another aspect, the disclosure provides a method of producing a polyketide, the method including the step of culturing a host cell engineered to express any of the foregoing polyketide synthases under conditions suitable for the polyketide synthase to produce a polyketide.

In another aspect, the disclosure provides a method of modulating the activity of a polyketide synthase, the method including the steps of: (a) providing a parent nucleic acid sequence encoding a parent polyketide synthase; and (b) modifying at least one codon of the parent nucleic acid sequence, wherein the codon specifies a residue in a conserved motif of at least one domain of the parent polyketide synthase, wherein the modification results in an alteration of an enzymatic or regulatory activity (e.g., the alteration results in inactivity of the domain) of the at least one domain.

In another aspect, the disclosure provides a method of producing a compound, the method including the steps of: (a) providing a parent nucleic acid encoding a parent polyketide synthase; (b) modifying at least one codon (e.g., a codon in the portion of the nucleic acid which encodes a β-ketone processing domain) of the parent nucleic acid to create a modified nucleic acid encoding a modified polyketide synthase capable of producing a compound, wherein the codon specifies a residue in a conserved domain of at least one domain of the polyketide synthase and wherein the modification results in an alteration of the enzymatic activity of the at least one domain of the polyketide synthase; (c) introducing the modified nucleic acid to a host cell; and (d) culturing the host cell under conditions suitable to allow expression of a compound by the modified polyketide synthase, thereby producing a compound.

In another aspect, the disclosure provides a method of producing a compound, the method including the steps of: (a) providing a parent polyketide synthase capable of producing a compound; (b) determining the amino acid sequence of the parent polyketide synthase; (c) providing a parent nucleic acid encoding the parent polyketide synthase; (d) modifying at least one codon of the parent nucleic acid to create a modified nucleic acid sequence encoding a modified polyketide synthase capable of producing a compound, wherein the codon specifies a residue in a conserved domain of at least one domain (e.g., a β-ketone processing domain) of the polyketide synthase and wherein the modification results in an alteration of the enzymatic activity (e.g., a decrease in activity) of the at least one domain; (e) introducing the modified nucleic acid to a host cell; (f) culturing the host cell under conditions suitable to allow expression of a compound by the modified polyketide synthase; and (g) recovering the compound produced by the modified polyketide synthase, thereby producing a compound.

In another aspect, the disclosure provides a method of producing a compound, the method of including the steps of: (a) determining the structure of a parent polyketide synthase; (b) producing a parent nucleic acid encoding the parent polyketide synthase; (c) modifying the nucleic acid to produce a modified nucleic acid encoding a modified polyketide synthase, wherein at least one domain (e.g., a β-ketone processing domain) of the modified polyketide synthase has altered enzymatic activity (e.g., decreased enzymatic activity) compared to the parent polyketide synthase; (d) introducing the modified nucleic acid sequence to a host cell; and (e) culturing the host cell under conditions suitable to allow expression of a compound by the modified polyketide synthase, thereby producing a compound.

In another aspect, the disclosure provides a method of producing a library of compounds, the method including the steps of: (a) providing a parent nucleic acid sequence encoding a parent polyketide synthase; (b) modifying at least one codon of the parent nucleic acid sequence to create a first modified nucleic acid encoding a first modified polyketide synthase capable of producing a compound; (c) modifying at least one codon of the parent nucleic acid to create a second modified nucleic acid encoding a second modified polyketide synthase capable of producing a compound, wherein the first and second modified nucleic acids are different; (d) introducing the first and the second modified nucleic acid sequences to one or more host cells; and (e) culturing the one or more host cells under conditions suitable to allow expression of a compound by the first and the second modified polyketide synthase, thereby producing a library of compounds.

In another aspect, the disclosure provides a compound produced by any of the foregoing methods.

Definitions

The term "conserved region of a domain," as used herein, refers to the portion of a domain of a polyketide synthase that is substantially the same in all domains of the same type which are active.

As used herein, the term "engineered polyketide synthase" is used to describe a non-natural polyketide synthase whose design and/or production involves action of the hand of man. For example, in some embodiments, an "engineered" polyketide synthase is prepared by production of a non-natural polynucleotide which encodes the polyketide synthase.

A cell that is "engineered to contain" and/or "engineered to express" refers to a cell that has been modified to contain and/or express a protein that does not naturally occur in the cell. A cell may be engineered to contain a protein, e.g., by introducing a nucleic acid encoding the protein by introduction of a vector including the nucleic acid.

The term "functionally inactive," as used herein, refers to a domain of a polyketide synthase that has no activity, or activity below the point of detection.

The term "gene cluster that produces a small molecule," as used herein refers to a cluster of genes which encodes one or more compound-producing proteins.

The term "heterologous," as used herein, refers to a relationship between two or more proteins, nucleic acids, compounds, and/or cell that is not present in nature. For example, the LAL having the sequence of SEQ ID NO: 38 is naturally occurring in the 518 *Streptomyces* strain and is thus homologous to that strain and would thus be heterologous to the S12 *Streptomyces* strain.

The term "homologous," as used herein, refers to a relationship between two or more proteins, nucleic acids, compounds, and/or cells that is present naturally. For example, the LAL having the sequence of SEQ ID NO: 38 is naturally occurring in the 518 *Streptomyces* strain and is thus homologous to that strain.

The term "modified domain," as used herein, refers to a domain of a polyketide synthase in which at least one amino acid residue has been altered from a reference sequence.

A "polyketide synthase" refers to an enzyme belonging to the family of multi-domain enzymes capable of producing a polyketide. A polyketide synthase may be expressed naturally in bacteria, fungi, plants, or animals.

The term "recombinant," as used herein, refers to a protein that is produced using synthetic methods.

As used herein, the term "reference polyketide synthase" refers to a polyketide synthase that has a sequence having at least 80% identity (e.g., at least 85% identity, at least 90% identity, at least 95% identity, at least 99% identity, or 100% identity) to the sequence of an engineered polyketide synthase except to the sequence of domains which are modified.

BRIEF DESCRIPTION OF THE DRAWINGS

FIGS. 4A and 4B are sequence alignments illustrating mutations resulting in inactive domains in polyketide synthases.

DETAILED DESCRIPTION

The present inventors have discovered that short protein sequences in polyketide synthases that result in deactivated β-ketone processing domains, i.e., ketoreductase (KR), dehydratase (DH), and enoylreductase (ER) domains, may be grafted onto live domains in another polyketide synthase to deactivate domain activity, and alter the chemical structure of the polyketide produced by the polyketide synthase.

Compounds

Compounds that may be produced with the methods of the invention include, but are not limited to, polyketides and polyketide macrolide antibiotics such as erythromycin; hybrid polyketides/non-ribosomal peptides such as rapamycin and FK506; carbohydrates including aminoglycoside antibiotics such as gentamicin, kanamycin, neomycin, tobramycin; benzofuranoids; benzopyranoids; flavonoids; glycopeptides including vancomycin; lipopeptides including daptomycin; tannins; lignans; polycyclic aromatic natural products, terpenoids, steroids, sterols, oxazolidinones including linezolid; amino acids, peptides and peptide antibiotics including polymyxins, non-ribosomal peptides, β-lactams antibiotics including carbapenems, cephalosporins, and penicillin; purines, pteridines, polypyrroles, tetracyclines, quinolones and fluoroquinolones; and sulfonamides.

Proteins

Polyketide Synthases

Polyketide synthases (PKSs) are a family of multi-domain enzymes that produce polyketides. Type I polyketide synthases are large, modular proteins which include several domains organized into modules. The modules generally present in a polyketide synthase include i) a loading module; ii) extending modules; and iii) releasing and/or cyclization modules depending on whether the final polyketide is linear or cyclic. The domains which generally are found in the modules are acyltransferase, acyl carrier protein, keto-synthase, ketoreductase, dehydratase, enoylreductase, methyltransferase, sulfhydrolase, and thioesterase.

A polyketide chain and the starter groups are generally bound to the thiol groups of the active site cysteines in the ketosynthase domain (the polyketide chain) and acyltransferase domain (the loading group and malonyl extender units) through a thioester linkage. Binding to acyl carrier protein (ACP) is mediated by the thiol of the phosphopantetheinyl group, which is bound to a serine hydroxyl of ACP, to form a thioester linkage to the growing polyketide chain. The growing polyketide chain is handed over from one thiol group to another by trans-acylations and is released after synthesis by hydrolysis or cyclization.

Figure 1:
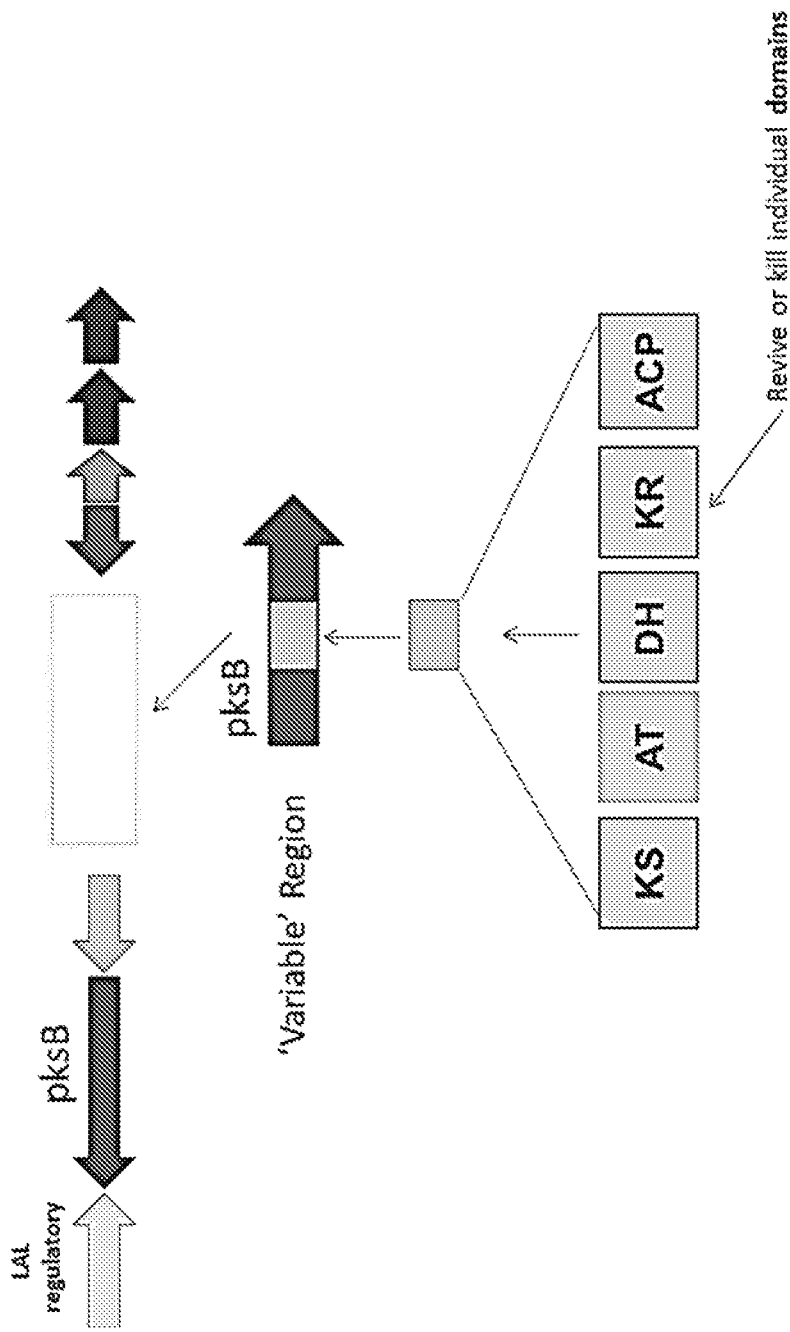
FIG. 1 is an image illustrating the biosynthesis of polyketides by a polyketide synthase.
Figure 2A:
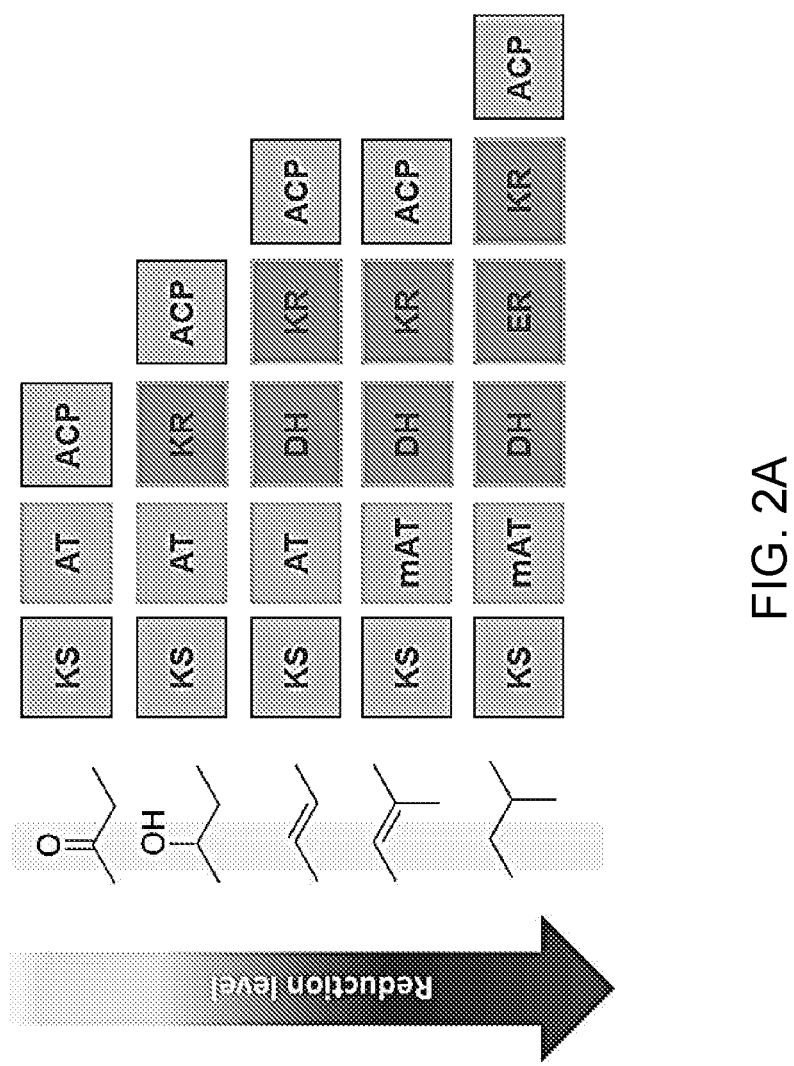
FIGS. 2A and 2B are images illustrating modification of malonyl β-ketones by domains of polyketide synthases.
Figure 2B:
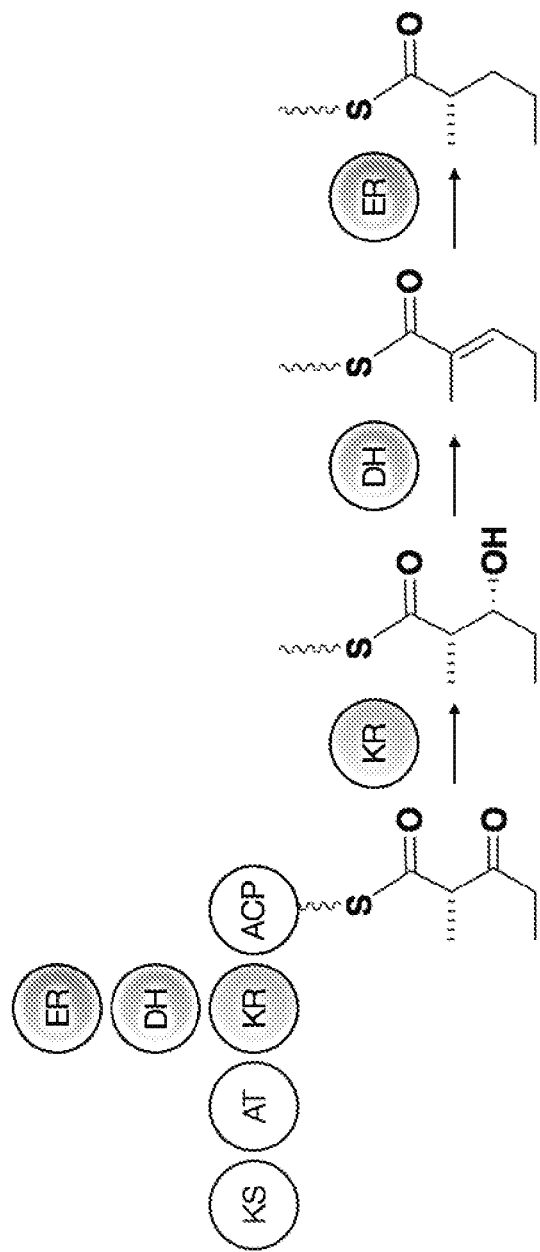
Figure 3:
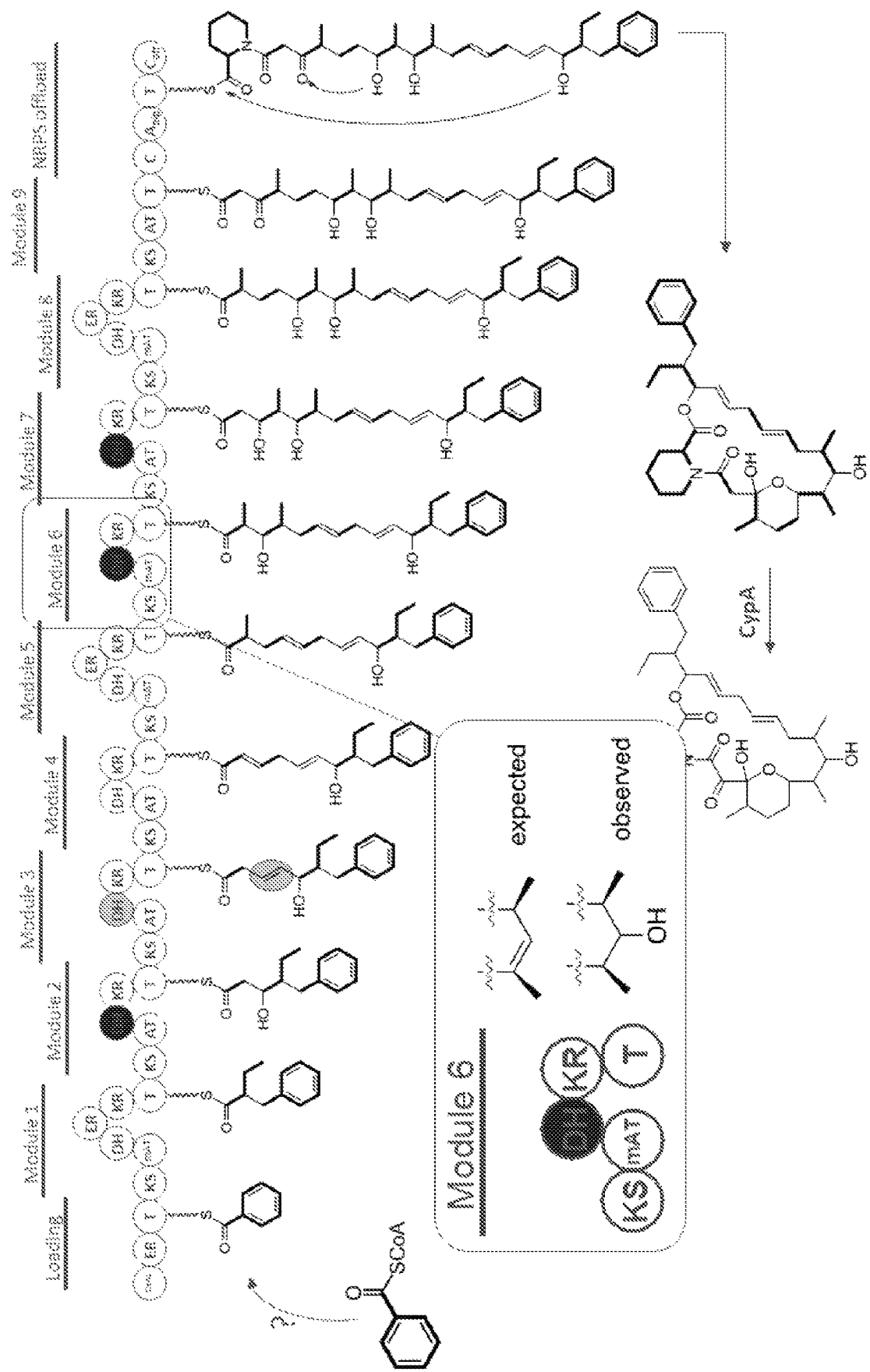
FIG. 3 is an image illustrating the biosynthesis of a polyketide.

The synthesis of a polyketide begins by a starter unit, being loaded onto the acyl carrier protein domain of the PKS catalyzed by the acyltransferase in the loading module. An extender unit, e.g., a malonyl-CoA, is loaded onto the acyl carrier protein domain of the current module catalyzed by another acyltransferase domain. The polyketide chain is then elongated by subsequent extender modules after being passed from the acyl carrier protein domain of module n to the ketosynthase domain of the n+1 module. The acyl carrier protein bound extender unit reacts with the polyketide chain bound to the ketosynthase domain with expulsion of $CO_2$ to produce an extended polyketide chain bound to the acyl carrier protein. Each added extender unit may then be modified by β-ketoprocessing domains, i.e., ketoreductase (which reduces the carbonyl of the elongation group to a hydroxy), dehydratase (which expels $H_2O$ to produce an alkene), and enoylreductase (which reduces alkenes to produce saturated hydrocarbons). Once the synthesis of the polyketide is complete, a thioesterase domain in the releasing modules hydrolyzes the completed polyketide chain from the acyl carrier protein of the last extending module. The compound released from the PKS may then be further modified by other proteins, e.g., nonribosomal peptide synthase. An example of the synthesis of a polyketide by a PKS is illustrated in FIG. 3. In some cases (e.g., rapamycin and X1, the cluster that encodes Compound 1), the biosynthetic cluster harbors polyketide megasynthases and a non-ribosomal peptide synthase (NRPS). This hybrid architecture is referred to as hybrid PKS/NRPS. In the case of rapamycin and Compound 1, the NRPS module inserts the pipecolate moiety in the FKBP12-binding region of the molecules (FIG. 3).

β-Ketone Processing Domains

β-ketone processing domains are the domains in a PKS which result in modification of the elongation groups added during the synthesis of a polyketide. Each β-ketone processing domain is capable of changing the oxidation state of an elongation group. The β-ketone processing domains include ketoreductase (which reduces the carbonyl of the elongation group to a hydroxy), dehydratase (which expels $H_2O$ to produce an alkene), and enoylreductase (which reduces alkenes to produce saturated hydrocarbons).

Non-Functional Domains

Figure 4A:
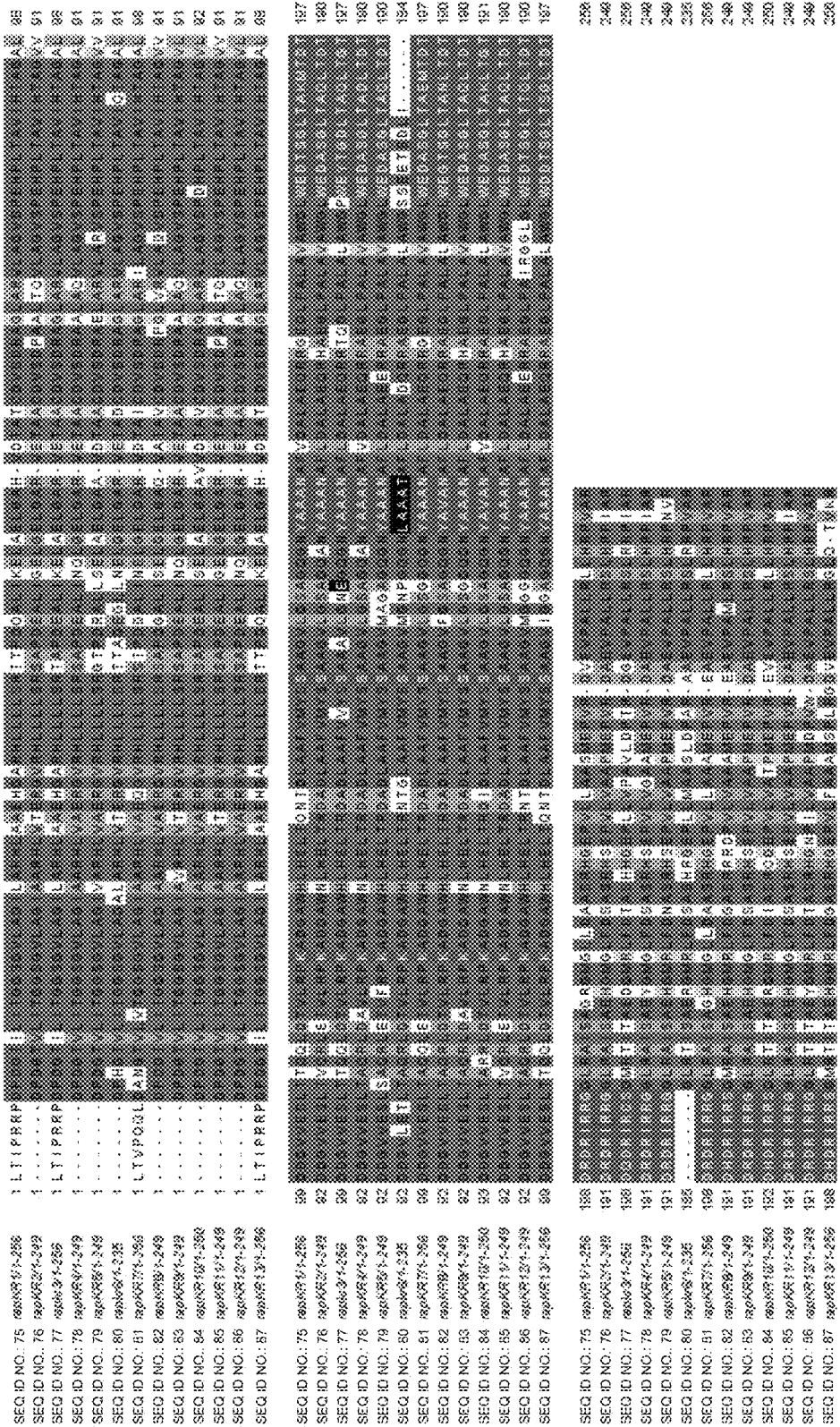
Figure 4B:
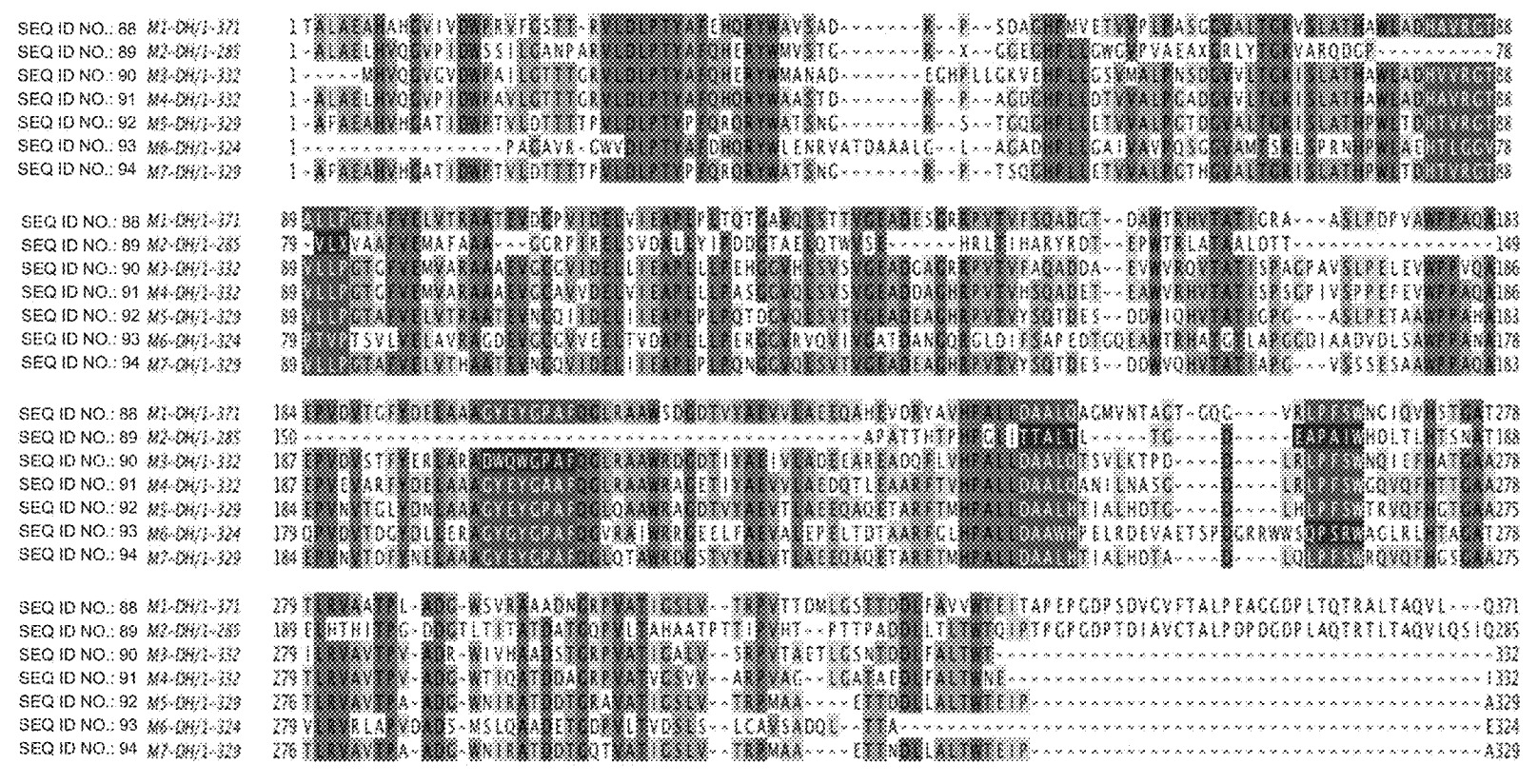

A comprehensive analysis of β-ketone modifying domains indicated the presence of non-functional β-ketone modifying domains which do not affect the final structure of the polyketide. These domains are likely "dead" (FIG. 3). Protein sequence alignments in combination with homology modeling using the crystal structures of functionally related domains as a template revealed that these non-functional domains have mutations in key catalytic and substrate binding motifs that render them inactive (FIGS. 4A and 4B). Nevertheless, these "dead" domains are retained in the gene cluster through evolution, suggesting that they instead play a structural role, i.e., maintaining proper spatial organization of the catalytic domains in the module for efficient assembly-line polyketide synthesis. Domain activity may have been selectively turned "off" by evolution, modifying the natural product chemical structure, protein target engagement, and the physiochemical properties of the evolved molecules.

For ketoreductase domain-level engineering, three KR dead domains have been analyzed: KR3 from S9, KR6-S303, and KR3-S399. KR3 from S9 includes single Ala to Glu substitution near the conserved catalytic YAAAN motif. While not being bound by the theory, homology modeling (using PDB 2FRO) suggested that a glutamic acid at this position might form a salt bridge with a nearby arginine, and that the resulting salt bridge would block the mobility of the substrate capping region (αFG) and prevent access of the ketoreductase active site to the polyketide substrate. The S303 and S399 dead KR6 domains include more prominent lesions. In S303, the catalytic Tyr is replaced by Phe and the αFG helix was deleted. In S399, a larger 150 residue deletion encompassing the catalytic and substrate binding residues is present.

In some embodiments, at least one ketoreductase domain of a polyketide synthase of the invention is encoded by a nucleic acid having at least 70% (e.g., at least 75%, at least 80%, at least 85%, at least 90%, at least 95%, at least 99%) sequence identity to any one of SEQ ID Nos: 12-23.

For dehydratase domain-level engineering, four "dead" DH domains were analyzed: S679-DH7, S12-DH6, S12-DH7, S679-DH4, and S12-DH2. The essential active site residues of the DH domain are distributed across four key conserved motifs: HXXXGXXXXP, GYXYGPXF, DXXX (Q/H) and LPFXW. S679-DH7 has a single Gly to Asp substitution in the HXXXGXXXXP motif, which contains the His residue that deprotonates the polyketide substrate to initiate the dehydration reaction. S12-DH6 and S12-DH7 have substitutions in the LPFXW motif. S679-DH4 contains a significant internal deletion, and S12-DH2 harbors mutations in all four key motifs comprising the DH active site. Hybrid PKS/NRPS clusters such as rapamycin require a hydroxyl for macrocyclization, and thus the S12-DH2 "dead" DH domain must remain inactive for cyclization and biological activity.

In some embodiments, at least one dehydratase domain of a polyketide synthase of the invention is encoded by a nucleic acid having at least 70% (e.g., at least 75%, at least 80%, at least 85%, at least 90%, at least 95%, at least 99%) sequence identity to any one of SEQ ID Nos: 24-35.

For enoyl-reductase domain level engineering, two ER domains from S12 and S61 were analyzed. Both dead ER domains are located in the loading modules of each cluster and are therefore associated with the chemistry of the starter unit and not the malonyl-derived polyketide chain. In both dead domains, the invariant Lys-Arg dyad is substituted or deleted.

In some embodiments, at least one enoyl reductase domain of a polyketide synthase of the invention is encoded by a nucleic acid having at least 70% (e.g., at least 75%, at least 80%, at least 85%, at least 90%, at least 95%, at least 99%) sequence identity to SEQ ID No: 36 or 37.

LALs

LALs include three domains, a nucleotide-binding domain, an inducer-binding domain, and a DNA-binding domain. A defining characteristic of the structural class of regulatory proteins that include the LALs is the presence of the AAA+ ATPase domain. Nucleotide hydrolysis is coupled to large conformational changes in the proteins and/or multimerization, and nucleotide binding and hydrolysis represents a "molecular timer" that controls the activity of the LAL (e.g., the duration of the activity of the LAL). The LAL is activated by binding of a small-molecule ligand to the inducer binding site. In most cases the allosteric inducer of the LAL is unknown. In the case of the related protein MalT, the allosteric inducer is maltotriose. Possible inducers for LAL proteins include small molecules found in the environment that trigger compound (e.g., polyketide) biosynthesis. The regulation of the LAL controls production of compound-producing proteins (e.g., polyketide synthases) resulting in activation of compound (e.g., polyketide) production in the presence of external environmental stimuli.

Therefore, there are gene clusters that produce small molecules (e.g., PKS gene clusters) which, while present in a strain, do not produce compound either because (i) the LAL has not been activated, (ii) the strain has LAL binding sites that differ from consensus, (iii) the strain lacks an LAL regulator, or (iv) the LAL regulator may be poorly expressed or not expressed under laboratory conditions. Since the DNA binding region of the LALs of the known PKS LALs are highly conserved, the known LALs may be used interchangeably to activate PKS gene clusters other than those which they naturally regulate. In some embodiments, the LAL is a fusion protein.

In some embodiments, an LAL may be modified to include a non-LAL DNA-binding domain, thereby forming a fusion protein including an LAL nucleotide-binding domain and a non-LAL DNA-binding domain. In certain embodiments, the non-LAL DNA-binding domain is capable of binding to a promoter including a protein-binding site positioned such that binding of the DNA-binding domain to the protein-binding site of the promoter promotes expression of a gene of interest (e.g., a gene encoding a compound-producing protein, as described herein). The non-LAL DNA binding domain may include any DNA binding domain known in the art. In some instances, the non-LAL DNA binding domain is a transcription factor DNA binding domain. Examples of non-LAL DNA binding domains include, without limitation, a basic helix-loop-helix (bHLH) domain, leucine zipper domain (e.g., a basic leucine zipper domain), GCC box domain, helix-turn-helix domain, homeodomain, srf-like domain, paired box domain, winged helix domain, zinc finger domain, HMG-box domain, Wor3 domain, OB-fold domain, immunoglobulin domain, B3 domain, TAL effector domain, Cas9 DNA binding domain, GAL4 DNA binding domain, and any other DNA binding domain known in the art. In some instances, the promoter is positioned upstream to the gene of interest, such that the fusion protein may bind to the promoter and induce or inhibit expression of the gene of interest. In certain instances, the promoter is a heterologous promoter introduced to the nucleic acid (e.g., a chromosome, plasmid, fosmid, or any other nucleic acid construct known in the art) containing the gene of interest. In other instances, the promoter is a pre-existing promoter positioned upstream to the gene of interest. The protein-binding site within the promoter may, for example, be a non-LAL protein-binding site. In certain embodiments, the protein-binding site binds to the non-LAL DNA binding domain, thereby forming a cognate DNA binding domain/protein-binding site pair.

In some embodiments, the LAL is encoded by a nucleic acid having at least 70% (e.g., at least 75%, at least 80%, at least 85%, at least 90%, at least 95%, at least 99%) sequence identity to any one of SEQ ID Nos: 41-62 or has a sequences with at least 70% (e.g., at least 75%, at least 80%, at least 85%, at least 90%, at least 95%, at least 99%) sequence identity to any one of SEQ ID Nos: 63-73.

```
SEQ ID NO: 41:
ATGCCTGCCGTGGAGTGCTATGAACTGGACGCCCGCGATGACGAGCTCAGAAAACTGGAGGAGGTT

GTGACCGGGCGGGCCAACGGCCGGGGTGTGGTGGTCACCATCACCGGACCGATCGCCTGCGGCA

AGACCGAACTGCTCGACGCAGCCGCCGCGAAGGCCGACGCCATCACGTTACGAGCGGTCTGCTCC

GCGGAGGAACAGGCACTCCCGTACGCCCTGATCGGGCAGCTCATCGACAACCCGGCGCTCGCCTC

CCACGCGCTGGAGCCGGCCTGCCCGACCCTCCCGGGCGAGCACCTGTCGCCGGAGGCCGAGAAC

CGGCTGCGCAGCGACCTCACCCGTACCCTGCTGGCGCTCGCCGCCGAACGGCCGGTGCTGATCGG

CATCGACGAGTCACACGCGAACGCTTTGTGTCTGCTCCACCTGGCCCGAAGGGTCGGCTCGGCCC

GGATCGCCATGGTCCTCACCGAGTTGCGCCGGCTCACCCCGGCCCACTCACAGTTCCAGGCCGAG

CTGCTCAGCCTGGGGCACCACCGCGAGATCGCGCTGCGCCCGCTCAGCCCGAAGCACACCGCCGA

GCTGGTCCGCGCCGGTCTCGGTCCCGACGTCGACGAGGACGTGCTCACGGGGTTGTACCGGGCGA

CCGGCGGCAACCTGAACCTCACCCGCGGACTGATCAACGATGTGCGGGAGGCCTGGGAGACGGGA

GGGACGGGCATCAGCGCGGGCCGCGCGTACCGGCTGGCATACCTCGGTTCCCTCTACCGCTGCGG

CCCGGTCCCGTTGCGGGTCGCACGGGTGGCCGCCGTGCTGGGCCAGAGCGCCAACACCACCCTG

GTGCGCTGGATCAGCGGGCTCAACGCGGACGCGGTGGGCGAGGCAACCGAGATCCTCACCGAAG

GCGGCCTGCTGCACGACCTGCGGTTCCCGCACCCGGCGGCCCGTTCGGTGGTACTCAACGACATG

TCCGCCCAGGAACGACGCCGCCTGCACCGGTCCGCTCTGGAAGTGCTGGACGACGTGCCCGTGGA

AGTGGTCGCGCACCACCAGGTCGGCGCCGGTCTCCTGCACGGCCCGAAGGCCGCCGAGATATTCG

CCAAGGCCGGCCAGGAGCTGCATGTGCGCGGCGAGTTGGACACCGCGTCCGACTATCTGCAACTG

GCCCACCAGGCCTCCGACGACGCCGTCACCGGGATGCGGGCCGAGGCCGTGGCGATCGAGCGCC

GCCGCAACCCGCTGGCCTCGAGCCGGCACCTCGACGAGCTGACCGTCGTCGCCCGTGCCGGGCT

GCTCTTCCCCGAGCACACGGCGCTGATGATCCGCTGGCTGGGCGTCGGCGGGCGGTCCGGCGAG

GCAGCCGGGCTGCTGGCCTCGCAGCGCCCCCGTGCGGTCACCGACCAGGACAGGGCCCATATGC
```

-continued

```
GGGCCGCCGAGGTATCGCTCGCGCTGGTCAGCCCCGGCACGTCCGGCCCGGACCGGCGGCCGCG

TCCGCTCACGCCGGATGAGCTCGCGAACCTGCCGAAGGCGGCCCGGCTCTGCGCGATCGCCGACA

ATGCCGTCATGTCGGCCCTGCGCGGTCGTCCCGAGCTCGCCGCGGCCGAGGCGGAGAACGTCCTG

CAGCACGCCGACTCGGCGGCGGCCGGCACCACCGCCCTCGCCGCGCTGACCGCCTTGCTGTACG

CGGAGAACACCGACACCGCTCAGCTCTGGGCCGACAAGCTGGTCTCCGAGACCGGGGCGTCGAAC

GAGGAGGAGGCGGGCTACGCGGGGCCGCGCGCCGAAGCCGCGTTGCGTCGCGGCGACCTGGCC

GCGGCGGTCGAGGCAGGCAGCACCGTTCTGGACCACCGGCGGCTCTCGACGCTCGGCATCACCG

CCGCGCTACCGCTGAGCAGCGCGGTGGCCGCCGCCATCCGGCTGGGCGAGACCGAGCGGGCGGA

GAAGTGGCTCGCCCAGCCGCTGCCGCAGGCCATCCAGGACGGCCTGTTCGGCCTGCACCTGCTCT

CGGCGCGCGGCCAGTACAGCCTCGCCACGGGCCAGCACGAGTCGGCGTACACGGCGTTTCGCAC

CTGCGGGAACGTATGCGGAACTGGGGCGTTGACGTGCCGGGTCTGTCCCTGTGGCGCGTCGACG

CCGCCGAGGCGCTGCTGCACGACCGCGACCGGGACGAGGGCCGACGGCTCGTCGACGAGCAACT

CACCCGTGCGATGGGACCCCGTTCCCGCGCCTTGACGCTGCGGGTGCAGGCGGCGTACAGCCCG

CCGGCGAAGCGGGTCGACCTGCTCGATGAAGCGGCCGACCTGCTGCTCTCCTGCAACGACCAGTA

CGAGCGGGCACGGGTGCTCGCCGACCTGAGCGAGACGTTCAGCGCGCTCCGGCACCACAGCCGG

GCGCGGGGACTGCTTCGGCAGGCCCGGCACCTGGCCGCCCAGCGCGGCGCGATACCGCTGCTGC

GCCGACTCGGGGCCAAGCCCGGAGGCCCCGGCTGGCTGGAGGAATCCGGCCTGCCGCAGCGGAT

CAAGTCGCTGACCGACGCGGAGCGGCGGGTGGCGTCGCTGGCCGCCGGCGGACAGACCAACCGC

GTGATCGCCGACCAGCTCTTCGTCACGGCCAGCACGGTGGAGCAGCACCTCACGGACGTCTCCACT

GGGTCAAGGCCGCCAGCACCTGCCGCCGAACTCGTCTAG

SEQ ID NO: 42
ATGCCTGCCGTGGAGTGCTATGAACTGGACGCCCGCGATGACGAGCTCAGAAAACTGGAGGAGGTT

GTGACCGGGCGGGCCAACGGCCGGGGTGTGGTGGTCACCATCACCGGACCGATCGCCTGCGGCA

AGACCGAACTGCTCGACGCAGCCGCCGCGAAGGCCGACGCCATCACGCTGCGAGCGGTCTGCTCC

GCGGAGGAACAGGCACTCCCGTACGCCCTGATCGGGCAGCTCATCGACAACCCGGCGCTCGCCTC

CCACGCGCTGGAGCCGGCCTGCCCGACCCTCCCGGGCGAGCACCTGTCGCCGGAGGCCGAGAAC

CGGCTGCGCAGCGACCTCACCCGTACCCTGCTGGCGCTCGCCGCCGAACGGCCGGTGCTGATCGG

CATCGACGAGTCACACGCGAACGCTTTGTGTCTGCTCCACCTGGCCCGAAGGGTCGGCTCGGCCC

GGATCGCCATGGTCCTCACCGAGTTGCGCCGGCTCACCCCGGCCCACTCACAGTTCCAGGCCGAG

CTGCTCAGCCTGGGGCACCACCGCGAGATCGCGCTGCGCCCGCTCAGCCCGAAGCACACCGCCGA

GCTGGTCCGCGCCGGTCTCGGTCCCGACGTCGACGAGGACGTGCTCACGGGGTTGTACCGGGCGA

CCGGCGGCAACCTGAACCTCACCCGCGGACTGATCAACGATGTGCGGGAGGCCTGGGAGACGGGA

GGGACGGGCATCAGCGCGGGCCGCGCGTACCGGCTGGCATACCTCGGTTCCCTCTACCGCTGCGG

CCCCGGTCCCGTTGCGGGTCGCACGGGTGGCCGCCGTGCTGGGCCAGAGCGCCAACACCACCCTG

GTGCGCTGGATCAGCGGGCTCAACGCGGACGCGGTGGGCGAGGCAACCGAGATCCTCACCGAAG

GCGGCCTGCTGCACGACCTGCGGTTCCCGCACCCGGCGGCCCGTTCGGTGGTACTCAACGACATG

TCCGCCCAGGAACGACGCCGCCTGCACCGGTCCGCTCTGGAAGTGCTGGACGACGTGCCCGTGGA

AGTGGTCGCGCACCACCAGGTCGGCGCCGGTCTCCTGCACGGCCCGAAGGCCGCCGAGATATTCG

CCAAGGCCGGCCAGGAGCTGCATGTGCGCGGCGAGTTGGACACCGCGTCCGACTATCTGCAACTG

GCCCACCAGGCCTCCGACGACGCCGTCACCGGGATGCGGGCCGAGGCCGTGGCGATCGAGCGCC

GCCGCAACCCGCTGGCCTCGAGCCGGCACCTCGACGAGCTGACCGTCGTCGCCCGTGCCGGGCT
```

-continued

```
GCTCTTCCCCGAGCACACGGCGCTGATGATCCGCTGGCTGGGCGTCGGCGGGCGGTCCGGCGAG

GCAGCCGGGCTGCTGGCCTCGCAGCGCCCCCGTGCGGTCACCGACCAGGACAGGGCCCATATGC

GGGCCGCCGAGGTATCGCTCGCGCTGGTCAGCCCCGGCACGTCCGGCCCGGACCGGCGGCCGCG

TCCGCTCACGCCGGATGAGCTCGCGAACCTGCCGAAGGCGGCCCGGCTCTGCGCGATCGCCGACA

ATGCCGTCATGTCGGCCCTGCGCGGTCGTCCCGAGCTCGCCGCGGCCGAGGCGGAGAACGTCCTG

CAGCACGCCGACTCGGCGGCGGCCGGCACCACCGCCCTCGCCGCGCTGACCGCCTTGCTGTACG

CGGAGAACACCGACACCGCTCAGCTCTGGGCCGACAAGCTGGTCTCCGAGACCGGGGCGTCGAAC

GAGGAGGAGGCGGGCTACGCGGGGCCGCGCGCCGAAGCCGCGTTGCGTCGCGGCGACCTGGCC

GCGGCGGTCGAGGCAGGCAGCACCGTTCTGGACCACCGGCGGCTCTCGACGCTCGGCATCACCG

CCGCGCTACCGCTGAGCAGCGCGGTGGCCGCCGCCATCCGGCTGGGCGAGACCGAGCGGGCGGA

GAAGTGGCTCGCCCAGCCGCTGCCGCAGGCCATCCAGGACGGCCTGTTCGGCCTGCACCTGCTCT

CGGCGCGCGGCCAGTACAGCCTCGCCACGGGCCAGCACGAGTCGGCGTACACGGCGTTTCGCAC

CTGCGGGAACGTATGCGGAACTGGGCGTTGACGTGCCGGGTCTGTCCCTGTGGCGCGTCGACG

CCGCCGAGGCGCTGCTGCACGGCCGCGACCGGGACGAGGGCCGACGGCTCGTCGACGAGCAACT

CACCCGTGCGATGGGACCCCGTTCCCGCGCCTTGACGCTGCGGGTGCAGGCGGCGTACAGCCCG

CCGGCGAAGCGGGTCGACCTGCTCGATGAAGCGGCCGACCTGCTGCTCTCCTGCAACGACCAGTA

CGAGCGGGCACGGGTGCTCGCCGACCTGAGCGAGACGTTCAGCGCGCTCCGGCACCACAGCCGG

GCGCGGGGACTGCTTCGGCAGGCCCGGCACCTGGCCGCCCAGCGCGGCGCGATACCGCTGCTGC

GCCGACTCGGGGCCAAGCCCGGAGGCCCCGGCTGGCTGGAGGAATCCGGCCTGCCGCAGCGGAT

CAAGTCGCTGACCGACGCGGAGCGGCGGGTGGCGTCGCTGGCCGCCGGCGGACAGACCAACCGC

GTGATCGCCGACCAGCTCTTCGTCACGGCCAGCACGGTGGAGCAGCACCTCACGGACGTCTCCACT

GGGTCAAGGCCGCCAGCACCTGCCGCCGAACTCGTCTAG

SEQ ID NO: 43
GTGGTTCCTGAAGTGCGAGCAGCCCCCGACGAACTGATCGCCCGCGATGACGAGCTGAGCCGCCT

CCAACGGGCACTCACCAGGGCGGGGAGCGGAAGGGGCGGCGTCGTCGCCATCACCGGGCCCATC

GCCAGCGGAAAGACGGCGCTGCTCGACGCCGGAGCGGCCAAGTCCGGCTTCGTCGCACTCCGTGC

GGTGTGCTCCTGGGAAGAGCGCACTCTGCCGTACGGGATGCTGGGCCAGCTCTTCGACCATCCCG

AACTGGCCGCCCAGGCGCCGGACCTTGCCCACTTCACGGCTTCGTGCGAGAGCCCTCAGGCCGGT

ACCGACAACCGCCTGCGGGCCGAGTTCACCCGCACCCTGCTGGCGCTCGCCGCGGACTGGCCCGT

CCTGATCGGCATCGACGACGTGCACCACGCCGACGCGGAATCACTGCGCTGTCTGCTCCACCTCGC

CCGCCGCATCGGCCCGGCCCGCATCGCGGTCGTACTGACCGAGCTGCGCAGACCGACGCCCGCC

GACTCCCGCTTCCAGGCGGAACTGCTGAGCCTGCGCTCCTACCAGGAGATCGCGCTCAGACCGCT

CACCGAGGCGCAGACCGGCGAACTCGTACGTCGGCACCTCGGCGCGGAGACCCACGAGGACGTCT

CCGCCGATACGTTCCGGGCGACCGGCGGGAACCTGCTCCTCGGGCACGGTTTGATCAATGACATC

CGGGAGGCGCGGACAGCGGGACGGCCGGGGGTCGTCGCGGGCGGGCGTACCGGCTCGCGTAC

CTCAGCTCGCTCTACCGCTGCGGCCCGAGCGCGCTGCGTGTCGCCCGGGCGTCCGCCGTGCTCG

GCGCGAGCGCCGAAGCCGTGCTCGTCCAGCGGATGACCGGACTGAACAAGGACGCGGTCGAACAG

GTCTATGAGCAGCTGAACGAGGGACGGCTGCTGCAGGGCGAGCGGTTTCCGCACCCGGCGGCCC

GCTCCATCGTCCTTGACGACCTGTCGGCCCTGGAACGCAGAAACCTGCACGAGTCGGCGCTGGAG

CTGCTGCGGGACCACGCGTGGCCGGCAACGTGCTCGCCCGCCACCAGATCGGCGCCGGCCGGG

TGCACGGCGAGGAGGCCGTCGAGCTGTTCACCGGGGCCGCACGGGAGCACCACCTGCGCGGTGA
```

-continued

ACTGGACGACGCGGCCGGATACCTGGAACTCGCCCACCGTGCCTCCGACGACCCCGTCACGCGCG

CCGCACTACGCGTCGGCGCCGCCGCGATCGAGCGCCTCTGCAATCCGGTACGGGCAGGCCGGCAT

CTGCCCGAGCTGCTCACCGCGTCGCGCGCGGGACTGCTCTCCAGCGAGCACGCCGTGTCGCTCGC

CGACTGGCTGGCGATGGGCGGGCGCCCGGGCGAGGCGGCCGAGGTCCTCGCGACGCAGCGTCC

CGCGGCCGACAGCGAGCAGCACCGCGCACTCCTGCGCAGCGGCGAGTTGTCCCTCGCGCTGGTC

CACCCCGGCGCGTGGGATCCGTTGCGCCGGACCGATCGGTTCGCCGCGGGCGGGCTCGGCTCGC

TTCCCGGACCCGCCCGGCACCGCGCGGTCGCCGACCAAGCCGTCATCGCGGCGCTGCGTGGACG

TCTCGACCGGGCGGACGCCAACGCGGAGAGCGTTCTCCAGCACACCGACGCCACGGCGGACCGG

ACCACGGCCATCATGGCGTTGCTGGCCCTGCTCTACGCGGAGAACACCGATGCTGTCCAGTTCTGG

GTCGACAAACTGGCCGGTGACGAGGGCACCAGGACACCGGCCGACGAGGCGGTCCACGCGGGGT

TCAACGCCGAGATCGCGCTGCGCCGCGGCGACTTGATGAGAGCCGTCGAGTACGGCGAGGCAGCG

CTCGGCCACCGGCACCTGCCCACCTGGGGAATGGCCGCCGCTCTGCCGCTGAGCAGCACCGTGGT

TGCCGCGATCCGGCTCGGCGACCTCGACAGGGCCGAGCGGTGGCTCGCCGAGCCGCTGCCGCAG

CAGACGCCGGAGAGCCTCTTCGGGCTGCACCTGCTCTGGGCCCGCGGGCAGCACCACCTCGCGAC

CGGGCGGCACGGGCGGCGTACACGGCGTTCAGGGAATGCGGCGAGCGGATGCGGCGGTGGGC

CGTCGACGTGCCGGGCCTGGCCCTGTGGCGGGTCGACGCCGCCGAATCGCTGCTGCTGCTCGGC

CGTGACCGTGCCGAAGGACTGCGGTCGTCTCCGAGCAGCTGTCCCGGCCGATGCGCCCTCGCGC

GCGCGTGCAGACGTTACGGGTACAGGCGGCCTACAGTCCGCCGCCCCAACGGATCGACCTGCTCG

AAGAGGCCGCCGACCTGCTGGTCACCTGCAACGACCAGTACGAACTGGCAAACGTACTCAGCGACT

TGGCAGAGGCCTCCAGCATGGTCCGGCAGCACAGCAGGGCGCGGGGTCTGCTCCGCCGGGCACG

GCACCTCGCCACCCAGTGCGGCGCCGTGCCGCTCCTGCGGCGGCTCGGCGCGGAACCCTCGGAC

ATCGGCGGAGCCTGGGACGCGACGCTGGGACAGCGGATCGCGTCACTGACGGAGTCGGAGCGGC

GGGTGGCCGCGCTCGCCGCGGTCGGGCGTACGAACAGGGAGATCGCCGAGCAGCTGTTCGTCAC

GGCCAGCACGGTGGAACAGCACCTCACGAACGTGTTCCGCAAACTGGCGGTGAAGGGCCGCCAGC

AGCTTCCGAAGGAACTGGCCGACGTCGGCGAGCCGGCGGACCGCGACCGCCGGTGCGGGTAG

SEQ ID NO: 44
ATGGTTCCTGAAGTGCGAGCAGCCCCCGACGAACTGATCGCCCGCGATGACGAGCTGAGCCGCCT

CCAACGGGCACTCACCAGGGCGGGGAGCGGAAGGGGCGGCGTCGTCGCCATCACCGGGCCCATC

GCCAGCGGAAAGACGGCGCTGCTCGACGCCGGAGCGGCCAAGTCCGGCTTCGTCGCACTCCGTGC

GGTGTGCTCCTGGGAAGAGCGCACTCTGCCGTACGGGATGCTGGCCAGCTCTTCGACCATCCCG

AACTGGCCGCCCAGGCGCCGGACCTTGCCCACTTCACGGCTTCGTGCGAGAGCCCTCAGGCCGGT

ACCGACAACCGCCTGCGGGCCGAGTTCACCCGCACCCTGCTGGCGCTCGCCGCGGACTGGCCCGT

CCTGATCGGCATCGACGACGTGCACCACGCCGACGCGGAATCACTGCGCTGTCTGCTCCACCTCGC

CCGCCGCATCGGCCCGGCCCGCATCGCGGTCGTACTGACCGAGCTGCGCAGACCGACGCCCGCC

GACTCCCGCTTCCAGGCGGAACTGCTGAGCCTGCGCTCCTACCAGGAGATCGCGCTCAGACCGCT

CACCGAGGCGCAGACCGGCGAACTCGTACGTCGGCACCTCGGCGCGGAGACCCACGAGGACGTCT

CCGCCCGATACGTTCCGGGCGACCGGCGGGAACCTGCTCCTCGGGCACGGTTTGATCAATGACATC

CGGGAGGCGCGGACAGCGGGACGGCCGGGGGTCGTCGCGGGGCGGGCGTACCGGCTCGCGTAC

CTCAGCTCGCTCTACCGCTGCGGCCCGAGCGCGCTGCGTGTCGCCCGGGCGTCCGCCGTGCTCG

GCGCGAGCGCCGAAGCCGTGCTCGTCCAGCGGATGACCGGACTGAACAAGGACGCGGTCGAACAG

GTCTATGAGCAGCTGAACGAGGGACGGCTGCTGCAGGGCGAGCGGTTTCCGCACCCGGCGGCCC

-continued

```
GCTCCATCGTCCTTGACGACCTGTCGGCCCTGGAACGCAGAAACCTGCACGAGTCGGCGCTGGAG

CTGCTGCGGGACCACGGCGTGGCCGGCAACGTGCTCGCCCGCCACCAGATCGGCGCCGGCCGGG

TGCACGGCGAGGAGGCCGTCGAGCTGTTCACCGGGGCCGCACGGGAGCACCACCTGCGCGGTGA

ACTGGACGACGCGGCCGGATACCTGGAACTCGCCCACCGTGCCTCCGACGACCCCGTCACGCGCG

CCGCACTACGCGTCGGCGCCGCCGCGATCGAGCGCCTCTGCAATCCGGTACGGGCAGGCCGGCAT

CTGCCCGAGCTGCTCACCGCGTCGCGCGCGGGACTGCTCTCCAGCGAGCACGCCGTGTCGCTCGC

CGACTGGCTGGCGATGGGCGGGCGCCCGGGCGAGGCGGCCGAGGTCCTCGCGACGCAGCGTCC

CGCGGCCGACAGCGAGCAGCACCGCGCACTCCTGCGCAGCGGCGAGTTGTCCCTCGCGCTGGTC

CACCCCGGCGCGTGGGATCCGTTGCGCCGGACCGATCGGTTCGCCGCGGGCGGGCTCGGCTCGC

TTCCCGGACCCGCCCGGCACCGCGCGGTCGCCGACCAAGCCGTCATCGCGGCGCTGCGTGGACG

TCTCGACCGGGCGGACGCCAACGCGGAGAGCGTTCTCCAGCACACCGACGCCACGGCGGACCGG

ACCACGGCCATCATGGCGTTGCTGGCCCTGCTCTACGCGGAGAACACCGATGCTGTCCAGTTCTGG

GTCGACAAACTGGCCGGTGACGAGGGCACCAGGACACCGGCCGACGAGGCGGTCCACGCGGGGT

TCAACGCCGAGATCGCGCTGCGCCGCGGCGACTTGATGAGAGCCGTCGAGTACGGCGAGGCAGCG

CTCGGCCACCGGCACCTGCCCACCTGGGGAATGGCCGCCGCTCTGCCGCTGAGCAGCACCGTGGT

TGCCGCGATCCGGCTCGGCGACCTCGACAGGGCCGAGCGGTGGCTCGCCGAGCCGCTGCCGCAG

CAGACGCCGGAGAGCCTCTTCGGGCTGCACCTGCTCTGGGCCCGCGGGCAGCACCACCTCGCGAC

CGGGCGGCACGGGGCGGCGTACACGGCGTTCAGGGAATGCGGCGAGCGGATGCGGCGGTGGGC

CGTCGACGTGCCGGGCCTGGCCCTGTGGCGGGTCGACGCCGCCGAATCGCTGCTGCTGCTCGGC

CGTGACCGTGCCGAAGGACTGCGGCTCGTCTCCGAGCAGCTGTCCCGGCCGATGCGCCCTCGCGC

GCGCGTGCAGACGCTGCGGGTACAGGCGGCCTACAGTCCGCCGCCCCAACGGATCGACCTGCTCG

AAGAGGCCGCCGACCTGCTGGTCACCTGCAACGACCAGTACGAACTGGCAAACGTACTCAGCGACT

TGGCAGAGGCCTCCAGCATGGTCCGGCAGCACAGCAGGGCGCGGGTCTGCTCCGCCGGGCACG

GCACCTCGCCACCCAGTGCGGCGCCGTGCCGCTCCTGCGGCGGCTCGGCGCGGAACCCTCGGAC

ATCGGCGGAGCCTGGGACGCGACGCTGGGACAGCGGATCGCGTCACTGACGGAGTCGGAGCGGC

GGGTGGCCGCGCTCGCCGCGGTCGGGCGTACGAACAGGGAGATCGCCGAGCAGCTGTTCGTCAC

GGCCAGCACGGTGGAACAGCACCTCACGAACGTGTTCCGCAAACTGGCGGTGAAGGGCCGCCAGC

AGCTTCCGAAGGAACTGGCCGACGTCGGCGAGCCGGCGGACCGCGACCGCCGGTGCGGGTAG

SEQ ID NO: 45
GTGATAGCGCGCTTATCTCCCCCAGACCTGATCGCCCGCGATGACGAGTTCGGTTCCCTCCACCGG

GCGCTCACCCGAGCGGGGGCGGGCGGGGCGTCGTCGCCGCCGTCACCGGGCCGATCGCCTGC

GGCAAGACCGAACTCCTCGACGCCGCCGCGGCCAAGGCCGGCTTCGTCACCCTTCGCGCGGTGTG

CTCCATGGAGGAGCGGGCCCTGCCGTACGGCATGCTCGGCCAGCTCCTCGACCAGCCCGAGCTGG

CCGCCCGGACACCGGAGCTGGTCCGGCTGACGGCATCGTGCGAAAACCTGCCGGCCGACGTCGAC

AACCGCCTGGGGACCGAACTCACCCGCACGGTGCTGACGCTCGCCGCGGAGCGGCCCGTACTGAT

CGGCATCGACGACGTGCACCACGCCGACGCGCCGTCGCTGCGCTGCCTGCTCCACCTCGCGCGCC

GCATCAGCCGGGCCCGTGTCGCCATCGTGCTGACCGAGCTGCTCCGGCCGACGCCCGCCCACTCC

CAATTCCGGGCGGCACTGCTGAGTCTGCGCCACTACCAGGAGATCGCGCTGCGCCCGCTCACCGA

GGCGCAGACCACCGAACTCGTGCGCCGGCACCTCGGCCAGGACGCGCACGACGACGTGGTGGCC

CAGGCGTTCCGGGCGACCGGCGGCAACCTGCTCCTCGGCCACGGCCTGATCGACGACATCCGGGA

GGCACGGACACGGACCTCAGGGTGCCTGGAAGTGGTCGCGGGGCGGGCGTACCGGCTCGCCTAC
```

-continued

CTCGGGTCGCTCTATCGTTGCGGCCCGGCCGCGCTGAGCGTCGCCCGAGCTTCCGCCGTGCTCGG

CGAGAGTGTCGAACTCACCCTCGTCCAGCGGATGACCGGCCTCGACACCGAGGCGGTCGAGCAGG

CCCACGAACAGCTGGTCGAGGGGCGGCTGCTGCGGGAAGGGCGGTTCCCGCACCCCGCGGCCCG

CTCCGTCGTACTCGACGACCTCTCCGCCGCCGAGCGGCGTGGCCTGCACGAGCTGGCGCTGGAAC

TGCTGCGGGACCGCGGCGTGGCCAGCAAGGTGCTCGCCCGCCACCAGATGGGTACCGGCCGGGT

GCACGGCGCCGAGGTCGCCGGGCTGTTCACCGACGCCGCGCGCGAGCACCACCTGCGCGGCGAG

CTCGACGAGGCCGTCACCTACCTGGAGTTCGCCTACCGGGCCTCCGACGACCCCGCCGTCCACGC

CGCACTGCGCGTCGACACCGCCGCCATCGAGCGGCTCTGCGATCCCGCCAGATCCGGCCGGCATG

TGCCCGAGCTGCTCACCGCGTCGCGGGAACGGCTCCTCTCCAGCGAGCACGCCGTGTCGCTCGCC

TGCTGGCTGGCGATGGACGGGCGGCCGGGCGAGGCCGCCGAGGTCCTGGCGGCCCAGCGCTCC

GCCGCCCCGAGCGAGCAGGGCCGGGCGCACCTGCGCGTCGCGGACCTGTCCCTCGCGCTGATCT

ATCCCGGCGCGGCCGATCCGCCGCGTCCGGCCGATCCGCCGGCCGAGGACGAGGTCGCCTCGTT

TTCCGGAGCCGTCCGGCACCGCGCCGTCGCCGACAAGGCCCTGAGCAACGCGCTGCGCGGCTGG

TCCGAACAGGCCGAGGCCAAAGCCGAGTACGTGCTCCAGCACTCCCGGGTCACGACGGACCGGAC

CACGACCATGATGGCGTTGCTGGCCCTGCTCTACGCCGAGGACACCGATGCCGTCCAGTCCTGGGT

CGACAAGCTGGCCGGTGACGACAACATGCGGACCCCGGCCGACGAGGCGGTCCACGCGGGGTTC

CGCGCCGAGGCCGCGCTGCGCCGCGGCGACCTGACCGCCGCCGTCGAATGCGGCGAGGCCGCG

CTCGCCCCCGGGTCGTGCCCTCCTGGGGATGGCCGCCGCATTGCCGCTGAGCAGCACCGTGG

CCGCCGCGATCCGACTGGGCGACCTGGACCGGGCGGAGCGGTGGCTCGCCGAGCCGTTGCCGGA

GGAGACCTCCGACAGCCTCTTCGGACTGCACATGGTCTGGGCCCGTGGGCAACACCATCTCGCGG

CCGGGCGGTACCGGCGGCGTACAACGCGTTCCGGGACTGCGGGGAGCGGATGCGACGCTGGTC

CGTCGACGTGCCGGGCCTGGCCCTGTGGCGGGTCGACGCCGCCGAAGCGCTTCTGCTGCTCGGC

CGCGGCCGTGACGAGGGGCTGAGGCTCATCTCCGAGCAGCTGTCCCGGCCGATGGGGTCCCGGG

CGCGGGTGATGACGCTGCGGGTGCAGGCGGCCTACAGTCCGCCGGCCAAGCGGATCGAACTGCTC

GACGAGGCCGCCGATCTGCTCATCATGTGCCGCGACCAGTACGAGCTGGCCCGCGTCCTCGCCGA

CATGGGCGAAGCGTGCGGCATGCTCCGGCGGCACAGCCGTGCGCGGGGACTGTTCCGCCGCGCA

CGGCACCTCGCGACCCAGTGCGGAGCCGTGCCGCTCCTCCGGCGGCTCGGTGGGGAGTCCTCGG

ACGCGGACGGCACCCAGGACGTGACGCCGGCGCAGCGGATCACATCGCTGACCGAGGCGGAGCG

GCGGGTGGCGTCGCACGCCGCGGTCGGGCGCACCAACAAGGAGATCGCCAGCCAGCTGTTCGTCA

CCTCCAGCACGGTGGAACAGCACCTCACCAACGTGTTCCGCAAGCTGGGGGTGAAGGGCCGTCAG

CAACTGCCCAAGGAACTGTCCGACGCCGGCTGA

SEQ ID NO: 46
ATGATAGCGCGCCTGTCTCCCCCAGACCTGATCGCCCGCGATGACGAGTTCGGTTCCCTCCACCGG

GCGCTCACCCGAGCGGGGGCGGGCGGGGCGTCGTCGCCGCCGTCACCGGGCCGATCGCCTGC

GGCAAGACCGAACTCCTCGACGCCGCCGCGGCCAAGGCCGGCTTCGTCACCCTTCGCGCGGTGTG

CTCCATGGAGGAGCGGGCCCTGCCGTACGGCATGCTCGGCCAGCTCCTCGACCAGCCCGAGCTGG

CCGCCCGGACACCGGAGCTGGTCCGGCTGACGGCATCGTGCGAAAACCTGCCGGCCGACGTCGAC

AACCGCCTGGGGACCGAACTCACCCGCACGGTGCTGACGCTCGCCGGGAGCGGCCCGTACTGAT

CGGCATCGACGACGTGCACCACGCCGACGCGCCGTCGCTGCGCTGCCTGCTCCACCTCGCGCGCC

GCATCAGCCGGGCCGTGTCGCCATCGTGCTGACCGAGCTGCTCCGGCCGACGCCCGCCCACTCC

CAATTCCGGGCGGCACTGCTGAGTCTGCGCCACTACCAGGAGATCGCGCTGCGCCCCGCTCACCGA

-continued

GGCGCAGACCACCGAACTCGTGCGCCGGCACCTCGGCCAGGACGCGCACGACGACGTGGTGGCC

CAGGCGTTCCGGGCGACCGGCGGCAACCTGCTCCTCGGCCACGGCCTGATCGACGACATCCGGGA

GGCACGGACACGGACCTCAGGGTGCCTGGAAGTGGTCGCGGGGCGGGCGTACCGGCTCGCCTAC

CTCGGGTCGCTCTATCGTTGCGGCCCGGCCGCGCTGAGCGTCGCCCGAGCTTCCGCCGTGCTCGG

CGAGAGTGTCGAACTCACCCTCGTCCAGCGGATGACCGGCCTCGACACCGAGGCGGTCGAGCAGG

CCCACGAACAGCTGGTCGAGGGGCGGCTGCTGCGGGAAGGGCGGTTCCCGCACCCCGCGGCCCG

CTCCGTCGTACTCGACGACCTCTCCGCCGCCGAGCGGCGTGGCCTGCACGAGCTGGCGCTGGAAC

TGCTGCGGGACCGCGGCGTGGCCAGCAAGGTGCTCGCCCGCCACCAGATGGGTACCGGCCGGGT

GCACGGCGCCGAGGTCGCCGGGCTGTTCACCGACGCCGCGCGCGAGCACCACCTGCGCGGCGAG

CTCGACGAGGCCGTCACCTACCTGGAGTTCGCCTACCGGGCCTCCGACGACCCCGCCGTCCACGC

CGCACTGCGCGTCGACACCGCCGCCATCGAGCGGCTCTGCGATCCCGCCAGATCCGGCCGGCATG

TGCCCGAGCTGCTCACCGCGTCGCGGGAACGGCTCCTCTCCAGCGAGCACGCCGTGTCGCTCGCC

TGCTGGCTGGCGATGGACGGGCGGCCGGGCGAGGCCGCCGAGGTCCTGGCGGCCCAGCGCTCC

GCCGCCCCGAGCGAGCAGGGCCGGGCGCACCTGCGCGTCGCGGACCTGTCCCTCGCGCTGATCT

ATCCCGGCGCGGCCGATCCGCCGCGTCCGGCCGATCCGCCGGCCGAGGACGAGGTCGCCCTCGTT

TTCCGGAGCCGTCCGGCACCGCGCCGTCGCCGACAAGGCCCTGAGCAACGCGCTGCGCGGCTGG

TCCGAACAGGCCGAGGCCAAAGCCGAGTACGTGCTCCAGCACTCCCGGGTCACGACGGACCGGAC

CACGACCATGATGGCGTTGCTGGCCCTGCTCTACGCCGAGGACACCGATGCCGTCCAGTCCTGGGT

CGACAAGCTGGCCGGTGACGACAACATGCGGACCCCGGCCGACGAGGCGGTCCACGCGGGGTTC

CGCGCCGAGGCCGCGCTGCGCCGCGGCGACCTGACCGCCGCCGTCGAATGCGGCGAGGCCGCG

CTCGCCCCCGGGTCGTGCCCTCCTGGGGGATGGCCGCCGCATTGCCGCTGAGCAGCACCGTGG

CCGCCGCGATCCGACTGGGCGACCTGGACCGGGCGGAGCGGTGGCTCGCCGAGCCGTTGCCGGA

GGAGACCTCCGACAGCCTCTTCGGACTGCACATGGTCTGGGCCCGTGGGCAACACCATCTCGCGG

CCGGGCGGTACCGGGCGGCGTACAACGCGTTCCGGGACTGCGGGGAGCGGATGCGACGCTGGTC

CGTCGACGTGCCGGGCCTGGCCCTGTGGCGGGTCGACGCCGCCGAAGCGCTTCTGCTGCTCGGC

CGCGGCCGTGACGAGGGGCTGAGGCTCATCTCCGAGCAGCTGTCCCGGCCGATGGGGTCCCGGG

CGCGGGTGATGACGCTGCGGGTGCAGGCGGCCTACAGTCCGCCGGCCAAGCGGATCGAACTGCTC

GACGAGGCCGCCGATCTGCTCATCATGTGCCGCGACCAGTACGAGCTGGCCCGCGTCCTCGCCGA

CATGGGCGAAGCGTGCGGCATGCTCCGGCGGCACAGCCGTGCGCGGGGACTGTTCCGCCGCGCA

CGGCACCTCGCGACCCAGTGCGGAGCCGTGCCGCTCCTCCGGCGGCTCGGTGGGGAGTCCTCGG

ACGCGGACGGCACCCAGGACGTGACGCCGGCGCAGCGGATCACATCGCTGACCGAGGCGGAGCG

GCGGGTGGCGTCGCACGCCGCGGTCGGGCGCACCAACAAGGAGATCGCCAGCCAGCTGTTCGTCA

CCTCCAGCACGGTGGAACAGCACCTCACCAACGTGTTCCGCAAGCTGGGGGTGAAGGGCCGTCAG

CAACTGCCCAAGGAACTGTCCGACGCCGGCTGA

SEQ ID NO: 47
GTGGAGTTTTACGACCTGGTCGCCCGCGATGACGAGCTCAGAAGGTTGGACCAGGCCCTCGGCCG

CGCCGCCGGCGGACGGGGTGTCGTGGTCACCGTCACCGGACCGGTCGGCTGCGGCAAGACCGAA

CTGCTGGACGCGGCCGCGGCCGAGGAGGAATTCATCACGTTGCGTGCGGTCTGCTCGGCCGAGGA

GCGGGCCCTGCCGTACGCCGTGATCGGCCAACTCCTCGACCATCCCGTACTCTCCGCACGCGCGC

CCGACCTGGCCTGCGTGACGGCTCCGGGCCGGACGCTGCCGGCCGACACCGAGAACCGCCTGCG

CCGCGACCTCACCCGGGCCCTGCTGGCCCTGGCCTCCGAACGACCGGTTCTGATCTGCATCGACG

-continued

```
ACGTGCACCAGGCCGACACCGCCTCGCTGAACTGCCTGCTGCACCTGGCCCGGCGGGTCGCCTCG

GCCCGGATCGCCATGATCCTCACCGAGTTGCGCCGGCTCACCCCGGCTCACTCCCGGTTCGAGGC

GGAACTGCTCAGCCTGCGGCACCGCCACGAGATCGCGCTGCGTCCCCTCGGCCCGGCCGACACCG

CCGAACTGGCCCGCGCCCGGCTCGGCGCCGGCGTCACCGCCGACGAGCTGGCCCAGGTCCACGA

GGCCACCAGCGGGAACCCCAACCTGGTCGGAGGCCTGGTCAACGACGTGCGAGAGGCCTGGGCG

GCCGGTGGCACGGGCATTGCGGCGGGGCGGGCGTACCGGCTGGCGTACCTCAGCTCCGTGTACC

GCTGTGGTCCGGTCCCGTTGCGGATCGCCCAGGCGGCGGCGGTGCTGGGTCCCAGCGCCACCGT

CACGCTGGTGCGCCGGATCAGCGGGCTCGACGCCGAGACGGTGGACGAGGCGACCGCGATCCTC

ACCGAGGGCGGCCTGCTCCGGGACCACCGGTTCCCGCATCCGGCGGCCCGCTCGGTCGTACTCGA

CGACATGTCCGCGCAGGAACGCCGCCGCCTGCACCGGTCCACGCTGGACGTGCTGGACGGCGTAC

CCGTCGACGTGCTCGCGCACCACCAGGCCGGCGCCGGTCTGCTGCACGGCCCGCAGGCGGCCGA

GATGTTCGCCCGGGCCAGCCAGGAGCTGCGGGTACGCGGCGAGCTGGACGCCGCGACCGAGTAC

CTGCAACTGGCCTACCGGGCCTCCGACGACGCCGGCGCCCGGGCCGCCCTGCAGGTGGAGACCG

TGGCCGGCGAGCGCCGCCGCAACCCGCTGGCCGCCAGCCGGCACCTGGACGAGCTGGCCGCCGC

CGCCCGGGCCGGCCTGCTGTCGGCCGAGCACGCCGCCCTGGTCGTGCACTGGCTGGCCGACGCC

GGACGACCCGGCGAGGCCGCCGAGGTGCTGGCGCTGCAGCGGGCGCTGGCCGTCACCGACCACG

ACCGGGCCCGCCTGCGGGCGGCCGAGGTGTCGCTCGCGCTGTTCCACCCCGGCGTCCCCGGTTC

GGACCCGCGGCCCCTCGCGCCGGAGGAGCTCGCGAGCCTGTCCCTGTCGGCCCGGCACGGTGTG

ACCGCCGACAACGCGGTGCTGGCGGCGCTGCGCGGCCGTCCCGAGTCGGCCGCCGCCGAGGCG

GAGAACGTGCTGCGCAACGCCGACGCCGCCGCGTCCGGCCCGACCGCCCTGGCCGCGCTGACGG

CCCTGCTCTACGCCGAGAACACCGACGCCGCCCAGCTCTGGGCGGACAAGCTGGCCGCGGGCATC

GGGGCGGGGAGGGGGAGGCCGGCTACGCGGGGCCGCGGACCGTGGCCGCCCTGCGTCGCGGC

GACCTGACCACCGCGGTCCAGGCGGCCGGCGCGGTCCTGGACCGCGGCCGGCCGTCGTCGCTCG

GCATCACCGCCGTGTTGCCGTTGAGCGGCGCGGTCGCCGCCGCGATCCGGCTGGGCGAGCTCGA

GCGGGCCGAGAAGTGGCTGGCCGAGCCGCTGCCCGAAGCCGTCCACGACAGCCTGTTCGGCCTG

CACCTGCTGATGGCGCGGGGCCGCTACAGCCTCGCGGTGGGCCGGCACGAGGCGGCGTACGCCG

CGTTCCGGGACTGCGGTGAACGGATGCGCCGGTGGGACGTCGACGTGCCCGGGCTGGCCCTGTG

GCGGGTGGACGCGGCCGAGGCGCTGCTGCCCGGCGATGACCGGGCGGAGGGCCGGCGGCTGAT

CGACGAGCAGCTCACCCGGCCGATGGGGCCCCGGTCACGAGCCCTGACCCTGCGGGTACGAGCG

GCCTACGCCCCGCCGGCGAAACGGATCGACCTGCTCGACGAAGCGGCCGACCTGCTGCTCTCCAG

CAACGACCAGTACGAGCGGGCACGGGTGCTGGCCGACCTGAGCGAGGCGTTCAGCGCGCTCCGG

CAGAACGGCCGGGCGCGCGGCATCCTGCGGCAGGCCCGGCACCTGGCCGCCCAGTGCGGGGCG

GTCCCCCTGCTGCGCCGGCTGGGCGTCAAGGCCGGCCGGTCCGGTCGGCTCGGCCGGCCGCCGC

AGGGAATCCGCTCCCTGACCGAGGCCGAGCGCCGGGTGGCCACGCTGGCCGCCGCCGGGCAGAC

CAACCGGGAGATCGCCGACCAGCTCTTCGTCACCGCCAGCACGGTCGAGCAGCACCTCACCAACG

TGTTCCGCAAGCTCGGCGTGAAGGGCCGCCAGCAATTGCCGGCCGAGCTGGCCGACCTGCGGCCG

CCGGGCTGA

SEQ ID NO: 48
ATGGAGTTTTACGACCTGGTCGCCCGCGATGACGAGCTCAGAAGGTTGGACCAGGCCCTCGGCCG

CGCCGCCGGCGGACGGGGTGTCGTGGTCACCGTCACCGGACCGGTCGGCTGCGGCAAGACCGAA

CTGCTGGACGCGGCCGCGGCCGAGGAGGAATTCATCACGTTGCGTGCGGTCTGCTCGGCCGAGGA
```

-continued

```
GCGGGCCCTGCCGTACGCCGTGATCGGCCAACTCCTCGACCATCCCGTACTCTCCGCACGCGCG
CCCGACCTGGCCTGCGTGACGGCTCCGGGCCGGACGCTGCCGGCCGACACCGAGAACCGCCTGCG
CCGCGACCTCACCCGGGCCCTGCTGGCCCTGGCCTCCGAACGACCGGTTCTGATCTGCATCGACG
ACGTGCACCAGGCCGACACCGCCTCGCTGAACTGCCTGCTGCACCTGGCCCGGCGGGTCGCCTCG
GCCCGGATCGCCATGATCCTCACCGAGTTGCGCCGGCTCACCCCGGCTCACTCCCGGTTCGAGGC
GGAACTGCTCAGCCTGCGGCACCGCCACGAGATCGCGCTGCGTCCCCTCGGCCCGGCCGACACCG
CCGAACTGGCCCGCGCCCGGCTCGGCGCCGGCGTCACCGCCGACGAGCTGGCCCAGGTCCACGA
GGCCACCAGCGGGAACCCCAACCTGGTCGGAGGCCTGGTCAACGACGTGCGAGAGGCCTGGGCG
GCCGGTGGCACGGGCATTGCGGCGGGGCGGGCGTACCGGCTGGCGTACCTCAGCTCCGTGTACC
GCTGTGGTCCGGTCCCGTTGCGGATCGCCCAGGCGGCGGCGGTGCTGGGTCCCAGCGCCACCGT
CACGCTGGTGCGCCGGATCAGCGGGCTCGACGCCGAGACGGTGGACGAGGCGACCGCGATCCTC
ACCGAGGGCGGCCTGCTCCGGGACCACCGGTTCCCGCATCCGGCGGCCCGCTCGGTCGTACTCGA
CGACATGTCCGCGCAGGAACGCCGCCGCCTGCACCGGTCCACGCTGGACGTGCTGGACGGCGTAC
CCGTCGACGTGCTCGCGCACCACCAGGCCGGCGCCGGTCTGCTGCACGGCCCGCAGGCGGCCGA
GATGTTCGCCCGGGCCAGCCAGGAGCTGCGGGTACGCGGCGAGCTGGACGCCGCGACCGAGTAC
CTGCAACTGGCCTACCGGGCCTCCGACGACGCCGGCGCCCGGGCCGCCCTGCAGGTGGAGACCG
TGGCCGGCGAGCGCCGCCGCAACCCGCTGGCCGCCAGCCGGCACCTGGACGAGCTGGCCGCCGC
CGCCCGGGCCGGCCTGCTGTCGGCCGAGCACGCCGCCCTGGTCGTGCACTGGCTGGCCGACGCC
GGACGACCCGGCGAGGCCGCCGAGGTGCTGGCGCTGCAGCGGGCGCTGGCCGTCACCGACCACG
ACCGGGCCCGCCTGCGGGCGGCCGAGGTGTCGCTCGCGCTGTTCCACCCCGGCGTCCCCGGTTC
GGACCCGCGGCCCCTCGCGCCGGAGGAGCTCGCGAGCCTGTCCCTGTCGGCCCGGCACGGTGTG
ACCGCCGACAACGCGGTGCTGGCGGCGCTGCGCGGCCGTCCCGAGTCGGCCGCCGCCGAGGCG
GAGAACGTGCTGCGCAACGCCGACGCCGCCGCGTCCGGCCCGACCGCCCTGGCCGCGCTGACGG
CCCTGCTCTACGCCGAGAACACCGACGCCGCCCAGCTCTGGGCGGACAAGCTGGCCGCGGGCATC
GGGGCGGGGAGGGGGAGGCCGGCTACGCGGGCCGCGGACCGTGGCCGCCCTGCGTCGCGGC
GACCTGACCACCGCGGTCCAGGCGGCCGGCGCGGTCCTGGACCGCGGCCGGCCGTCGTCGCTCG
GCATCACCGCCGTGTTGCCGTTGAGCGGCGCGGTCGCCGCCGCGATCCGGCTGGGCGAGCTCGA
GCGGGCCGAGAAGTGGCTGGCCGAGCCGCTGCCCGAAGCCGTCCACGACAGCCTGTTCGGCCTG
CACCTGCTGATGGCGCGGGGCCGCTACAGCCTCGCGGTGGGCCGGCACGAGGCGGCGTACGCCG
CGTTCCGGGACTGCGGTGAACGGATGCGCCGGTGGGACGTCGACGTGCCCGGGCTGGCCCTGTG
GCGGGTGGACGCGGCCGAGGCGCTGCTGCCCGGCGATGACCGGGCGGAGGGCCGGCGGCTGAT
CGACGAGCAGCTCACCCGGCCGATGGGGCCCCGGTCACGAGCCCTGACCCTGCGGGTACGAGCG
GCCTACGCCCCGCCGGCGAAACGGATCGACCTGCTCGACGAAGCGGCCGACCTGCTGCTCTCCAG
CAACGACCAGTACGAGCGGGCACGGGTGCTGGCCGACCTGAGCGAGGCGTTCAGCGCGCTCCGG
CAGAACGGCCGGGCGCGCGGCATCCTGCGGCAGGCCCGGCACCTGGCCGCCCAGTGCGGGGCG
GTCCCCCTGCTGCGCCGGCTGGGCGTCAAGGCCGGCCGGTCCGGTCGGCTCGGCCGGCCGCCGC
AGGGAATCCGCTCCCTGACCGAGGCCGAGCGCGGGTGGCCACGCTGGCCGCCGCCGGGCAGAC
CAACCGGGAGATCGCCGACCAGCTCTTCGTCACCGCCAGCACGGTCGAGCAGCACCTCACCAACG
TGTTCCGCAAGCTCGGCGTGAAGGGCCGCCAGCAATTGCCGGCCGAGCTGGCCGACCTGCGGCCG
CCGGGCTGA
```

-continued

SEQ ID NO: 49
GTGGTCACCGTCACCGGCCCAATCGCCTGCGGCAAGACAGAACTGCTTGACGCGGCTGCCGCGAA

GGCTGAGGCCATCATTCTGCGCGCGGTCTGCGCGCCAGAAGAGCGGGCTATGCCGTACGCCATGA

TCGGGCAGCTCATCGACGACCCGGCGCTCGCGCATCGGGCGCCGGGGCTGGCTGATCGGATAGC

CCAGGGCGGGCAGCTGTCGCTGAGGGCCGAGAACCGACTGCGCAGGGATCTCACCCGTGCCCTG

CTGGCGCTTGCCGTCGACCGGCCTGTGCTGATCGGCGTCGACGATGTGCATCACGCCGACACCGC

CTCTTTGAACTGTCTGCTGCATTTGGCGCGCCGGGTCCGTCCGGCCCGGATATCCATGATCTTCACC

GAGTTGCGCAGCCTCACCCCTACTCAGTCACGGTTCAAGGCGGAGCTGCTCAGCCTGCCGTACCAC

CACGAGATCGCGCTGCGTCCGTTCGGACCGGAGCAATCGGCGGAGCTGGCCCGCGCCGCCTTCG

GCCCGGGCCTCGCCGAGGATGTGCTCGTGGGGTTGTATAAAACGACCAGGGGCAATCTGAGTCTCA

GCCGTGGACTGATCAGCGATGTGCGGGAGGCCCTGGCCAACGGAGAGAGCGCCTTCGAGGCGGG

CCGCGCGTTCCGGCTGGCGTACCTCGGCTCGCTCTACCGCTGTGGCCCGGTCGCGCTGCGGGTCG

CCCGAGTGGCTGCCGTGCTGGGCCCGAGCGCCACCACCACGCTGGTGCGCCGTCTAAGCGGGCT

CAGCGCGGAGACGATAGACCGGGCAACCAAGATCCTCACCGAGGGCGGGCTGCTGCTCGACCAGC

AGTTCCCGCACCCGGCCGCCCGCTCGGTGGTGCTTGATGACATGTCCGCCCAGGAACGACGCGGC

CTGCACACTCTCGCCCTGGAACTGCTGGACGAGGCGCCGGTTGAAGTGCTCGCGCACCACCAGGT

CGGCGCCGGTCTCATACACGGGCCCAAGGCTGCGGAGATGTTCGCCAAGGCCGGCAAGGCTCTGG

TCGTACGCAACGAGTTGGGCGACGCGGCAGAATACCTGCAACTGGCTCACCGGGCCTCCGACGAT

GTCTCCACCCGGGCCGCCTTACGGGTCGAGGCCGTGGCGATCGAGCGCCGCCGCAATCCGCTGG

CCTCCAGTCGGCACATGGACGAGCTGAGCGCCGCCGGCCGCGCCGGTCTGCTTTCCCCCAAGCAT

GCGGCGCTGGCCGTCTTCTGGCTGGCCGACGGCGGGCGATCCGGCGAGGCAGCCGAGGTGCTGG

CGTCGGAACGCCCGCTAGCGACCACCGATCAGAACCGGGCCCACTTGCGATTTGTCGAGGTGACTC

TCGCGCTGTTCTCTCCCGGCGCCTTCGGATCGGACCGGCGCCCACCTCCGCTGACGCCGGACGAA

CTCGCCAGCCTGCCGAAGGCGGCCTGGCAATGCGCGGTCGCCGACAACGCGGCCATGACCGCCTT

GCACGGTCATCCAGAACTTGCCACCGCTCAGGCGGAAACAGTTCTGCGGCAGGCTGATTCGGCAGC

CGACGCGATCCCCGCCGCGCTGATCGCCCTGTTGTACGCGGAGAACACCGAGTCCGCTCATATCTG

GGCCGACAAGCTGGGCAGCACGAATGGCGGGGTATCGAACGAGGCGGAAGCGGGCTACGCCGGC

CCGTGCGCCGAGATCGCCCTGCGGCGCGGCGACCTGGCCACGGCGTTCGAGGCTGGTAGCACCG

TCCTGGACGACCGGTCGCTGCCGTCGCTCGGCATCACCGCCGCATTGCTGTTGAGCAGCAAGACG

GCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCATACGGCCAGTACAGCCTCGCGAT

GGGCCGATATGAATCGGCTCTCCGGGCGTTTCACACCTGCGGAGAACGTATGCGCAGCTGGGATGT

TGACGTGCCTGGTCTGGCCCTGTGGCGTGTCGACGCCGCCGAGGCGCTGCTCAGCCTCGACCGGA

ACGAGGGCCAGCGGCTCATCGACGAACAACTCACCCGTCCGATGGGGCCTCGTTCCCGCGCGTTA

ACGCTGCGGATCAAGGCGGCATACCTCCCGCGGACGAAGCGGATCCCCCTGCTCCATGAGGCGGC

CGAGCTGCTGCTCCCCTGCCCCGACCCGTACGAGCAAGCGCGGGTGCTCGCCGATCTGGGCGACA

CGCTCAGCGCGCTCAGACGCTATAGCCGGGCGCGGGAGTTCTCCGGCAGGCTCGTCACCTGGCC

GCCCAGTGCGGTGCTGTCCCGCTGCTGCGCAGGCTCGGGGGCGAGCCCGGCCGGATCGACGACG

-continued

CCGGCCTGCCGCAGCGGAGCACATCGTTGACCGATGCGGAGCGGCGGGTGGCGGCGCTGGCCGC

GGCCGGACAGACCAACCGGGAGATCGCCAAACAGCTGTTCGTCACGGCCAGCACAGTGGAACAGC

ACCTCACAAGCGTCTTCCGCAAACTGGGGGTCAAGGGTCGCAAGCAGCTGCCGACCGCGCTGGCC

GACGTGGAACAGACCTGA

SEQ ID NO: 50
ATGTATAGCGGTACCTGCCGTGAAGGATACGAACTCGTCGCACGCGAGGACGAACTCGGCATTCTA

CAGAGGTCTCTGGAACAAGCGAGCAGCGGCCAGGGCGTCGTGGTCACCGTCACCGGCCCAATCGC

CTGCGGCAAGACAGAACTGCTTGACGCGGCTGCCGCGAAGGCTGAGGCCATCATTCTGCGCGCGG

TCTGCGCGCCAGAAGAGCGGGCTATGCCGTACGCCATGATCGGGCAGCTCATCGACGACCCGGCG

CTCGCGCATCGGGCGCCGGGGCTGGCTGATCGGATAGCCCAGGGCGGGCAGCTGTCGCTGAGGG

CCGAGAACCGACTGCGCAGGGATCTCACCCGTGCCCTGCTGGCGCTTGCCGTCGACCGGCCTGTG

CTGATCGGCGTCGACGATGTGCATCACGCCGACACCGCCTCTTTGAACTGTCTGCTGCATTTGGCG

CGCCGGGTCCGTCCGGCCCGGATATCCATGATCTTCACCGAGTTGCGCAGCCTCACCCCTACTCAG

TCACGGTTCAAGGCGGAGCTGCTCAGCCTGCCGTACCACCACGAGATCGCGCTGCGTCCGTTCGG

ACCGGAGCAATCGGCGGAGCTGGCCCGCGCCGCCTTCGGCCCGGGCCTCGCCGAGGATGTGCTC

GTGGGGTTGTATAAAACGACCAGGGGCAATCTGAGTCTCAGCCGTGGACTGATCAGCGATGTGCGG

GAGGCCCTGGCCAACGAGAGAGCGCCTTCGAGGCGGGCCGCGCGTTCCGGCTGGCGTACCTCG

GCTCGCTCTACCGCTGTGGCCCGGTCGCGCTGCGGGTCGCCCGAGTGGCTGCCGTGCTGGGCCC

GAGCGCCACCACCACGCTGGTGCGCCGTCTAAGCGGGCTCAGCGCGGAGACGATAGACCGGGCAA

CCAAGATCCTCACCGAGGGCGGGCTGCTGCTCGACCAGCAGTTCCCGCACCCGGCCGCCCGCTCG

GTGGTGCTTGATGACATGTCCGCCCAGGAACGACGCGGCCTGCACACTCTCGCCCTGGAACTGCTG

GACGAGGCGCCGGTTGAAGTGCTCGCGCACCACCAGGTCGGCGCCGGTCTCATACACGGGCCCAA

GGCTGCGGAGATGTTCGCCAAGGCCGGCAAGGCTCTGGTCGTACGCAACGAGTTGGGCGACGCGG

CAGAATACCTGCAACTGGCTCACCGGGCCTCCGACGATGTCTCCACCCGGGCCGCCCTGCGGGTC

GAGGCCGTGGCGATCGAGCGCCGCCGCAATCGCTGGCCTCCAGTCGGCACATGGACGAGCTGAG

CGCCGCCGGCCGCGCCGGTCTGCTTTCCCCCAAGCATGCGGCGCTGGCCGTCTTCTGGCTGGCCG

ACGGCGGGCGATCCGGCGAGGCAGCCGAGGTGCTGGCGTCGGAACGCCCGCTAGCGACCACCGA

TCAGAACCGGGCCCACTTGCGATTTGTCGAGGTGACTCTCGCGCTGTTCTCTCCCGGCGCCTTCGG

ATCGGACCGGCGCCCACCTCCGCTGACGCCGGACGAACTCGCCAGCCTGCCGAAGGCGGCCTGG

CAATGCGCGGTCGCCGACAACGCGGCCATGACCGCCTTGCACGGTCATCCAGAACTTGCCACCGCT

CAGGCGGAAACAGTTCTGCGGCAGGCTGATTCGGCAGCCGACGCGATCCCCGCCGCGCTGATCGC

CCTGTTGTACGCGGAGAACACCGAGTCCGCTCATATCTGGGCCGACAAGCTGGGCAGCACGAATGG

CGGGGTATCGAACGAGGCGGAAGCGGGCTACGCCGGCCCGTGCGCCGAGATCGCCCTGCGGCGC

GGCGACCTGGCCACGGCGTTCGAGGCTGGTAGCACCGTCCTGGACGACCGGTCGCTGCCGTCGCT

CGGCATCACCGCCGCATTGCTGTTGAGCAGCAAGACGGCCGCCGCTGTCCGGCTGGGCGAACTCG

AGCGTGCGGAGAAGCTGCTCGCCGAGCCGCTTCCGAACGGCGTCCAGGACAGCCTTTTCGGTCTG

CACCTGCTCTCGGCATACGGCCAGTACAGCCTCGCGATGGGCCGATATGAATCGGCTCTCCGGGC

GTTTCACACCTGCGGAGAACGTATGCGCAGCTGGGATGTTGACGTGCCTGGTCTGGCCCTGTGGCG

TGTCGACGCCGCCGAGGCGCTGCTCAGCCTCGACCGGAACGAGGGCCAGCGGCTCATCGACGAAC

AACTCACCCGTCCGATGGGGCCTCGTTCCCGCGCGCTGACGCTGCGGATCAAGGCGGCATACCTC

CCGCGGACGAAGCGGATCCCCCTGCTCCATGAGGCGGCCGAGCTGCTGCTCCCCTGCCCCGACCC

```
GTACGAGCAAGCGCGGGTGCTCGCCGATCTGGGCGACACGCTCAGCGCGCTCAGACGCTATAGCC

GGGCGCGGGGAGTTCTCCGGCAGGCTCGTCACCTGGCCGCCCAGTGCGGTGCTGTCCCGCTGCT

GCGCAGGCTCGGGGGCGAGCCCGGCCGGATCGACGACGCCGGCCTGCCGCAGCGGAGCACATCG

TTGACCGATGCGGAGCGGCGGGTGGCGGCGCTGGCCGCGGCCGGACAGACCAACCGGGGAGATCG

CCAAACAGCTGTTCGTCACGGCCAGCACAGTGGAACAGCACCTCACAAGCGTCTTCCGCAAACTGG

GGGTCAAGGGTCGCAAGCAGCTGCCGACCGCGCTGGCCGACGTGGAACAGACCTGA

SEQ ID NO: 51
ATGCCTGCCGTGGAGAGCTATGAACTGGACGCCCGCGATGACGAGCTCAGAAGACTGGAGGAGGC

GGTAGGCCAGGCGGGCAACGGCCGGGGTGTGGTGGTCACCATCACCGGGCCGATCGCCTGCGGC

AAGACCGAACTGCTCGACGCGGCCGCCGCGAAGAGCGACGCCATCACATTACGTGCGGTCTGCTC

CGAGGAGGAACGGGCCCTCCCGTACGCCCTGATCGGGCAGCTCATCGACAACCCGGCGGTCGCCT

CCCAGCTGCCGGATCCGGTCTCCATGGCCCTCCCGGGCGAGCACCTGTCGCCGGAGGCCGAGAAC

CGGCTGCGCGGCGACCTCACCCGTACCCTGCTGGCGCTCGCCGCCGAACGGCCGGTGCTGATCG

GCATCGACGACATGCACCACGCCGACACCGCCTCTTTGAACTGCCTGCTCCACCTGGCCCGGAGG

GTCGGCCCGGCCCGGATCGCCATGGTCCTCACCGAGCTGCGCCGGCTCACCCCGGCCCACTCCCA

GTTCCACGCCGAGCTGCTCAGCCTGGGGCACCACCGCGAGATCGCGCTGCGCCCGCTCGGCCCGA

AGCACATCGCCGAGCTGGCCCGCGCCGGCCTCGGTCCCGATGTCGACGAGGACGTGCTCACGGG

GTTGTACCGGGCGACCGGCGGCAACCTGAACCTCGGCCACGGACTGATCAAGGATGTGCGGGAGG

CCTGGGCGACGGGCGGGACGGGCATCAACGCGGGCCGCGCGTACCGGCTGGCGTACCTCGGTTC

CCTCTACCGCTGCGGCCCGGTCCCGTTGCGGGTCGCACGGGTGGCCGCCGTGCTGGGCCAGAGC

GCCAACACCACCCTGGTGCGCTGGATCAGCGGGCTCAACGCGGACGCGGTGGGCGAGGCGACCG

AGATCCTCACCGAGGGCGGCCTGCTGCACGACCTGCGGTTCCCGCATCCGGCGGCCCGTTCGGTC

GTACTCAACGACCTGTCCGCCCGGGAACGCCGCCGACTGCACCGGTCCGCTCTGGAAGTGCTGGA

TGACGTACCCGTTGAAGTGGTCGCGCACCACCAGGCCGGTGCCGGTTTCATCCACGGTCCCAAGG

CCGCCGAGATCTTCGCCAAGGCCGGCCAGGAGCTGCATGTGCGCGGCGAGCTGGACGCCGCGTC

CGACTATCTGCAACTGGCCCACCACGCCTCCGACGACGCCGTCACCCGGGCCGCGCTGCGGGTCG

AGGCCGTGGCGATCGAGCGCCGCCGCAACCCGCTGGCCTCCAGCCGCCACCTCGACGAGCTGAC

CGTCGCCGCCCGTGCCGGTCTGCTCTCCCTCGAGCACGCCGCGCTGATGATCCGCTGGCTGGCTC

TCGGCGGGCGGTCCGGCGAGGCGGCCGAGGTGCTGGCCGCGCAGCGCCCGCGTGCGGTCACCG

ACCAGGACAGGGCCCACCTGCGGGCCGCCGAGGTATCGCTGGCGCTGGTCAGCCCGGGCGCGTC

CGGCGTCAGCCCGGGTGCGTCCGGCCCGGATCGGCGGCCGCGTCCGCTCCCGCCGGATGAGCTC

GCGAACCTGCCGAAGGCGGCCCGGCTTTGTGCGATCGCCGACAACGCCGTCATATCGGCCCTGCA

CGGTCGTCCCGAGCTTGCCTCGGCCGAGGCGGAGAACGTCCTGAAGCAGGCTGACTCGGCGGCG

GACGGCGCCACCGCCCTCTCCGCGCTGACGGCCTTGCTGTACGCGGAGAACACCGACACCGCTCA

GCTCTGGGCCGACAAGCTCGTCTCCGAGACCGGGCGTCGAACGAGGAGGAAGGCGCGGGCTAC

GCGGGGCCGCGCGCCGAGACCGCGTTGCGCCGCGGCGACCTGGCCGGCGGTCGAGGCGGGC

AGCGCCATTCTGGACCACCGGCGGGGTCGTTGCTCGGCATCACCGCCGCGCTACCGCTGAGCAG

CGCGGTAGCCGCCGCCATCCGGCTGGGCGAGACCGAGCGGGCGGAGAAGTGGCTCGCCGAGCCG

CTGCCGGAGGCCATTCGGGACAGCCTGTTCGGGCTGCACCTGCTCTCGGCGCGCGGCCAGTACTG

CCTCGCGACGGGCCGGCACGAGTCGGCGTACACGGCGTTCCGCACCTGCGGGGAACGGATGCGG

AACTGGGCGTCGACGTGCCGGGTCTGTCCCTGTGGCGCGTCGACGCCGCCGAGGCGCTGCTGC
```

-continued

ACGGCCGCGACCGGGACGAGGGCCGACGGCTCATCGACGAGCAGCTCACCCATGCGATGGGACC
CCGTTCCCGCGCTTTGACGCTGCGGGTGCAGGCGGCGTACAGCCCGCAGGCGCAGCGGGTCGAC
CTGCTCGAAGAGGCGGCCGACCTGCTGCTCTCCTGCAACGACCAGTACGAGCGGGCGCGGGTGCT
CGCCGATCTGAGCGAGGCGTTCAGCGCGCTCAGGCACCACAGCCGGGCGCGGGGACTGCTCCGG
CAGGCCCGGCACCTGGCCGCCCAGTGCGGCGCGACCCCGCTGCTGCGCCGGCTCGGGGCCAAGC
CCGGAGGCCCCGGCTGGCTGGAGGAATCCGGCCTGCCGCAGCGGATCAAGTCGCTGACCGACGC
GGAGCGGCGGGTGGCGTCGCTGGCCGCCGGCGGCCAGACCAACCGCGTGATCGCCGACCAGCTC
TTCGTCACGGCCAGCACGGTGGAGCAGCACCTCACGAACGTCTTCCGCAAGCTGGGCGTCAAGGG
CCGCCAGCACCTGCCGGCCGAACTCGCCAACGCGGAATAG

SEQ ID NO: 52
ATGCCTGCCGTGGAGAGCTATGAACTGGACGCCCGCGATGACGAGCTCAGAAGACTGGAGGAGGC
GGTAGGCCAGGCGGGCAACGGCCGGGGTGTGGTGGTCACCATCACCGGGCCGATCGCCTGCGGC
AAGACCGAACTGCTCGACGCGGCCGCCGCGAAGAGCGACGCCATCACACTGCGTGCGGTCTGCTC
CGAGGAGGAACGGGCCCTCCCGTACGCCCTGATCGGGCAGCTCATCGACAACCCGGCGGTCGCCT
CCCAGCTGCCGGATCCGGTCTCCATGGCCCTCCCGGGCGAGCACCTGTCGCCGGAGGCCGAGAAC
CGGCTGCGCGGCGACCTCACCCGTACCCTGCTGGCGCTCGCCGCCGAACGGCCGGTGCTGATCG
GCATCGACGACATGCACCACGCCGACACCGCCTCTTTGAACTGCCTGCTCCACCTGGCCCGGAGG
GTCGGCCCGGCCCGGATCGCCATGGTCCTCACCGAGCTGCGCCGGCTCACCCCGGCCCACTCCCA
GTTCCACGCCGAGCTGCTCAGCCTGGGGCACCACCGCGAGATCGCGCTGCGCCCGCTCGGCCCGA
AGCACATCGCCGAGCTGGCCCGCGCCGGCCTCGGTCCCGATGTCGACGAGGACGTGCTCACGGG
GTTGTACCGGGCGACCGGCGGCAACCTGAACCTCGGCCACGGACTGATCAAGGATGTGCGGGAGG
CCTGGGCGACGGGCGGGACGGGCATCAACGCGGGCCGCGCGTACCGGCTGGCGTACCTCGGTTC
CCTCTACCGCTGCGGCCCGGTCCCGTTGCGGGTCGCACGGGTGGCCGCCGTGCTGGGCCAGAGC
GCCAACACCACCCTGGTGCGCTGGATCAGCGGGCTCAACGCGGACGCGGTGGGCGAGGCGACCG
AGATCCTCACCGAGGGCGGCCTGCTGCACGACCTGCGGTTCCCGCATCCGGCGGCCCGTTCGGTC
GTACTCAACGACCTGTCCGCCCGGGAACGCCGCCGACTGCACCGGTCCGCTCTGGAAGTGCTGGA
TGACGTACCCGTTGAAGTGGTCGCGCACCACCAGGCCGGTGCCGGTTTCATCCACGGTCCCAAGG
CCGCCGAGATCTTCGCCAAGGCCGGCCAGGAGCTGCATGTGCGCGGCGAGCTGGACGCCGCGTC
CGACTATCTGCAACTGGCCCACCACGCCTCCGACGACGCCGTCACCCGGGCCGCGCTGCGGGTCG
AGGCCGTGGCGATCGAGCGCCGCCGCAACCCGCTGGCCTCCAGCCGCCACCTCGACGAGCTGAC
CGTCGCCGCCCGTGCCGGTCTGCTCTCCCTCGAGCACGCCGCGCTGATGATCCGCTGGCTGGCTC
TCGGCGGGCGGTCCGGCGAGGCGGCCGAGGTGCTGGCCGCGCAGCGCCCGCGTGCGGTCACCG
ACCAGGACAGGGCCCACCTGCGGGCCGCCGAGGTATCGCTGGCGCTGGTCAGCCCGGGCGCGTC
CGGCGTCAGCCCGGGTGCGTCCGGCCCGGATCGGCGGCCGCGTCCGCTCCCGCCGGATGAGCTC
GCGAACCTGCCGAAGGCGGCCCGGCTTTGTGCGATCGCCGACAACGCCGTCATATCGGCCCTGCA
CGGTCGTCCCGAGCTTGCCTCGGCCGAGGCGGAGAACGTCCTGAAGCAGGCTGACTCGGCGGCG
GACGGCGCCACCGCCCTCTCCGCGCTGACGGCCTTGCTGTACGCGGAGAACACCGACACCGCTCA
GCTCTGGGCCGACAAGCTCGTCTCCGAGACCGGGGCGTCGAACGAGGAGGAAGGCGCGGGCTAC
GCGGGGCCGCGCGCCGAGACCGCGTTGCGCCGCGGCGACCTGGCCGCGGCGGTCGAGGCGGGC
AGCGCCATTCTGGACCACCGGCGGGGGTCGTTGCTCGGCATCACCGCCGCGCTACCGCTGAGCAG
CGCGGTAGCCGCCGCCATCCGGCTGGGCGAGACCGAGCGGGCGGAGAAGTGGCTCGCCGAGCCG

-continued

CTGCCGGAGGCCATTCGGGACAGCCTGTTCGGGCTGCACCTGCTCTCGGCGCGCGGCCAGTACTG

CCTCGCGACGGGCCGGCACGAGTCGGCGTACACGGCGTTCCGCACCTGCGGGGAACGGATGCGG

AACTGGGGCGTCGACGTGCCGGGTCTGTCCCTGTGGCGCGTCGACGCCGCCGAGGCGCTGCTGC

ACGGCCGCGACCGGGACGAGGGCCGACGGCTCATCGACGAGCAGCTCACCCATGCGATGGGACC

CCGTTCCCGCGCTTTGACGCTGCGGGTGCAGGCGGCGTACAGCCCGCAGGCGCAGCGGGTCGAC

CTGCTCGAAGAGGCGGCCGACCTGCTGCTCTCCTGCAACGACCAGTACGAGCGGGCGCGGGTGCT

CGCCGATCTGAGCGAGGCGTTCAGCGCGCTCAGGCACCACAGCCGGGCGCGGGGACTGCTCCGG

CAGGCCCGGCACCTGGCCGCCCAGTGCGGCGCGACCCCGCTGCTGCGCCGGCTCGGGGCCAAGC

CCGGAGGCCCCGGCTGGCTGGAGGAATCCGGCCTGCCGCAGCGGATCAAGTCGCTGACCGACGC

GGAGCGGCGGGTGGCGTCGCTGGCCGCCGGCGGCCAGACCAACCGCGTGATCGCCGACCAGCTC

TTCGTCACGGCCAGCACGGTGGAGCAGCACCTCACGAACGTCTTCCGCAAGCTGGGCGTCAAGGG

CCGCCAGCACCTGCCGGCCGAACTCGCCAACGCGGAATAG

SEQ ID NO: 53
GTGAAGCGCAACGATCTGGTTGCCCGCGATGGCGAGCTCAGGTGGATGCAAGAGATTCTCAGTCAG

GCGAGCGAGGGCCGGGGGGCCGTGGTCACCATCACGGGGGCGATCGCCTGTGGCAAGACGGTGC

TGCTGGACGCCGCGGCAGCCAGTCAAGACGTGATCCAACTGCGTGCGGTCTGCTCGGCGGAGGAG

CAGGAGCTGCCGTACGCGATGGTCGGACAACTACTCGACAATCCGGTGCTCGCCGCGCGAGTGCC

GGCCCTGGGCAACCTGGCTGCGGCGGGCGAGCGGCTGCTGCCGGGCACCGAGAACAGGATCCGG

CGGGAGCTCACCCGCACCCTGCTGGCTCTCGCCGACGAACGACCGGTGCTGATCGGCGTCGACGA

CATGCACCATGCGGACCCCGCCTCGCTGGACTGCCTGCTGCACCTGGCCCGGCGGGTCGGCCCG

GCCCGCATCGCGATCGTTCTGACCGAGTTGCGCCGGCTCACCCCGGCTCACTCGCGCTTCCAGTCC

GAGCTGCTCAGCCTGCGGTACCACCACGAGATCGGGTTGCAGCCGCTCACCGCGGAGCACACCGC

CGACCTGGCCCGCGTCGGCCTCGGTGCCGAGGTCGACGACGACGTGCTCACCGAGCTCTACGAGG

CGACCGGCGGCAACCCGAGTCTGTGCTGCGGCCTGATCAGGGACGTGCGGCAGGACTGGGAGGC

CGGGGTCACCGGTATCCACGTCGGCCGGGCGTACCGGCTGGCCTATCTCAGTTCGCTCTACCGCT

GCGGCCCGGCGGCGCTGCGGACCGCCCGCGCGGCCGCGGTGCTGGGCGACAGCGCCGACGCCT

GCCTGATCCGCCGGGTCAGCGGCCTCGGTACGGAGGCCGTGGGCCAGGCGATCCAGCAGCTCAC

CGAGGGCGGCCTGCTGCGTGACCAGCAGTTCCCGCACCCGGCGGCCCGCTCGGTCGTGCTCGAC

GACATGTCCGCGCAGGAACGCCACGCGATGTATCGCAGCGCCCGGGAGGCAGCCGCCGAAGGTCA

GGCCGACCCCGGCACCCCGGGCGAGCCGCGGGCGGCTACGGCGTACGCCGGGTGTGGTGAGCAA

GCCGGTGACTACCCGGAGCCGGCCGGCCGGGCCTGCGTGGACGGTGCCGGTCCGGCCGAGTACT

GCGGCGACCCGCACGGCGCCGACGACGACCCGGACGAGCTGGTCGCCGCGCTGGGCGGGCTGCT

GCCGAGCCGGCTCGTGGCGATGAAGATCCGGCGCCTGGCGGTGGCCGGGCGCCCCGGGGCGGC

TGCCGAGCTGCTGACCTCGCAGCGGTTGCACGCGGTGACCAGCGAGGACCGGGCCAGCCTGCGG

GCCGCCGAGGTGGCGCTCGCCACGCTGTGGCCGGGTGCGACCGGCCCGGACCGGCATCCGCTCA

CGGAGCAGGAGGCGGCGAGCCTGCCGGAGGGTCCGCGCCTGCTCGCTGCCGCCGACGATGCCGT

CGGGGCCGCCCTGCGCGGTCGCGCCGAGTACGCCGCGGCCGAGGCGGAGAACGTCCTGCGGCAC

GCCGATCCGGCAGCCGGTGGTGACGCCTACGCCGCCATGATCGCCCTGCTGTACACGGAGCACCC

CGAGAACGTGCTGTTCTGGGCCGACAAGCTCGACGCGGGCCGCCCCGACGAGGAGACCAGTTATC

CCGGGCTGCGGGCCGAGACCGCGGTGCGGCTCGGTGACCTGGAAACGGCGATGGAGCTGGGCCG

CACGGTGCTGGACCAGCGGCGGCTGCCGTCCCTGGGTGTCGCCGCGGGCCTGCTCCTGGGCGGC

-continued

GCGGTGACGGCCGCCATCCGGCTCGGCGACCTCGACCGGGCGGAGAAGTGGCTCGCCGAGCCGA

TCCCCGACGCCATCCGTACCAGCCTCTACGGCCTGCACGTGCTGGCCGCGCGGGGCCGGCTCGAC

CTGGCCGCGGGCCGCTACGAGGCGGCGTACACGGCGTTCCGGCTGTGTGGCGAGCGGATGGCAG

GCTGGGATGCCGATGTCTCCGGGCTGGCGCTGTGGCGCGTCGACGCCGCCGAGGCCCTGCTGTC

CGCGGGCATCCGCCCGGACGAGGGCCGCAAGCTCATCGACGACCAGCTCACCCGTGAGATGGGG

GCCCGCTCCCGGGCGCTGACGCTGCGGGCGCAAGCGGCGTACAGCCTGCCGGTGCACCGGGTGG

GCCTGCTCGACGAGGCGGCCGGCCTGCTGCTCGCCTGCCATGACGGGTACGAGCGGGCGCGGGT

GCTCGCGGACCTGGGGGAGACCCTGCGCACGCTGCGGCACACCGACGCGGCCCAGCGGGTGCTC

CGGCAGGCCGAGCAGGCGGCCGCGCGGTGCGGGTCGGTCCCGCTGCTGCGGCGGCTCGGGGCC

GAACCCGTACGCATCGGCACCCGGCGTGGTGAACCCGGCCTGCCGCAGCGGATCAGGCTGCTGAC

CGATGCCGAGCGGCGGGTTGCCGCGATGGCCGCCGCCGGGCAGACCAACCGGGAGATCGCCGGT

CGGCTCTTCGTCACGGCCAGCACGGTGGAGCAGCACCTGACCAGCGTCTTCCGCAAGCTGGGCGT

CAAGGGCCGCCGGTTCCTGCCGACCGAGCTCGCCCAAGCCGTCTGA

SEQ ID NO: 54
ATGCCTGCCGTGAAGCGCAACGATCTGGTTGCCCGCGATGGCGAGCTCAGGTGGATGCAAGAGATT

CTCAGTCAGGCGAGCGAGGGCCGGGGGCCGTGGTCACCATCACGGGGGCGATCGCCTGTGGCA

AGACGGTGCTGCTGGACGCCGCGGCAGCCAGTCAAGACGTGATCCAACTGCGTCGGTCTGCTCG

GCGGAGGAGCAGGAGCTGCCGTACGCGATGGTCGGACAACTACTCGACAATCCGGTGCTCGCCGC

GCGAGTGCCGGCCCTGGGCAACCTGGCTGCGGCGGGCGAGCGGCTGCTGCCGGGCACCGAGAAC

AGGATCCGGCGGGAGCTCACCCGCACCCTGCTGGCTCTCGCCGACGAACGACCGGTGCTGATCGG

CGTCGACGACATGCACCATGCGGACCCCGCCTCGCTGGACTGCCTGCTGCACCTGGCCCGGCGGG

TCGGCCCGGCCCGCATCGCGATCGTTCTGACCGAGTTGCGCCGGCTCACCCCGGCTCACTCGCGC

TTCCAGTCCGAGCTGCTCAGCCTGCGGTACCACCACGAGATCGGGTTGCAGCCGCTCACCGCGGA

GCACACCGCCGACCTGGCCCGCGTCGGCCTCGGTGCCGAGGTCGACGACGACGTGCTCACCGAG

CTCTACGAGGCGACCGGCGGCAACCCGAGTCTGTGCTGCGGCCTGATCAGGGACGTGCGGCAGGA

CTGGGAGGCCGGGGTCACCGGTATCCACGTCGGCCGGGCGTACCGGCTGGCCTATCTCAGTTCGC

TCTACCGCTGCGGCCCGGCGGCGCTGCGGACCGCCCGCGCGGCCGCGGTGCTGGGCGACAGCG

CCGACGCCTGCCTGATCCGCCGGGTCAGCGGCCTCGGTACGGAGGCCGTGGGCCAGGCGATCCA

GCAGCTCACCGAGGGCGGCCTGCTGCGTGACCAGCAGTTCCCGCACCCGGCGGCCCGCTCGGTC

GTGCTCGACGACATGTCCGCGCAGGAACGCCACGCGATGTATCGCAGCGCCCGGGAGGCAGCCGC

CGAAGGTCAGGCCGACCCCGGCACCCCGGGCGAGCCGCGGGCGGCTACGGCGTACGCCGGGTGT

GGTGAGCAAGCCGGTGACTACCCGGAGCCGGCCGGCCGGGCCTGCGTGGACGGTGCCGGTCCGG

CCGAGTACTGCGGCGACCCGCACGGCGCCGACGACGACCCGGACGAGCTGGTCGCCGCGCTGGG

CGGGCTGCTGCCGAGCCGGCTCGTGGCGATGAAGATCCGGCGCCTGGCGGTGGCCGGGCGCCCC

GGGGCGGCTGCCGAGCTGCTGACCTCGCAGCGGTTGCACGCGGTGACCAGCGAGGACCGGGCCA

GCCTGCGGGCCGCCGAGGTGGCGCTCGCCACGCTGTGGCCGGTGCGACCGGCCCGGACCGGC

ATCCGCTCACGGAGCAGGAGGCGGCGAGCCTGCCGGAGGGTCCGCGCCTGCTCGCTGCCGCCGA

CGATGCCGTCGGGGCCGCCCTGCGCGGTCGCGCCGAGTACGCCGCGGCCGAGGCGGAGAACGTC

CTGCGGCACGCCGATCCGGCAGCCGGTGGTGACGCCTACGCCGCCATGATCGCCCTGCTGTACAC

GGAGCACCCCGAGAACGTGCTGTTCTGGGCCGACAAGCTCGACGCGGGCCGCCCCGACGAGGAG

ACCAGTTATCCCGGGCTGCGGGCCGAGACCGCGGTGCGGCTCGGTGACCTGGAAACGGCGATGGA

-continued

GCTGGGCCGCACGGTGCTGGACCAGCGGCGGCTGCCGTCCCTGGGTGTCGCCGCGGGCCTGCTC

CTGGGCGGCGCGGTGACGGCCGCCATCCGGCTCGGCGACCTCGACCGGGCGGAGAAGTGGCTCG

CCGAGCCGATCCCCGACGCCATCCGTACCAGCCTCTACGGCCTGCACGTGCTGGCCGCGCGGGC

CGGCTCGACCTGGCCGCGGGCCGCTACGAGGCGGCGTACACGGCGTTCCGGCTGTGTGGCGAGC

GGATGGCAGGCTGGGATGCCGATGTCTCCGGGCTGGCGCTGTGGCGCGTCGACGCCGCCGAGGC

CCTGCTGTCCGCGGGCATCCGCCCGGACGAGGGCCGCAAGCTCATCGACGACCAGCTCACCCGTG

AGATGGGGGCCCGCTCCCGGGCGCTGACGCTGCGGGCGCAAGCGGCGTACAGCCTGCCGGTGCA

CCGGGTGGGCCTGCTCGACGAGGCGGCCGGCCTGCTGCTCGCCTGCCATGACGGGTACGAGCGG

GCGCGGGTGCTCGCGGACCTGGGGGAGACCCTGCGCACGCTGCGGCACACCGACGCGGCCCAGC

GGGTGCTCCGGCAGGCCGAGCAGGCGGCCGCGCGGTGCGGGTCGGTCCCGCTGCTGCGGCGGC

TCGGGGCCGAACCCGTACGCATCGGCACCCGGCGTGGTGAACCCGGCCTGCCGCAGCGGATCAG

GCTGCTGACCGATGCCGAGCGGCGGGTTGCCGCGATGGCCGCCGCCGGGCAGACCAACCGGGAG

ATCGCCGGTCGGCTCTTCGTCACGGCCAGCACGGTGGAGCAGCACCTGACCAGCGTCTTCCGCAA

GCTGGGCGTCAAGGGCCGCCGGTTCCTGCCGACCGAGCTCGCCCAAGCCGTCTGA

SEQ ID NO: 55
GTGGTCACCGTCACCGGCCCAATCGCCTGCGGCAAGACAGAACTGCTTGACGCGGCTGCCGCGAA

GGCTGAGGCCATCATTCTGCGCGCGGTCTGCGCGCCAGAAGAGCGGGCTATGCCGTACGCCATGA

TCGGGCAGCTCATCGACGACCCGGCGCTCGCGCATCGGGCGCCGGGGCTGGCTGATCGGATAGC

CCAGGGCGGGCAGCTGTCGCTGAGGGCCGAGAACCGACTGCGCAGGGATCTCACCCGTGCCCTG

CTGGCGCTTGCCGTGGACCGGCCTGTGCTGATCGGCGTCGACGATGTGCATCACGCCGACACCGC

CTCTTTGAACTGTCTGCTGCATTTGGCCCGCCGGGTCCGTCCGGCCCGGATATCCATGATCTTCACC

GAGTTGCGCAGCCTCACCCCTACTCAGTCACGGTTCAAGGCGGAGCTGCTCAGCCTGCCATACCAC

CACGAGATCGCGCTGCGTCCATTCGGACCGGAGCAATCGGCGGAGCTGGCTCGCGCCGCCTTCGG

CCCGGGCCTCGCCGAGGATGTGCTCGCGGGGTTGTATAAAACGACCAGGGGCAATCTGAGTCTCA

GCCGTGGACTGATCAGCGATGTGCGGGAGGCCCTGGCCAACGGAGAGAGCGCTTTCGAGGCGGG

CCGCGCGTTCCGGCTGGCGTACCTCAGCTCGCTCTACCGCTGTGGCCCGGTCGCGCTGCGGGTCG

CCCGAGTGGCTGCCGTGCTGGGCCCAAGCGCCACCACCACGCTGGTGCGCCGGCTAAGCGGGCT

CAGCGCGGAGACGATAGACCGGGCAACCAAGATCCTCACTGAGGGCGGGCTGCTGCTCGACCAGC

AGTTCCCGCACCCGGCCGCCCGCTCGGTGGTGCTCGATGACATGTCCGCCCAGGAACGACGCAGC

CTGCACACTCTCGCCCTGGAACTGCTGGACGAGGCGCCGGTTGAAGTGCTCGCGCACCACCAGGT

CGGCGCCGGTCTCATACACGGGCCCAAGGCTGCGGAGATGTTCGCCAAGGCCGGCAAGGCTCTGG

TCGTACGCAACGAGTTGGGCGACGCGGCCGAATACCTGCAACTGGCTCACCGGGCCTCCGACGAT

GTCTCCACCCGGGCCGCCTTACGGGTCGAGGCCGTGGCCATCGAGCGCCGCCGCAATCCGCTGGC

CTCCAGTCGGCACATGGACGAACTGAGCGCCGCCGGCCGCGCCGGTCTGCTTTCCCCCAAGCATG

CGGCGCTGGCCGTCTTCTGGCTAGCCGACGGCGGGCGATCCGGCGAGGCAGCCGAAGTGCTGGC

GTCGGAACGCCCGCTCGCGACCACCGATCAGAACCGGGCCCACCTGCGATTTGTCGAGGTGACTC

TCGCGCTGTTCTCTCCCGGCGCCTTCGGATCGGACCGGCGCCCACCTCCGCTGACGCCGGACGAA

CTCGCCAGCCTGCCGAAGGCGGCCTGGCAATGCGCGGTCGCCGACAACGCGGCCATGACCGCCTT

GCACGGCCATCCAGAACTTGCCACCGCTCAGGCGGAAACAGTTCTGCGGCAGGCTGATTCGGCAG

CCGACGCGATCCCCGCCGCGCTGATCGCCCTGTTGTACGCGGAGAACACCGAGTCCGCTCATATCT

GGGCCGACAAGCTGGGCAGCACGAATGCCGGGGTATCGAACGAGGCGGAAGCGGGCTACGCCGG

-continued

CCCGTGCGCCGAGATCGCCCTGCGGCGCGGCGACCTGGCCACGGCGTTCGAGGCTGGTAGCGCC

GTCCTGGACGACCGGTCGCTGCCGTCGCTCGGCATCACCGCCGCATTGCTGTTGAGCAGCAAGAC

GGCCGCCGCTGTCCGGCTGGGCGAACTCGAGCGTGCGGAGAAGCTGCTCGCCGAGCCGCTTCCG

AACGGCGTCCAGGACAGCCTTTTCGGTCTGCACCTGCTCTCGGCGTACGGCCAGTACAGCCTCGCG

ATGGGCCGATATGAATCAGCTCACCGGGCGTTTCGCACCTGCGGAGAACGTATGCGCAGCTGGGAT

GTTGACGTGCCTGGTCTGGCCCTGTGGCGTGTCGACGCCGCCGAGGCGCTGCTCAGCCTCGACCG

GAACGAGGGCCAGCGGCTCATCGACGAACAACTCACCCGTCCGATGGGGCCTCGTTCCCACGCGT

TAACGCTGCGGATCAAGGCGGCATACCTCCCGCGGACGAAGCGGATCCCCCTGCTCCATGAGGCG

GCCGAGCTGCTGCTCCCCTGCCCCGACCCGTACGAGCAAGCGCGGGTGCTCGCCGATCTGGGCGA

CACGCTCAGCGCGCTCAGACGCTATAGCCGGGCGCGGGGAGTTCTCCGGCAGGCTCGTCACCTGG

CCACCCAGTGCGGTGCTGTCCCGCTGCTGCGCAGGCTCGGGGGCGAGCCCGGCCGGATCGACGA

CGCCGGCCTGCCGCAGCGGAGCACATCGTTGACCGATGCGGAGCGGCGGGTGGCGGCGCTGGCC

GCGGCCGGACAGACCAACCGGGAGATCGCCGAACAGCTGTTCGTCACGGCCAGCACAGTGGAACA

GCACCTCACAAGCGTCTTCCGCAAGCTGGGCGTCAAGGGCCGCAAGCAGCTGCCGACCGCGCTGG

CCGACGTGGAACAGACCTGA

SEQ ID NO: 56
ATGTATAGCGGTACCTGCCGTGAAGGATACGAACTCGTCGCACGCGAGGACGAACTCGGTATTCTA

CAGAGGTCTCTGGAACAAGCGAGCAGCGGCCAGGGCGTCGTGGTCACCGTCACCGGCCCAATCGC

CTGCGGCAAGACAGAACTGCTTGACGCGGCTGCCGCGAAGGCTGAGGCCATCATTCTGCGCGCGG

TCTGCGCGCCAGAAGAGCGGGCTATGCCGTACGCCATGATCGGGCAGCTCATCGACGACCCGGCG

CTCGCGCATCGGGCGCCGGGGCTGGCTGATCGGATAGCCCAGGGCGGGCAGCTGTCGCTGAGGG

CCGAGAACCGACTGCGCAGGGATCTCACCCGTGCCCTGCTGGCGCTTGCCGTGGACCGGCCTGTG

CTGATCGGCGTCGACGATGTGCATCACGCCGACACCGCCTCTTTGAACTGTCTGCTGCATTTGGCC

CGCCGGGTCCGTCCGGCCCGGATATCCATGATCTTCACCGAGTTGCGCAGCCTCACCCCTACTCAG

TCACGGTTCAAGGCGGAGCTGCTCAGCCTGCCATACCACCACGAGATCGCGCTGCGTCCATTCGGA

CCGGAGCAATCGGCGGAGCTGGCTCGCGCCGCCTTCGGCCCGGGCCTCGCCGAGGATGTGCTCG

CGGGGTTGTATAAAACGACCAGGGGCAATCTGAGTCTCAGCCGTGGACTGATCAGCGATGTGCGGG

AGGCCCTGGCCAACGGAGAGAGCGCTTTCGAGGCGGGCCGCGCGTTCCGGCTGGCGTACCTCAG

CTCGCTCTACCGCTGTGGCCCGGTCGCGCTGCGGGTCGCCCGAGTGGCTGCCGTGCTGGGCCCAA

GCGCCACCACCACGCTGGTGCGCCGGCTAAGCGGGCTCAGCGCGGAGACGATAGACCGGGCAAC

CAAGATCCTCACTGAGGGCGGGCTGCTGCTCGACCAGCAGTTCCCGCACCCGGCCGCCCGCTCGG

TGGTGCTCGATGACATGTCCGCCCAGGAACGACGCAGCCTGCACACTCTCGCCCTGGAACTGCTGG

ACGAGGCGCCGGTTGAAGTGCTCGCGCACCACCAGGTCGGCGCCGGTCTCATACACGGGCCCAAG

GCTGCGGAGATGTTCGCCAAGGCCGGCAAGGCTCTGGTCGTACGCAACGAGTTGGGCGACGCGGC

CGAATACCTGCAACTGGCTCACCGGGCCTCCGACGATGTCTCCACCCGGGCCGCCCTGCGGGTCG

AGGCCGTGGCCATCGAGCGCCGCCGCAATCCGCTGGCCTCCAGTCGGCACATGGACGAACTGAGC

GCCGCCGGCCGCGCCGGTCTGCTTTCCCCCAAGCATGCGGCGCTGGCCGTCTTCTGGCTAGCCGA

CGGCGGGCGATCCGGCGAGGCAGCCGAAGTGCTGGCGTCGGAACGCCCGCTCGCGACCACCGAT

CAGAACCGGGCCCACCTGCGATTTGTCGAGGTGACTCTCGCGCTGTTCTCTCCCGGCGCCTTCGGA

TCGGACCGGCGCCCACCTCCGCTGACGCCGGACGAACTCGCCAGCCTGCCGAAGGCGGCCTGGC

AATGCGCGGTCGCCGACAACGCGGCCATGACCGCCTTGCACGGCCATCCAGAACTTGCCACCGCT

-continued

CAGGCGGAAACAGTTCTGCGGCAGGCTGATTCGGCAGCCGACGCGATCCCCGCCGCGCTGATCGC

CCTGTTGTACGCGGAGAACACCGAGTCCGCTCATATCTGGGCCGACAAGCTGGGCAGCACGAATGC

CGGGGTATCGAACGAGGCGGAAGCGGGCTACGCCGGCCCGTGCGCCGAGATCGCCCTGCGGCGC

GGCGACCTGGCCACGGCGTTCGAGGCTGGTAGCGCCGTCCTGGACGACCGGTCGCTGCCGTCGCT

CGGCATCACCGCCGCATTGCTGTTGAGCAGCAAGACGGCCGCCGCTGTCCGGCTGGGCGAACTCG

AGCGTGCGGAGAAGCTGCTCGCCGAGCCGCTTCCGAACGGCGTCCAGGACAGCCTTTTCGGTCTG

CACCTGCTCTCGGCGTACGGCCAGTACAGCCTCGCGATGGGCCGATATGAATCAGCTCACCGGGC

GTTTCGCACCTGCGGAGAACGTATGCGCAGCTGGGATGTTGACGTGCCTGGTCTGGCCCTGTGGC

GTGTCGACGCCGCCGAGGCGCTGCTCAGCCTCGACCGGAACGAGGGCCAGCGGCTCATCGACGAA

CAACTCACCCGTCCGATGGGGCCTCGTTCCCACGCGCTGACGCTGCGGATCAAGGCGGCATACCT

CCCGCGGACGAAGCGGATCCCCCTGCTCCATGAGGCGGCCGAGCTGCTGCTCCCCTGCCCCGACC

CGTACGAGCAAGCGCGGGTGCTCGCCGATCTGGGCGACACGCTCAGCGCGCTCAGACGCTATAGC

CGGGCGCGGGGAGTTCTCCGGCAGGCTCGTCACCTGGCCACCCAGTGCGGTGCTGTCCCGCTGCT

GCGCAGGCTCGGGGGCGAGCCCGGCCGGATCGACGACGCCGGCCTGCCGCAGCGGAGCACATCG

TTGACCGATGCGGAGCGGCGGGTGGCGGCGCTGGCCGCGGCCGGACAGACCAACCGGGAGATCG

CCGAACAGCTGTTCGTCACGGCCAGCACAGTGGAACAGCACCTCACAAGCGTCTTCCGCAAGCTGG

GCGTCAAGGGCCGCAAGCAGCTGCCGACCGCGCTGGCCGACGTGGAACAGACCTGA

SEQ ID NO: 57
GTGTATAGCGGTACCTGCCGTGAAGGATACGAACTCGTCGCCCGCGAGGACGAACTCGGCATTCTG

CAGAGGTCTCTGGAAGAAGCAGGCAGCGGCCAGGGCGCCGTGGTCACCGTCACCGGCCCGATCG

CCTGCGGCAAGACAGAACTGCTTGACGCGGCTGCCGCGAAGGCTGACGCCATCATTCTGCGCGCG

GTCTGCGCGCCCGAAGAGCGCGCTATGCCGTACGCCATGATCGGGCAGCTCATCGACGACCCGGC

GCTCGCGCATCGGGCGCCGGAGCTGGCTGATCGGATAGCCCAGGGCGGGCATCTGTCGCTGAGG

GCCGAGAACCGACTGCGCAGGGATCTCACCCGTGCCCTGCTGGCGCTTGCCGTCGACCGGCCTGT

GCTGATCGGCGTCGACGATGTGCATCACGCCGACACCGCCTCTTTGAACTGTCTGCTGCATTTAGC

CCGCCGGGTCCGTCCGGCCCGGATATCCATGATCTTCACCGAGTTGCGCAGCCTCACCCCTACTCA

GTCACGATTCAAGGCGGAGCTGCTCAGCCTGCCGTACCACCACGAGATCGCGCTGCGTCCACTCG

GACCGGAGCAATCGGCGGAGCTGGCCCACGCCGCCTTCGGCCCGGGCCTCGCCGAGGATGTGCT

CGCGGGGTTGTATGGGATGACCAGGGGCAACCTGAGTCTCAGCCGTGGACTGATCAGCGATGTGC

GGGAGGCCCAGGCCAACGGAGAGAGCGCTTTCGAGGTGGGCCGCGCGTTCCGGCTGGCGTACCT

CAGCTCGCTCTACCGCTGTGGCCCGATCGCGCTGCGGGTCGCCCGAGTGGCTGCCGTGCTGGGCC

CAAGCGCCACCACCACGCTGGTGCGCCGTCTAAGCGGGCTCAGCGCGGAGACGATAGACCGGGCA

ACCAAGATCCTCACTGAGGGCGGGCTGCTGCTCGACCACCAGTTCCCGCACCCGGCCGCCCGCTC

GGTGGTGCTCGATGACATGTCCGCCCAGGAACGACGCAGCCTGCACACTCTCGCCCTGGAACTGCT

GGACGAGGCGCCGGTTGAAGTGCTCGCGCACCACCAGGTCGGCGCCGGTCTCATACACGGGCCCA

AGGCTGCGGAGATATTCGCCAGGGCTGGCCAGGCTCTGGTTGTACGCAACGAGTTGGGCGACGCG

GCCGAATACCTGCAACTGGCTCACCGAGCCTCCGACGATGTCTCCACCCGGGCCGCCTTACGGGTC

GAGGCCGTGGCAATCGAGCGCCGCCGCAATCCGCTGGCCTCCAGTCGTCACATGGACGAGCTGAG

CGCCGCCGGCCGCGCCGGTCTGCTTTCCCCCAAGCATGCAGCGCTGGCTGTCTTCTGGCTGGCCG

ACGGCGGGCGATCCGGCGAGGCAGCCGAGGTGCTGGCGTCGGAACACCCGCTCGCGACCACCGA

TCAGAACCGAGCACACCTGCGATTTGCCGAGGTGACTCTCGCGCTGTTCTGTCCCGGCGCCTTCGG

-continued

GTCGGACCGGCGCCCACCTCCGCTGGCGCCGGACGAGCTCGCCAGCTTGCCGAAGGCGGCCTGG

CAATGCGCGGTCGCCGACAACGCGGTCATGACAGCGTTGCATGCTCATCCAGAACTTGCCACCGCT

CAGGCGGAAACAGTTCTGCGGCAGGCTGATTCGGCAGCCGACGCAATCCCCGCCGCACTGATCGC

CCTGTTGTACGCAGAGAACACCGAGTCCGCTCAGATCTGGGCCGACAAGCTGGGCAGCACCAATGC

CGGGGTATCGAACGAGGCGGAAGCGGGCTACGCCGGCCCGTGCGCCGAGATCGCCCTGCGGCGC

GGCGACCTGGCCACGGCGTTCGAGGCTGGTGGCACCGTCCTGGACGACCGGCCGCTGCCGTCGC

TCGGCATCACCGCCGCATTGCTGTTGAGCAGCAAGACGGCAGCCGCTGTCCGCCTGGGCGAACTC

GAGCGTGCGGAGAAGCTGCTCGCTGAGCCGCTTCCGAACGGTGTCCAGGACAGCCTTTTCGGTCT

GCACCTGCTCTCGGCGCACGGCCAGTACAGCCTCGCGATGGGCCGATATGAATCGGCTCACCGGG

CGTTTCACACCTGCGGAGAACGTATGCGCAGCTGGGGTGTTGACGTGCCTGGTCTAGCCCTGTGGC

GTGTCGACGCCGCCGAGGCACTGCTCAGCCTCGACCGGAACGAGGGCCAGCGGCTCATCGACGAA

CAACTCGCCCGTCCGATGGGACCTCGTTCCCGCGCATTAACGCTGCGGATCAAGGCGGCATACCTC

CCGCGGACGAAGCGGATCCCCCTGCTCCATGAGGCAGCTGAGCTGCTGCTCTCCTGCCCCGACCC

GTACGAGCAAGCGCGGGTGCTCGCCGATCTGGGCGACACGCTCAGCGCGCTCAGACGCTATAGCC

GGGCGCGGGGAGTTCTCCGGCAGGCTCGTCACCTGGCCACCCAGTGCGGTGCTGTCCCGCTGCTG

CGCCGACTCGGGGGCGAGCCCGGCCGGATCGACGACGCCGGCCTGCCGCAGCGGAGCACATCGT

TGACCGATGCGGAGCGGCGGGTGTCGGCCCTGGCCGCGGCCGGACAGACCAACCGGGAGATCGC

CAAACAGCTATTCGTCACGGCCAGCACCGTGGAACAGCACCTCACAAGCGTCTTCCGCAAGCTGGG

CGTTAAGGGCCGCAGGCAGCTACCGACCGCGCTGGCCGACGTGGAATAG

SEQ ID NO: 58
ATGTATAGCGGTACCTGCCGTGAAGGATACGAACTCGTCGCCCGCGAGGACGAACTCGGCATTCTG

CAGAGGTCTCTGGAAGAAGCAGGCAGCGGCCAGGGCGCCGTGGTCACCGTCACCGGCCCGATCG

CCTGCGGCAAGACAGAACTGCTTGACGCGGCTGCCGCGAAGGCTGACGCCATCATTCTGCGCGCG

GTCTGCGCGCCCGAAGAGCGCGCTATGCCGTACGCCATGATCGGGCAGCTCATCGACGACCCGGC

GCTCGCGCATCGGGCGCCGGAGCTGGCTGATCGGATAGCCCAGGGCGGGCATCTGTCGCTGAGG

GCCGAGAACCGACTGCGCAGGGATCTCACCCGTGCCCTGCTGGCGCTTGCCGTCGACCGGCCTGT

GCTGATCGGCGTCGACGATGTGCATCACGCCGACACCGCCTCTTTGAACTGTCTGCTGCATCTGGC

CCGCCGGGTCCGTCCGGCCCGGATATCCATGATCTTCACCGAGTTGCGCAGCCTCACCCCTACTCA

GTCACGATTCAAGGCGGAGCTGCTCAGCCTGCCGTACCACCACGAGATCGCGCTGCGTCCACTCG

GACCGGAGCAATCGGCGGAGCTGGCCCACGCCGCCTTCGGCCCGGGCCTCGCCGAGGATGTGCT

CGCGGGGTTGTATGGGATGACCAGGGGCAACCTGAGTCTCAGCCGTGGACTGATCAGCGATGTGC

GGGAGGCCCAGGCCAACGGAGAGAGCGCTTTCGAGGTGGGCCGCGCGTTCCGGCTGGCGTACCT

CAGCTCGCTCTACCGCTGTGGCCCGATCGCGCTGCGGGTCGCCCGAGTGGCTGCCGTGCTGGGCC

CAAGCGCCACCACCACGCTGGTGCGCCGTCTAAGCGGGCTCAGCGCGGAGACGATAGACCGGGCA

ACCAAGATCCTCACTGAGGGCGGGCTGCTGCTCGACCACCAGTTCCCGCACCCGGCCGCCCGCTC

GGTGGTGCTCGATGACATGTCCGCCCAGGAACGACGCAGCCTGCACACTCTCGCCCTGGAACTGCT

GGACGAGGCGCCGGTTGAAGTGCTCGCGCACCACCAGGTCGGCGCCGGTCTCATACACGGGCCCA

AGGCTGCGGAGATATTCGCCAGGGCTGGCCAGGCTCTGGTTGTACGCAACGAGTTGGGCGACGCG

GCCGAATACCTGCAACTGGCTCACCGAGCCTCCGACGATGTCTCCACCCGGGCCGCCCTGCGGGT

CGAGGCCGTGGCAATCGAGCGCCGCCGCAATCCGCTGGCCTCCAGTCGTCACATGGACGAGCTGA

GCGCCGCCGGCCGCGCCGGTCTGCTTTCCCCCAAGCATGCAGCGCTGGCTGTCTTCTGGCTGGCC

```
GACGGCGGGCGATCCGGCGAGGCAGCCGAGGTGCTGGCGTCGGAACACCCGCTCGCGACCACCG

ATCAGAACCGAGCACACCTGCGATTTGCCGAGGTGACTCTCGCGCTGTTCTGTCCCGGCGCTTCG

GGTCGGACCGGCGCCCACCTCCGCTGGCGCCGGACGAGCTCGCCAGCTTGCCGAAGGCGGCCTG

GCAATGCGCGGTCGCCGACAACGCGGTCATGACAGCGTTGCATGCTCATCCAGAACTTGCCACCGC

TCAGGCGGAAACAGTTCTGCGGCAGGCTGATTCGGCAGCCGACGCAATCCCCGCCGCACTGATCG

CCCTGTTGTACGCAGAGAACACCGAGTCCGCTCAGATCTGGGCCGACAAGCTGGGCAGCACCAATG

CCGGGGTATCGAACGAGGCGGAAGCGGGCTACGCCGGCCCGTGCGCCGAGATCGCCCTGCGGCG

CGGCGACCTGGCCACGGCGTTCGAGGCTGGTGGCACCGTCCTGGACGACCGGCCGCTGCCGTCG

CTCGGCATCACCGCCGCATTGCTGTTGAGCAGCAAGACGGCAGCCGCTGTCCGCCTGGGCGAACT

CGAGCGTGCGGAGAAGCTGCTCGCTGAGCCGCTTCCGAACGGTGTCCAGGACAGCCTTTTCGGTCT

GCACCTGCTCTCGGCGCACGGCCAGTACAGCCTCGCGATGGGCCGATATGAATCGGCTCACCGGG

CGTTTCACACCTGCGGAGAACGTATGCGCAGCTGGGGTGTTGACGTGCCTGGTCTAGCCCTGTGGC

GTGTCGACGCCGCCGAGGCACTGCTCAGCCTCGACCGGAACGAGGGCCAGCGGCTCATCGACGAA

CAACTCGCCCGTCCGATGGGACCTCGTTCCCGCGCACTGACGCTGCGGATCAAGGCGGCATACCT

CCCGCGGACGAAGCGGATCCCCCTGCTCCATGAGGCAGCTGAGCTGCTGCTCTCCTGCCCCGACC

CGTACGAGCAAGCGCGGGTGCTCGCCGATCTGGGCGACACGCTCAGCGCGCTCAGACGCTATAGC

CGGGCGCGGGGAGTTCTCCGGCAGGCTCGTCACCTGGCCACCCAGTGCGGTGCTGTCCCGCTGCT

GCGCCGACTCGGGGGCGAGCCCGGCCGGATCGACGACGCCGGCCTGCCGCAGCGGAGCACATCG

TTGACCGATGCGGAGCGGCGGGTGTCGGCCCTGGCCGCGGCCGGACAGACCAACCGGGAGATCG

CCAAACAGCTATTCGTCACGGCCAGCACCGTGGAACAGCACCTCACAAGCGTCTTCCGCAAGCTGG

GCGTTAAGGGCCGCAGGCAGCTACCGACCGCGCTGGCCGACGTGGAATAG

SEQ ID NO: 59
GTGTATAGCGGTACCTGCCGTGAAGGATACGAACTCGTCGCACGCGAGGACGAACTCGGCATTCTA

CAGAGGTCTCTGGAACAAGCGAGCAGCGGCCAGGGCGTCGTGGTCACCGTCACCGGCCCAATCGC

CTGCGGCAAGACAGAACTGCTTGACGCGGCTGCCGCGAAGGCTGAGGCCATCATTCTGCGCGCGG

TCTGCGCGCCCGAAGAGCGGGCTATGCCGTACGCCATGATCGGGCAGCTCATCGACGACCCGGCG

CTCGCGCATCGGGCGCCGGGGCTGGCTGATCGGATAGCCCAGGGCGGGCAGCTGTCGCTGAGGG

CCGAGAACCGACTGCGCAGGGATCTCACCCGTGCCCTGCTGGCGCTTGCCGTGCACCGGCCTGTG

CTGATCGGCGTCGATGATGTGCATCACGCCGACACCGCCTCTTTGAACTGTCTGCTGCATTTGGCG

CGCCGGGTCCGTCCGGCCCGGATATCCATGATCTTCACCGAGTTGCGCAGCCTCACCCCTACTCAG

TCACGATTCAAGGCGGAGCTGCTCAGCCTGCCGTACCACCACGAGATCGCGCTGCGTCCATTCGGA

CCGGAGCAATCGGCGGAGCTGGCTCGCGCCGCCTTCGGCCCGGGCCTCGCCGAGGATGTGCTCG

CGGGGTTGTATAAAACGACCAGGGGCAATCTGAGTCTCAGCCGTGGACTGATCAGCGATGTGCGGG

AGGCCCTGGCCAACGGAGAGAGCGCTTTCGAGGCGGGCCGCGCGTTCCGGCTGGCGTACCTCAG

CTCGCTCTACCGCTGTGGCCCGGTCGCGCTGCGGGTCGCCCGAGTGGCTGCCGTGCTGGGCCCAA

GCGCCACCACCACGCTGGTGCGCCGGCTAAGCGGGCTCAGCGCGGAGACGATAGACCGGGCAAC

CAAGATCCTCACCGAGGGCGGGCTGCTGCTCGACCAGCAGTTTCCGCACCCGGCCGCCCGCTCGG

TGGTGCTCGATGACATGTCCGCCCAGGAACGACGCGGCCTGCACACTCTCGCCCTGGAACTGCTG

GACGAGGCGCCGGTTGAAGTGCTCGCGCACCACCAGGTCGGCGCCGGTCTCATACACGGGCCCAA

GGCTGCGGAGATGTTCGCCAAGGCCGGCAAGGCTCTGGTCGTACGCAACGAGTTGGGCGACGCGG

CCGAATACCTGCAACTGGCTCACCGGGCCTCCGACGATGTCTCCACCCGGGCCGCCTTACGGGTC
```

-continued

GAGGCCGTGGCGATCGAGCGCCGCCGCAATCCGCTGGCCTCCAGTCGGCACATGGACGAGCTGAG

CGCCGCCGGCCGCGCCGGTCTGCTTTCCCCCAAGCATGCGGCGCTGGCCGTCTTCTGGCTGGCCG

ACGGCGGGCGATCCGGCGAGGCAGCCCAGGTGCTGGCGTCGGAACGCCCGCTCGCGACCACCGA

TCAGAACCGGGCCCACCTGCGATTTGTCGAGGTGACTCTCGCGCTGTTCTCTCCCGGCGCCTTCGG

ATCGGACCGGCGCCCACCTCCGCTGACGCCGGACGAACTCGCCAGCCTGCCGAAGGCGGCCTGG

CAATGCGCGGTCGCCGACAACGCGGCCATGACCGCCTTGCACGGCCATCCAGAACTTGCCACCGC

TCAGGCGGAAACAGTTCTGCGGCAGGCTGATTCGGCAGCCGACGCGATCCCCGCCGCGCTGATCG

CCCTGTTGTACGCGGAGAACACCGAGTCCGCTCATATCTGGGCCGACAAGCTGGGCAGCATGAATG

CCGGGGTATCGAACGAGGCGGAAGCGGGCTACGCCGGCCCGTGCGCCGAGATCGCCCTGCGGCG

CGGCGACCTGGCCACGGCGTTCGAGGCTGGTAGCACCGTCCTGGACGACCGGTCACTGCCGTCGC

TCGGCATCACCGCCGCATTGCTGTTGAGCAGCAAGACGGCCGCCGCTGTCCGGCTGGGCGAACTC

GAGCGTGCGGAGAAGCTGCTCGCCGAGCCGCTTCCGAACGGCGTCCAGGACAGCCTTTTCGGTCT

GCACCTGCTCTCGGCGTACGGCCAGTACAGCCTCGCGATGGGCCGATATGAATCGGCTCACCGGG

CGTTTCGCACCTGCGGAGAACGTATGCGCAGCTGGGATGTTGACGTGCCTGGTCTGGCCCTGTGGC

GTGTCGACGCCGCCGAGGCGCTGCTCAGCCTCGACCGGAACGAGGGCCAGCGGCTCATCGACGAA

CAACTCACCCGTCCGATGGGACCTCGTTCCCGCGCGTTAACGCTGCGGATCAAGGCGGCATACCTC

CCGCGGACGAAGCGGATCCCCCTGCTCCATGAGGCGGCCGAGCTGCTGCTCCCCTGCCCCGACCC

GTACGAGCAAGCGCGGGTGCTCGCCGATCTGGGCGACACGCTCAGCGCGCTCAGACGCTATAGCC

GGGCGCGGGGAGTTCTCCGGCAGGCTCGTCACCTGGCCACCCAGTGCGGTGCTGTCCCGCTGCTG

CGCCGACTCGGGGGCGAGCCCGGCCGGATCGACGACGCCGGCCTGCCGCAGCGGAGCACATCGT

TGACCGATGCGGAGCGGCGGGTGGCGGCGCTGGCCGCGGCCGGACAGACCAACCGGGAGATCGC

CGAACAGCTGTTCGTCACGGCCAGCACAGTGGAACAGCACCTCACAAGCGTCTTCCGCAAGCTGGG

CGTCAAGGGCCGCAAGCAGCTGCCGACCGCGCTGGCCGACGTGGAACAGACCTGA

SEQ ID NO: 60
ATGTATAGCGGTACCTGCCGTGAAGGATACGAACTCGTCGCACGCGAGGACGAACTCGGCATTCTA

CAGAGGTCTCTGGAACAAGCGAGCAGCGGCCAGGGCGTCGTGGTCACCGTCACCGGCCCAATCGC

CTGCGGCAAGACAGAACTGCTTGACGCGGCTGCCGCGAAGGCTGAGGCCATCATTCTGCGCGCGG

TCTGCGCGCCCGAAGAGCGGGCTATGCCGTACGCCATGATCGGGCAGCTCATCGACGACCCGGCG

CTCGCGCATCGGGCGCCGGGGCTGGCTGATCGGATAGCCCAGGGCGGGCAGCTGTCGCTGAGGG

CCGAGAACCGACTGCGCAGGGATCTCACCCGTGCCCTGCTGGCGCTTGCCGTGCACCGGCCTGTG

CTGATCGGCGTCGATGATGTGCATCACGCCGACACCGCCTCTTTGAACTGTCTGCTGCATTTGGCG

CGCCGGGTCCGTCCGGCCCGGATATCCATGATCTTCACCGAGTTGCGCAGCCTCACCCCTACTCAG

TCACGATTCAAGGCGGAGCTGCTCAGCCTGCCGTACCACCACGAGATCGCGCTGCGTCCATTCGGA

CCCGGAGCAATCGGCGGAGCTGGCTCGCGCCGCCTTCGGCCCGGGCCTCGCCGAGGATGTGCTCG

CGGGGTTGTATAAAACGACCAGGGGCAATCTGAGTCTCAGCCGTGGACTGATCAGCGATGTGCGGG

AGGCCCTGGCCAACGGAGAGAGCGCTTTCGAGGCGGGCCGCGCGTTCCGGCTGGCGTACCTCAG

CTCGCTCTACCGCTGTGGCCCGGTCGCGCTGCGGGTCGCCCGAGTGGCTGCCGTGCTGGGCCCAA

GCGCCACCACCACGCTGGTGCGCCGGCTAAGCGGGCTCAGCGCGGAGACGATAGACCGGGCAAC

CAAGATCCTCACCGAGGGCGGGCTGCTGCTCGACCAGCAGTTTCCGCACCCGGCCGCCCGCTCGG

TGGTGCTCGATGACATGTCCGCCCAGGAACGACGCGGCCTGCACACTCTCGCCCTGGAACTGCTG

GACGAGGCGCCGGTTGAAGTGCTCGCGCACCACCAGGTCGGCGCCGGTCTCATACACGGGCCCAA

-continued

```
GGCTGCGGAGATGTTCGCCAAGGCCGGCAAGGCTCTGGTCGTACGCAACGAGTTGGGCGACGCGG
CCGAATACCTGCAACTGGCTCACCGGGCCTCCGACGATGTCTCCACCCGGGCCGCCCTGCGGGTC
GAGGCCGTGGCGATCGAGCGCCGCCGCAATCCGCTGGCCTCCAGTCGGCACATGGACGAGCTGAG
CGCCGCCGGCCGCGCCGGTCTGCTTTCCCCCAAGCATGCGGCGCTGGCCGTCTTCTGGCTGGCCG
ACGGCGGGCGATCCGGCGAGGCAGCCCAGGTGCTGGCGTCGGAACGCCCGCTCGCGACCACCGA
TCAGAACCGGGCCCACCTGCGATTTGTCGAGGTGACTCTCGCGCTGTTCTCTCCCGGCGCCTTCGG
ATCGGACCGGCGCCCACCTCCGCTGACGCCGGACGAACTCGCCAGCCTGCCGAAGGCGGCCTGG
CAATGCGCGGTCGCCGACAACGCGGCCATGACCGCCTTGCACGGCCATCCAGAACTTGCCACCGC
TCAGGCGGAAACAGTTCTGCGGCAGGCTGATTCGGCAGCCGACGCGATCCCCGCCGCGCTGATCG
CCCTGTTGTACGCGGAGAACACCGAGTCCGCTCATATCTGGGCCGACAAGCTGGGCAGCATGAATG
CCGGGGTATCGAACGAGGCGGAAGCGGGCTACGCCGGCCCGTGCGCCGAGATCGCCCTGCGGCG
CGGCGACCTGGCCACGGCGTTCGAGGCTGGTAGCACCGTCCTGGACGACCGGTCACTGCCGTCGC
TCGGCATCACCGCCGCATTGCTGTTGAGCAGCAAGACGGCCGCCGCTGTCCGGCTGGGCGAACTC
GAGCGTGCGGAGAAGCTGCTCGCCGAGCCGCTTCCGAACGGCGTCCAGGACAGCCTTTTCGGTCT
GCACCTGCTCTCGGCGTACGGCCAGTACAGCCTCGCGATGGGCCGATATGAATCGGCTCACCGGG
CGTTTCGCACCTGCGGAGAACGTATGCGCAGCTGGGATGTTGACGTGCCTGGTCTGGCCCTGTGGC
GTGTCGACGCCGCCGAGGCGCTGCTCAGCCTCGACCGGAACGAGGGCCAGCGGCTCATCGACGAA
CAACTCACCCGTCCGATGGGACCTCGTTCCCGCGCGCTGACGCTGCGGATCAAGGCGGCATACCT
CCCGCGGACGAAGCGGATCCCCCTGCTCCATGAGGCGGCCGAGCTGCTGCTCCCCTGCCCCGACC
CGTACGAGCAAGCGCGGGTGCTCGCCGATCTGGGCGACACGCTCAGCGCGCTCAGACGCTATAGC
CGGGCGCGGGGAGTTCTCCGGCAGGCTCGTCACCTGGCCACCCAGTGCGGTGCTGTCCCGCTGCT
GCGCCGACTCGGGGGCGAGCCCGGCCGGATCGACGACGCCGGCCTGCCGCAGCGGAGCACATCG
TTGACCGATGCGGAGCGGCGGGTGGCGGCGCTGGCCGCGGCCGGACAGACCAACCGGGAGATCG
CCGAACAGCTGTTCGTCACGGCCAGCACAGTGGAACAGCACCTCACAAGCGTCTTCCGCAAGCTGG
GCGTCAAGGGCCGCAAGCAGCTGCCGACCGCGCTGGCCGACGTGGAACAGACCTGA
```

SEQ ID NO: 61
```
GTGCGAGCTATTAATGCGTCCGACACCGGTCCTGAACTGGTCGCCCGCGAAGACGAACTGGGACGT
GTACGAAGTGCCCTGAACCGAGCGAACGGCGGCCAAGGTGTCCTGATCTCCATTACCGGTCCGATC
GCCTGCGGCAAGACCGAACTGCTTGAGGCTGCCGCCTCGGAAGTTGACGCCATCACTCTGCGCGC
GGTCTGTGCCGCCGAGGAACGGGCGATACCTTATGCCCTGATCGGGCAGCTTATCGACAACCCCGC
GCTCGGCATTCCGGTTCCGGATCCGGCCGGCCTGACCGCCCAGGGCGGACGACTGTCATCGAGCG
CCGAGAACCGACTGCGTCGCGACCTCACCCGTGCCCTGCTGACGCTCGCCACCGACCGGCTGGTG
CTGATCTGTGTCGATGACGTGCAGCACGCCGACAACGCCTCGTTGAGCTGCCTTCTGTATCTGGCC
CGACGGCTTGTCCCGGCTCGAATCGCTCTGGTATTCACCGAGTTGCGAGTCCTCACCTCGTCTCAG
TTACGGTTCAACGCGGAGCTGCTCAGCTTGCGGAACCACTGCGAGATCGCGCTGCGCCCACTCGG
CCCGGGGCATGCGGCCGAGCTGGCCCGCGCCACCCTCGGCCCCGGCCTCTCCGACGAAACACTC
ACGGAGCTGTACCGGGTGACCGGAGGCAACCTGAGTCTCAGCCGCGGGCTGATCGACGATGTGCG
GGACGCCTGGGCACGAGGGGAAACGGGCGTCCAGGTGGGCCGGGCGTTCCGGCTGGCCTACCTC
GGTTCCCTCCACCGCTGTGGTCCGCTGGCGTTGCGGGTCGCCCGCGTAGCCGCCGTACTGGGCCC
GAGCGCCACCAGCGTCCTGGTGCGCCGGATCAGTGGGCTCAGCGCGGAGGCCATGGCCCAGGCG
ACCGATATCCTCGCTGACGGCGGCCTCCTGCGCGACCAGCGGTTCACACATCCAGCGGCCCGCTC
```

-continued

GGTGGTGCTCGACGACATGTCCGCCGAGGAACGACGCAGCGTGCACAGCCTCGCCCTGGAACTGC
TGGACGAGGCACCGGCCGAGATGCTCGCGCACCACCGGGTCGGCGCCGGTCTCGTGCACGGGCC
GAAGGCCGCGGAGACATTCACCGGGGCCGGCCGGGCACTGGCCGTTCGCGGCATGCTGGGCGAG
GCAGCCGACTACCTGCAACTGGCGTACCGGGCCTCCGGCGACGCCGCTACCAAGGCCGCGATACG
CGTCGAGTCCGTGGCGGTCGAGCGCCGACGCAATCCGCTGGTCGTCAGTCGCCATTGGGACGAGC
TGAGCGTCGCGGCCCGCGCCGGTCTGCTCTCCTGCGAGCACGTGTCCAGGACGGCCCGCTGGCTG
ACCGTCGGTGGGCGGCCCGGCGAGGCGGCCAGGGTGCTGGCGTCGCAACACCGACGGGTCGTCA
CCGATCAGGACCGGGCCCACCTGCGGGTCGCCGAGTTCTCGCTCGCGCTGCTGTACCCCGGTACG
TCCGGCTCGGACCGGCGCCCGCACCCGCTCACGTCGGACGAACTCGCGGCCCTACCGACTGCGAC
CAGACACTGCGCGATCGCCGATAACGCTGTCATGGCTGCCTTGCGTGGTCATCCGGAGCTTGCCAC
CGCCGAGGCAGAAGCCGTTCTGCAGCAAGCCGACGCGGCGGACGGCGCTGCTCTCACCGCGCTG
ATGGCCCTGCTGTACGCGGAGAGCATCGAGGTCGCTGAAGTCTGGGCGGACAAGCTGGCGGCAGA
GGCCGGAGCATCGAACGGGCAGGACGCGGAGTACGCCGGTATACGCGCCGAAATCGCCCTGCGG
CGCGGCGATCTGACCGCGGCCGTCGAGACCGCCGGCATGGTCCTGGACGGCCGGCCGCTGCCGT
CGCTCGACATCACCGCCACGTTGCTGTTGGCCGGCAGGGCGTCCGTCGCCGTCCGGCTGGGCGAA
CTCGACCACGCGGAGGAGCTGTTCGCCGCGCCGCCGGAGGACGCCTTCCAGGACAGCCTCTTCGG
TCTGCATCTGCTCTCGGCGCACGGCCAGTACAGCCTCGCGACAGGCCGGCCCGAGTCGGCATACC
GGGCCTTTCGTGCCTGCGGCGAACGTATGCGCGATTGGGGCTTCGACGCGCCCGGTGTGGCCCTG
TGGCGCGTCGGCGCCGCCGAGGCGCTGCTCGGCCTCGACCGGAACGAGGGCCGACGGCTCATCG
ACGAACAGCTGAGCCGGACGATGGCCCCCCGGTCCCACGCGTTGACGCTGCGGATAAAAGCGGCG
TACATGCCGGAGCCGAAGCGGGTCGACCTGCTCTACGAAGCGGCTGAGCTGCTGCTCTCCTGCCG
GGACCAGTATGAGCGAGCGCGGGTGCTCGCCGATCTGGGCGAGGCGCTCAGCGCGCTCGGGAAC
TACCGGCAGGCGCGAGGTGTGCTCCGGCAGGCTCGGCATCTGGCCATGCGAACCGGCGCGGACC
CGCTGCTGCGCCGGCTCGGAATCAGGCCCGGCCGGCAGGACGACCCCGACCCGCAGCCGCGGAG
CAGATCGCTGACCAACGCTGAGCGGCGTGCGGCGTCGCTGGCCGCGACCGGACTGACCAACCGG
GAGATCGCCGACCGGCTCTTCGTCACCGCCAGCACCGTGGAGCAGCACCTCACCAACGTCTTCCGC
AAGCTGGGCGTCAAGGGCCGCAAGCAGCTGCCGGCCGAGTTGGACGACATGGAATAG

SEQ ID NO: 62
ATGCGAGCTATTAATGCGTCCGACACCGGTCCTGAACTGGTCGCCCGCGAAGACGAACTGGGACGT
GTACGAAGTGCCCTGAACCGAGCGAACGGCGGCCAAGGTGTCCTGATCTCCATTACCGGTCCGATC
GCCTGCGGCAAGACCGAACTGCTTGAGGCTGCCGCCTCGGAAGTTGACGCCATCACTCTGCGCGC
GGTCTGTGCCGCCGAGGAACGGGCGATACCTTATGCCCTGATCGGGCAGCTTATCGACAACCCCGC
GCTCGGCATTCCGGTTCCGGATCCGGCCGGCCTGACCGCCCAGGGCGGACGACTGTCATCGAGCG
CCGAGAACCGACTGCGTCGCGACCTCACCCGTGCCCTGCTGACGCTCGCCACCGACCGGCTGGTG
CTGATCTGTGTCGATGACGTGCAGCACGCCGACAACGCCTCGTTGAGCTGCCTTCTGTATCTGGCC
CGACGGCTTGTCCCGGCTCGAATCGCTCTGGTATTCACCGAGTTGCGAGTCCTCACCTCGTCTCAG
CTGCGGTTCAACGCGGAGCTGCTCAGCTTGCGGAACCACTGCGAGATCGCGCTGCGCCCACTCGG
CCCGGGGCATGCGGCCGAGCTGGCCCGCGCCACCCTCGGCCCCGGCCTCTCCGACGAAACACTC
ACGGAGCTGTACCGGGTGACCGGAGGCAACCTGAGTCTCAGCCGCGGGCTGATCGACGATGTGCG
GGACGCCTGGGCACGAGGGGAAACGGGCGTCCAGGTGGGCCGGGCGTTCCGGCTGGCCTACCTC
GGTTCCCTCCACCGCTGTGGTCCGCTGGCGTTGCGGGTCGCCCGCGTAGCCGCCGTACTGGGCCC

-continued

```
GAGCGCCACCAGCGTCCTGGTGCGCCGGATCAGTGGGCTCAGCGCGGAGGCCATGGCCCAGGCG

ACCGATATCCTCGCTGACGGCGGCCTCCTGCGCGACCAGCGGTTCACACATCCAGCGGCCCGCTC

GGTGGTGCTCGACGACATGTCCGCCGAGGAACGACGCAGCGTGCACAGCCTCGCCCTGGAACTGC

TGGACGAGGCACCGGCCGAGATGCTCGCGCACCACCGGGTCGGCGCCGGTCTCGTGCACGGGCC

GAAGGCCGCGGAGACATTCACCGGGGCCGGCCGGGCACTGGCCGTTCGCGGCATGCTGGGCGAG

GCAGCCGACTACCTGCAACTGGCGTACCGGGCCTCCGGCGACGCCGCTACCAAGGCCGCGATACG

CGTCGAGTCCGTGGCGGTCGAGCGCCGACGCAATCCGCTGGTCGTCAGTCGCCATTGGGACGAGC

TGAGCGTCGCGGCCCGCGCCGGTCTGCTCTCCTGCGAGCACGTGTCCAGGACGGCCCGCTGGCTG

ACCGTCGGTGGGCGGCCCGGCGAGGCGGCCAGGGTGCTGGCGTCGCAACACCGACGGGTCGTCA

CCGATCAGGACCGGGCCCACCTGCGGGTCGCCGAGTTCTCGCTCGCGCTGCTGTACCCCGGTACG

TCCGGCTCGGACCGGCGCCCGCACCCGCTCACGTCGGACGAACTCGCGGCCCTACCGACTGCGAC

CAGACACTGCGCGATCGCCGATAACGCTGTCATGGCTGCCTTGCGTGGTCATCCGGAGCTTGCCAC

CGCCGAGGCAGAAGCCGTTCTGCAGCAAGCCGACGCGGCGGACGCGCTGCTCTCACCGCGCTG

ATGGCCCTGCTGTACGCGGAGAGCATCGAGGTCGCTGAAGTCTGGGCGGACAAGCTGGCGGCAGA

GGCCGGAGCATCGAACGGGCAGGACGCGGAGTACGCCGGTATACGCGCCGAAATCGCCCTGCGG

CGCGGCGATCTGACCGCGGCCGTCGAGACCGCCGGCATGGTCCTGGACGGCCGGCCGCTGCCGT

CGCTCGACATCACCGCCACGTTGCTGTTGGCCGGCAGGGCGTCCGTCGCCGTCCGGCTGGGCGAA

CTCGACCACGCGGAGGAGCTGTTCGCCGCGCCGCCGGAGGACGCCTTCCAGGACAGCCTCTTCGG

TCTGCATCTGCTCTCGGCGCACGGCCAGTACAGCCTCGCGACAGGCCGGCCCGAGTCGGCATACC

GGGCCTTTCGTGCCTGCGGCGAACGTATGCGCGATTGGGGCTTCGACGCGCCCGGTGTGGCCCTG

TGGCGCGTCGGCGCCGCCGAGGCGCTGCTCGGCCTCGACCGGAACGAGGGCCGACGGCTCATCG

ACGAACAGCTGAGCCGGACGATGGCCCCCCGGTCCCACGCGTTGACGCTGCGGATAAAAGCGGCG

TACATGCCGGAGCCGAAGCGGGTCGACCTGCTCTACGAAGCGGCTGAGCTGCTGCTCTCCTGCCG

GGACCAGTATGAGCGAGCGCGGGTGCTCGCCGATCTGGGCGAGGCGCTCAGCGCGCTCGGGAAC

TACCGGCAGGCGCGAGGTGTGCTCCGGCAGGCTCGGCATCTGGCCATGCGAACCGGCGCGGACC

CGCTGCTGCGCCGGCTCGGAATCAGGCCCGGCCGGCAGGACGACCCCGACCCGCAGCCGCGGAG

CAGATCGCTGACCAACGCTGAGCGGCGTGCGGCGTCGCTGGCCGCGACCGGACTGACCAACCGG

GAGATCGCCGACCGGCTCTTCGTCACCGCCAGCACCGTGGAGCAGCACCTCACCAACGTCTTCCGC

AAGCTGGGCGTCAAGGGCCGCAAGCAGCTGCCGGCCGAGTTGGACGACATGGAATAG
```

SEQ ID NO: 63
```
MPAVECYELDARDDELRKLEEVVTGRANGRGVVVTITGPIACGKTELLDAAAAKADAITLRAVCSAEEQAL

PYALIGQLIDNPALASHALEPACPTLPGEHLSPEAENRLRSDLTRTLLALAAERPVLIGIDESHANALCLLHL

ARRVGSARIAMVLTELRRLTPAHSQFQAELLSLGHHREIALRPLSPKHTAELVRAGLGPDVDEDVLTGLYR

ATGGNLNLTRGLINDVREAWETGGTGISAGRAYRLAYLGSLYRCGPVPLRVARVAAVLGQSANTTLVRWI

SGLNADAVGEATEILTEGGLLHDLRFPHPAARSVVLNDMSAQERRRLHRSALEVLDDVPVEVVAHHQVG

AGLLHGPKAAEIFAKAGQELHVRGELDTASDYLQLAHQASDDAVTGMRAEAVAIERRRNPLASSRHLDEL

TVVARAGLLFPEHTALMIRWLGVGGRSGEAAGLLASQRPRAVTDQDRAHMRAAEVSLALVSPGTSGPD

RRPRPLTPDELANLPKAARLCAIADNAVMSALRGRPELAAAEAENVLQHADSAAAGTTALAALTALLYAE

NTDTAQLWADKLVSETGASNEEEAGYAGPRAEAALRRGDLAAAVEAGSTVLDHRRLSTLGITAALPLSSA

VAAAIRLGETERAEKWLAQPLPQAIQDGLFGLHLLSARGQYSLATGQHESAYTAFRTCGERMRNWGVDV

PGLSLWRVDAAEALLHGRDRDEGRRLVDEQLTRAMGPRSRALTLRVQAAYSPPAKRVDLLDEAADLLLS
```

-continued

CNDQYERARVLADLSETFSALRHHSRARGLLRQARHLAAQRGAIPLLRRLGAKPGGPGWLEESGLPQRI

KSLTDAERRVASLAAGGQTNRVIADQLFVTASTVEQHLTDVSTGSRPPAPAAELV

SEQ ID NO: 64
MVPEVRAAPDELIARDDELSRLQRALTRAGSGRGGVVAITGPIASGKTALLDAGAAKSGFVALRAVCSWE

ERTLPYGMLGQLFDHPELAAQAPDLAHFTASCESPQAGTDNRLRAEFTRTLLALAADWPVLIGIDDVHHA

DAESLRCLLHLARRIGPARIAVVLTELRRPTPADSRFQAELLSLRSYQEIALRPLTEAQTGELVRRHLGAET

HEDVSADTFRATGGNLLLGHGLINDIREARTAGRPGVVAGRAYRLAYLSSLYRCGPSALRVARASAVLGA

SAEAVLVQRMTGLNKDAVEQVYEQLNEGRLLQGERFPHPAARSIVLDDLSALERRNLHESALELLRDHG

VAGNVLARHQIGAGRVHGEEAVELFTGAAREHHLRGELDDAAGYLELANRASDDPVTRAALRVGAAAIE

RLCNPVRAGRHLPELLTASRAGLLSSEHAVSLADWLAMGGRPGEAAEVLATQRPAADSEQHRALLRSG

ELSLALVHPGAWDPLRRTDRFAAGGLGSLPGPARHRAVADQAVIAALRGRLDRADANAESVLQHTDATA

DRTTAIMALLALLYAENTDAVQFWVDKLAGDEGTRTPADEAVHAGFNAEIALRRGDLMRAVEYGEAALG

HRHLPTWGMAAALPLSSTVVAAIRLGDLDRAERWLAEPLPQQTPESLFGLHLLWARGQHHLATGRHGAA

YTAFRECGERMRRWAVDVPGLALWRVDAAESLLLLGRDRAEGLRLVSEQLSRPMRPRARVQTLRVQAA

YSPPPQRIDLLEEAADLLVTCNDQYELANVLSDLAEASSMVRQHSRARGLLRRARHLATQCGAVPLLRRL

GAEPSDIGGAWDATLGQRIASLTESERRVAALAAVGRTNREIAEQLFVTASTVEQHLTNVFRKLAVKGRQ

QLPKELADVGEPADRDRRCG

SEQ ID NO: 65
MIARLSPPDLIARDDEFGSLHRALTRAGGGRGVVAAVTGPIACGKTELLDAAAAKAGFVTLRAVCSMEER

ALPYGMLGQLLDQPELAARTPELVRLTASCENLPADVDNRLGTELTRTVLTLAAERPVLIGIDDVHHADAP

SLRCLLHLARRISRARVAIVLTELLRPTPAHSQFRAALLSLRHYQEIALRPLTEAQTTELVRRHLGQDAHDD

VVAQAFRATGGNLLLGHGLIDDIREARTRTSGCLEVVAGRAYRLAYLGSLYRCGPAALSVARASAVLGES

VELTLVQRMTGLDTEAVEQAHEQLVEGRLLREGRFPHPAARSVVLDDLSAAERRGLHELALELLRDRGV

ASKVLARHQMGTGRVHGAEVAGLFTDAAREHHLRGELDEAVTYLEFAYRASDDPAVHAALRVDTAAIER

LCDPARSGRHVPELLTASRERLLSSEHAVSLACWLAMDGRPGEAAEVLAAQRSAAPSEQGRAHLRVAD

LSLALIYPGAADPPRPADPPAEDEVASFSGAVRHRAVADKALSNALRGWSEQAEAKAEYVLQHSRVTTD

RTTTMMALLALLYAEDTDAVQSWVDKLAGDDNMRTPADEAVHAGFRAEAALRRGDLTAAVECGEAALA

PRVVPSWGMAAALPLSSTVAAAIRLGDLDRAERWLAEPLPEETSDSLFGLHMVWARGQHHLAAGRYRA

AYNAFRDCGERMRRWSVDVPGLALWRVDAAEALLLLGRGRDEGLRLISEQLSRPMGSRARVMTLRVQA

AYSPPAKRIELLDEAADLLIMCRDQYELARVLADMGEACGMLRRHSRARGLFRRARHLATQCGAVPLLR

RLGGESSDADGTQDVTPAQRITSLTEAERRVASHAAVGRTNKEIASQLFVTSSTVEQHLTNVFRKLGVKG

RQQLPKELSDAG

SEQ ID NO: 66
MEFYDLVARDDELRRLDQALGRAAGGRGVVVTVTGPVGCGKTELLDAAAAEEEFITLRAVCSAEERALP

YAVIGQLLDHPVLSARAPDLACVTAPGRTLPADTENRLRRDLTRALLALASERPVLICIDDVHQADTASLN

CLLHLARRVASARIAMILTELRRLTPAHSRFEAELLSLRHRHEIALRPLGPADTAELARARLGAGVTADELA

QVHEATSGNPNLVGGLVNDVREAWAAGGTGIAAGRAYRLAYLSSVYRCGPVPLRIAQAAAVLGPSATVT

LVRRISGLDAETVDEATAILTEGGLLRDHRFPHPAARSVVLDDMSAQERRRLHRSTLDVLDGVPVDVLAH

HQAGAGLLHGPQAAEMFARASQELRVRGELDAATEYLQLAYRASDDAGARAALQVETVAGERRRNPLA

ASRHLDELAAAARAGLLSAEHAALVVHWLADAGRPGEAAEVLALQRALAVTDHDRARLRAAEVSLALFH

PGVPGSDPRPLAPEELASLSLSARHGVTADNAVLAALRGRPESAAAEAENVLRNADAAASGPTALAALTA

LLYAENTDAAQLWADKLAAGIGAGEGEAGYAGPRTVAALRRGDLTTAVQAAGAVLDRGRPSSLGITAVLP

-continued

LSGAVAAAIRLGELERAEKWLAEPLPEAVHDSLFGLHLLMARGRYSLAVGRHEAAYAAFRDCGERMRRW

DVDVPGLALWRVDAAEALLPGDDRAEGRRLIDEQLTRPMGPRSRALTLRVRAAYAPPAKRIDLLDEAADL

LLSSNDQYERARVLADLSEAFSALRQNGRARGILRQARHLAAQCGAVPLLRRLGVKAGRSGRLGRPPQG

IRSLTEAERRVATLAAAGQTNREIADQLFVTASTVEQHLTNVFRKLGVKGRQQLPAELADLRPPG

SEQ ID NO: 67
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVDRPVLIGVDDVHHAD

TASLNCLLHLARRVRPARISMIFTELRSLTPTQSRFKAELLSLPYHHEIALRPFGPEQSAELARAAFGPGLA

EDVLVGLYKTTRGNLSLSRGLISDVREALANGESAFEAGRAFRLAYLGSLYRCGPVALRVARVAAVLGPS

ATTTLVRRLSGLSAETIDRATKILTEGGLLLDQQFPHPAARSVVLDDMSAQERRGLHTLALELLDEAPVEV

LAHHQVGAGLIHGPKAAEMFAKAGKALVVRNELGDAAEYLQLAHRASDDVSTRAALRVEAVAIERRRNPL

ASSRHMDELSAAGRAGLLSPKHAALAVFWLADGGRSGEAAEVLASERPLATTDQNRAHLRFVEVTLALF

SPGAFGSDRRPPPLTPDELASLPKAAWQCAVADNAAMTALHGHPELATAQAETVLRQADSAADAIPAALI

ALLYAENTESAHIWADKLGSTNGGVSNEAEAGYAGPCAEIALRRGDLATAFEAGSTVLDDRSLPSLGITAA

LLLSSKTAAAVRLGELERAEKLLAEPLPNGVQDSLFGLHLLSAYGQYSLAMGRYESALRAFHTCGERMRS

WDVDVPGLALWRVDAAEALLSLDRNEGQRLIDEQLTRPMGPRSRALTLRIKAAYLPRTKRIPLLHEAAELL

LPCPDPYEQARVLADLGDTLSALRRYSRARGVLRQARHLAAQCGAVPLLRRLGGEPGRIDDAGLPQRST

SLTDAERRVAALAAAGQTNREIAKQLFVTASTVEQHLTSVFRKLGVKGRKQLPTALADVEQT

SEQ ID NO: 68
MPAVESYELDARDDELRRLEEAVGQAGNGRGVVVTITGPIACGKTELLDAAAAKSDAITLRAVCSEEERA

LPYALIGQLIDNPAVASQLPDPVSMALPGEHLSPEAENRLRGDLTRTLLALAAERPVLIGIDDMHHADTASL

NCLLHLARRVGPARIAMVLTELRRLTPAHSQFHAELLSLGHHREIALRPLGPKHIAELARAGLGPDVDEDV

LTGLYRATGGNLNLGHGLIKDVREAWATGGTGINAGRAYRLAYLGSLYRCGPVPLRVARVAAVLGQSAN

TTLVRWISGLNADAVGEATEILTEGGLLHDLRFPHPAARSVVLNDLSARERRRLHRSALEVLDDVPVEVVA

HHQAGAGFIHGPKAAEIFAKAGQELHVRGELDAASDYLQLAHHASDDAVTRAALRVEAVAIERRRNPLAS

SRHLDELTVAARAGLLSLEHAALMIRWLALGGRSGEAAEVLAAQRPRAVTDQDRAHLRAAEVSLALVSP

GASGVSPGASGPDRRPRPLPPDELANLPKAARLCAIADNAVISALHGRPELASAEAENVLKQADSAADGA

TALSALTALLYAENTDTAQLWADKLVSETGASNEEEGAGYAGPRAETALRRGDLAAAVEAGSAILDHRRG

SLLGITAALPLSSAVAAAIRLGETERAEKWLAEPLPEAIRDSLFGLHLLSARGQYCLATGRHESAYTAFRTC

GERMRNWGVDVPGLSLWRVDAAEALLHGRDRDEGRRLIDEQLTHAMGPRSRALTLRVQAAYSPQAQR

VDLLEEAADLLLSCNDQYERARVLADLSEAFSALRHHSRARGLLRQARHLAAQCGATPLLRRLGAKPGG

PGWLEESGLPQRIKSLTDAERRVASLAAGGQTNRVIADQLFVTASTVEQHLTNVFRKLGVKGRQHLPAEL

ANAE

SEQ ID NO: 69
MPAVKRNDLVARDGELRWMQEILSQASEGRGAVVTITGAIACGKTVLLDAAAASQDVIQLRAVCSAEEQE

LPYAMVGQLLDNPVLAARVPALGNLAAAGERLLPGTENRIRRELTRTLLALADERPVLIGVDDMHHADPA

SLDCLLHLARRVGPARIAIVLTELRRLTPAHSRFQSELLSLRYHHEIGLQPLTAEHTADLARVGLGAEVDDD

VLTELYEATGGNPSLCCGLIRDVRQDWEAGVTGIHVGRAYRLAYLSSLYRCGPAALRTARAAAVLGDSA

DACLIRRVSGLGTEAVGQAIQQLTEGGLLRDQQFPHPAARSVVLDDMSAQERHAMYRSAREAAAEGQA

DPGTPGEPRAATAYAGCGEQAGDYPEPAGRACVDGAGPAEYCGDPHGADDDPDELVAALGGLLPSRL

VAMKIRRLAVAGRPGAAAELLTSQRLHAVTSEDRASLRAAEVALATLWPGATGPDRHPLTEQEAASLPE

GPRLLAAADDAVGAALRGRAEYAAAEAENVLRHADPAAGGDAYAAMIALLYTEHPENVLFWADKLDAGR

```
-continued
PDEETSYPGLRAETAVRLGDLETAMELGRTVLDQRRLPSLGVAAGLLLGGAVTAAIRLGDLDRAEKWLAE

PIPDAIRTSLYGLHVLAARGRLDLAAGRYEAAYTAFRLCGERMAGWDADVSGLALWRVDAAEALLSAGIR

PDEGRKLIDDQLTREMGARSRALTLRAQAAYSLPVHRVGLLDEAAGLLLACHDGYERARVLADLGETLRT

LRHTDAAQRVLRQAEQAAARCGSVPLLRRLGAEPVRIGTRRGEPGLPQRIRLLTDAERRVAAMAAAGQT

NREIAGRLFVTASTVEQHLTSVFRKLGVKGRRFLPTELAQAV

SEQ ID NO: 70
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVDRPVLIGVDDVHHAD

TASLNCLLHLARRVRPARISMIFTELRSLTPTQSRFKAELLSLPYHHEIALRPFGPEQSAELARAAFGPGLA

EDVLAGLYKTTRGNLSLSRGLISDVREALANGESAFEAGRAFRLAYLSSLYRCGPVALRVARVAAVLGPS

ATTTLVRRLSGLSAETIDRATKILTEGGLLLDQQFPHPAARSVVLDDMSAQERRSLHTLALELLDEAPVEVL

AHHQVGAGLIHGPKAAEMFAKAGKALVVRNELGDAAEYLQLAHRASDDVSTRAALRVEAVAIERRRNPL

ASSRHMDELSAAGRAGLLSPKHAALAVFWLADGGRSGEAAEVLASERPLATTDQNRAHLRFVEVTLALF

SPGAFGSDRRPPPLTPDELASLPKAAWQCAVADNAAMTALHGHPELATAQAETVLRQADSAADAIPAALI

ALLYAENTESAHIWADKLGSTNAGVSNEAEAGYAGPCAEIALRRGDLATAFEAGSAVLDDRSLPSLGITAA

LLLSSKTAAAVRLGELERAEKLLAEPLPNGVQDSLFGLHLLSAYGQYSLAMGRYESAHRAFRTCGERMR

SWDVDVPGLALWRVDAAEALLSLDRNEGQRLIDEQLTRPMGPRSHALTLRIKAAYLPRTKRIPLLHEAAEL

LLPCPDPYEQARVLADLGDTLSALRRYSRARGVLRQARHLATQCGAVPLLRRLGGEPGRIDDAGLPQRS

TSLTDAERRVAALAAAGQTNREIAEQLFVTASTVEQHLTSVFRKLGVKGRKQLPTALADVEQT

SEQ ID NO: 71
MYSGTCREGYELVAREDELGILQRSLEEAGSGQGAVVTVTGPIACGKTELLDAAAAKADAIILRAVCAPEE

RAMPYAMIGQLIDDPALAHRAPELADRIAQGGHLSLRAENRLRRDLTRALLALAVDRPVLIGVDDVHHADT

ASLNCLLHLARRVRPARISMIFTELRSLTPTQSRFKAELLSLPYHHEIALRPLGPEQSAELAHAAFGPGLAE

DVLAGLYGMTRGNLSLSRGLISDVREAQANGESAFEVGRAFRLAYLSSLYRCGPIALRVARVAAVLGPSA

TTTLVRRLSGLSAETIDRATKILTEGGLLLDHQFPHPAARSVVLDDMSAQERRSLHTLALELLDEAPVEVLA

HHQVGAGLIHGPKAAEIFARAGQALVVRNELGDAAEYLQLAHRASDDVSTRAALRVEAVAIERRRNPLAS

SRHMDELSAAGRAGLLSPKHAALAVFWLADGGRSGEAAEVLASEHPLATTDQNRAHLRFAEVTLALFCP

GAFGSDRRPPPLAPDELASLPKAAWQCAVADNAVMTALHAHPELATAQAETVLRQADSAADAIPAALIAL

LYAENTESAQIWADKLGSTNAGVSNEAEAGYAGPCAEIALRRGDLATAFEAGGTVLDDRPLPSLGITAALL

LSSKTAAAVRLGELERAEKLLAEPLPNGVQDSLFGLHLLSAHGQYSLAMGRYESAHRAFHTCGERMRSW

GVDVPGLALWRVDAAEALLSLDRNEGQRLIDEQLARPMGPRSRALTLRIKAAYLPRTKRIPLLHEAAELLL

SCPDPYEQARVLADLGDTLSALRRYSRARGVLRQARHLATQCGAVPLLRRLGGEPGRIDDAGLPQRSTS

LTDAERRVSALAAAGQTNREIAKQLFVTASTVEQHLTSVFRKLGVKGRRQLPTALADVE

SEQ ID NO: 72
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVHRPVLIGVDDVHHAD

TASLNCLLHLARRVRPARISMIFTELRSLTPTQSRFKAELLSLPYHHEIALRPFGPEQSAELARAAFGPGLA

EDVLAGLYKTTRGNLSLSRGLISDVREALANGESAFEAGRAFRLAYLSSLYRCGPVALRVARVAAVLGPS

ATTTLVRRLSGLSAETIDRATKILTEGGLLLDQQFPHPAARSVVLDDMSAQERRGLHTLALELLDEAPVEV

LAHHQVGAGLIHGPKAAEMFAKAGKALVVRNELGDAAEYLQLAHRASDDVSTRAALRVEAVAIERRRNPL

ASSRHMDELSAAGRAGLLSPKHAALAVFWLADGGRSGEAAQVLASERPLATTDQNRAHLRFVEVTLALF

SPGAFGSDRRPPPLTPDELASLPKAAWQCAVADNAAMTALHGHPELATAQAETVLRQADSAADAIPAALI
```

-continued

ALLYAENTESAHIWADKLGSMNAGVSNEAEAGYAGPCAEIALRRGDLATAFEAGSTVLDDRSLPSLGITA

ALLLSSKTAAAVRLGELERAEKLLAEPLPNGVQDSLFGLHLLSAYGQYSLAMGRYESAHRAFRTCGERM

RSWDVDVPGLALWRVDAAEALLSLDRNEGQRLIDEQLTRPMGPRSRALTLRIKAAYLPRTKRIPLLHEAA

ELLLPCPDPYEQARVLADLGDTLSALRRYSRARGVLRQARHLATQCGAVPLLRRLGGEPGRIDDAGLPQ

RSTSLTDAERRVAALAAAGQTNREIAEQLFVTASTVEQHLTSVFRKLGVKGRKQLPTALADVEQT

SEQ ID NO: 73
MRAINASDTGPELVAREDELGRVRSALNRANGGQGVLISITGPIACGKTELLEAAASEVDAITLRAVCAAE

ERAIPYALIGQLIDNPALGIPVPDPAGLTAQGGRLSSSAENRLRRDLTRALLTLATDRLVLICVDDVQHADN

ASLSCLLYLARRLVPARIALVFTELRVLTSSQLRFNAELLSLRNHCEIALRPLGPGHAAELARATLGPGLSD

ETLTELYRVTGGNLSLSRGLIDDVRDAWARGETGVQVGRAFRLAYLGSLHRCGPLALRVARVAAVLGPS

ATSVLVRRISGLSAEAMAQATDILADGGLLRDQRFTHPAARSVVLDDMSAEERRSVHSLALELLDEAPAE

MLAHHRVGAGLVHGPKAAETFTGAGRALAVRGMLGEAADYLQLAYRASGDAATKAAIRVESVAVERRR

NPLVVSRHWDELSVAARAGLLSCEHVSRTARWLTVGGRPGEAARVLASQHRRVVTDQDRAHLRVAEFS

LALLYPGTSGSDRRPHPLTSDELAALPTATRHCAIADNAVMAALRGHPELATAEAEAVLQQADAADGAAL

TALMALLYAESIEVAEVWADKLAAEAGASNGQDAEYAGIRAEIALRRGDLTAAVETAGMVLDGRPLPSLDI

TATLLLAGRASVAVRLGELDHAEELFAAPPEDAFQDSLFGLHLLSAHGQYSLATGRPESAYRAFRACGER

MRDWGFDAPGVALWRVGAAEALLGLDRNEGRRLIDEQLSRTMAPRSHALTLRIKAAYMPEPKRVDLLYE

AAELLLSCRDQYERARVLADLGEALSALGNYRQARGVLRQARHLAMRTGADPLLRRLGIRPGRQDDPDP

QPRSRSLTNAERRAASLAATGLTNREIADRLFVTASTVEQHLTNVFRKLGVKGRKQLPAELDDME

LAL Binding Sites

In some embodiments, a gene cluster (e.g., a PKS gene cluster) includes one or more promoters that include one or more LAL binding sites. The LAL binding sites may include a polynucleotide consensus LAL binding site sequence (e.g., as described herein). In some instances, the LAL binding site includes a core AGGGGG (SEQ ID NO: 74) motif. In certain instances, the LAL binding site includes a sequence having at least 80% (e.g., 80%, 85%, 90%, 95%, 97%, 98%, 99%, or 100%) homology to SEQ ID NO: 39. The LAL binding site may include mutation sites that have been restored to match the sequence of a consensus or optimized LAL binding site. In some embodiments, the LAL binding site is a synthetic LAL binding site. In some embodiments, synthetic LAL binding sites may be identified by (a) providing a plurality of synthetic nucleic acids including at least eight nucleotides; (b) contacting one or more of the plurality of nucleotides including at least eight nucleotides with one or more LALs; (c) determining the binding affinity between a nucleic acid of step (a) and an LAL of step (b), wherein a synthetic nucleic acid is identified as a synthetic LAL binding site if the affinity between the synthetic nucleic acid and an LAL is greater than X. The identified synthetic LAL binding sites may then be introduced into a host cell in a compound-producing cluster (e.g., a PKS cluster).

In some embodiments, a pair of LAL binding site and a heterologous LAL or a heterologous LAL binding site and an LAL that have increased expression compared to a natural pair may be identified by (a) providing one or more LAL binding sites; (b) contacting one or more of the LAL binding sites with one or more LALs; (c) determining the binding affinity between a LAL binding site and an LAL, wherein a pair having increased expression is identified if the affinity between the LAL binding site and the LAL is greater than the affinity between the LAL binding site and its homologous LAL and/or the LAL at its homologous LAL binding site. In some embodiments, the binding affinity between the LAL binding site and the LAL is determined by determining the expression of a protein or compound by a cell which includes both the LAL and the LAL binding site.

Constitutively Active LALs

In some embodiments, the recombinant LAL is a constitutively active LAL. For example, the amino acid sequence of the LAL has been modified in such a way that it does not require the presence of an inducer compound for the altered LAL to engage its cognate binding site and activate transcription of a compound producing protein (e.g., polyketide synthase). Introduction of a constitutively active LAL to a host cell would likely result in increased expression of the compound-producing protein (e.g., polyketide synthase) and, in turn, increased production of the corresponding compound (e.g., polyketide).

Engineering Unidirectional LALs

FkPhD gene clusters are arranged with a multicistronic architecture driven by multiple bidirectional promoter-operators that harbor conserved (in single or multiple, and inverted to each other and/or directly repeating) GGGGGT (SEQ ID NO: 40) motifs presumed to be LAL binding sites. Bidirectional LAL promoters may be converted to unidirectional ones (UniLALs) by strategically deleting one of the opposing promoters, but maintaining the tandem LAL binding sites (in case binding of LALs in the native promoter is cooperative, as was demonstrated for MalT). Functionally this is achieved by removal of all sequences 3' of the conserved GGGGGT (SEQ ID NO: 40) motif present on the antisense strand (likely containing the −35 and −10 promoter sequences), but leaving intact the entire sequence on the sense strand. As a consequence of this deletion, transcription would be activated in one direction only. The advantages of this feed-forward circuit architecture would be to tune and/or maximize LAL expression during the complex life cycle of *Streptomyces* vegetative and fermentation growth conditions.

Host Cells

In some embodiments, the host cell is a bacteria such as an Actiobacterium. For example, in some embodiments, the host cell is a *Streptomyces* strain. In some embodiments, the host cell is *Streptomyces anulatus, Streptomyces antibioticus, Streptomyces coelicolor, Streptomyces peucetius, Streptomyces* sp. ATCC 700974, *Streptomyces canus, Streptomyces nodosus, Streptomyces* (multiple sp.), *Streptoalloteicus hindustanus, Streptomyces hygroscopicus, Streptomyces avermitilis, Streptomyces viridochromogenes, Streptomyces verticillus, Streptomyces chartruensis, Streptomyces* (multiple sp.), *Saccharothrix mutabilis, Streptomyces halstedii, Streptomyces clavuligerus, Streptomyces venezuelae, Streptomyces roseochromogenes, Amycolatopsis orientalis, Streptomyces clavuligerus, Streptomyces rishiriensis, Streptomyces lavendulae, Streptomyces roseosporus, Nonomuraea* sp., *Streptomyces peucetius, Saccharopolyspora erythraea, Streptomyces filipinensis, Streptomyces hygroscopicus, Micromonospora purpurea, Streptomyces hygroscopicus, Streptomyces narbonensis, Streptomyces kanamyceticus, Streptomyces collinus, Streptomyces lasaliensis, Streptomyces lincolnensis, Dactosporangium aurantiacum, Streptomyces toxitricini, Streptomyces hygroscopicus, Streptomyces plicatus, Streptomyces lavendulae, Streptomyces ghanaensis, Streptomyces cinnamonensis, Streptomyces aureofaciens, Streptomyces natalensis, Streptomyces chattanoogensis* L10, *Streptomyces lydicus* A02, *Streptomyces fradiae, Streptomyces ambofaciens, Streptomyces tendae, Streptomyces noursei, Streptomyces avermitilis, Streptomyces rimosus, Streptomyces wedmorensis, Streptomyces cacaoi, Streptomyces pristinaespiralis, Streptomyces pristinaespiralis, Actinoplanes* sp. ATCC 33076, *Streptomyces hygroscopicus, Lechevalieria aerocolonegenes, Amycolatopsis mediterranei, Amycolatopsis lurida, Streptomyces albus, Streptomyces griseolus, Streptomyces spectabilis, Saccharopolyspora spinosa, Streptomyces ambofaciens, Streptomyces staurosporeus, Streptomyces griseus, Streptomyces* (multiple species), *Streptomyces acromogenes, Streptomyces tsukubaensis, Actinoplanes teichomyceticus, Streptomyces glaucescens, Streptomyces rimosus, Streptomyces cattleya, Streptomyces azureus, Streptoalloteicus hindustanus, Streptomyces chartreusis, Streptomyces fradiae, Streptomyces coelicolor, Streptomyces hygroscopicus, Streptomyces* sp. 11861, *Streptomyces virginiae, Amycolatopsis japonicum, Amycolatopsis balhimycini, Streptomyces albus* J1074, *Streptomyces coelicolor* M1146, *Streptomyces lividans, Streptomyces incarnates, Streptomyces violaceoruber,* or *Streptomyces griseofuscus*. In some embodiments, the host cell is an *Escherichia* strain such as *Escherichia coli*. In some embodiments, the host cell is a *Bacillus* strain such as *Bacillus subtilis*. In some embodiments, the host cell is a *Pseudomonas* strain such as *Pseudomonas putida*. In some embodiments, the host cell is a *Myxococcus* strain such as *Myxococcus xanthus*.

Methods

The proteins, nucleic acids, vectors, and host cells of the invention may be used for production of compounds (e.g., polyketides). Introduction of heterologous domains to proteins allow alteration of the chemical structure of polyketides produced by the proteins.

Introduction of Heterologous Domains

The activity of β-ketone processing domains can be altered by introducing the sequences of domains from other polyketide synthases. Multiple heterologous sequences can be tested for their ability to alter the activity of a specific domain without drastically reducing the amount of polyketide expressed. New variants of the polyketide synthase can be subjected to rigorous quality control (Sanger sequencing of region of interest, PCR-based "tiling" to confirm cluster integrity and Illumina sequencing to sequence the entire BAC). BACs may then be conjugated to two optimized *Streptomyces* producer strains, and solid-phase extracted (SPE) samples can be subjected to Top-Down mass spectrometry with purified FKBP12 protein to identify produced compounds.

A representative example of a workflow to generate a compound from a chimeric polyketide synthase includes grafting a short peptide sequence from the domain of one polyketide synthase, e.g., a ketoreductase domain, onto another polyketide synthase using homology-based cloning. For example, the catalytic Tyr of one ketoreductase may be replaced with Phe and the active site αFG loop may also deleted to inactive the domain. The resulting clone may then be conjugated into a *Streptomyces* expression host and fermented. Compounds may then be identified using comparative LC-TOF analysis of unfractionated SPE samples. Top Down mass spectrometry analysis may also be performed by co-injecting purified native FKBP12 and a compound from the modified polyketide synthase with a compound from the unmodified polyketide synthase. This analysis can show a mass difference between the two compounds consistent with the change in activity of the domain, e.g., a difference of 2 for an inactivated ketoreductase domain.

Compounds with multiple structural changes may be generated using combinations of KR, DH or ER single variants.

Production of Libraries of Engineered Polyketide Synthases

Combinatorial domain level engineering may be performed by combining multiple domain-level variants on a single protein backbone, thus enabling library-scale construction of diverse PKS/NRPS molecules for drug development.

Alternately, multiplex parallel engineering (e.g., by site-directed mutagenesis) may be used to produce libraries of engineered PKS/NRPS molecules for drug development. For example, site-directed mutagenesis of a polynucleotide encoding a parent polyketide synthase may be used to generate, in parallel, a plurality of polynucleotides encoding a plurality of engineered polyketide synthases. In some embodiments, each of the plurality of engineered polyketide synthases includes at least one codon modification relative to of the parent polyketide synthase (e.g., a codon that specifies a residue in a conserved motif of at least one domain of the parent polyketide synthase).

Characterization of Engineered PKS Libraries by Single-Molecule Long-Read Sequencing In some embodiments of the invention, single-molecule long-read sequencing technology (e.g., Nanopore sequencing or SMRT sequencing) may be used to characterize libraries of engineered polyketide synthases or non-ribosomal peptide synthases which are produced by any of the methods described herein. In particular, single-molecule long-read sequencing (e.g., Nanopore sequencing or SMRT sequencing) may be used to characterize (e.g., deconvolute) combinatorial or multiplex libraries of engineered polyketide synthases or non-ribosomal peptide synthases (e.g., multiplex libraries generated by parallel engineering). Single-molecule long-read sequencing enables the identification of the module or modules which are incorporated into the combinatorial library. This further enables the prediction of the chemistry of the resulting plurality of engineered polyketide synthases or non-ribosomal peptide synthases. The predicted enzymatic chemistry can therefore be connected to the compounds produced by the engineered polyketide synthases or non-ribosomal peptide synthases. The resulting compounds may be identified by chemical methods of analysis known to one of skill in the art (e.g., mass spectrometry or high performance liquid chromatography). Furthermore, the predicted enzymatic chemistry can be connected to the function of the resulting compounds (e.g., binding to a target protein or inducing a phenotype, such as a cell based phenotype). Accordingly, long-read sequencing of a genetically encoded molecule may allow for genotypic-phenotypic linkage.

Single-molecule long-read sequencing technologies may be considered to include any sequencing technology which enables the sequencing of a single molecule of a biopolymer (e.g., a polynucleotide such as DNA or RNA), and which enables read lengths of greater than 2 kilobases (e.g., greater than 5 kilobases, greater than 10 kilobases, greater than 20 kilobases, greater than 50 kilobases, or greater 100 kilobases). Single-molecule long-read sequencing technologies may enable the sequencing of multiple single molecules of DNA or RNA in parallel. Single-molecule long-read sequencing technologies may include sequencing technologies that rely on individual compartmentalization of each molecule of DNA or RNA being sequenced.

Nanopore sequencing is an exemplary single-molecule long-read sequencing technology that may be used to characterize libraries of engineered polyketide synthases or non-ribosomal peptide synthases that are prepared by any of the methods described herein. Nanopore sequencing enables the long-read sequencing of single molecules of biopolymers (e.g., polynucleotides such as DNA or RNA). Nanopore sequencing relies on protein nanopores set in an electrically resistant polymer membrane. An ionic current is passed through the nanopores by setting a voltage across this membrane. If an analyte (e.g., a biopolymer such as DNA or RNA) passes through the pore or near its aperture, this event creates a characteristic disruption in current. The magnitude of the electric current density across a nanopore surface depends on the composition of DNA or RNA (e.g., the specific base) that is occupying the nanopore. Therefore, measurement of the current makes it possible to identify the sequence of the molecule in question.

Single molecule real-time (SMRT) sequencing (PacBio) is an exemplary single-molecule long-read sequencing technology that may be used to characterize libraries of engineered polyketide synthases or non-ribosomal peptide synthases that are prepared by any of the methods described herein. SMRT is a parallelized single molecule DNA sequencing method. SMRT utilizes a zero-mode waveguide (ZMW). A single DNA polymerase enzyme is affixed at the bottom of a ZMW with a single molecule of DNA as a template. The ZMW is a structure that creates an illuminated observation volume that is small enough to observe only a single nucleotide of DNA being incorporated by DNA polymerase. Each of the four DNA bases is attached to one of four different fluorescent dyes. When a nucleotide is incorporated by the DNA polymerase, the fluorescent tag is cleaved off and diffuses out of the observation area of the ZMW where its fluorescence is no longer observable. A detector detects the fluorescent signal of the nucleotide incorporation, and the base call is made according to the corresponding fluorescence of the dye.

EXAMPLES

Example 1. Inactivation of a Ketoreductase Domain

Figure 5A:
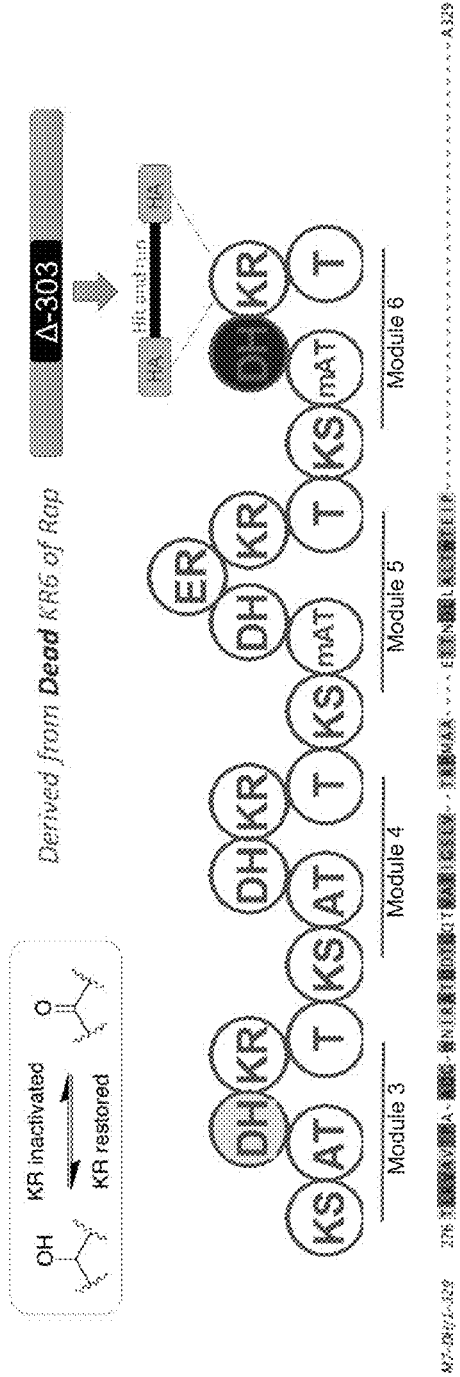
FIG. 5A is an image illustrating the deactivation of a ketoreductase domain.
Figure 5B:
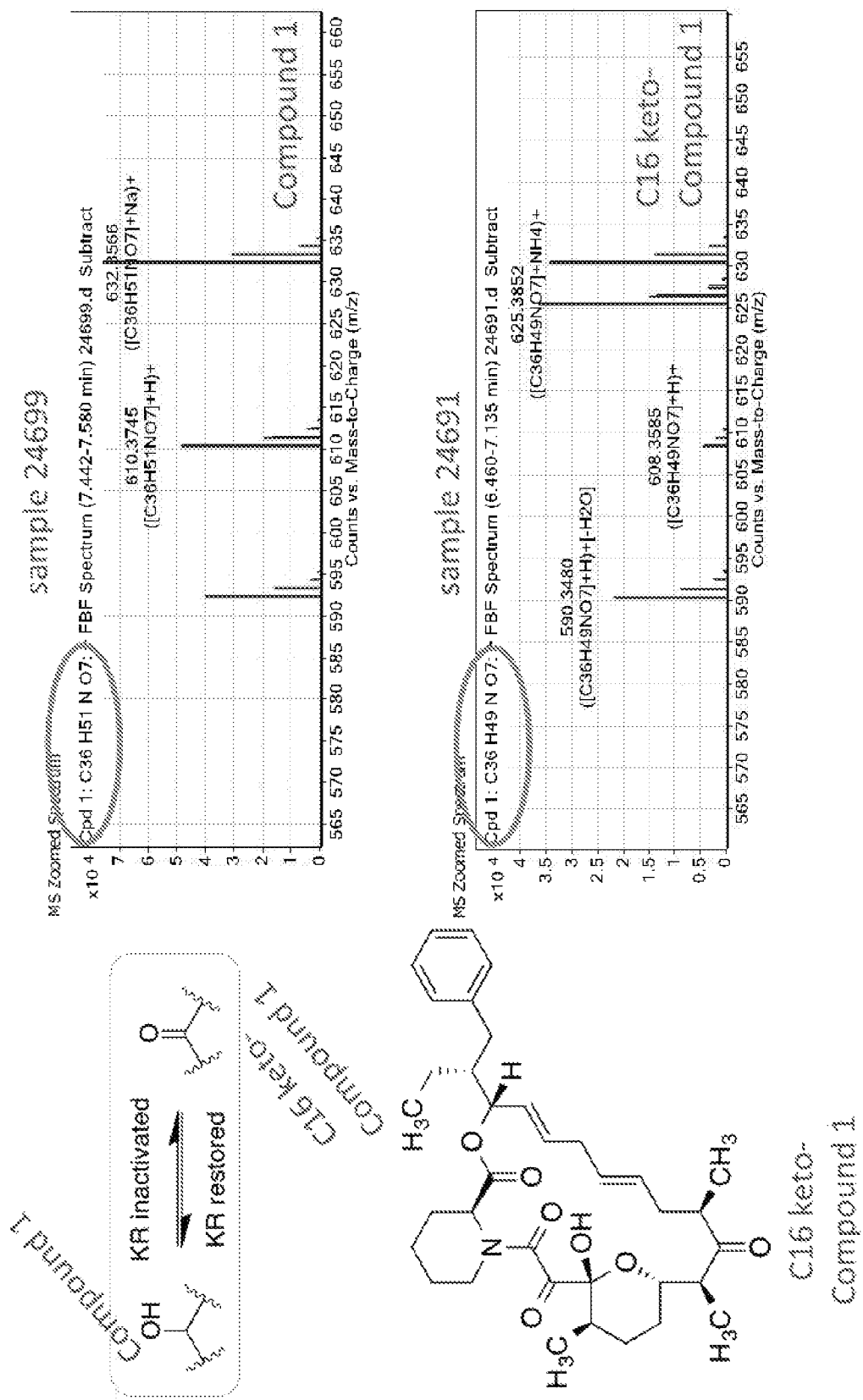
FIGS. 5B and 5C are images illustrating the generation of a compound by a modified polyketide synthase.
Figure 5C:
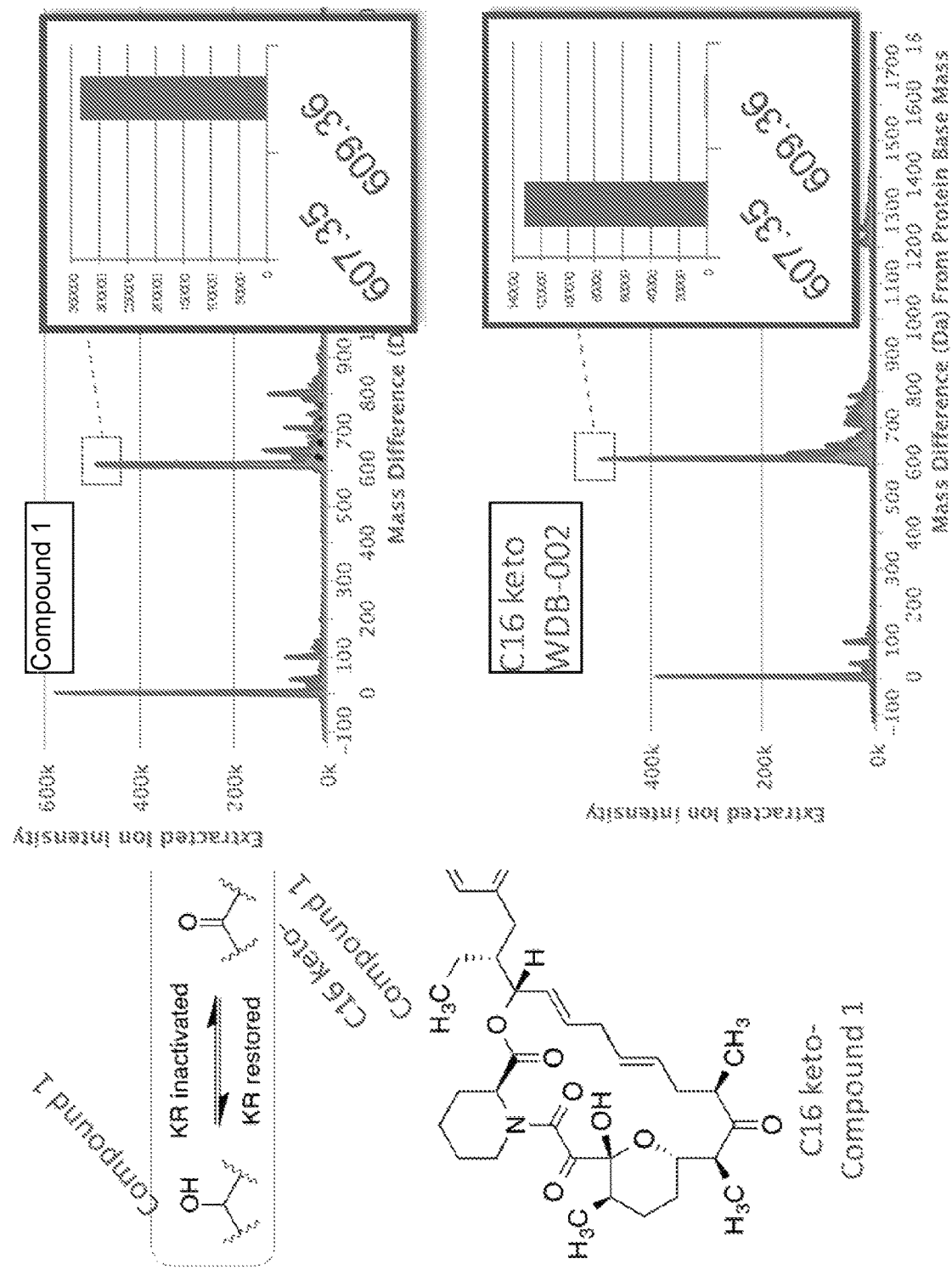

A short peptide sequence from 5303-KR6 was grafted onto X1-KR6 using homology-based cloning. The catalytic Tyr is replaced with Phe (shown in red) and the active site αFG loop (show in blue) is also deleted (FIG. 5A). The resulting clone was conjugated into a *Streptomyces* expression host and fermented. Comparative LC-TOF analysis of unfractionated SPE samples of Compound 1 and C16-keto-Compound 1 indicated that the new compound had the desired M+H mass of 608.35 (FIG. 5B). We then performed Top Down mass spectrometry analysis by co-injecting purified native FKBP12 and Compound 1 or C16-keto-Compound 1. This analysis again showed a mass difference of 2 consistent with the conversion at C16 of the hydroxyl to the ketone (FIG. 5C). C16-keto-Compound 1 was re-fermented at large scale, purified to homogeneity and the structure was confirmed by NMR spectroscopy.

Example 2. Inactivation of Dehydratase and Enoyl Reductase Domains

Figure 6A:
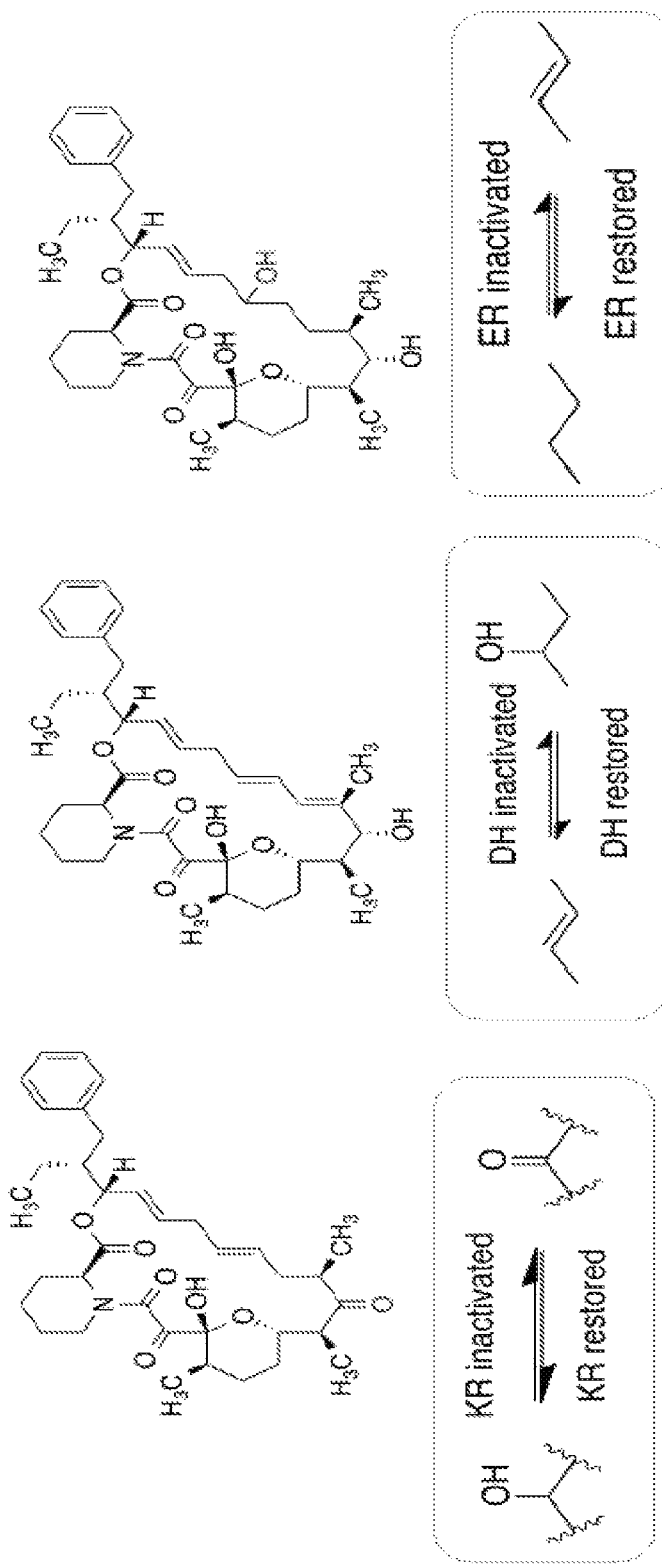
FIGS. 6A-6C are images illustrating the generation of compounds by modified polyketide synthases.

Using the protocol from Example 1, DH and ER domains in the PKS which produces Compound 1 were successfully deactivated as shown in FIG. 6A.

Example 3. Inactivation of Multiple Domains Simultaneously

Figure 6B:
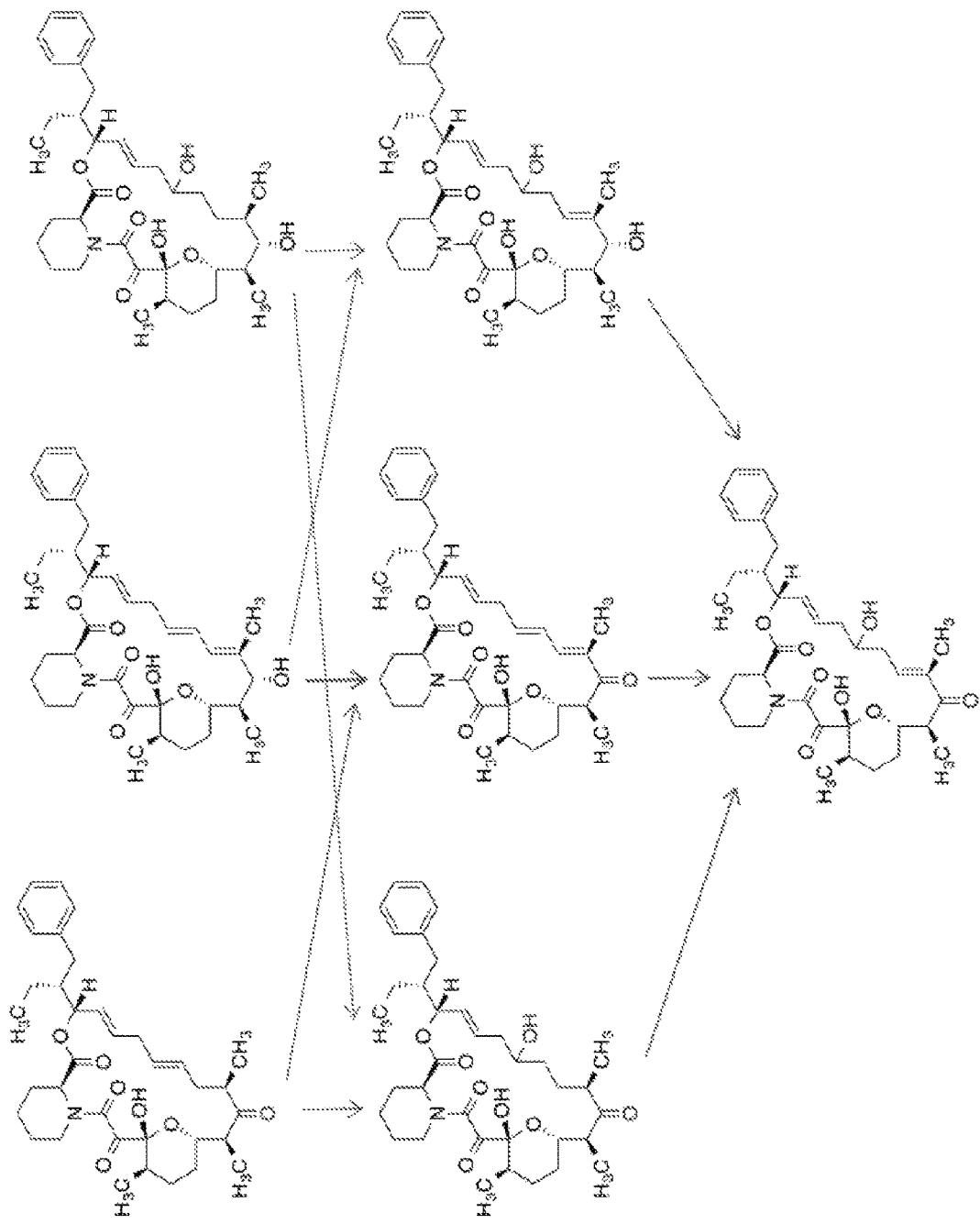

Using the protocol from Example 1, two domains were simultaneously deactivated as shown in FIG. 6B.

Figure 6C:
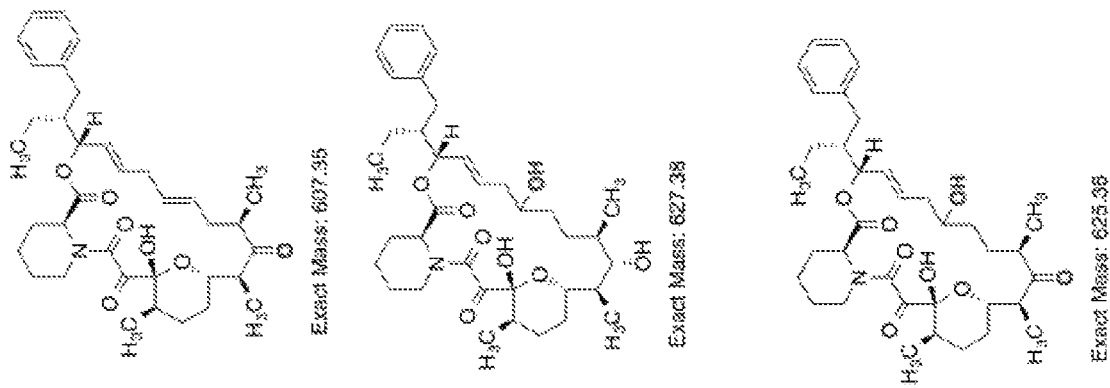
Figure 6C:
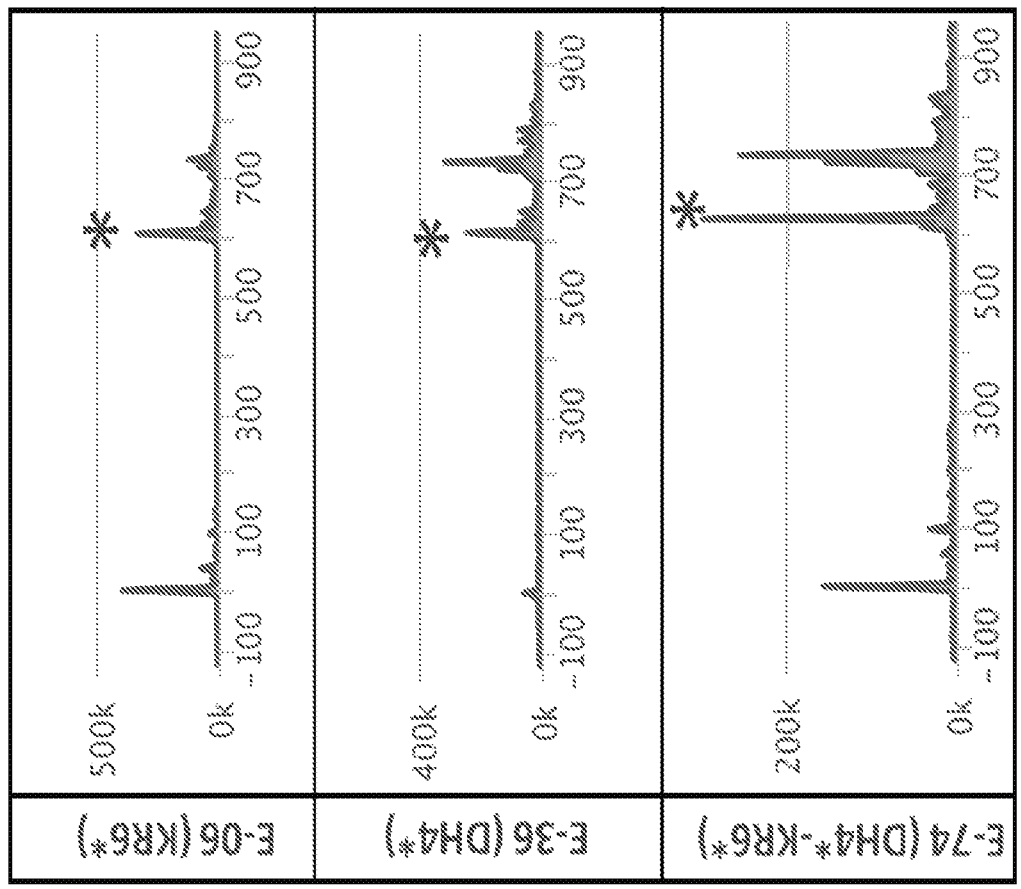

Further, the expression profiles of E-06 (KR6*), a C16-keto-Compound 1 compound generated by inactivating the KR domain of module 6, and E36 (DH4*), a hydroxy-Compound 1 analog generated by inactivating the DH domain of module 4 were compared. When the validated KR and DH modifications were combined on a single construct, the resulting combinatorial compound E-74(KR6*-DH4*) produced the expected compound mass of 625.36 in good yield as detected by the Top-Down assay (FIG. 6c).

Example 4. Engineering of the Constant Region

Figure 7A:
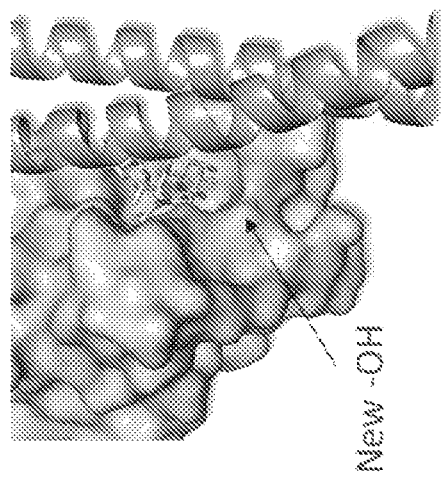
FIG. 7A is an image of a compound generated by a modified polyketide synthase.
Figure 7B:
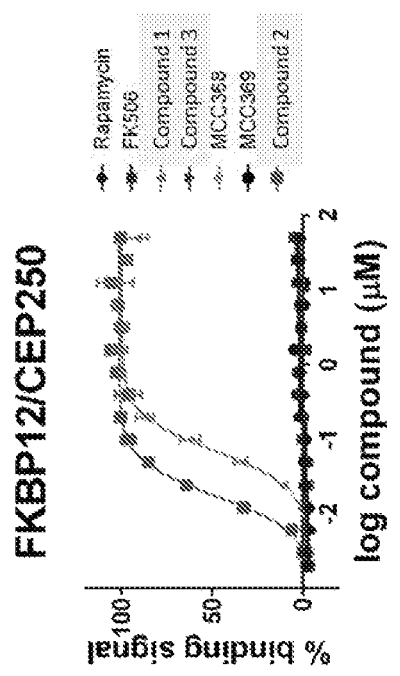
FIG. 7B is a graph illustrating generation of a compound by a modified polyketide synthase.
Figure 7C:
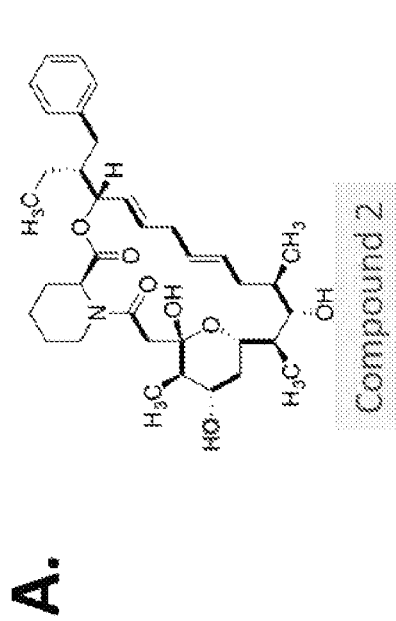
FIG. 7C is an image illustrating binding of a compound to CEP250.
Figure 7D:
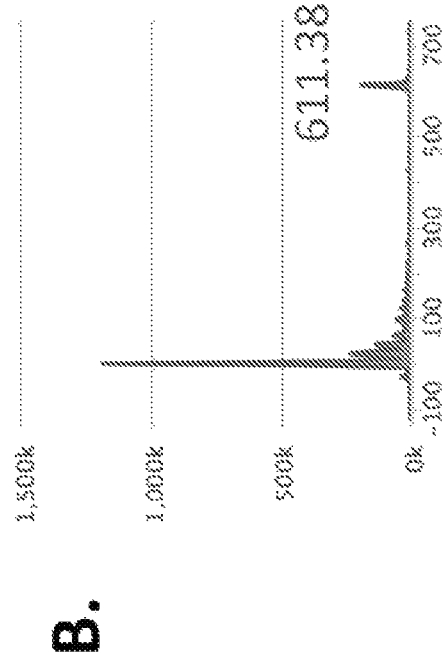
FIG. 7D is a graph illustrating binding of compounds to CEP250.

The rapamycin/FK506 "constant region" is the conserved portion of the macrolide ring that binds FKBP12. DH8 in the PKS which produces Compound 1 was inactivated by mutating the LPFXW motif to generate Compound 2 with a hydroxyl in the pyran ring of the constant region (FIG. 7A). The expected mass of 611.38 (FIG. 7B) was observed by a Top-Down assay, which confirmed that Compound 2 retained FKBP12 binding affinity. The structure of the FKBP12: Compound 2:CEP250 complex (FIG. 7C) was solved by crystallization. The structure confirmed that (1) the FKBP12:CEP250 interface can accommodate the addition of the hydroxyl on the pyran ring, (2) the stereochemistry of the newly installed —OH group, and, as expected, (3) that CEP250 binding is also retained. The FKBP12-dependent CEP250 binding to Compound 2, as measured by TR-FRET, was increased as compared to Compound 2 (FIG. 7D).

The above data establish the utility of domain-level engineering to generate chemically-novel derivatives of PKS natural products which retaining biological function (i.e., target protein binding).

Example 5. Combinatorial Domain Engineering

Figure 8A:
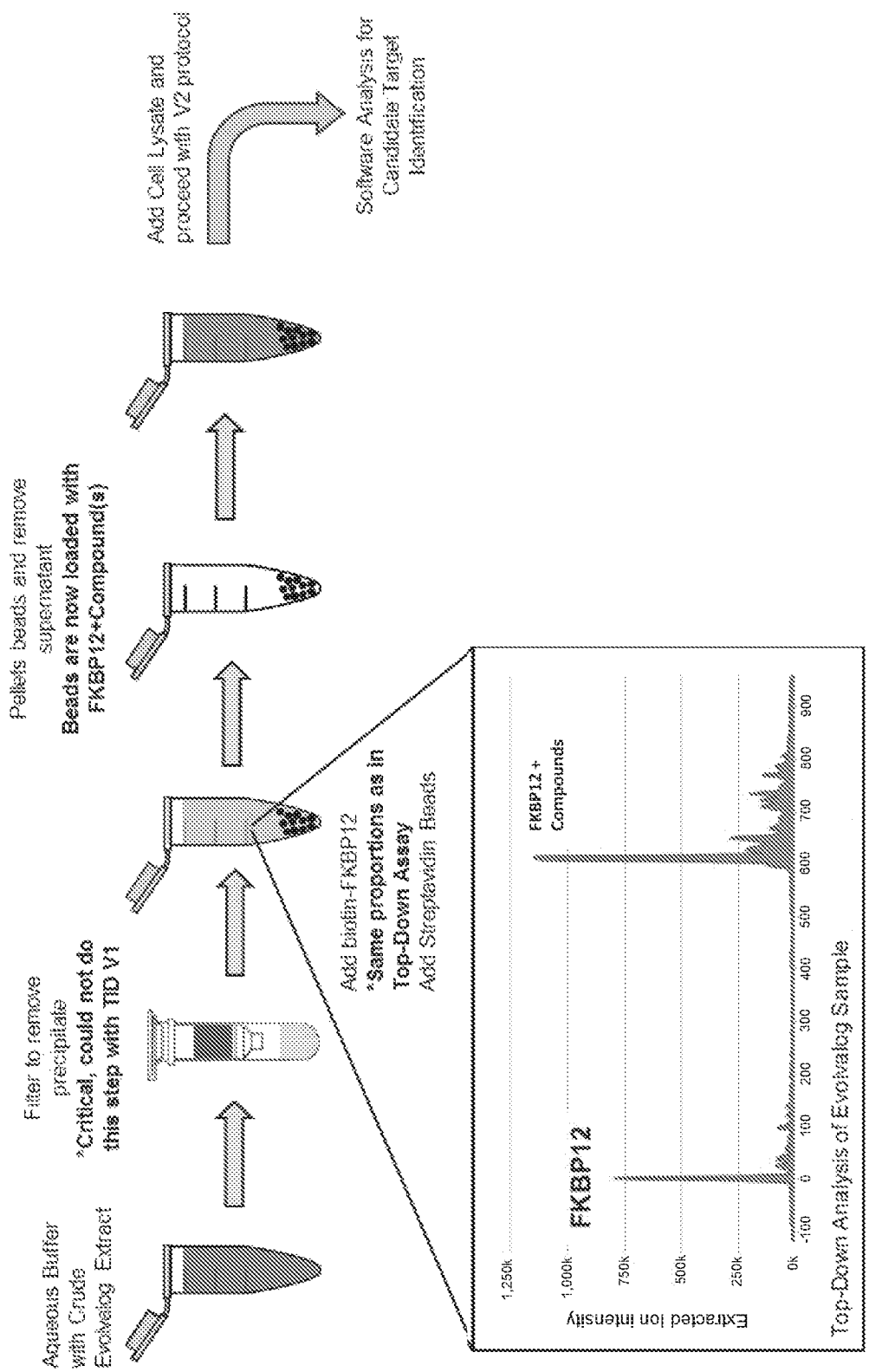
FIG. 8A is an image illustrating a target-ID method used for assaying compounds in crude extracts.
Figure 8B:
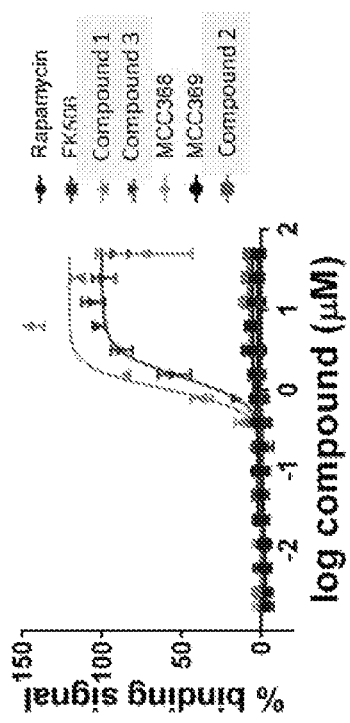
FIG. 8B is an image illustrating binding of compounds to CEP250 and CBY1.
Figure 8B:
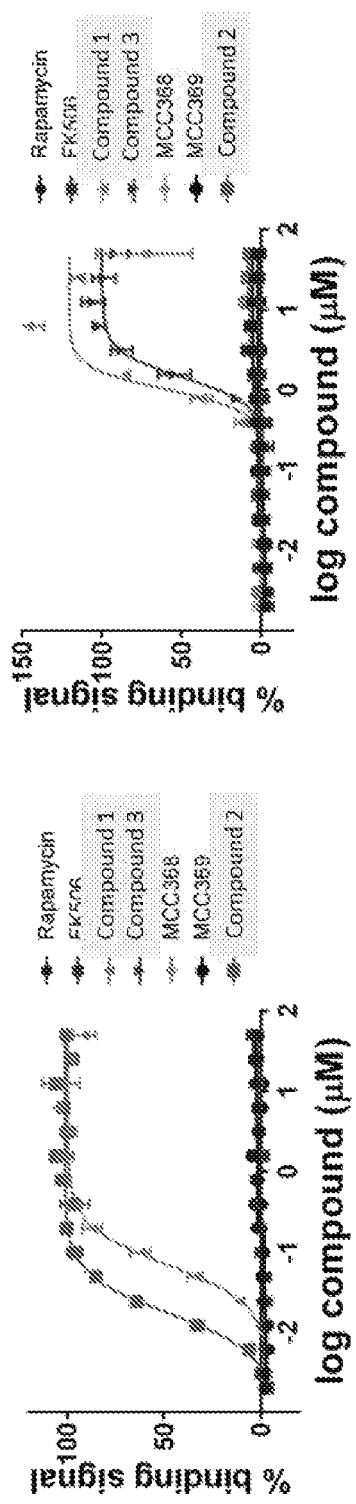

An optimized Target-ID assay based on FKBP12 affinity enrichment and LC-MS/MS sequencing of tryptic peptides that allows for the identification of the protein targets of compounds in crude extracts was developed (FIG. 8A). Target-ID analysis confirmed that Compound 1 bound both CEP250 and CBY1A in 293T lysates, whereas Compound 3, a combinatorial compound derivative of Compound 1, selectively bound CBY1 and not CEP250. The mass spectrometry-based Target-ID results were validated with TR-FRET data. The TR-FRET assay confirmed that CBY1 binds to Compound 1 (FIG. 8B). The data also confirmed that Compound 3 is specific for CBY1 and can no longer engage CEP250. Furthermore, Compound 2 (FIG. 7A) is specific for CEP250 and not CBY1. The structure of Compound 3 was confirmed by NMR, which indicated the successful inactivation of KR6, DH4 and ER5 domains via the domain-level engineering approach described above. Compound 2 also lacked the third carbonyl in the constant region, suggesting that CypB, the final tailoring step in Compound 1 biosynthesis, was unable to utilize Compound 2 as a productive substrate.

The above data demonstrates that domain-level engineering results in compounds with "reprogrammed" or altered target binding and therefore domain engineering can be utilized to generate molecules with new potential biological function.

Example 6. Ring Expansion Resulting from Ketoreductase Deactivation

Figure 9A:
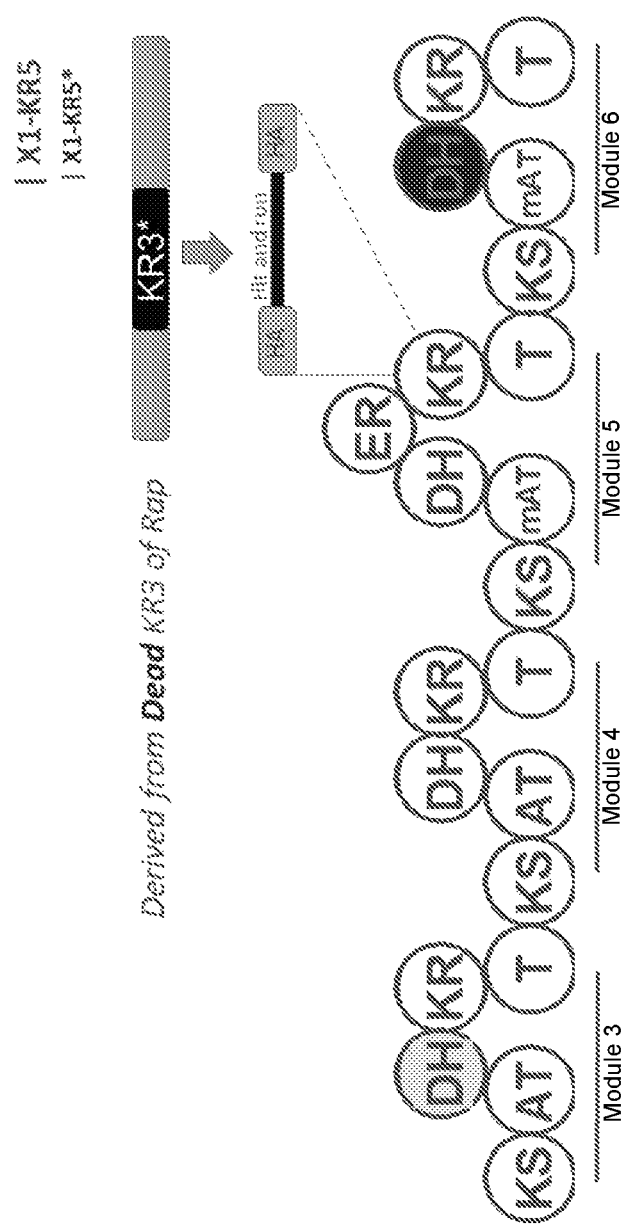
FIG. 9A is an image illustrating deactivation of a ketoreductase domain in a polyketide synthase.
Figure 9B:
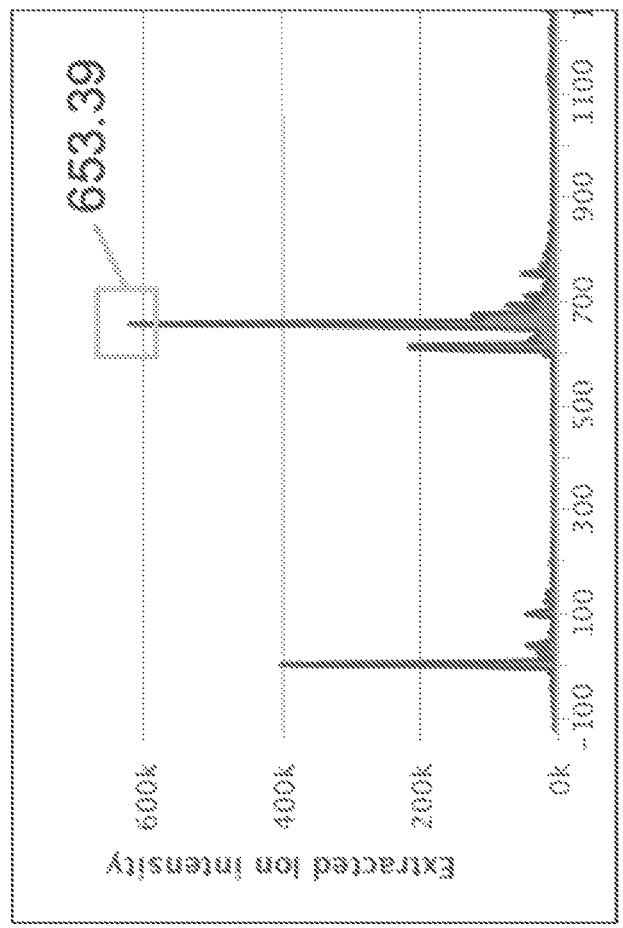
FIG. 9B is an image illustrating generation of a ring expanded compound by deactivation of a ketoreductase domain in a polyketide synthase.
Figure 9B:
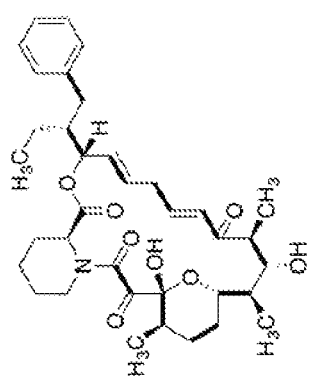
Figure 9B:
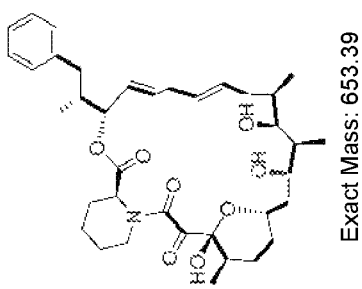

Each KR domain in modules 3-6 of the PKS which produces Compound 1 was systematically deactivated. Six sequences were tested for their ability to inactivate the KR domain (FIG. 9A). Unexpectedly, a +44 mass in compound, Compound 4, was observed which was purified and the structure determined by NMR. The structure indicated that rather than installing a keto by inactivation of KR5, the ring size Compound 4 was expanded by 2 carbons, corresponding to an additional round of malonyl incorporation via PKS chain extension (FIG. 9B). The domain-level compound variant in the PKS which produces Compound 1 that yielded Compound 4 was a single Ala to Glu substitution in KR5 near the conserved catalytic YAAAN motif. This mutation may prevent access of the ketoreductase active site and, in doing so, may alter the kinetic balance between intramodular domain-domain handoff and intermodule transfer in the next cycle of polyketide elongation. This model predicts that module iteration is favored as a consequence of the KR5 mutation, which results in an additional malonyl incorporation event and expanded ring size.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

---

The invention claimed is:

1. A method of producing a compound, the method comprising:
   (a) providing a parent nucleic acid encoding a parent polyketide synthase;
   (b) modifying at least a first codon of a ketoreductase domain of the parent nucleic acid to produce a modified nucleic acid encoding a modified polyketide synthase capable of producing a compound, wherein modifying the first codon produces a modified ketoreductase domain comprising at least one of the following modifications:
      (i) a substitution of an amino acid other than tyrosine at a position corresponding to a tyrosine in a conserved YAAAN (SEQ ID NO: 97) catalytic motif and a deletion of a region corresponding to a conserved αFG helix of SEQ ID NO: 1,
      (ii) a substitution of a glutamic acid residue at a position corresponding to alanine 6632 of an S9-pksA ORF of SEQ ID NO: 2, or
      (iii) a deletion of amino acids corresponding to amino acids 3386 to 3516 of a WT S12-pksB ORF of SEQ ID NO: 3; and
   wherein the one or more modifications decrease the enzymatic activity of the modified ketoreductase domain in comparison to the enzymatic activity of the ketoreductase domain of the parent polyketide synthase
   (c) introducing the modified nucleic acid to one or more host cells; and
   (d) culturing the one or more host cells under conditions suitable to allow expression of the compound by the modified polyketide synthase;
   thereby producing the compound.

2. The method of claim 1, wherein (b) further comprises modifying at least a second codon of the parent nucleic acid, wherein modifying the second codon produces a second modified domain, and
   wherein the second modified domain is a β-ketone processing domain.

3. The method of claim 2, wherein the β-ketone processing domain is a ketoreductase, a dehydratase, or an enoyl-reductase.

4. The method of claim 3, wherein the β-ketone processing domain is a ketoreductase, wherein the ketoreductase (a) comprises a substitution of an amino acid other than tyrosine at a position corresponding to a tyrosine in a conserved YAAAN (SEQ ID NO: 97) catalytic motif and a deletion of a region corresponding to a conserved αFG helix of SEQ ID NO: 1; (b) comprises a substitution of a glutamic acid residue at a position corresponding to alanine 6632 of an S9-pksA ORF of SEQ ID NO: 2; or (c) comprises a deletion of amino acids corresponding to amino acids 3386 to 3516 of a WT S12-pksB ORF of SEQ ID NO: 3.

5. The method of claim 3, wherein the β-ketone processing domain is a dehydratase, wherein the dehydratase comprises (a) a substitution of an aspartic acid at a position corresponding to a glycine at position 4288 in pksB of an S679-pksB ORF in a conserved HXXXGXXXXP (SEQ ID NO: 98) motif of SEQ ID NO: 4; (b) a substitution in a conserved LPFXW (SEQ ID NO: 99) motif at a position corresponding to position 3066 to 3070 in an S12-pksB ORF of SEQ ID NO: 5; (c) a deletion corresponding to a region between Pro 6844 and Trp 6874 of an S679-pksA ORF of SEQ ID NO: 6; or (d) a substitution or deletion at the positions corresponding to A, B, C, and D of SEQ ID NO: 7.

6. The method of claim 3, wherein the β-ketone processing domain is an enoylreductase, wherein the enoylreductase comprises a substitution or deletion of a lysine at a position corresponding to position 1546 of an S12-pksB ORF of SEQ ID NO: 8 and/or a substitution or deletion of an aspartic acid at a position corresponding to position 1568 of an S12-pksB ORF of SEQ ID NO: 8 or SEQ ID NO: 9.

7. The method of claim 1, wherein the modified nucleic acid further encodes a Large ATP-binding regulator of the LuxR family (LAL).

8. The method of claim 7, wherein the LAL comprises the amino acid sequence of SEQ ID NO: 38.

9. The method of claim 1, wherein the modified nucleic acid further comprises an LAL binding site, wherein the nucleic acid sequence encoding the LAL binding site is operatively linked to the nucleic acid sequence encoding the first modified polyketide synthase.

10. The method of claim 9, wherein the LAL binding site comprises the nucleic acid sequence of SEQ ID NO: 39.

11. The method of claim 9, wherein the LAL binding site comprises the nucleic acid sequence of SEQ ID NO: 40.

12. The method of claim 10, wherein binding of an LAL to the LAL binding site promotes the expression of the first modified polyketide synthase.

13. The method of claim 1, wherein the modified nucleic acid further encodes a nonribosomal peptide synthase.

14. The method of claim 1, wherein the modified nucleic acid further encodes a P450 enzyme.

15. The method of claim 1, wherein the modified ketoreductase domain is functionally inactive.

\* \* \* \* \*

SEQUENCE LISTING

```
<160> NUMBER OF SEQ ID NOS: 99

<210> SEQ ID NO 1
<211> LENGTH: 327
<212> TYPE: PRT
<213> ORGANISM: Streptomyces hygroscopicus S303

<400> SEQUENCE: 1

Asp Pro Asp Gly Thr Val Leu Ile Thr Gly Gly Ser Gly Val Arg Ala
1               5                   10                  15
```

Gly Ala Leu Ala Arg His Leu Val Thr Glu Arg Gly Val Arg His Leu
            20                  25                  30

Leu Leu Leu Ser Arg Thr Thr Ala Asp Glu Glu Leu Leu Asn Glu Leu
        35                  40                  45

Gly Glu Leu Gly Ala Arg Val Asp Thr Ala Ile Cys Asp Val Ser Asp
50                  55                  60

Arg Ala Arg Leu Ala Gln Val Leu Ala Gly Val Ser Pro Glu His Pro
65                  70                  75                  80

Leu Thr Ala Val Ile His Thr Ala Gly Ala Leu Asp Asp Asp Val Val
                85                  90                  95

Glu Ser Leu Thr Ala Gln Arg Leu Asp Thr Val Leu Arg Pro Lys Ala
            100                 105                 110

Asp Gly Ala Trp His Leu His Glu Leu Thr Arg Asp Thr Asp Leu Ala
        115                 120                 125

Ala Phe Val Met Tyr Ser Ser Ala Ala Gly Val Met Gly Asn Pro Gly
130                 135                 140

Gln Gly Asn Phe Ala Ala Ala Thr Ala Phe Leu Asp Ala Leu Ala Glu
145                 150                 155                 160

Gln Arg Arg Ala Glu Gly Leu Pro Ala Leu Ala Leu Ala Trp Gly Ser
                165                 170                 175

Ser Glu Glu Thr Gly Gly Leu Thr Gly Leu Arg Ala Ile Ser Ala Glu
            180                 185                 190

His Gly Met Arg Leu Phe Asp Ser Ala Ser His Arg Arg Glu Pro Leu
        195                 200                 205

Leu Val Ala Ala Ser Met Asp Pro Val Leu Ala Ala Glu Val Pro Ala
210                 215                 220

Leu Leu Arg Ser Leu Arg Arg Pro Ile Ala Arg Arg Ala Ala Ser Ala
225                 230                 235                 240

Asp Gly Val Gln Trp Leu Ala Gly Leu Ala Pro Glu Glu Arg Ala Lys
                245                 250                 255

Ala Leu Leu Lys Val Val Cys Asp Thr Ala Thr Val Leu Gly His
            260                 265                 270

Ala Asp Ala Arg Thr Ile Pro Leu Thr Gly Ala Phe Lys Asp Leu Gly
        275                 280                 285

Val Asp Ser Leu Thr Ala Val Glu Leu Arg Asn Ser Leu Thr Lys Ala
290                 295                 300

Thr Gly Leu Arg Leu Pro Ala Thr Leu Val Phe Asp Tyr Pro Thr Pro
305                 310                 315                 320

Thr Ala Leu Ala Val Arg Leu
                325

<210> SEQ ID NO 2
<211> LENGTH: 342
<212> TYPE: PRT
<213> ORGANISM: Streptomyces rapamycinicus NRRL 5491

<400> SEQUENCE: 2

Asp Pro Asp Gly Thr Ile Leu Ile Thr Gly Gly Ser Gly Val Leu Ala
1               5                   10                  15

Gly Ile Leu Ala Arg His Leu Ala Ala Glu His Gly Ala Arg His Leu
            20                  25                  30

Leu Leu Leu Ser Arg Thr Ala Pro Asp Glu Ala Leu Ile Lys Glu Leu
        35                  40                  45

Ala Glu Leu Gly Ala Arg Val Glu Thr Ala Ala Cys Asp Val Ser Asp

```
                50                  55                  60
Arg Ala Gly Leu Ala Arg Val Leu Ala Gly Val Ser Pro Glu His Pro
 65                  70                  75                  80

Leu Thr Ala Val Ile His Thr Ala Gly Ala Leu Asp Asp Gly Val Val
                     85                  90                  95

Glu Ser Leu Thr Thr Gln Gln Leu Asp Thr Val Leu Arg Pro Lys Ala
                100                 105                 110

Asp Gly Ala Trp His Leu His Glu Leu Thr Arg Asp Ala Asp Leu Ala
                115                 120                 125

Ala Phe Val Val Tyr Ser Ala Ala Ala Val Leu Gly Asn Glu Gly
            130                 135                 140

Gln Gly Asn Tyr Ala Ala Asn Ala Phe Leu Asp Ala Leu Ala Glu
145                 150                 155                 160

Gln Arg Arg Thr Gln Gly Leu Pro Ala Leu Ala Leu Ala Trp Gly Pro
                165                 170                 175

Trp Glu Tyr Thr Gly Asp Leu Thr Ala Gln Leu Thr Gly Thr Asp Gln
                180                 185                 190

Asp Arg Ile Arg Cys Ser Gly Met Arg Thr Ile Thr Ala Glu Asp Gly
                195                 200                 205

Met Arg Leu Phe Asp Thr Ala Ser His His Gly Glu Pro Leu Leu Val
210                 215                 220

Pro Ala Val Leu Asp Pro Thr Arg Asp Gly Glu Val Pro Ala Leu Leu
225                 230                 235                 240

Arg Ser Leu Arg Arg Pro Ile Ala Arg Ala Ala Ser Ala Asp Gly
                245                 250                 255

Gly Val Gln Trp Leu Ala Ala Leu Ala Pro Ala Glu Arg Glu Lys Ala
                260                 265                 270

Leu Leu Lys Leu Val Cys Asp Ser Ala Ala Met Val Leu Gly His Ala
                275                 280                 285

Asp Ala Arg Ser Ile Pro Ala Ala Gly Ala Phe Lys Asp Leu Gly Val
            290                 295                 300

Asp Ser Leu Met Ala Val Glu Leu Arg Asn Gly Leu Val Lys Ala Thr
305                 310                 315                 320

Gly Leu Arg Leu Pro Ala Thr Leu Val Phe Asp Tyr Pro Thr Pro Thr
                325                 330                 335

Val Leu Ala Ala Arg Leu
            340

<210> SEQ ID NO 3
<211> LENGTH: 202
<212> TYPE: PRT
<213> ORGANISM: Actinoplanes sp. S399

<400> SEQUENCE: 3

Asp Pro Asp Gly Thr Val Leu Ile Thr Gly Glu Arg Ala Gly Ala Val
 1               5                  10                  15

Ala Arg Arg Met Ala Glu Arg Gly Val Arg His Leu Leu Leu Ala Ser
                20                  25                  30

Gly Arg Val Pro Asp Glu Leu Met Asp Leu Asp Thr Ser Val Glu Val
            35                  40                  45

Ala Val Cys Asp Val Ser Asp Arg Ala Leu Ala Gly Val Leu Ala
            50                  55                  60

Gly Leu Pro Ser Leu Thr Gly Val Ile Gln Thr Ala Gly Glu Asp Val
 65                  70                  75                  80
```

```
Leu Pro Val Leu Ala Gly Ala Ile Thr Pro Thr Arg Asp Gly Glu Ile
                85                  90                  95

Pro Ala Ser Leu Arg Leu Leu Arg Arg Pro Leu Val Arg Arg Val
            100                 105                 110

Ser Ala Ala Gly Asp Ser Ser Leu Ala Ala Leu Pro Pro Ala Glu Arg
            115                 120                 125

Glu Arg Ala Leu Leu Lys Val Val Arg Asp Ser Ala Ala Val Val Leu
        130                 135                 140

Gly His Ala Asp Gly Arg Thr Val Pro Ala Thr Ala Phe Lys Asp
145                 150                 155                 160

Leu Gly Leu Asp Ser Leu Thr Ala Val Glu Leu Arg Asn Ser Leu Arg
                165                 170                 175

Lys Ala Thr Gly Leu Gln Leu Pro Ala Thr Leu Val Phe Asp Tyr Pro
            180                 185                 190

Ser Pro Val Ala Leu Ala Ala Arg Leu Gly
            195                 200
```

<210> SEQ ID NO 4
<211> LENGTH: 235
<212> TYPE: PRT
<213> ORGANISM: Micromonospora sp. S679

<400> SEQUENCE: 4

```
His Pro Phe Leu Gly Ala Ala Leu Pro Ala Pro Asp Gly Asp Ser Leu
1               5                   10                  15

Thr Leu Thr Gly Arg Ile Thr Leu Asp Ala His Pro Trp Leu Ala Asp
            20                  25                  30

His Ile Ile Arg Asp Thr Leu Ile Leu Pro Gly Ala Ala Phe Ala Glu
        35                  40                  45

Cys Val Leu Arg Ala Gly Arg Glu Val Gly Cys Asp Leu Leu Glu Glu
    50                  55                  60

Leu Val Ile Glu Ala Pro Leu Val Leu Pro Ala Thr Gly Gly Val Ala
65                  70                  75                  80

Val Arg Ile Ala Val Gly Glu Pro Asp Asp Ala Gly Arg Arg Thr Phe
                85                  90                  95

Asp Leu Tyr Ala Arg Pro Asp Ala Ala Pro Gly Trp Asn Arg His Ala
            100                 105                 110

Gly Gly Thr Leu Lys Pro Gly Asp Ala Leu Pro Ala Thr Glu Ala Ala
        115                 120                 125

Thr Glu Thr Val Ala Trp Pro Pro Ala Asp Ala Glu Pro Val Asp Val
    130                 135                 140

Asp Asp Leu Tyr Asp Arg Leu Ala Ala Ala Gly Tyr Ala Tyr Gly Pro
145                 150                 155                 160

Ala Phe Gln Ser Val His Ala Ala Trp Arg Thr Pro Asp Ala Ile Trp
                165                 170                 175

Ala Glu Val Val Leu Asp Gly Glu Pro Ala Gly Phe Gly Leu His Pro
            180                 185                 190

Ala Leu Leu Asp Gly Ala Leu Gln Leu Ser Ala Leu Ala Ala Thr Gly
        195                 200                 205

Gly Asp Val Ala Gln Leu Pro Phe Ala Trp His Asp Val Arg Leu Pro
    210                 215                 220

Gly His Gly Ala Asp Arg Leu Arg Val Arg Leu
225                 230                 235
```

<210> SEQ ID NO 5

<211> LENGTH: 271
<212> TYPE: PRT
<213> ORGANISM: Streptomyces malaysiensis DSM4137

<400> SEQUENCE: 5

His Pro Leu Leu Gly Ala Ile Val Ala Pro Gln Ser Gly Gly Val
1               5                   10                  15

Ala Met Thr Ser Arg Leu Ser Pro Arg Asn His Pro Trp Leu Ala Glu
            20                  25                  30

His Thr Leu Gly Gly Val Pro Thr Val Pro Thr Ser Val Leu Val Glu
        35                  40                  45

Leu Ala Val Arg Ala Gly Asp Glu Val Gly Cys Gly Val Val Glu Glu
50                  55                  60

Leu Thr Val Asp Ala Pro Leu Leu Pro Glu Arg Gly Gly Val Arg
65                  70                  75                  80

Val Gln Val Ile Val Gly Ala Thr Asp Ala Asn Gly Gln Arg Gly Leu
                85                  90                  95

Asp Ile Phe Ser Ala Pro Glu Asp Thr Gly Gln Glu Ala Trp Thr Arg
            100                 105                 110

His Ala Thr Gly Thr Leu Ala Pro Gly Gly Asp Ile Ala Ala Asp Val
        115                 120                 125

Asp Leu Ser Ala Trp Pro Pro Ala Asn Ala Gln Pro Val Asp Val Thr
130                 135                 140

Asp Gly Tyr Asp Leu Leu Glu Arg Ala Gly Tyr Gly Tyr Gly Pro Ala
145                 150                 155                 160

Phe Gln Gly Val Arg Ala Ile Trp Arg Arg Gly Glu Glu Leu Phe Ala
                165                 170                 175

Glu Val Ala Leu Glu Pro Glu Leu Thr Asp Thr Ala Ala Arg Phe Gly
            180                 185                 190

Leu His Pro Ala Leu Leu Asp Ala Ala Trp His Pro Glu Leu Arg Asp
        195                 200                 205

Glu Val Ala Glu Thr Ser Pro Asp Gly Arg Arg Trp Trp Ser Gln Pro
    210                 215                 220

Ser Arg Trp Ala Gly Leu Arg Leu His Thr Ala Gly Ala Thr Val Leu
225                 230                 235                 240

Arg Val Arg Leu Ala Pro Val Asp Ala Asp Ser Met Ser Leu Gln Ala
                245                 250                 255

Ala Asp Glu Thr Gly Asp Pro Val Leu Thr Val Asp Ser Leu Ser
            260                 265                 270

<210> SEQ ID NO 6
<211> LENGTH: 185
<212> TYPE: PRT
<213> ORGANISM: Micromonospora sp. S679

<400> SEQUENCE: 6

His Pro Leu Leu Gly Ala Gly Met Pro Ile Ala Gly Thr Gly Ala Val
1               5                   10                  15

Leu Phe Gly Thr Glu Val Ala His Pro Trp Phe Asp Gly His Glu Thr
            20                  25                  30

Leu Pro Ala Ala Ala Phe Ala Glu Ile Ala Val Arg Ala Ala Ala Glu
        35                  40                  45

Val Gly Ser Pro Val Val Gly Glu Leu His Val Glu Leu Leu Pro Arg
    50                  55                  60

Ile Pro Ala Asp Gly Arg Leu Arg Leu Gln Thr Trp Val Asp Gly Pro
65                  70                  75                  80

```
Asp Pro Thr Gly Val Arg Arg Phe Thr Val His Ala Arg Pro Asp Pro
                85                  90                  95

Thr Ala Ala Trp Leu Arg Val Ala Ser Gly Val Leu Thr Gly Ala Glu
            100                 105                 110

Ala Pro Val Pro Ala Phe Ala Gly Gly Glu Pro Leu His Ile Ala Asp
        115                 120                 125

Gly Thr Pro Ala Gly Phe Leu Leu His Pro Asp Ala Thr Pro Ala Ala
    130                 135                 140

Asp Trp Phe Gly Leu Val Ala His Gly Ser Gly Ala Arg Gln Gln His
145                 150                 155                 160

Val Tyr Gln Ala Gly Glu Gly Leu Cys Val Thr Asp Asp Ala Gly Arg
                165                 170                 175

Pro Ile Val Thr Ala Ala Arg Val Arg
                180                 185

<210> SEQ ID NO 7
<211> LENGTH: 171
<212> TYPE: PRT
<213> ORGANISM: Streptomyces malaysiensis DSM4137

<400> SEQUENCE: 7

His Pro Leu Leu Gly Trp Gly Val Pro Val Ala Glu Ala Gly Gly Arg
1               5                   10                  15

Leu Tyr Thr Gly Arg Val Ala Arg Gln Asp Gly Pro Val Leu Ser Val
            20                  25                  30

Ala Ala Phe Val Glu Met Ala Phe Ala Ala Gly Gly Arg Pro Ile
        35                  40                  45

Arg Glu Leu Ser Val Asp Ala Leu Leu Tyr Ile Pro Asp Asp Gly Thr
    50                  55                  60

Ala Glu Leu Gln Thr Trp Val Ser Glu His Arg Leu Thr Ile His Ala
65                  70                  75                  80

Arg Tyr Arg Asp Thr Glu Pro Trp Thr Arg Leu Ala Thr Ala Ala Leu
                85                  90                  95

Asp Thr Thr Ala Pro Ala Thr Thr His Thr Pro His Pro Gly Leu Ile
            100                 105                 110

Thr Thr Ala Leu Thr Leu Thr Gly Asp Glu Ala Pro Ala Ile Trp His
        115                 120                 125

Asp Leu Thr Leu His Thr Ser Asn Ala Thr Glu Leu His Thr His Ile
    130                 135                 140

Thr Pro Gly Asp Asp Gly Thr Leu Thr Ile Thr Ala Thr Asp Thr Thr
145                 150                 155                 160

Gly Gln Pro Val Leu Thr Ala His Thr Ala Thr
                165                 170

<210> SEQ ID NO 8
<211> LENGTH: 637
<212> TYPE: PRT
<213> ORGANISM: Streptomyces malaysiensis DSM4137

<400> SEQUENCE: 8

Arg Leu Ser Ala Leu Ala Ser Leu Gly Glu Pro Gln Ile Val Val Arg
1               5                   10                  15

Asp Asp Thr Pro Leu Val Ala Arg Leu Ala Arg Glu Lys Ser Pro Ala
            20                  25                  30

Leu Thr Ile Pro Gly Glu Arg Ala Trp Val Leu Glu Pro Asp His Ser
        35                  40                  45
```

```
Gly Val Leu Gln Glu Leu Ala Leu Val Ala Ala Asp Thr Asp Val Arg
 50                  55                  60

Pro Leu Arg Pro Gly Glu Val Arg Ile Glu Val Arg Ala Ala Gly Leu
 65                  70                  75                  80

Asn Phe Arg Asp Val Leu Val Ala Leu Gly Thr Asp Leu Gly Asp Gly
                 85                  90                  95

Val Phe Gly Ala Glu Gly Ala Gly Val Val Leu Glu Thr Gly Ser Asp
            100                 105                 110

Val Arg Asp Leu Arg Pro Gly Asp Arg Val Phe Gly Leu Leu Glu Gly
            115                 120                 125

Gly His Gly Ser Ile Ala Ile Ala Asp Arg Arg Met Leu Ala Val Ile
            130                 135                 140

Pro Glu Gly Trp Ser Phe Ala Thr Ala Ala Ser Val Pro Glu Val Phe
145                 150                 155                 160

Val Ile Ala Tyr Tyr Gly Leu Val Asp Leu Ala Gly Leu Arg Ala Gly
                165                 170                 175

Glu Ser Val Leu Ile His Ala Ala Thr Gly Gly Val Gly Met Ala Ala
            180                 185                 190

Thr Gln Ile Ala Arg His Leu Gly Ala Gln Val Tyr Ala Thr Ala Gly
            195                 200                 205

Val Gly Lys Gln His Ile Leu Arg Asp Ala Gly Leu Gly Asp Asp Arg
210                 215                 220

Ile Ala Asp Ser Arg Thr Thr Asp Phe Arg Glu Ala Phe Arg Asp Ser
225                 230                 235                 240

Thr Gln Gly Arg Gly Val Asp Val Val Leu Asn Ser Leu Lys Gly Asp
                245                 250                 255

Phe Val Asp Ala Ser Leu Asp Leu Leu Ala Asp Gly Gly Arg Phe Leu
            260                 265                 270

Glu Leu Gly Gln Thr Asp Ile Arg Asp Ala Gly Glu Ile Ala Ala Glu
            275                 280                 285

Arg Pro Gly Thr Thr Tyr His Ser Phe Thr Arg Met Asn Ala Gly Pro
290                 295                 300

Asp Arg Leu Arg Glu Ile Ile Ala Glu Leu Leu Ala Leu Phe Glu Gln
305                 310                 315                 320

Gly Val Leu Arg Pro Ser Pro Val His Thr Trp Asp Ile Arg His Ala
                325                 330                 335

Arg Glu Ala Phe Ser Trp Met Ser Gly Gly Arg His Thr Gly Lys Met
            340                 345                 350

Val Leu Thr Met Pro Gln Arg Ile Asp Pro Gly Gly Thr Val Leu Ile
            355                 360                 365

Ala Gly Asp Ser Glu Ala Leu Ala Arg Ile Ala Ala Arg His Leu Gly
370                 375                 380

Val Arg His Leu Leu Leu Asp Arg Gly Val Ala Asp Ala Ala Pro Asp
385                 390                 395                 400

Ala Val Val Cys Asp Val Ser Asp His Asp Ala Leu Glu Arg Val Leu
                405                 410                 415

Ala Asp Leu Ser Pro Glu His Pro Leu Thr Ala Val Ile His Thr Gly
            420                 425                 430

Gly Ala Ala Val Thr Asp Glu Ile Arg Arg Leu His Asp Leu Thr Glu
            435                 440                 445

Ser Leu Asp Leu Thr Asp Phe Val Val Phe Ser Gln Asp Ala Pro Ala
450                 455                 460
```

```
Ala Val Glu Ala Phe Ala Arg Ser Arg Arg Ala His Gly Leu Pro Val
465                 470                 475                 480

Arg Thr Ile Ala Trp Gly Ile Pro Glu Ala Asp Pro Val Val Ala Asp
            485                 490                 495

Glu His Leu Leu Gly Arg Ala Leu Ala Ser Ala Glu Gln Ala Gln Ile
            500                 505                 510

Val Ala Arg Val Asn Thr Ala Gly Leu Arg Ala Leu Thr Ala Ala Asn
            515                 520                 525

Ala Leu Pro Thr Leu Leu Arg Asn Leu Ile Arg Ala Glu Pro Glu Glu
            530                 535                 540

Thr Gly Gln Ser Ala Trp Pro His Arg Phe Glu Ala Ala Gly Ala Asp
545                 550                 555                 560

Arg Glu Glu Ala Leu Leu Asp Leu Ile Arg Ala Asn Val Val Asp Ile
            565                 570                 575

Leu Ser Leu Pro Thr Ala Asp Arg Tyr Ala Pro Asp Arg Thr Phe Arg
            580                 585                 590

Glu Met Gly Ile Asp Ser Leu Thr Ala Val Gly Leu Arg Asn Ser Leu
            595                 600                 605

Ala Lys Ala Thr Gly Leu Pro Leu Pro Thr Thr Met Val Phe Asp Tyr
            610                 615                 620

Pro Thr Pro Ala Val Leu Thr Ala Arg Met Arg Glu Leu
625                 630                 635

<210> SEQ ID NO 9
<211> LENGTH: 652
<212> TYPE: PRT
<213> ORGANISM: Streptomyces sp. S61

<400> SEQUENCE: 9

Arg Leu Ser Thr Leu Val Ala Leu Gly Glu Pro Gln Ile Ala Leu Arg
1               5                   10                  15

Asp Ser Thr Pro Leu Val Pro Arg Leu Ala Pro Glu Ser Ser Thr Ala
            20                  25                  30

Leu Thr Thr Pro Ala Ala Arg Ala Trp Val Leu Glu Pro Ala Arg Ser
            35                  40                  45

Gly Thr Leu Arg Glu Leu Ser Leu Val Ala Ala Asp Thr Asp Ala Arg
50                  55                  60

Pro Leu Arg Pro Gly Glu Val Arg Val Asp Val Arg Ala Ala Gly Leu
65                  70                  75                  80

Asn Phe Arg Asp Val Leu Ile Ala Leu Gly Thr Tyr Pro Gly Asp Gly
            85                  90                  95

Val Met Gly Gly Glu Ala Ala Gly Val Val Leu Glu Val Gly Pro Glu
            100                 105                 110

Val Asn Asp Leu Ser Val Gly Asp Arg Val Phe Gly Leu Val Thr Asp
            115                 120                 125

Gly Phe Gly Pro Val Thr Ile Thr Asp Arg Arg Leu Leu Ala Ala Met
130                 135                 140

Pro Gln Asp Trp Ser Phe Thr Thr Ala Ala Ser Ala Ala Met Ala Phe
145                 150                 155                 160

Ala Thr Ala His Tyr Gly Leu Val Glu Leu Ala Gly Leu Lys Ala Gly
            165                 170                 175

Glu Ser Val Leu Ile His Ala Ala Thr Gly Gly Val Gly Met Ala Ala
            180                 185                 190

Thr Gln Ile Ala His His Leu Gly Ala His Ile Tyr Ala Thr Ala Ser
            195                 200                 205
```

```
Ser Gly Lys Gln His Leu Leu Arg Ala Ala Gly Ile Asp Asp Arg
    210                 215                 220

Ile Ala Asn Ser Arg Thr Thr Gly Phe Arg Asp Ala Phe Leu Asp Ser
225                 230                 235                 240

Thr Gly Gly Arg Gly Val Asp Val Val Leu Asn Ser Leu Ser Gly Glu
                245                 250                 255

Phe Val Asp Ser Ser Leu Asp Leu Leu Ala His Gly Gly Arg Phe Ile
            260                 265                 270

Glu Met Ser Thr Asp Ile Arg Asp Ala Gly Arg Ile Ala Ala Glu Arg
        275                 280                 285

Pro Gly Thr Thr Tyr Gln Ala Phe His Leu Val Asp Ala Asp Pro Asp
    290                 295                 300

Arg Leu Arg Glu Ile Leu Thr Glu Leu Leu Ala Leu Phe Asp Gln Gly
305                 310                 315                 320

Ile Leu Asp Pro Leu Pro Val Gln Ala Trp Asp Ile Arg Gln Ala Arg
                325                 330                 335

Glu Ala Phe Ser Trp Met Ser Arg Ala Arg His Thr Gly Lys Leu Val
            340                 345                 350

Leu Thr Ile Pro Gln His Ile Asp Pro Asp Gly Thr Val Leu Ile Thr
        355                 360                 365

Gly Gly Ser Gly Gly Leu Ala Gly Val Val Ala Arg His Leu Val Ala
    370                 375                 380

Asp Lys Gly Ala Arg Arg Leu Leu Leu Leu Ser Cys Asp Thr Leu Asp
385                 390                 395                 400

Ala Thr Leu Ala Ala Glu Leu Thr Glu Ser Gly Ala Arg Val Asp Thr
                405                 410                 415

Ala Val Cys Asp Val Ser Asp Arg Ala Ala Leu Ala Gln Val Leu Ala
            420                 425                 430

Gly Val Ser Pro Glu His Pro Leu Thr Ala Ile Val His Ala Gly Gly
        435                 440                 445

Ala Ala Val Ala Asp Glu Ser Arg Gln Leu His His Leu Thr Lys Asn
    450                 455                 460

Arg Asp Leu Ala Ala Phe Val Val Phe Ser Gln Asp Ala Pro Ala Ala
465                 470                 475                 480

Thr Glu Ala Phe Ala Gly Ile Arg Gln Ala Glu Gly Leu Pro Val Thr
                485                 490                 495

Thr Ile Ala Trp Gly Ile Pro Glu Ala Glu Pro Val Val Gly Gln
            500                 505                 510

His Leu Leu Asp Arg Ala Met Ala Ser Ala Asp Arg Ala His Val Ala
        515                 520                 525

Ala Arg Val Asn Thr Ala Gly Leu Arg Ala Leu Ala Ala Asn Ala
    530                 535                 540

Leu Pro Pro Val Leu Lys Asn Leu Val Gly Ala Glu Thr Asp Gly Thr
545                 550                 555                 560

Gly His Gln Asp Trp Ser Arg Arg Phe Met Val Ala Glu Ala Ala Arg
                565                 570                 575

Gln Gln Glu Leu Leu Asp Leu Ile Arg Thr Thr Val Met Glu Ile Leu
            580                 585                 590

Ser Leu Pro Thr Thr Ala Arg Tyr Phe Pro Asp Arg Thr Phe Arg Glu
        595                 600                 605

Asn Gly Ile Asp Ser Leu Thr Ala Val Glu Leu Val Asn Ser Leu Ala
    610                 615                 620
```

```
Lys Thr Thr Gly Leu Arg Leu Ser Ala Thr Met Val Phe Asp Tyr Pro
625                 630                 635                 640

Thr Pro Thr Ala Leu Ala Gly Arg Met Arg Glu Leu
            645                 650

<210> SEQ ID NO 10
<211> LENGTH: 7934
<212> TYPE: PRT
<213> ORGANISM: Streptomyces malaysiensis DSM4137

<400> SEQUENCE: 10

Met Ser Arg Glu Glu Phe Ile Gln Pro Ile His Asp Leu Leu Arg Val
1               5                   10                  15

Asn Ala Glu Arg Leu Gly Asp Lys Ile Ala Tyr Ala Asp Ser Arg Arg
            20                  25                  30

Glu Leu Thr His Ala Glu Leu Arg Thr Arg Thr Gly Arg Ile Ala Gly
        35                  40                  45

His Leu Val Asp Leu Ala Val Glu Arg Gly Asp Arg Val Ala Ile Leu
    50                  55                  60

Leu Gly Asn Arg Val Glu Thr Ile Glu Ser Tyr Leu Ala Ile Ala Arg
65              70                  75                  80

Ala Gly Ala Ile Ala Val Pro Leu Asn Pro Asp Ala Thr Gly Ala Glu
                85                  90                  95

Val Ala His Phe Leu Ala Asp Ser Gly Ala Val Leu Val Ile Thr Asp
            100                 105                 110

Ser Ala His Leu Asp Asp Val Arg Arg Ala Ala Ala Val Thr Val
        115                 120                 125

Val Leu Val Asp Glu Gly Pro Leu Pro Ala Gly Thr Arg Ser Phe Ala
130                 135                 140

Glu Leu Ala Thr Ala Glu Pro Pro Thr Pro Ala Arg Asp Asp Leu Gly
145                 150                 155                 160

Leu Asp Glu Ala Ala Trp Met Leu Tyr Thr Ser Gly Thr Thr Gly Thr
                165                 170                 175

Pro Lys Gly Val Val Ser Thr Gln Gly Ser Gly Leu Trp Ser Ala Ala
            180                 185                 190

Asn Cys Asp Val Pro Ala Trp Glu Leu Thr Glu Asn Asp Val Leu Leu
        195                 200                 205

Trp Pro Ala Pro Leu Phe His Ser Leu Ala His Leu Cys Leu Leu
    210                 215                 220

Ala Thr Thr Ala Val Gly Ala Thr Ala Arg Ile Met Ser Gly Phe Val
225                 230                 235                 240

Ala Gly Glu Val Leu His Glu Leu Glu Glu His Ala Cys Thr Val Leu
                245                 250                 255

Val Gly Val Pro Thr Met Tyr His Tyr Leu Leu Gly Ala Val Gly Glu
            260                 265                 270

Ala Gly Pro Arg Leu Pro Ser Leu Lys Met Gly Leu Val Ala Gly Ala
        275                 280                 285

Val Ser Pro Pro Ala Leu Ile Glu Gly Phe Glu Arg Val Phe Gly Val
    290                 295                 300

Pro Leu Leu Asp Thr Tyr Gly Cys Thr Glu Thr Thr Gly Ser Leu Thr
305                 310                 315                 320

Val Asn Arg Leu Ser Gly Pro Arg Met Pro Gly Ser Cys Gly Gln Ala
                325                 330                 335

Val Pro Gly Ile Ser Leu Arg Phe Val Asp Pro His Thr Gly Ala Glu
            340                 345                 350
```

-continued

Val Ala Glu Gly Glu Gly Glu Leu Trp Ala Ser Gly Pro Ser Leu
            355                 360                 365

Met Ile Gly Tyr His Gly Arg Pro Asp Ala Thr Arg Glu Val Leu Ser
    370                 375                 380

Asp Gly Trp Tyr Arg Thr Gly Asp Leu Ala Arg Arg Ser Glu Thr Gly
385                 390                 395                 400

His Val Thr Ile Thr Gly Arg Val Lys Glu Leu Ile Arg Gly Gly
                405                 410                 415

Glu Asn Ile His Pro Arg Asp Ile Glu Ala Val Ala Leu Glu Leu Pro
                420                 425                 430

Gly Val Arg Asp Ala Ala Ala Gly Lys Gln His Pro Val Leu Gly
            435                 440                 445

Glu Ile Pro Ala Leu Tyr Leu Val Pro Asp Ala Asp Gly Val Asp Ala
                450                 455                 460

Glu Ala Val Leu Ala Ala Cys Arg Glu Lys Leu Ser Tyr Phe Lys Val
465                 470                 475                 480

Pro Glu Glu Ile Tyr Arg Val Asp Ala Ile Pro Arg Thr Leu Ser Gly
                485                 490                 495

Lys Val Lys Arg Ala Ala Leu Thr Glu Ala Pro Ala Glu Leu Leu Ser
            500                 505                 510

Ala Ala Ser Gly Asn Gly Ser Leu Tyr Arg Leu Glu Trp Val Pro Ala
            515                 520                 525

Glu Thr Pro Pro Ala Gly Thr Gly Pro Val Ala Val His Val Thr
            530                 535                 540

Arg Arg Ala Val Ala Thr Gly Pro Ala Asp Leu Pro Asp Gln Glu Gln
545                 550                 555                 560

Ala Ala Thr Trp Asp Ala Leu Arg Gly Glu Gln Thr Gly Pro Gly Gly
                565                 570                 575

Pro Val Leu Ile Asp Leu Asp Gly Ala Asp Ile Asp Asp Ala Arg Leu
                580                 585                 590

Ser Ala Leu Ala Ser Leu Gly Glu Pro Gln Ile Val Val Arg Asp Asp
            595                 600                 605

Thr Pro Leu Val Ala Arg Leu Ala Arg Glu Lys Ser Pro Ala Leu Thr
            610                 615                 620

Ile Pro Gly Glu Arg Ala Trp Val Leu Glu Pro Asp His Ser Gly Val
625                 630                 635                 640

Leu Gln Glu Leu Ala Leu Val Ala Ala Asp Thr Asp Val Arg Pro Leu
                645                 650                 655

Arg Pro Gly Glu Val Arg Ile Glu Val Arg Ala Ala Gly Leu Asn Phe
            660                 665                 670

Arg Asp Val Leu Val Ala Leu Gly Thr Asp Leu Gly Asp Gly Val Phe
            675                 680                 685

Gly Ala Glu Gly Ala Gly Val Val Leu Glu Thr Gly Ser Asp Val Arg
            690                 695                 700

Asp Leu Arg Pro Gly Asp Arg Val Phe Gly Leu Glu Gly Gly His
705                 710                 715                 720

Gly Ser Ile Ala Ile Ala Asp Arg Arg Met Leu Ala Val Ile Pro Glu
                725                 730                 735

Gly Trp Ser Phe Ala Thr Ala Ala Ser Val Pro Glu Val Phe Val Ile
                740                 745                 750

Ala Tyr Tyr Gly Leu Val Asp Leu Ala Gly Leu Arg Ala Gly Glu Ser
            755                 760                 765

```
Val Leu Ile His Ala Ala Thr Gly Gly Val Gly Met Ala Ala Thr Gln
770                 775                 780

Ile Ala Arg His Leu Gly Ala Gln Val Tyr Ala Thr Ala Gly Val Gly
785                 790                 795                 800

Lys Gln His Ile Leu Arg Asp Ala Gly Leu Gly Asp Asp Arg Ile Ala
                805                 810                 815

Asp Ser Arg Thr Thr Asp Phe Arg Glu Ala Phe Arg Asp Ser Thr Gln
                820                 825                 830

Gly Arg Gly Val Asp Val Val Leu Asn Ser Leu Lys Gly Asp Phe Val
                835                 840                 845

Asp Ala Ser Leu Asp Leu Leu Ala Asp Gly Gly Arg Phe Leu Glu Leu
850                 855                 860

Gly Gln Thr Asp Ile Arg Asp Ala Gly Glu Ile Ala Ala Glu Arg Pro
865                 870                 875                 880

Gly Thr Thr Tyr His Ser Phe Thr Arg Met Asn Ala Gly Pro Asp Arg
                885                 890                 895

Leu Arg Glu Ile Ile Ala Glu Leu Leu Ala Leu Phe Glu Gln Gly Val
                900                 905                 910

Leu Arg Pro Ser Pro Val His Thr Trp Asp Ile Arg His Ala Arg Glu
                915                 920                 925

Ala Phe Ser Trp Met Ser Gly Gly Arg His Thr Gly Lys Met Val Leu
930                 935                 940

Thr Met Pro Gln Arg Ile Asp Pro Gly Gly Thr Val Leu Ile Ala Gly
945                 950                 955                 960

Asp Ser Glu Ala Leu Ala Arg Ile Ala Ala Arg His Leu Gly Val Arg
                965                 970                 975

His Leu Leu Leu Asp Arg Gly Val Ala Asp Ala Ala Pro Asp Ala Val
                980                 985                 990

Val Cys Asp Val Ser Asp His Asp Ala Leu Glu Arg Val Leu Ala Asp
                995                 1000                1005

Leu Ser Pro Glu His Pro Leu Thr Ala Val Ile His Thr Gly Gly
    1010                1015                1020

Ala Ala Val Thr Asp Glu Ile Arg Arg Leu His Asp Leu Thr Glu
    1025                1030                1035

Ser Leu Asp Leu Thr Asp Phe Val Val Phe Ser Gln Asp Ala Pro
    1040                1045                1050

Ala Ala Val Glu Ala Phe Ala Arg Ser Arg Arg Ala His Gly Leu
    1055                1060                1065

Pro Val Arg Thr Ile Ala Trp Gly Ile Pro Glu Ala Asp Pro Val
    1070                1075                1080

Val Ala Asp Glu His Leu Leu Gly Arg Ala Leu Ala Ser Ala Glu
    1085                1090                1095

Gln Ala Gln Ile Val Ala Arg Val Asn Thr Ala Gly Leu Arg Ala
    1100                1105                1110

Leu Thr Ala Ala Asn Ala Leu Pro Thr Leu Leu Arg Asn Leu Ile
    1115                1120                1125

Arg Ala Glu Pro Glu Glu Thr Gly Gln Ser Ala Trp Pro His Arg
    1130                1135                1140

Phe Glu Ala Ala Gly Ala Asp Arg Glu Glu Ala Leu Leu Asp Leu
    1145                1150                1155

Ile Arg Ala Asn Val Val Asp Ile Leu Ser Leu Pro Thr Ala Asp
    1160                1165                1170

Arg Tyr Ala Pro Asp Arg Thr Phe Arg Glu Met Gly Ile Asp Ser
```

```
            1175                1180                1185

Leu  Thr  Ala  Val  Gly  Leu  Arg  Asn  Ser  Leu  Ala  Lys  Ala  Thr  Gly
     1190                1195                1200

Leu  Pro  Leu  Pro  Thr  Thr  Met  Val  Phe  Asp  Tyr  Pro  Thr  Pro  Ala
     1205                1210                1215

Val  Leu  Thr  Ala  Arg  Met  Arg  Glu  Leu  Ala  Gly  Glu  Ser  Pro
     1220                1225                1230

Ala  Pro  Ala  Arg  Thr  Ala  Ala  Arg  Ala  Val  Ala  Gln  Asp  Glu  Pro
     1235                1240                1245

Leu  Ala  Ile  Val  Gly  Met  Ala  Cys  Arg  Leu  Pro  Gly  Gly  Val  Ser
     1250                1255                1260

Ser  Pro  Asp  Asp  Leu  Trp  Arg  Leu  Val  Ala  Ala  Gly  Thr  Asp  Ala
     1265                1270                1275

Ile  Ser  Glu  Phe  Pro  Ala  Asp  Arg  Gly  Trp  Asp  Val  Asp  Asn  Leu
     1280                1285                1290

Tyr  Asp  Pro  Asp  Pro  Asp  Ala  Pro  Gly  Lys  Thr  Tyr  Thr  Val  Leu
     1295                1300                1305

Gly  Gly  Phe  Leu  Asp  Gly  Val  Ala  Gly  Phe  Asp  Ala  Ser  Phe  Phe
     1310                1315                1320

Gly  Ile  Ser  Pro  Arg  Glu  Ala  Leu  Ala  Met  Asp  Pro  Gln  Gln  Arg
     1325                1330                1335

Leu  Met  Leu  Glu  Val  Ser  Trp  Glu  Ala  Phe  Glu  His  Ala  Gly  Ile
     1340                1345                1350

Pro  Pro  Arg  Ser  Val  Arg  Gly  Ser  Asp  Ala  Gly  Val  Phe  Met  Gly
     1355                1360                1365

Ala  Phe  Pro  Ser  Gly  Tyr  Asp  Ala  Gly  Leu  Glu  Glu  Phe  Gly  Met
     1370                1375                1380

Thr  Gly  Asp  Ala  Val  Ser  Val  Leu  Ser  Gly  Arg  Val  Ser  Tyr  Phe
     1385                1390                1395

Phe  Gly  Leu  Glu  Gly  Pro  Ala  Ile  Thr  Val  Asp  Thr  Ala  Cys  Ser
     1400                1405                1410

Ser  Ser  Leu  Val  Ala  Leu  His  Gln  Ala  Ser  Ser  Ala  Leu  Arg  Gln
     1415                1420                1425

Gly  Glu  Cys  Ser  Leu  Ala  Leu  Val  Gly  Gly  Val  Thr  Val  Leu  Ala
     1430                1435                1440

Thr  Pro  Gln  Thr  Phe  Val  Glu  Phe  Ser  Arg  Gln  Arg  Gly  Leu  Ala
     1445                1450                1455

Leu  Asp  Gly  Arg  Ser  Lys  Ala  Phe  Ala  Asp  Ala  Ala  Asp  Gly  Ala
     1460                1465                1470

Gly  Trp  Ala  Glu  Gly  Val  Gly  Val  Leu  Val  Val  Glu  Arg  Leu  Ser
     1475                1480                1485

Asp  Ala  Arg  Ala  Lys  Gly  His  Gln  Ile  Trp  Gly  Val  Ile  Arg  Gly
     1490                1495                1500

Ser  Ala  Val  Asn  Gln  Asp  Gly  Ala  Ser  Asn  Gly  Leu  Ser  Ala  Pro
     1505                1510                1515

Asn  Gly  Pro  Ser  Gln  Gln  Arg  Val  Ile  Arg  Gln  Ala  Leu  Ala  Asn
     1520                1525                1530

Ala  Gly  Leu  Ala  Pro  His  Glu  Val  Asp  Val  Val  Glu  Ala  His  Gly
     1535                1540                1545

Thr  Gly  Thr  Thr  Leu  Gly  Asp  Pro  Ile  Glu  Ala  Gln  Ala  Val  Ile
     1550                1555                1560

Ala  Thr  Tyr  Gly  Gln  Asp  Arg  Glu  Gln  Pro  Leu  Leu  Leu  Gly  Ser
     1565                1570                1575
```

```
Leu Lys Ser Asn Val Gly His Thr Gln Ala Ala Ala Gly Val Ser
    1580            1585                1590

Gly Val Ile Lys Met Val Met Ala Leu Gln His Asp Thr Val Pro
    1595            1600                1605

Ala Thr Leu His Val Asp Ala Pro Ser Arg His Val Asp Trp Thr
    1610            1615                1620

Ala Gly Ala Val Glu Leu Val Thr Glu Asn Arg Pro Trp Pro Glu
    1625            1630                1635

Thr Gly Arg Val Arg Arg Ala Gly Val Ser Ser Phe Gly Ile Ser
    1640            1645                1650

Gly Thr Asn Ala His Val Ile Leu Glu Ser Ala Pro Glu Gln Pro
    1655            1660                1665

Val Ser Pro Pro Glu Ala Val Ala Pro Val Val Ala Ser Asp Arg
    1670            1675                1680

Val Pro Leu Val Ile Ser Ala Lys Thr Pro Ala Ala Leu Ala Glu
    1685            1690                1695

Met Glu Asn Arg Leu Arg Ala Tyr Leu Ala Ala Ala Pro Gly Ala
    1700            1705                1710

Asp Pro Arg Ala Val Ala Ser Thr Leu Ala Thr Ala Arg Ser Val
    1715            1720                1725

Phe Glu His Arg Ala Val Leu Leu Gly Glu Asn Thr Ile Thr Gly
    1730            1735                1740

Thr Val Ala Gly Ala Asp Pro Arg Val Val Phe Val Phe Pro Gly
    1745            1750                1755

Gln Gly Trp Gln Gln Leu Gly Met Gly Arg Ala Leu Arg Glu Ser
    1760            1765                1770

Ser Pro Val Phe Ala Ala Arg Met Ala Glu Cys Ala Ala Ala Leu
    1775            1780                1785

Ser Glu Phe Val Asp Trp Asp Leu Phe Thr Met Leu Asp Asp Pro
    1790            1795                1800

Ala Val Ile Asp Arg Ile Asp Val Leu Gln Pro Ala Cys Trp Ala
    1805            1810                1815

Val Met Met Ser Leu Ala Ala Val Trp Gln Ala Ala Gly Val Arg
    1820            1825                1830

Pro Asp Ala Val Ile Gly His Ser Gln Gly Glu Ile Ala Ala Ala
    1835            1840                1845

Cys Val Ala Gly Ala Leu Ser Leu Arg Asp Ala Ala Arg Ile Val
    1850            1855                1860

Ala Leu Arg Ser Gln Leu Leu Ala Arg Glu Met Val Gly His Gly
    1865            1870                1875

Val Met Ala Ala Val Ala Leu Pro Ala Asp Asp Ile Pro Leu Val
    1880            1885                1890

Asp Gly Val Trp Ile Gly Ala Cys Asn Gly Pro Ser Ser Thr Val
    1895            1900                1905

Ile Ser Gly Thr Pro Glu Ala Val Glu Val Val Ala Ala Cys
    1910            1915                1920

Glu Glu Arg Gly Ala Arg Val Arg Arg Ile Thr Ala Ala Val Ala
    1925            1930                1935

Ser His Ser Pro Leu Gly Glu Lys Ile Arg Thr Glu Leu Leu Gly
    1940            1945                1950

Ile Ser Ala Ser Ile Pro Ser Arg Thr Pro Val Val Pro Trp Leu
    1955            1960                1965
```

```
Ser Thr Ala Asp Gly Ile Trp Ile Glu Ala Pro Leu Asp Pro Ala
    1970            1975            1980

Tyr Trp Trp Arg Asn Leu Arg Glu Pro Val Gly Phe Gly Pro Ala
    1985            1990            1995

Val Asp Leu Leu Gln Ala Arg Gly Glu Asn Val Phe Leu Glu Met
    2000            2005            2010

Ser Ala Ser Pro Val Leu Leu Pro Ala Met Asn Asp Ala Val Thr
    2015            2020            2025

Val Ala Thr Leu Arg Arg Asp Asp Gly Thr Pro Asp Arg Met Leu
    2030            2035            2040

Thr Ala Leu Ala Glu Ala His Ala His Gly Val Ile Val Asp Trp
    2045            2050            2055

Pro Arg Val Phe Gly Ser Thr Thr Arg Val Leu Asp Leu Pro Thr
    2060            2065            2070

Tyr Ala Phe Glu His Gln Arg Tyr Trp Ala Val Ser Ala Asp Arg
    2075            2080            2085

Pro Ser Asp Ala Gly His Pro Met Val Glu Thr Val Val Pro Leu
    2090            2095            2100

Pro Ala Ser Gly Gly Val Ala Leu Thr Gly Arg Val Ser Leu Ala
    2105            2110            2115

Thr His Ala Trp Leu Ala Asp His Ala Val Arg Gly Thr Ala Leu
    2120            2125            2130

Leu Pro Gly Thr Ala Phe Val Glu Leu Val Thr Arg Ala Ala Thr
    2135            2140            2145

Glu Val Asp Cys Pro Val Ile Asp Glu Leu Val Ile Glu Ala Pro
    2150            2155            2160

Leu Pro Leu Thr Gln Thr Gly Ala Val Gln Leu Ser Thr Thr Val
    2165            2170            2175

Gly Glu Ala Asp Glu Ser Gly Arg Arg Pro Val Thr Val Phe Ser
    2180            2185            2190

Gln Ala Asp Gly Thr Asp Ala Trp Thr Arg His Val Thr Ala Thr
    2195            2200            2205

Ile Gly Arg Ala Ala Ser Leu Pro Asp Pro Val Ala Trp Pro Pro
    2210            2215            2220

Ala Gln Ala Glu Pro Val Asp Val Thr Gly Phe Tyr Asp Glu Leu
    2225            2230            2235

Ala Ala Ala Gly Tyr Glu Tyr Gly Pro Ala Phe Gln Gly Leu Arg
    2240            2245            2250

Ala Ala Trp Ser Asp Gly Asp Thr Val Tyr Ala Glu Val Val Leu
    2255            2260            2265

Ala Glu Glu Gln Ala His Glu Val Asp Arg Tyr Ala Val His Pro
    2270            2275            2280

Ala Leu Leu Asp Ala Ala Leu Gln Ala Gly Met Val Asn Thr Ala
    2285            2290            2295

Gly Thr Gly Gln Gly Val Arg Leu Pro Phe Ser Trp Asn Gly Ile
    2300            2305            2310

Gln Val His Ser Thr Gly Ala Thr Thr Leu Arg Val Ala Ala Thr
    2315            2320            2325

Pro Leu Ala Asp Gly Trp Ser Val Arg Ala Ala Ala Asp Asn Gly
    2330            2335            2340

Arg Pro Val Ala Thr Ile Gly Ser Leu Val Thr Arg Pro Val Thr
    2345            2350            2355

Thr Asp Met Leu Gly Ser Thr Thr Asp Asp Leu Phe Ala Val Val
```

-continued

```
                2360                2365                2370

Trp Thr Glu Ile Thr Ala Pro Glu Pro Gly Asp Pro Ser Asp Val
        2375                2380                2385

Gly Val Phe Thr Ala Leu Pro Glu Ala Gly Gly Asp Pro Leu Thr
        2390                2395                2400

Gln Thr Arg Ala Leu Thr Ala Gln Val Leu Gln Thr Val Gln Gln
        2405                2410                2415

Trp Leu Ala Gly Glu Asp Arg Pro Leu Val Val Arg Thr Gly Thr
        2420                2425                2430

Asp Leu Ala Ser Ala Ala Val Ser Gly Leu Val Arg Ser Ala Gln
        2435                2440                2445

Ser Glu His Pro Gly Arg Leu Ile Leu Val Glu Ser Asp Asp Glu
        2450                2455                2460

Leu Thr Pro Glu Gln Leu Ala Gly Thr Ala Gly Leu Asp Glu Pro
        2465                2470                2475

Arg Ile Arg Ile Asp Gly Gly His Tyr Glu Val Pro Arg Leu Ala
        2480                2485                2490

Arg Glu Asp Ala Ser Leu Thr Val Pro Glu Asp Arg Ala Trp Leu
        2495                2500                2505

Leu Glu Leu Pro Gly Ser Gly Thr Leu Arg Asp Leu Arg Val Ile
        2510                2515                2520

Pro Thr Asp Thr Ala Glu Arg Pro Leu Arg Trp Gly Glu Val Arg
        2525                2530                2535

Val Gly Val Arg Ala Gly Gly Leu Asn Phe Arg Asp Val Val Val
        2540                2545                2550

Ala Leu Gly Met Val Thr Asp Pro Arg Pro Ala Gly Gly Glu Ala
        2555                2560                2565

Ala Gly Val Val Leu Glu Thr Gly Pro Gly Val Glu Asp Leu Ser
        2570                2575                2580

Pro Gly Asp Arg Val Phe Gly Ile Leu Asp Gly Gly Phe Gly Ser
        2585                2590                2595

Val Ala Ile Ala Asp Arg Arg Leu Leu Ala Val Ile Pro Asp Gly
        2600                2605                2610

Trp Ser Phe Thr Thr Ala Ala Ser Ile Pro Val Val Phe Ala Thr
        2615                2620                2625

Ala Tyr Tyr Gly Leu Val Asp Leu Ala Gly Leu Arg Ala Gly Glu
        2630                2635                2640

Ser Val Leu Ile His Ala Ala Thr Gly Gly Val Gly Met Ala Ala
        2645                2650                2655

Thr Gln Ile Ala Arg His Leu Gly Ala Glu Ile Tyr Gly Thr Ala
        2660                2665                2670

Gly Ile Ala Lys Gln His Val Leu Arg Asp Ala Gly Leu Gly Asp
        2675                2680                2685

Asp Arg Ile Ala Asp Ser Arg Thr Thr Gly Phe Arg Glu Thr Phe
        2690                2695                2700

Arg Asp Ser Thr Gln Gly Arg Gly Val Asp Val Val Leu Asn Ser
        2705                2710                2715

Leu Ser Gly Asp Phe Val Asp Ala Ser Leu Asp Val Leu Ala Glu
        2720                2725                2730

Gly Gly Arg Phe Ile Glu Met Gly Lys Thr Asp Ile Arg Asp Ala
        2735                2740                2745

Glu Gln Ile Thr His Ala Thr Tyr Arg Ala Phe Asp Leu Met Asp
        2750                2755                2760
```

Ala Gly Pro Asp Arg Val Arg Glu Ile Ile Ala Glu Leu Leu Gly
         2765              2770                2775

Leu Phe Glu Gln Gly Val Leu Arg Pro Leu Pro Val Gln Ala Trp
         2780              2785                2790

Asp Ile Arg Gln Ala Arg Asp Ala Phe Thr Trp Met Ser Arg Ala
         2795              2800                2805

Arg His Ile Gly Lys Ile Val Leu Thr Ile Pro Gln Gln Leu Asp
         2810              2815                2820

Pro Asp Gly Thr Val Leu Ile Ser Gly Gly Ser Gly Val Leu Ala
         2825              2830                2835

Gly Ile Leu Ala Arg His Leu Val Ala Glu Arg Gly Val Arg His
         2840              2845                2850

Leu Leu Leu Val Ser Arg Ser Ala Pro Ser Glu Ala Leu Ile Ser
         2855              2860                2865

Glu Leu Thr Ala Leu Gly Ala Gln Val Glu Thr Val Ala Cys Asp
         2870              2875                2880

Val Ser Asp Arg Val Ala Leu Glu Gln Val Leu Asp Gly Val Pro
         2885              2890                2895

Leu Thr Ala Val Phe His Thr Ala Ala Leu Asp Asp Gly Val
         2900              2905                2910

Val Glu Ser Leu Thr Pro Gln Arg Val Asp Thr Val Leu Arg Pro
         2915              2920                2925

Lys Ala Asp Ala Ala Trp Tyr Leu His Glu Leu Thr Arg Asp Ala
         2930              2935                2940

Asp Leu Ala Ala Phe Val Met Tyr Ser Ser Val Ala Gly Ile Met
         2945              2950                2955

Gly Ala Ala Gly Gln Gly Asn Tyr Ala Ala Ala Asn Ala Phe Leu
         2960              2965                2970

Asp Ala Leu Ala Ala His Arg Arg Arg Glu Gly Leu Pro Ala Leu
         2975              2980                2985

Ser Leu Ala Trp Gly Leu Trp Glu Asp Ala Ser Gly Leu Ser Ala
         2990              2995                3000

Gly Leu Thr Glu Thr Asp His Asp Arg Ile Arg Arg Gly Gly Leu
         3005              3010                3015

Glu Ala Ile Ala Ala Glu His Gly Met Arg Leu Phe Asp Thr Ala
         3020              3025                3030

Thr Arg Gln Gly Glu Pro Val Leu Leu Ala Ser Pro Leu Asn Leu
         3035              3040                3045

Thr Arg Gln Gly Glu Val Pro Ala Leu Leu Arg Thr Leu His Arg
         3050              3055                3060

Pro Val Ala Arg Arg Ala Ala Thr Ala Asn Gly Arg Pro Ala Asp
         3065              3070                3075

Leu Thr Pro Glu Ala Leu Leu Lys Leu Val Cys Gly Arg Ala Ala
         3080              3085                3090

Ala Val Leu Gly His Val Asp Ala Asp Ala Val Pro Val Ala Val
         3095              3100                3105

Ala Phe Arg Asp Leu Gly Val Asp Ser Leu Thr Ala Val Glu Leu
         3110              3115                3120

Arg Asn Ser Leu Ala Lys Ala Thr Gly Leu Arg Leu Pro Ala Thr
         3125              3130                3135

Leu Val Phe Asp Tyr Pro Thr Pro Thr Val Leu Ala Gly Arg Leu
         3140              3145                3150

```
Gly Glu Leu Leu Ala Gly Gly Thr Ala Pro Val Arg Ala Ala Val
    3155                3160                3165

Val Arg Arg Ala Ala Ala Ser Asp Glu Pro Leu Ala Ile Val Gly
    3170                3175                3180

Met Ala Cys Arg Leu Pro Gly Gly Val Leu Ser Pro Glu Asp Leu
    3185                3190                3195

Trp Arg Leu Val Glu Ser Gly Asp Ala Ile Ser Gly Phe Pro
    3200                3205                3210

Val Asp Arg Gly Trp Asp Val Glu Asn Leu Phe Asp Pro Asp Pro
    3215                3220                3225

Asp Ala Ala Gly Arg Thr Tyr Ala Val Arg Gly Gly Phe Leu Asp
    3230                3235                3240

Gly Ala Ala Gly Phe Asp Ala Ser Phe Phe Gly Ile Ser Pro Arg
    3245                3250                3255

Glu Ala Gln Ala Met Asp Pro Gln Gln Arg Leu Val Leu Glu Val
    3260                3265                3270

Ser Trp Glu Ala Phe Glu Arg Ala Gly Ile Glu Pro Gly Ser Val
    3275                3280                3285

Arg Gly Ser Asp Thr Gly Val Phe Met Gly Ala Tyr Pro Gly Gly
    3290                3295                3300

Tyr Gly Val Gly Thr Asp Leu Gly Gly Phe Gly Met Thr Ser Val
    3305                3310                3315

Ala Val Ser Val Leu Ala Gly Arg Val Ser Tyr Phe Phe Gly Leu
    3320                3325                3330

Glu Gly Pro Ala Met Thr Val Asp Thr Ala Cys Ser Ser Ser Leu
    3335                3340                3345

Val Ala Leu His Gln Ala Gly Ser Ala Leu Arg Gln Gly Glu Cys
    3350                3355                3360

Ser Leu Ala Leu Val Gly Gly Val Thr Val Met Pro Thr Pro Gln
    3365                3370                3375

Thr Phe Val Glu Phe Ser Arg Gln Arg Gly Leu Ala Ala Asp Gly
    3380                3385                3390

Arg Cys Lys Ala Phe Ala Asp Ala Ala Asp Gly Thr Gly Phe Ser
    3395                3400                3405

Glu Gly Val Gly Val Leu Leu Val Glu Arg Leu Ser Asp Ala Gln
    3410                3415                3420

Ala Arg Gly His Asn Ile Leu Ala Val Val Arg Gly Ser Ala Val
    3425                3430                3435

Asn Gln Asp Gly Ala Ser Asn Gly Leu Thr Ala Pro Asn Gly Pro
    3440                3445                3450

Ser Gln Gln Arg Val Ile Arg Gln Ala Leu Ala Asn Ala Gly Leu
    3455                3460                3465

Ala Gly Ala Glu Val Asp Val Val Glu Ala His Gly Thr Gly Thr
    3470                3475                3480

Thr Leu Gly Asp Pro Ile Glu Ala Gln Ala Val Ile Ala Thr Tyr
    3485                3490                3495

Gly Gln Asp Arg Asp Gln Pro Val Leu Leu Gly Ser Leu Lys Ser
    3500                3505                3510

Asn Leu Gly His Thr Gln Ala Ala Ala Gly Val Ser Gly Val Ile
    3515                3520                3525

Lys Met Val Met Ala Leu Arg His Asp Thr Val Pro Ala Thr Leu
    3530                3535                3540

His Ile Asp Glu Pro Ser Arg His Ile Asp Trp Thr Ala Gly Ala
```

|  | 3545 |  |  | 3550 |  |  |  | 3555 |  |  |
|---|---|---|---|---|---|---|---|---|---|---|
| Val | Glu | Leu | Val | Thr | Glu | Asn | Gln | Ser | Trp | Pro | Glu | Thr | Gly | Arg |
| 3560 | | | | | 3565 | | | | 3570 | |
| Ala | Arg | Arg | Ala | Ala | Val | Ser | Ser | Phe | Gly | Ile | Ser | Gly | Thr | Asn |
| 3575 | | | | | 3580 | | | | 3585 | |
| Ala | His | Val | Ile | Leu | Glu | Ser | Ala | Pro | Ala | Gln | Pro | Val | Pro | Leu |
| 3590 | | | | | 3595 | | | | 3600 | |
| Val | Asp | Thr | Pro | Val | Ser | Ala | Val | Thr | Ala | Gly | Val | Val | Pro | Leu |
| 3605 | | | | | 3610 | | | | 3615 | |
| Pro | Ile | Ser | Ala | Arg | Thr | Val | Pro | Ala | Leu | Ala | Asp | Leu | Glu | Asp |
| 3620 | | | | | 3625 | | | | 3630 | |
| Arg | Leu | Arg | Ala | Tyr | Leu | Thr | Thr | Thr | Pro | Glu | Thr | Asp | Leu | Pro |
| 3635 | | | | | 3640 | | | | 3645 | |
| Ala | Val | Ala | Ser | Thr | Leu | Ala | Val | Thr | Arg | Ser | Val | Phe | Glu | His |
| 3650 | | | | | 3655 | | | | 3660 | |
| Arg | Ala | Val | Leu | Leu | Gly | Glu | Glu | Thr | Val | Thr | Gly | Ile | Ala | Val |
| 3665 | | | | | 3670 | | | | 3675 | |
| Ser | Asp | Pro | Arg | Val | Val | Phe | Val | Phe | Ser | Gly | Gln | Gly | Ser | Gln |
| 3680 | | | | | 3685 | | | | 3690 | |
| Arg | Val | Gly | Met | Gly | Glu | Glu | Leu | Ala | Ala | Ala | Phe | Pro | Leu | Phe |
| 3695 | | | | | 3700 | | | | 3705 | |
| Ala | Arg | Leu | His | Arg | Gln | Val | Trp | Asp | Leu | Leu | Asp | Val | Pro | Asp |
| 3710 | | | | | 3715 | | | | 3720 | |
| Leu | Glu | Val | Asp | Asp | Thr | Gly | Tyr | Val | Gln | Pro | Ala | Leu | Phe | Ala |
| 3725 | | | | | 3730 | | | | 3735 | |
| Leu | Gln | Val | Ala | Leu | Phe | Gly | Leu | Leu | Glu | Ser | Trp | Gly | Val | Arg |
| 3740 | | | | | 3745 | | | | 3750 | |
| Pro | Glu | Ala | Val | Ile | Gly | His | Ser | Val | Gly | Glu | Val | Ala | Ala | Gly |
| 3755 | | | | | 3760 | | | | 3765 | |
| Tyr | Val | Ala | Gly | Val | Trp | Ser | Leu | Glu | Asp | Ala | Cys | Thr | Leu | Val |
| 3770 | | | | | 3775 | | | | 3780 | |
| Ser | Ala | Arg | Ala | Arg | Leu | Met | Gln | Ala | Leu | Pro | Ala | Gly | Gly | Ala |
| 3785 | | | | | 3790 | | | | 3795 | |
| Met | Val | Ala | Val | Pro | Val | Ser | Glu | Glu | Arg | Ala | Arg | Ala | Val | Leu |
| 3800 | | | | | 3805 | | | | 3810 | |
| Val | Asp | Gly | Val | Glu | Ile | Ala | Ala | Val | Asn | Gly | Pro | Ala | Ser | Val |
| 3815 | | | | | 3820 | | | | 3825 | |
| Val | Leu | Ser | Gly | Asp | Glu | Ser | Ala | Val | Leu | Arg | Val | Ala | Glu | Gly |
| 3830 | | | | | 3835 | | | | 3840 | |
| Leu | Gly | Arg | Trp | Thr | Arg | Leu | Ser | Ala | Ser | His | Ala | Phe | His | Ser |
| 3845 | | | | | 3850 | | | | 3855 | |
| Val | Arg | Met | Glu | Pro | Met | Leu | Glu | Glu | Phe | Arg | Gln | Val | Ala | Ser |
| 3860 | | | | | 3865 | | | | 3870 | |
| Glu | Leu | Thr | Tyr | Arg | Glu | Pro | Arg | Ile | Val | Met | Ala | Ala | Gly | Glu |
| 3875 | | | | | 3880 | | | | 3885 | |
| Gln | Val | Thr | Thr | Pro | Glu | Tyr | Trp | Val | Arg | Gln | Val | Arg | Asp | Thr |
| 3890 | | | | | 3895 | | | | 3900 | |
| Val | Arg | Phe | Gly | Asp | Gln | Val | Ala | Ala | Phe | Gly | Asp | Ala | Val | Phe |
| 3905 | | | | | 3910 | | | | 3915 | |
| Leu | Glu | Ile | Gly | Pro | Asp | Arg | Thr | Leu | Ser | Arg | Leu | Ile | Asp | Gly |
| 3920 | | | | | 3925 | | | | 3930 | |
| Ile | Pro | Thr | Leu | His | Gly | Asp | Asp | Glu | Gln | His | Ala | Val | Val | Ala |
| 3935 | | | | | 3940 | | | | 3945 | |

```
Ala Leu Ala Glu Leu His Val Gln Gly Val Pro Ile Asp Trp Ser
3950                3955                3960

Ser Ile Leu Gly Ala Asn Pro Ala Arg Val Leu Asp Leu Pro Thr
    3965                3970                3975

Tyr Ala Phe Gln His Glu Arg Tyr Trp Met Val Ser Thr Gly Arg
3980                3985                3990

Val Gly Gly Glu Gly His Pro Leu Leu Gly Trp Gly Val Pro Val
3995                4000                4005

Ala Glu Ala Gly Gly Arg Leu Tyr Thr Gly Arg Val Ala Arg Gln
4010                4015                4020

Asp Gly Pro Val Leu Ser Val Ala Ala Phe Val Glu Met Ala Phe
4025                4030                4035

Ala Ala Ala Gly Gly Arg Pro Ile Arg Glu Leu Ser Val Asp Ala
4040                4045                4050

Leu Leu Tyr Ile Pro Asp Asp Gly Thr Ala Glu Leu Gln Thr Trp
4055                4060                4065

Val Ser Glu His Arg Leu Thr Ile His Ala Arg Tyr Arg Asp Thr
4070                4075                4080

Glu Pro Trp Thr Arg Leu Ala Thr Ala Ala Leu Asp Thr Thr Ala
4085                4090                4095

Pro Ala Thr Thr His Thr Pro His Pro Gly Leu Ile Thr Thr Ala
4100                4105                4110

Leu Thr Leu Thr Gly Asp Glu Ala Pro Ala Ile Trp His Asp Leu
4115                4120                4125

Thr Leu His Thr Ser Asn Ala Thr Glu Leu His Thr His Ile Thr
4130                4135                4140

Pro Gly Asp Asp Gly Thr Leu Thr Ile Thr Ala Thr Asp Thr Thr
4145                4150                4155

Gly Gln Pro Val Leu Thr Ala His Thr Ala Thr Pro Thr Thr Ile
4160                4165                4170

Pro Val His Thr Pro Thr Thr Pro Ala Asp Asp Leu Leu Thr Leu
4175                4180                4185

Thr Trp Thr Gln Ile Pro Thr Pro Gly Pro Gly Asp Pro Thr Asp
4190                4195                4200

Ile Ala Val Cys Thr Ala Leu Pro Asp Pro Asp Gly Asp Pro Leu
4205                4210                4215

Ala Gln Thr Arg Thr Leu Thr Ala Gln Val Leu Gln Ser Ile Gln
4220                4225                4230

Thr Thr Leu Thr Gly Glu Asp Arg Pro Leu Val Val His Thr Gly
4235                4240                4245

Thr Gly Leu Ala Ser Ala Ala Val Ser Gly Leu Val Arg Ser Ala
4250                4255                4260

Gln Ser Glu His Pro Asp Arg Phe Ile Leu Val Glu Ser Asp Asp
4265                4270                4275

Ser Leu Pro Gln Ala Gln Leu Ala Ala Val Ala Gly Leu Asp Glu
4280                4285                4290

Pro Trp Leu Arg Ile Thr Gly Ser Cys Tyr Glu Val Pro Arg Leu
4295                4300                4305

Thr Lys Thr Thr Thr Ala Thr Ala Thr Ala Val Ser Glu Pro Val
4310                4315                4320

Trp Asn Pro Asp Gly Thr Val Leu Ile Thr Gly Gly Ser Gly Ala
4325                4330                4335
```

```
Leu Ala Gly Ile Leu Ala Arg His Leu Val Thr Glu Arg Gly Val
4340                4345                4350

Arg His Leu Leu Leu Ile Ser Arg Ser Thr Pro Ser Thr Thr Leu
4355                4360                4365

Thr Asp Glu Leu Arg Glu Leu Gly Ala His Val Asp Val Ala Ala
4370                4375                4380

Cys Asp Val Ser Asp Arg Asp Ala Leu Ala Arg Val Leu Asp Gly
4385                4390                4395

Val Asp Leu Thr Ala Val Phe His Thr Ala Gly Ala Leu Asp Asp
4400                4405                4410

Gly Val Val Glu Ser Leu Thr Pro Gln Arg Leu Asp Thr Val Leu
4415                4420                4425

Thr Pro Lys Ala Asp Gly Ala Trp His Leu His Glu Leu Thr Arg
4430                4435                4440

Asp Arg Asp Leu Thr Ala Phe Val Met Tyr Ser Ser Ala Ala Gly
4445                4450                4455

Val Met Gly Ala Ala Gly Gln Gly Asn Tyr Ala Ala Ala Asn Ala
4460                4465                4470

Phe Leu Asp Ala Leu Ala Glu His Arg His Ala Asp Gly Leu Pro
4475                4480                4485

Ala Leu Ser Leu Ala Trp Gly Met Trp Asp Asp Thr Asp Gly Met
4490                4495                4500

Thr Ala Ser Leu Ser Gly Thr Asp His Arg Arg Ile Arg Arg Ser
4505                4510                4515

Gly Gln Arg Ala Ile Thr Ala Glu His Gly Met Arg Leu Leu Asp
4520                4525                4530

Lys Ala Ser Gly Arg Ser Glu Pro Val Leu Val Ala Thr Ala Met
4535                4540                4545

Asn Pro Ile Pro Asp Thr Asp Leu Pro Ala Leu Leu Arg Ser Leu
4550                4555                4560

Tyr Pro Lys Thr Ala Arg Lys Ser Gln Pro Ile Gln Glu Leu Ser
4565                4570                4575

Pro Glu Ala Leu Leu Lys Ile Val Arg Asp Ser Ala Ala Leu Met
4580                4585                4590

Leu Gly His Pro Asn Thr Asp Ala Ile Ala Ala Thr Thr Ala Phe
4595                4600                4605

Arg Asp Leu Gly Val Asp Ser Leu Ile Ala Val Glu Leu Arg Asn
4610                4615                4620

Ser Leu Ala Lys Ala Thr Gly Leu Arg Leu Pro Ala Thr Leu Val
4625                4630                4635

Phe Asp Tyr Pro Thr Pro Val Leu Ala Gly Arg Leu Gly Glu
4640                4645                4650

Leu Leu Ala Gly Val Thr Pro Gln Arg His Ala Thr Val Arg Thr
4655                4660                4665

Gly Thr Ala Ser Asp Glu Pro Leu Ala Ile Val Gly Met Ala Cys
4670                4675                4680

Arg Leu Pro Gly Gly Val Ser Ser Pro Glu Asp Leu Trp Arg Leu
4685                4690                4695

Val Glu Ser Gly Thr Asp Ala Ile Thr Asp Phe Pro Thr Asp Arg
4700                4705                4710

Gly Trp Asp Thr Asp Asp Leu Phe Asp Pro Asp Pro Asp Thr Ala
4715                4720                4725

Gly Lys Thr Tyr Thr Val His Gly Gly Phe Leu Asp Asp Val Ala
```

-continued

```
            4730                4735                4740
Gly Phe Asp Ala Ser Phe Phe Gly Ile Ser Pro Arg Glu Ala Gln
            4745                4750                4755
Ala Met Asp Pro Gln Gln Arg Leu Val Leu Glu Ala Ala Trp Glu
            4760                4765                4770
Ala Phe Glu Arg Ala Gly Ile Glu Pro Gly Ser Val Arg Gly Ser
            4775                4780                4785
Asp Thr Gly Val Phe Met Gly Ala Tyr Pro Gly Gly Tyr Gly Ile
            4790                4795                4800
Gly Ala Asp Leu Gly Gly Phe Gly Ala Thr Ala Gly Ala Gly Ser
            4805                4810                4815
Val Leu Ser Gly Arg Leu Ser Tyr Phe Phe Gly Leu Glu Gly Pro
            4820                4825                4830
Ala Met Thr Val Asp Thr Ala Cys Ser Ser Ser Leu Val Ala Leu
            4835                4840                4845
His Gln Ala Gly Ser Ala Leu Arg Gln Gly Glu Cys Ser Leu Ala
            4850                4855                4860
Leu Val Gly Gly Val Thr Val Ile Ala Asn Pro Gln Ile Phe Val
            4865                4870                4875
Glu Phe Ser Arg Gln Arg Gly Leu Ala Ala Asp Gly Arg Cys Lys
            4880                4885                4890
Ala Phe Ala Asp Ser Ala Asp Gly Thr Gly Trp Ser Glu Gly Val
            4895                4900                4905
Gly Val Leu Leu Val Glu Arg Leu Ser Asp Ala Gln Ala Arg Gly
            4910                4915                4920
His Asn Ile Leu Ala Val Val Arg Gly Ser Ala Val Asn Gln Asp
            4925                4930                4935
Gly Ala Ser Asn Gly Leu Thr Ala Pro Asn Gly Pro Ser Gln Gln
            4940                4945                4950
Arg Val Ile Arg Gln Ala Leu Ala Asn Ala Gly Leu Ala Gly Ala
            4955                4960                4965
Glu Val Asp Val Val Glu Ala His Gly Thr Gly Thr Thr Leu Gly
            4970                4975                4980
Asp Pro Ile Glu Ala Gln Ala Val Ile Ala Thr Tyr Gly Gln Asp
            4985                4990                4995
Arg Asp Gln Ser Val Leu Leu Gly Ser Leu Lys Ser Asn Leu Gly
            5000                5005                5010
His Thr Gln Ala Ala Ala Gly Val Ser Gly Val Ile Lys Met Val
            5015                5020                5025
Met Ala Leu Gln Asn Gly Val Val Pro Arg Thr Leu His Ala Asp
            5030                5035                5040
Gln Pro Ser Arg His Ile Asp Trp Thr Ala Gly Ala Val Glu Leu
            5045                5050                5055
Val Thr Glu Asn Gln Pro Trp Pro Glu Leu Asp Arg Pro Arg Arg
            5060                5065                5070
Ala Ala Val Ser Ala Phe Gly Val Ser Gly Thr Asn Ala His Val
            5075                5080                5085
Ile Leu Glu Ser Ala Pro Asp Gln Pro Val Pro Leu Val Asp Thr
            5090                5095                5100
Pro Val Ser Ala Val Thr Ala Gly Val Val Pro Leu Pro Ile Ser
            5105                5110                5115
Ala Arg Thr Val Pro Ala Leu Ala Asp Leu Glu Asp Gln Leu Arg
            5120                5125                5130
```

```
Ala Tyr Leu Thr Thr Ala Pro Glu Thr Asp Leu Pro Ala Val Ala
    5135                5140                5145

Ser Thr Leu Ala Thr Thr Arg Ser Val Phe Glu His Arg Ala Val
    5150                5155                5160

Leu Leu Gly Glu Asp Thr Val Thr Gly Thr Ala Ile Pro Asp Pro
    5165                5170                5175

Arg Ile Val Phe Val Phe Ser Gly Gln Gly Ser Gln Arg Ala Gly
    5180                5185                5190

Met Gly Glu Glu Leu Ala Ala Ala Phe Pro Leu Phe Ala Arg Leu
    5195                5200                5205

His Arg Gln Val Trp Asp Leu Leu Asp Val Pro Asp Leu Asp Val
    5210                5215                5220

Asp Asp Thr Gly Tyr Val Gln Pro Ala Leu Phe Ala Leu Gln Val
    5225                5230                5235

Ala Leu Phe Gly Leu Leu Glu Ser Trp Gly Val Arg Pro Arg Ala
    5240                5245                5250

Val Ile Gly His Ser Val Gly Glu Val Ala Ala Gly Tyr Val Ala
    5255                5260                5265

Gly Val Trp Ser Leu Glu Asp Ala Cys Ala Leu Val Ser Ala Arg
    5270                5275                5280

Ala Arg Leu Met Gln Ala Leu Pro Ala Gly Gly Ala Met Val Ala
    5285                5290                5295

Val Pro Val Ser Glu Glu Arg Ala Arg Ala Val Leu Val Asp Gly
    5300                5305                5310

Val Glu Ile Ala Ala Val Asn Gly Pro Ala Ser Val Val Leu Ser
    5315                5320                5325

Gly Asp Glu Ala Ala Val Leu Arg Val Ala Glu Gly Leu Gly Arg
    5330                5335                5340

Trp Thr Arg Leu Ser Ala Ser His Ala Phe His Ser Val Arg Met
    5345                5350                5355

Glu Pro Met Leu Glu Glu Phe Arg Gln Val Val Ser Arg Leu Thr
    5360                5365                5370

Tyr Arg Glu Pro Arg Ile Val Met Ala Ala Gly Glu Gln Val Thr
    5375                5380                5385

Thr Pro Glu Tyr Trp Val Arg Gln Val Arg Glu Thr Val Arg Phe
    5390                5395                5400

Gly Asp Gln Val Ala Ala Phe Gly Asp Ala Val Phe Leu Glu Ile
    5405                5410                5415

Gly Pro Asp Arg Thr Leu Ser Arg Leu Ile Asp Gly Ile Ala Met
    5420                5425                5430

Leu Asp Gly Asp Glu Val Arg Ala Ala Val Ala Ala Leu Ala
    5435                5440                5445

Met Met His Val Gln Gly Val Gly Val Asp Trp Pro Ala Ile Leu
    5450                5455                5460

Gly Thr Thr Thr Gly Arg Val Leu Asp Leu Pro Thr Tyr Ala Phe
    5465                5470                5475

Gln His Glu Arg Tyr Trp Met Ala Asn Ala Asp Glu Gly His Pro
    5480                5485                5490

Leu Leu Gly Lys Val Glu His Pro Leu Leu Gly Ser Val Met Ala
    5495                5500                5505

Leu Pro Asn Ser Asp Gly Val Val Leu Thr Gly Arg Ile Ser Leu
    5510                5515                5520
```

| | | | | | | | | | | |
|---|---|---|---|---|---|---|---|---|---|---|
|Ala|Thr|His|Ala|Trp|Leu|Ala|Asp|His|Val|Val|Arg|Gly|Thr|Val|
| |5525| | | |5530| | | |5535| |
|Leu|Leu|Pro|Gly|Thr|Gly|Phe|Val|Glu|Met|Val|Ala|Arg|Ala|Ala|
| |5540| | | |5545| | | |5550| |
|Ala|Glu|Val|Gly|Cys|Gly|Val|Ile|Asp|Glu|Leu|Leu|Ile|Glu|Ala|
| |5555| | | |5560| | | |5565| |
|Pro|Leu|Leu|Leu|Pro|Glu|His|Gly|Gly|Val|His|Leu|Ser|Val|Ser|
| |5570| | | |5575| | | |5580| |
|Val|Gly|Glu|Ala|Asp|Gly|Ala|Gly|Arg|Arg|Pro|Val|Thr|Val|Phe|
| |5585| | | |5590| | | |5595| |
|Ala|Gln|Ala|Asp|Asp|Ala|Glu|Val|Trp|Val|Arg|Gln|Val|Thr|Ala|
| |5600| | | |5605| | | |5610| |
|Thr|Ile|Ser|Pro|Ala|Gly|Pro|Ala|Val|Ser|Leu|Pro|Glu|Leu|Glu|
| |5615| | | |5620| | | |5625| |
|Val|Trp|Pro|Pro|Val|Gln|Ala|Glu|Pro|Val|Asp|Val|Ser|Thr|Phe|
| |5630| | | |5635| | | |5640| |
|Tyr|Glu|Arg|Leu|Ala|Arg|Ala|Asp|Trp|Gln|Trp|Gly|Pro|Ala|Phe|
| |5645| | | |5650| | | |5655| |
|Gln|Gly|Leu|Arg|Ala|Ala|Trp|Arg|Asp|Gly|Asp|Thr|Ile|Tyr|Ala|
| |5660| | | |5665| | | |5670| |
|Glu|Ile|Val|Leu|Ala|Asp|Glu|Glu|Ala|Arg|Glu|Ala|Asp|Gln|Phe|
| |5675| | | |5680| | | |5685| |
|Leu|Val|His|Pro|Ala|Leu|Leu|Asp|Ala|Ala|Leu|Gln|Thr|Ser|Val|
| |5690| | | |5695| | | |5700| |
|Leu|Lys|Thr|Pro|Asp|Asp|Leu|Arg|Leu|Pro|Phe|Ser|Trp|Asn|Gln|
| |5705| | | |5710| | | |5715| |
|Ile|Glu|Phe|His|Ala|Thr|Gly|Ala|Ala|Ile|Leu|Arg|Val|Ala|Val|
| |5720| | | |5725| | | |5730| |
|Thr|Pro|Val|Ala|Asp|Arg|Trp|Ile|Val|His|Ala|Ala|Asp|Ser|Thr|
| |5735| | | |5740| | | |5745| |
|Gly|Arg|Pro|Val|Ala|Thr|Ile|Gly|Ala|Leu|Val|Ser|Arg|Pro|Val|
| |5750| | | |5755| | | |5760| |
|Thr|Ala|Glu|Thr|Leu|Gly|Ser|Asn|Thr|Asp|Asp|Leu|Phe|Ala|Leu|
| |5765| | | |5770| | | |5775| |
|Thr|Trp|Thr|Glu|Ile|Pro|Thr|Pro|Gly|Pro|Gly|Asp|Pro|Ala|Asp|
| |5780| | | |5785| | | |5790| |
|Val|Ala|Val|Cys|Thr|Ala|Leu|Pro|Glu|Pro|Asp|Ser|Asp|Pro|Leu|
| |5795| | | |5800| | | |5805| |
|Thr|Gln|Thr|Arg|Thr|Leu|Thr|Ala|Gln|Val|Leu|Gln|Ser|Ile|Gln|
| |5810| | | |5815| | | |5820| |
|Thr|Ser|Leu|Thr|Gly|Glu|Asp|Arg|Pro|Leu|Val|Val|His|Thr|Gly|
| |5825| | | |5830| | | |5835| |
|Thr|Gly|Leu|Ala|Ser|Ala|Ala|Val|Ser|Gly|Leu|Val|Arg|Ser|Ala|
| |5840| | | |5845| | | |5850| |
|Gln|Ser|Glu|His|Pro|Asp|Arg|Phe|Ile|Leu|Val|Glu|Cys|Asp|Asp|
| |5855| | | |5860| | | |5865| |
|Glu|Thr|Leu|Thr|Pro|Asp|Gln|Leu|Ala|Ala|Thr|Ala|Gly|Leu|Asp|
| |5870| | | |5875| | | |5880| |
|Glu|Pro|Trp|Leu|Arg|Ile|Thr|Gly|Gly|His|Tyr|Glu|Val|Pro|Arg|
| |5885| | | |5890| | | |5895| |
|Leu|Thr|Lys|Thr|Thr|Thr|Ala|Ala|Ala|Thr|Thr|Val|Ser|Glu|Pro|
| |5900| | | |5905| | | |5910| |
|Val|Trp|Asp|Pro|Asp|Gly|Thr|Val|Leu|Ile|Thr|Gly|Gly|Ser|Gly|

-continued

```
                5915                5920                5925

Ala Leu Ala Gly Ile Leu Ala Arg His Leu Val Thr Glu Arg Ser
        5930                5935                5940

Val Arg His Leu Leu Leu Ile Ser Arg Ser Thr Pro Ser Thr Thr
        5945                5950                5955

Leu Ile Asn Glu Leu Arg Glu Leu Gly Ala His Ile Glu Thr Ala
        5960                5965                5970

Ala Cys Asp Val Ser Asp Arg Asp Ala Leu Ala Arg Val Leu Asp
        5975                5980                5985

Gly Val Asp Leu Thr Ala Val Phe His Thr Ala Gly Ala Leu Asp
        5990                5995                6000

Asp Gly Val Val Glu Ser Leu Thr Pro Gln Arg Leu Asp Thr Val
        6005                6010                6015

Leu Met Pro Lys Ala Asp Ala Ala Trp His Leu His Glu Leu Thr
        6020                6025                6030

Arg Asp Arg Asp Leu Ala Ala Phe Val Met Tyr Ser Ser Ala Ala
        6035                6040                6045

Gly Val Met Gly Ala Ala Gly Gln Gly Asn Tyr Ala Ala Ala Asn
        6050                6055                6060

Ala Phe Leu Asp Ala Leu Ala Glu His Arg Arg Ala Asp Gly Leu
        6065                6070                6075

Pro Ala Leu Ser Leu Ala Trp Gly Met Trp Asp Ala Asp Gly
        6080                6085                6090

Met Thr Ala Ser Leu Ser Gly Thr Asp His Arg Arg Ile Arg Arg
        6095                6100                6105

Ser Gly Gln Arg Ala Ile Thr Ala Glu His Gly Met Arg Leu Leu
        6110                6115                6120

Asp Lys Ala Ser Gly Arg Ser Glu Pro Val Leu Val Ala Thr Ala
        6125                6130                6135

Met Asn Pro Ala Gly Glu Gly Glu Val Pro Ala Leu Leu Arg Thr
        6140                6145                6150

Leu His Arg Pro Val Ala Arg Arg Ala Ala Thr Thr Asn Gly Arg
        6155                6160                6165

Pro Ala Asp Leu Thr Pro Glu Ala Leu Leu Lys Val Val Arg Asp
        6170                6175                6180

Ser Ala Ala Val Val Leu Gly His Ala Ser Ala Asp Thr Val Pro
        6185                6190                6195

Ala Ala Thr Ala Phe Gln Glu Leu Gly Leu Asp Ser Leu Ile Ala
        6200                6205                6210

Val Glu Leu Arg Asn Ser Leu Ala Lys Ala Thr Gly Leu Arg Leu
        6215                6220                6225

Pro Ala Thr Met Val Phe Asp Tyr Pro Thr Pro Ala Ala Leu Ala
        6230                6235                6240

Gly Arg Leu Gly Glu Leu Leu Ala Gly Glu Thr Thr Pro Ala Thr
        6245                6250                6255

Ala Ala Val Val Arg Arg Ala Thr Ala Ser Asp Glu Pro Leu Ala
        6260                6265                6270

Ile Val Gly Met Ala Cys Arg Leu Pro Gly Gly Val Ser Ser Pro
        6275                6280                6285

Glu Asp Leu Trp Arg Leu Val Glu Ser Gly Phe Asp Ala Ile Thr
        6290                6295                6300

Gly Phe Pro Thr Asp Arg Gly Trp Asp Val Asp Asn Leu Tyr Asp
        6305                6310                6315
```

```
Pro Asp Pro Asp Ala Pro Gly Lys Ser Thr Thr Leu His Gly Gly
6320                6325                6330

Phe Leu Asp Asp Val Ala Gly Phe Asp Ala Ser Phe Phe Gly Ile
    6335                6340                6345

Ser Pro Arg Glu Ala Val Ala Met Asp Pro Gln Gln Arg Leu Ala
6350                6355                6360

Met Glu Val Ser Trp Glu Ala Phe Glu Arg Ala Gly Ile Glu Pro
6365                6370                6375

Gly Ser Val Arg Gly Ser Asp Thr Gly Val Phe Met Gly Ala Tyr
6380                6385                6390

Pro Gly Gly Tyr Gly Ile Gly Ala Glu Leu Gly Gly Phe Met Leu
6395                6400                6405

Thr Gly Arg Ala Gly Ser Val Leu Ala Gly Arg Val Ser Tyr Phe
6410                6415                6420

Phe Gly Leu Glu Gly Pro Ala Met Thr Val Asp Thr Ala Cys Ser
6425                6430                6435

Ser Ser Leu Val Ala Leu His Gln Ala Ala Tyr Ala Leu Arg Gln
6440                6445                6450

Gly Glu Cys Ser Leu Ala Leu Val Gly Gly Val Thr Val Met Pro
6455                6460                6465

Thr Pro Val Met Phe Val Glu Phe Ser Gln Gln Gln Asn Leu Ala
6470                6475                6480

Asp Asp Gly Arg Cys Lys Ala Phe Ala Asp Ser Ala Asp Gly Thr
6485                6490                6495

Gly Trp Ser Glu Gly Val Gly Val Leu Leu Val Glu Arg Leu Ser
6500                6505                6510

Asp Ala Gln Ala Arg Gly His Asn Ile Leu Ala Val Val Arg Gly
6515                6520                6525

Ser Ala Val Asn Gln Asp Gly Ala Ser Asn Gly Leu Thr Ala Pro
6530                6535                6540

Asn Gly Pro Ser Gln Gln Arg Val Ile Arg Ser Ala Leu Thr Ser
6545                6550                6555

Ala Gly Leu Thr Thr Ala Asp Val Asp Val Val Glu Ala His Gly
6560                6565                6570

Thr Gly Thr Thr Leu Gly Asp Pro Ile Glu Ala Gln Ala Val Leu
6575                6580                6585

Ala Thr Tyr Gly Gln Asp Arg Asp Gln Pro Val Leu Leu Gly Ser
6590                6595                6600

Leu Lys Ser Asn Leu Gly His Thr Gln Ala Ala Ala Gly Val Ser
6605                6610                6615

Gly Val Ile Lys Met Val Met Ala Leu Gln Asn Gly Val Val Pro
6620                6625                6630

Arg Thr Leu His Val Glu Glu Pro Ser Arg His Val Asp Trp Thr
6635                6640                6645

Ala Gly Ala Val Glu Leu Val Thr Glu Asn Gln Ser Trp Pro Glu
6650                6655                6660

Thr Gly Arg Ala Arg Arg Ala Ala Val Ser Ser Phe Gly Phe Ser
6665                6670                6675

Gly Thr Asn Ala His Val Ile Leu Glu Ser Ala Pro Ala Gln Pro
6680                6685                6690

Val Pro Pro Met Asp Thr Pro Ala Pro Ala Val Thr Thr Gly Val
6695                6700                6705
```

```
Val Pro Leu Pro Ile Ser Ala Lys Ser Leu Pro Ala Leu Ala Asp
6710                6715                6720

Leu Glu Asp Gln Leu Arg Ala Tyr Leu Thr Ala Thr Pro Glu Thr
    6725                6730                6735

Asp Leu Pro Ala Val Ala Ser Thr Leu Ala Met Thr Arg Ser Val
        6740                6745                6750

Phe Glu His Arg Ala Val Leu Leu Gly Glu Glu Thr Val Thr Gly
    6755                6760                6765

Thr Ala Ile Pro Asp Pro Arg Ile Val Phe Val Phe Ser Gly Gln
6770                6775                6780

Gly Ser Gln Arg Val Gly Met Gly Glu Glu Leu Ala Ala Ala Phe
    6785                6790                6795

Pro Leu Phe Ala Arg Leu His Arg Gln Val Trp Asp Leu Leu Asp
6800                6805                6810

Val Pro Asp Leu Asp Val Asp Asp Thr Gly Tyr Val Gln Pro Ala
6815                6820                6825

Leu Phe Ala Leu Gln Val Ala Leu Phe Gly Leu Leu Glu Ser Trp
    6830                6835                6840

Gly Val Arg Pro Arg Ala Val Ile Gly His Ser Val Gly Glu Val
6845                6850                6855

Ala Ala Gly Tyr Val Ala Gly Val Trp Ser Leu Glu Asp Ala Cys
6860                6865                6870

Ala Leu Val Ser Ala Arg Ala Arg Leu Met Gln Ala Leu Pro Ala
    6875                6880                6885

Gly Gly Ala Met Val Ala Val Pro Val Ser Glu Glu Arg Ala Arg
6890                6895                6900

Val Ala Leu Val Asp Gly Val Glu Ile Ala Ala Val Asn Gly Pro
    6905                6910                6915

Ala Ser Val Val Leu Ser Gly Asp Glu Ala Ala Val Leu Gln Ile
    6920                6925                6930

Ala Glu Gly Leu Gly Arg Trp Thr Arg Leu Ser Ala Ser His Ala
    6935                6940                6945

Phe His Ser Val Arg Met Glu Pro Met Leu Glu Glu Phe Gly Gln
    6950                6955                6960

Val Ala Ser Glu Leu Thr Tyr Gln Glu Pro Arg Ile Val Met Ala
    6965                6970                6975

Ala Gly Glu Gln Val Thr Thr Pro Glu Tyr Trp Val Arg Gln Val
    6980                6985                6990

Arg Asp Thr Val Arg Phe Gly Asp Gln Val Ala Ala Phe Gly Asp
    6995                7000                7005

Ala Val Phe Leu Glu Ile Gly Pro Asp Arg Thr Leu Ser Arg Leu
    7010                7015                7020

Ile Asp Gly Ile Ala Met Leu Asp Gly Asp Asp Glu Val Arg Ala
    7025                7030                7035

Ala Val Ala Ala Leu Ala Glu Leu His Val Gln Gly Val Pro Ile
    7040                7045                7050

Asp Trp Pro Ala Val Leu Gly Thr Thr Thr Gly Arg Val Leu Asp
    7055                7060                7065

Leu Pro Thr Tyr Ala Phe Gln His Gln Arg Tyr Trp Ala Ala Ser
    7070                7075                7080

Thr Asp Arg Pro Ala Gly Asp Gly His Pro Leu Leu Asp Thr Val
    7085                7090                7095

Val Ala Leu Pro Gly Ala Asp Gly Val Val Leu Thr Gly Arg Ile
```

```
                    7100                 7105               7110
Ser Leu Ala Thr His Ala Trp Leu Ala Asp His Ala Val Arg Gly
    7115             7120               7125

Thr Val Leu Leu Pro Gly Thr Gly Phe Val Glu Met Val Ala Arg
    7130             7135               7140

Ala Ala Ala Glu Val Gly Cys Ala Val Val Asp Glu Leu Val Ile
    7145             7150               7155

Glu Ala Pro Leu Leu Pro Ala Ser Gly Gly Val Gln Leu Ser
    7160             7165               7170

Val Ser Val Gly Glu Ala Asp Asp Ala Gly His Arg Pro Val Thr
    7175             7180               7185

Val His Ser Gln Ala Asp Glu Thr Glu Ala Trp Val Arg His Val
    7190             7195               7200

Thr Ala Thr Ile Ser Pro Ser Gly Pro Ile Val Ser Pro Pro Glu
    7205             7210               7215

Phe Glu Val Trp Pro Pro Ala Gln Ala Glu Pro Val Glu Val Ala
    7220             7225               7230

Arg Phe Tyr Asp Glu Leu Ala Ala Ala Gly Tyr Glu Tyr Gly Ala
    7235             7240               7245

Ala Phe Gln Gly Leu Arg Ala Ala Trp Arg Ala Gly Glu Thr Ile
    7250             7255               7260

Tyr Ala Glu Val Val Leu Ala Glu Asp Gln Thr Leu Glu Ala Ala
    7265             7270               7275

Arg Phe Thr Val His Pro Ala Leu Leu Asp Ala Ala Leu Gln Ala
    7280             7285               7290

Asn Ile Leu Asn Ala Ser Gly Asp Leu Arg Leu Pro Phe Ser Trp
    7295             7300               7305

Gly Gln Val Gln Phe His Thr Thr Gly Ala Ala Thr Leu Arg Val
    7310             7315               7320

Ala Val Thr Pro Val Ala Asp Gly Trp Thr Ile Gln Ala Thr Asp
    7325             7330               7335

Asp Ala Gly Arg Pro Val Ala Thr Val Gly Ser Val Val Ala Arg
    7340             7345               7350

Pro Val Ala Gly Leu Gly Ala Thr Ala Glu Asp Leu Phe Ala Leu
    7355             7360               7365

Thr Trp Asn Glu Ile Pro Ala Pro Gly Gln Gly Gly Arg Thr Val
    7370             7375               7380

Gly Arg Phe Glu Asp Leu Ala Asp Asp Gly Pro Val Pro Glu Leu
    7385             7390               7395

Val Val Phe Thr Ala Leu Pro Asp Val Asp Ala Asp Pro Leu Val
    7400             7405               7410

Arg Thr Arg Ala Leu Thr Ala Arg Val Leu Glu Ala Ile Gln Arg
    7415             7420               7425

Trp Leu Gly Glu Pro Arg Phe Ala Asp Ser Thr Leu Val Val Arg
    7430             7435               7440

Thr Gly Thr Asp Leu Ala Ser Ala Ala Val Ser Gly Leu Val Arg
    7445             7450               7455

Ser Ala Gln Ser Glu His Pro Asp Arg Phe Ile Leu Val Glu Gly
    7460             7465               7470

Asp Ser Ser Pro Val Glu Ile Gly Leu Asp Glu Pro Trp Leu Arg
    7475             7480               7485

Val Asp Gly Gly Arg Tyr Glu Val Pro Arg Leu Ile Arg Leu Ser
    7490             7495               7500
```

Ala Glu Pro Val Gln Glu Ala Ala Trp Asn Pro Asp Gly Met Val
7505                    7510                7515

Leu Ile Thr Gly Gly Thr Gly Ala Leu Ala Gly Ile Leu Ala Arg
7520                    7525                7530

His Leu Val Ala Glu Asn Lys Ala Arg Arg Leu Leu Leu Val Ser
7535                    7540                7545

Arg Ser Val Pro Asp Asp Ala Leu Ile Ser Glu Leu Thr Glu Leu
7550                    7555                7560

Gly Ala Glu Val Gly Thr Ala Val Cys Asp Val Ser Asp Arg Ala
7565                    7570                7575

Ala Leu Ala Arg Val Leu Ala Gly Val Pro Ser Leu Thr Ala Val
7580                    7585                7590

Ile His Thr Ala Gly Val Leu Asp Asp Gly Val Met Glu Ser Leu
7595                    7600                7605

Thr Pro Gln Arg Leu Asp Thr Val Leu Arg Ala Lys Ala Asp Gly
7610                    7615                7620

Ala Trp His Leu His Glu Leu Thr Arg Asp Arg Asp Leu Ala Ala
7625                    7630                7635

Phe Val Met Tyr Ser Ser Ala Ala Gly Leu Met Gly Ser Pro Gly
7640                    7645                7650

Gln Gly Asn Tyr Ala Ala Ala Asn Ala Phe Leu Asp Ala Leu Ala
7655                    7660                7665

Val Glu Arg Arg Ala Glu Gly Leu Pro Ala Leu Ser Leu Ala Trp
7670                    7675                7680

Gly Phe Trp Glu Glu Thr Thr Gly Leu Thr Ala Asn Leu Thr Gly
7685                    7690                7695

Ala Asp Arg Asp Arg Ile Arg Arg Gly Gly Leu Gln Thr Ile Thr
7700                    7705                7710

Ala Glu Arg Gly Met Arg Met Phe Asp Thr Ala Thr Gln His Gly
7715                    7720                7725

Glu Pro Val Leu Leu Ala Ala Pro Ile Ser Pro Val Arg Asp Gly
7730                    7735                7740

Glu Val Pro Ala Leu Leu Arg Ser Leu His Arg Arg Gly Thr Arg
7745                    7750                7755

Arg Gly Thr Thr Ala Asp Ala Ser Ala Gln Trp Leu Ala Gly Leu
7760                    7765                7770

Ala Pro Glu Glu Arg Glu Gly Ala Leu Ile Lys Val Val Arg Asp
7775                    7780                7785

Thr Ala Ala Val Val Leu Gly His Ala Asp Ala Gly Thr Ile Pro
7790                    7795                7800

Val Thr Ala Ala Phe Lys Asp Leu Gly Leu Asp Ser Leu Thr Ala
7805                    7810                7815

Val Glu Leu Arg Asn Ser Leu Ala Lys Ser Thr Gly Leu Arg Leu
7820                    7825                7830

Pro Ala Thr Met Val Phe Asp Tyr Pro Thr Pro Ala Ser Leu Ala
7835                    7840                7845

Ala Arg Leu Asp Asp Leu Met Asn Pro Arg Val Ser Ser Thr Ala
7850                    7855                7860

Leu Leu Ala Glu Leu Asp Arg Ile Glu Gly Met Phe Asp Ser Val
7865                    7870                7875

Thr Phe Asp Glu Lys Gln Ala Ser Leu Val Lys Asp Arg Leu Ser
7880                    7885                7890

Ala Ala Leu Gly Lys Trp Gln Gln Ile Ser Arg Ser Ala Asp Val
    7895                7900                7905

Ala Thr Val Ala Leu Ala Asn Ala Asp Ala Gly Glu Ile Leu Asp
    7910                7915                7920

Phe Ile Asp Arg Glu Phe Gly Asn Pro Thr Ile
    7925                7930

<210> SEQ ID NO 11
<211> LENGTH: 8134
<212> TYPE: PRT
<213> ORGANISM: Streptomyces malaysiensis DSM4137

<400> SEQUENCE: 11

Met Pro Asp His Asp Lys Leu Val Glu Tyr Leu Arg Trp Ala Thr Ala
1               5                   10                  15

Glu Leu His Thr Thr Arg Ala Lys Leu Gln Ala Ala Thr Glu Ala Gly
                20                  25                  30

Thr Gln Pro Leu Ala Ile Val Gly Met Ala Cys Arg Leu Pro Gly Gly
            35                  40                  45

Val Ser Ser Pro Glu Asp Leu Trp Arg Leu Val Glu Ser Gly Thr Asp
    50                  55                  60

Ala Ile Ser Gly Phe Pro Val Asp Arg Gly Trp Asp Val Asp Gly Leu
65                  70                  75                  80

Tyr Asp Pro Asp Pro Asp Val Pro Gly Lys Ser Tyr Thr Val Glu Gly
                85                  90                  95

Gly Phe Leu Asp Ala Val Thr Gly Phe Asp Ala Pro Phe Phe Gly Ile
            100                 105                 110

Ser Pro Arg Glu Ala Leu Ala Met Asp Pro Gln Gln Arg Leu Val Leu
        115                 120                 125

Glu Ala Ser Trp Glu Ala Phe Glu Arg Ala Gly Ile Glu Pro Gly Ser
    130                 135                 140

Val Arg Gly Ser Asp Thr Gly Val Phe Met Gly Ala Phe Pro Gly Gly
145                 150                 155                 160

Tyr Gly Thr Gly Ala Asp Leu Gly Gly Phe Gly Met Thr Gly Gly Ala
                165                 170                 175

Ala Ser Val Leu Ser Gly Arg Val Ser Tyr Phe Phe Gly Leu Glu Gly
            180                 185                 190

Pro Ala Met Thr Val Asp Thr Val Cys Ser Ser Ser Leu Val Ala Leu
        195                 200                 205

His Gln Ala Gly Tyr Ala Leu Arg His Gly Glu Cys Ser Leu Ala Leu
    210                 215                 220

Val Gly Gly Val Thr Val Met Ser Thr Pro Gln Thr Phe Val Glu Phe
225                 230                 235                 240

Ser Arg Gln Arg Gly Leu Ala Ala Asp Gly Arg Cys Lys Ala Phe Ala
                245                 250                 255

Asp Asn Ala Asp Gly Thr Gly Trp Ser Glu Gly Val Gly Val Leu Leu
            260                 265                 270

Val Glu Arg Leu Ser Asp Ala Gln Ala Arg Gly His Asn Ile Leu Ala
        275                 280                 285

Val Val Arg Gly Ser Ala Val Asn Gln Asp Gly Ala Ser Asn Gly Leu
    290                 295                 300

Thr Ala Pro Asn Gly Pro Ser Gln Gln Arg Val Ile Arg Gln Ala Leu
305                 310                 315                 320

Ala Asn Ala Gly Leu Thr Gly Ala Asp Val Asp Val Val Glu Ala His
                325                 330                 335

```
Gly Thr Gly Thr Thr Leu Gly Asp Pro Ile Glu Ala Gln Ala Val Ile
            340                 345                 350

Ala Thr Tyr Gly Arg Asp Arg Asp Gln Pro Val Leu Leu Gly Ser Leu
        355                 360                 365

Lys Ser Asn Leu Gly His Thr Gln Ala Ala Gly Val Ser Gly Val
370                 375                 380

Ile Lys Met Val Met Ala Leu Gln Asn Gly Val Val Pro Arg Thr Leu
385                 390                 395                 400

His Ile Glu Glu Pro Ser Arg His Val Asp Trp Thr Ala Gly Ala Val
                405                 410                 415

Gln Leu Val Thr Glu Asn Arg Pro Trp Pro Glu Leu Gly Arg Ala Arg
            420                 425                 430

Arg Ala Ala Val Ser Ser Phe Gly Leu Ser Gly Thr Asn Ala His Val
        435                 440                 445

Ile Leu Glu Ser Ala Pro Asp Gln Pro Pro Ala Pro Thr Thr Asp Thr
450                 455                 460

Pro Val Ser Ala Val Thr Ala Gly Val Val Pro Leu Pro Ile Ser Ala
465                 470                 475                 480

Lys Thr Val Pro Ala Leu Ala Asp Leu Glu Asp Arg Leu Arg Thr Tyr
            485                 490                 495

Leu Thr Thr Thr Pro Asp Thr Asp Leu Pro Ala Val Ala Ser Thr Leu
            500                 505                 510

Ala Thr Thr Arg Ser Leu Phe Glu His Arg Ala Val Leu Leu Gly Glu
        515                 520                 525

Asp Thr Val Thr Gly Thr Ala Ile Pro Asp Pro Arg Val Val Phe Val
    530                 535                 540

Phe Pro Gly Gln Gly Trp Gln Trp Gln Gly Met Gly Ser Ala Leu Leu
545                 550                 555                 560

Thr Ser Ser Thr Val Phe Ala Glu Arg Met Ala Glu Cys Ala Ala Ala
            565                 570                 575

Leu Ser Glu Phe Val Asp Trp Asp Leu Leu Thr Val Leu Asp Asp Pro
        580                 585                 590

Ser Val Val Asp Arg Val Asp Val Gln Pro Ala Cys Trp Ala Val
    595                 600                 605

Met Ile Ser Leu Ala Ala Val Trp Gln Ala Ala Gly Ile His Pro Asp
610                 615                 620

Ile Val Leu Gly His Ser Gln Gly Glu Ile Ala Ala Cys Leu Ala
625                 630                 635                 640

Gly Ala Ile Ser Leu Pro Asp Ala Ala Arg Ile Val Ala Gln Arg Ser
            645                 650                 655

Gln Leu Ile Ala His Gln Leu Thr Gly His Gly Ala Met Ala Ser Ile
        660                 665                 670

Ser Leu Pro Ala Asp Asp Ile Pro Thr Thr Asp Lys Val Trp Ile Ala
    675                 680                 685

Ala His Asn Gly Thr Ser Thr Val Ile Ala Gly Asp Pro Gln Ala Val
        690                 695                 700

Glu Ala Val Leu Ala Thr Cys Glu Thr Arg Gly Ala Arg Val Arg Lys
705                 710                 715                 720

Ile Asn Val Asp Tyr Ala Ser His Thr Pro His Val Glu Gln Ile Arg
                725                 730                 735

Thr Glu Leu Leu Asp Ile Thr Thr Gly Ile Glu Ala His Thr Pro Ala
            740                 745                 750
```

```
Val Pro Trp Leu Ser Thr Thr Asp Asn Thr Trp Ile Asp Gln Pro Leu
        755                 760                 765

Asp Pro Thr Tyr Trp Tyr Arg Asn Leu Arg Glu Pro Val Arg Phe Gly
770                 775                 780

Pro Ala Ile Asp Leu Leu Gln Thr Gln Asp Asn Asn Leu Phe Ile Glu
785                 790                 795                 800

Ile Ser Ala Ser Pro Val Leu Gln Thr Met Asp Asn Ala Ala Thr
                805                 810                 815

Val Ala Thr Leu Arg Arg Asp Glu Asp Thr Thr Gln Arg Leu Leu Thr
                820                 825                 830

Ala Phe Ala Glu Ala His Val His Gly Ala Thr Ile Asp Trp Pro Thr
        835                 840                 845

Val Leu Asp Thr Thr Thr Thr Pro Val Leu Asp Leu Pro Thr Tyr Pro
        850                 855                 860

Phe Gln Arg Gln Arg Tyr Trp Ala Thr Ser Asn Gly Arg Ser Thr Gly
865                 870                 875                 880

Gln Gly His Pro Leu Leu Glu Thr Val Val Ala Leu Pro Gly Thr Asp
                885                 890                 895

Gly Val Ala Leu Thr Gly Arg Ile Ser Leu Ala Thr His Pro Trp Leu
        900                 905                 910

Thr Asp His Thr Val Arg Gly Thr Val Leu Leu Pro Gly Thr Ala Phe
        915                 920                 925

Val Glu Leu Val Thr Arg Ala Ala Thr Glu Val Asn Cys Gln Ile Ile
        930                 935                 940

Asp Glu Leu Ile Ile Glu Ala Pro Leu Pro Leu Pro Gln Thr Asp Gly
945                 950                 955                 960

Val Gln Leu Ser Val Thr Val Gly Glu Ala Asp Glu Ala Gly His Arg
                965                 970                 975

Pro Val Thr Val Tyr Ser Gln Thr Asp Glu Ser Asp Asp Trp Ile Gln
                980                 985                 990

His Val Thr Ala Thr Ile Gly Pro Gly Ala Ser Leu Pro Glu Thr Ala
                995                 1000                1005

Ala Trp Pro Pro Ala His Ala Glu Pro Val Asn Val Thr Gly Leu
    1010                1015                1020

Tyr Asp Asn Leu Ala Ala Ala Gly Tyr Glu Tyr Gly Pro Ala Phe
    1025                1030                1035

Gln Gly Leu Gln Ala Ala Trp Arg Ala Gly Asp Thr Val Tyr Ala
    1040                1045                1050

Glu Val Thr Leu Ala Glu Glu Gln Ala Gln Glu Thr Ala Arg Phe
    1055                1060                1065

Thr Met His Pro Ala Leu Leu Asp Ala Ala Leu His Thr Ile Ala
    1070                1075                1080

Leu His Asp Thr Gly Asp Leu His Leu Pro Phe Ser Trp Thr Arg
    1085                1090                1095

Val Gln Phe His Gly Thr Gly Ala Ala Thr Leu Arg Val Ala Val
    1100                1105                1110

Thr Pro Ala Ala Asp Gly Trp Asn Ile Arg Ala Thr Asp Asp Thr
    1115                1120                1125

Gly Arg Ala Val Ala Thr Ile Gly Ser Leu Val Thr Arg Pro Met
    1130                1135                1140

Ala Ala Glu Thr Thr Asp Asp Leu Leu Ala Leu Thr Trp Thr Glu
    1145                1150                1155

Ile Pro Ala Pro Glu Pro Val Asp Pro Thr Asp Val Val Val Phe
```

```
          1160                1165                1170

Thr Ala Leu Pro Asp Thr Val Glu Asp Val Pro Ala Gln Thr Arg
          1175                1180                1185

Ala Leu Thr Thr Arg Val Leu His Thr Ile Gln Glu Trp Leu Ala
          1190                1195                1200

Asp Asp Asp Arg Thr Leu Ile Val Arg Thr Gly Thr Asp Leu Ala
          1205                1210                1215

Ser Ala Ala Val Ser Gly Leu Val Arg Ser Ala Gln Ser Glu His
          1220                1225                1230

Pro Gly Arg Phe Ile Leu Val Glu Ser Ala Asp Glu Ala Leu Thr
          1235                1240                1245

Gln Glu Gln Leu Ala Ala Thr Ala Gly Leu Asp Glu Pro Arg Leu
          1250                1255                1260

Arg Ile Thr Gly Gly Arg Tyr Glu Val Pro Arg Leu Thr Arg Glu
          1265                1270                1275

Asp Thr Ala Leu Ala Val Pro Thr Asp Arg Ala Trp Leu Leu Glu
          1280                1285                1290

Gln Pro Arg Ser Gly Ser Leu Glu Asp Leu Ala Leu Leu Pro Thr
          1295                1300                1305

Asp Ala Ala Glu Arg Pro Leu Gln Ala Gly Glu Val Arg Ile Gly
          1310                1315                1320

Val Arg Ala Ala Gly Met Asn Phe Arg Asp Val Val Val Ala Leu
          1325                1330                1335

Gly Met Val Thr Asp Thr Arg Leu Ala Gly Gly Glu Ala Ala Gly
          1340                1345                1350

Val Val Leu Glu Val Gly Thr Asp Val Asn Asp Phe Arg Pro Gly
          1355                1360                1365

Asp Arg Val Phe Gly Ile Leu Glu Gly Gly Phe Gly Ser Val Ala
          1370                1375                1380

Ile Cys Asp His Arg Thr Leu Ala Val Ile Pro Asp Gly Trp Ser
          1385                1390                1395

Phe Thr Thr Ala Ala Ser Val Pro Ile Ala Phe Ala Thr Ala Tyr
          1400                1405                1410

Tyr Gly Leu Val Asp Leu Ala Gly Leu Arg Ala Gly Glu Ser Val
          1415                1420                1425

Leu Ile His Ala Ala Thr Gly Gly Val Gly Ile Ala Ala Thr Gln
          1430                1435                1440

Ile Ala Arg His Leu Gly Ala Glu Ile Tyr Gly Thr Ala Ser Val
          1445                1450                1455

Gly Lys Gln His Val Leu Arg Asp Ala Gly Leu Ala Asp Asp Arg
          1460                1465                1470

Ile Ala Asp Ser Arg Thr Thr Asp Phe Arg Asp Thr Phe Arg Asp
          1475                1480                1485

Gly Thr Gln Gly Arg Gly Val Asp Val Val Leu Asn Ser Leu Arg
          1490                1495                1500

Gly Glu Phe Ile Asp Ala Ser Leu Asp Leu Leu Val Asp Gly Gly
          1505                1510                1515

Arg Phe Ile Glu Met Gly Lys Thr Asp Ile Arg Asp Ala Ala Gln
          1520                1525                1530

Ile Pro Asp Ala Thr Tyr His Ala Phe Asp Leu Met Asp Ala Gly
          1535                1540                1545

His Asp Arg Leu Arg Glu Ile Met Thr Glu Leu Leu Ala Leu Phe
          1550                1555                1560
```

```
Glu Gln Gly Val Leu His Pro Met Pro Val His Ala Phe Asp Ile
    1565            1570            1575

Arg Gln Ala Arg Glu Ala Phe Ser Trp Met Ser Arg Ala Arg His
    1580            1585            1590

Ile Gly Lys Leu Val Leu Thr Ile Pro Gln Pro Ile Asp Pro Asp
    1595            1600            1605

Gly Thr Val Leu Ile Thr Gly Gly Ser Gly Val Leu Ala Gly Ile
    1610            1615            1620

Val Ala Arg Tyr Leu Val Thr Glu Asn Arg Ala Arg His Leu Leu
    1625            1630            1635

Leu Leu Ser Arg Ser Ala Pro Ser Ala Ser Leu Ile Asp Glu Leu
    1640            1645            1650

Thr Ala Leu Gly Ala His Val Asp Val Ala Ala Cys Asp Val Ala
    1655            1660            1665

Asp Arg Ala Ala Leu Ala Glu Ile Leu Asp Gly Val Asp Leu Thr
    1670            1675            1680

Ala Val Ile His Thr Ala Gly Ala Leu Asp Asp Gly Val Val Glu
    1685            1690            1695

Ser Leu Thr Pro Gln Arg Leu Asp Thr Val Leu Thr Pro Lys Ala
    1700            1705            1710

Asp Gly Ala Trp His Leu His Glu Leu Thr Arg Asp Arg Asp Leu
    1715            1720            1725

Ala Ala Phe Ile Val Tyr Ser Ser Ala Ala Gly Val Leu Gly Ala
    1730            1735            1740

Ala Gly Gln Gly Asn Tyr Ala Ala Ala Asn Ala Phe Leu Asp Ala
    1745            1750            1755

Leu Ala Val His Arg Arg Leu Glu Gly Leu Pro Gly Leu Ser Leu
    1760            1765            1770

Ala Trp Gly Leu Trp Glu Asp Ala Ser Gly Leu Thr Ala Asp Leu
    1775            1780            1785

Thr Asp Ala Asp Arg Asp Arg Ile Arg Arg Ser Gly Gln Arg Ala
    1790            1795            1800

Ile Thr Ala Ala Tyr Gly Met Arg Met Leu Asp Ala Ala Thr Arg
    1805            1810            1815

Gln Ser Glu Ala Ile Leu Leu Ala Ala Pro Ile Ser Pro Ile Gln
    1820            1825            1830

Asp Gly Asp Val Pro Ala Ile Leu Arg Ser Leu His Arg Arg Val
    1835            1840            1845

Gly Arg Arg Ala Ser Val Ala His Gly His Pro Ala Asp Leu Thr
    1850            1855            1860

Pro Glu Ala Leu Leu Lys Val Val Arg Asp Ser Ala Ala Met Val
    1865            1870            1875

Leu Gly His Thr Asn Ala Asp Thr Val Pro Thr Ala Thr Ala Phe
    1880            1885            1890

Gln Glu Leu Gly Leu Asp Ser Leu Thr Ala Val Glu Leu Arg Asn
    1895            1900            1905

Ser Leu Thr Lys Ala Thr Gly Leu Arg Leu Pro Ala Thr Met Ala
    1910            1915            1920

Phe Asp Tyr Pro Thr Pro Asp Ala Leu Ala Ala Arg Leu Gly Glu
    1925            1930            1935

Leu Leu Ala Gly Glu Ala Ala Pro Lys Ala Ala Ala Ala Val Arg
    1940            1945            1950
```

Arg Ala Thr Ala Ser Asp Glu Pro Leu Ala Ile Val Gly Met Ala
1955                1960                1965

Cys Arg Leu Pro Gly Gly Val Ser Ser Pro Glu Asp Leu Trp Arg
1970                1975                1980

Leu Val Glu Ser Gly Thr Asp Ala Ile Thr Asp Phe Pro Thr Asp
1985                1990                1995

Arg Gly Trp Asp Thr Asp Thr Leu Phe Asp Pro Asp Pro Asp Thr
2000                2005                2010

Pro Gly Lys Thr Tyr Thr Val His Gly Gly Phe Leu Asn Asp Val
2015                2020                2025

Ala Gly Phe Asp Ala Pro Phe Phe Gly Ile Ser Pro Arg Glu Ala
2030                2035                2040

Val Ala Met Asp Pro Gln Gln Arg Leu Val Leu Glu Ser Ser Trp
2045                2050                2055

Glu Ala Phe Glu Arg Ala Gly Ile Gln Pro Asp Ser Ile Arg Gly
2060                2065                2070

Ser Asp Thr Gly Val Phe Met Gly Ala Tyr Pro Asp Gly Tyr Gly
2075                2080                2085

Ile Gly Ala Asp Leu Ala Gly Phe Gly Val Thr Ala Gly Ala Gly
2090                2095                2100

Ser Val Leu Ser Gly Arg Val Ser Tyr Phe Phe Gly Leu Glu Gly
2105                2110                2115

Pro Ala Met Thr Val Asp Thr Ala Cys Ser Ser Ser Leu Val Ala
2120                2125                2130

Leu His Gln Ala Ala Tyr Ala Leu Arg Gln Gly Glu Cys Ser Leu
2135                2140                2145

Ala Leu Val Gly Gly Val Thr Val Met Pro Ser Pro Arg Thr Phe
2150                2155                2160

Ile Glu Phe Ser Arg Gln Arg Gly Leu Ala Ala Asp Gly Arg Ser
2165                2170                2175

Lys Ala Phe Ala Asp Ala Ala Asp Gly Thr Gly Phe Ser Glu Gly
2180                2185                2190

Val Gly Val Leu Leu Val Glu Arg Leu Ser Asp Ala Gln Ala Lys
2195                2200                2205

Gly His Asn Ile Leu Ala Leu Val Arg Ser Ser Ala Val Asn Gln
2210                2215                2220

Asp Gly Ala Ser Asn Gly Leu Thr Ala Pro Asn Gly Pro Ser Gln
2225                2230                2235

Gln Arg Val Ile Gln Ser Ala Leu Ala Gly Ala Gly Leu Thr Ser
2240                2245                2250

Ala Asp Val Asp Val Val Glu Ala His Gly Thr Gly Thr Thr Leu
2255                2260                2265

Gly Asp Pro Ile Glu Ala Gln Ala Val Leu Ala Thr Tyr Gly Gln
2270                2275                2280

Asp Arg Asp Gln Pro Val Leu Leu Gly Ser Leu Lys Ser Asn Leu
2285                2290                2295

Gly His Thr Gln Ala Ala Ala Gly Val Ser Gly Val Ile Lys Met
2300                2305                2310

Val Met Ala Leu Gln His Asn Thr Val Pro Ala Thr Leu His Val
2315                2320                2325

Asp Ala Pro Ser Arg His Val Asp Trp Thr Ala Gly Ala Val Arg
2330                2335                2340

Leu Ala Thr Glu Asn Gln Pro Trp Pro Glu Thr Asn Arg Pro Arg

```
                 2345                2350                2355

Arg Ala Gly Val Ser Ser Phe Gly Val Ser Gly Thr Asn Ala His
        2360                2365                2370

Val Ile Leu Glu Gln Ala Pro Ala Ala Ser Pro Val Glu Pro Val
        2375                2380                2385

Asp Thr Thr Asp Val Val Ile Pro Leu Val Val Ser Ala Arg Ser
        2390                2395                2400

Ser Gly Ser Leu Ser Asp Gln Ala Asp Arg Leu Ala Ala Leu Val
        2405                2410                2415

Gly Ser Pro Asp Ala Pro Ala Leu Thr Ser Leu Ala Asp Ala Leu
        2420                2425                2430

Leu Thr Arg Arg Thr Val Phe Ser Gln Arg Ala Val Val Val Ala
        2435                2440                2445

Gly Ser His Glu Gln Ala Ala Ala Gly Leu Arg Ala Leu Ala Ser
        2450                2455                2460

Gly Asp Ser His Pro Ala Leu Val Thr Gly Ala Ala Gly Pro Ala
        2465                2470                2475

Arg Gly Val Val Leu Val Phe Pro Gly Gln Gly Ser Gln Trp Ala
        2480                2485                2490

Gly Met Gly Ala Glu Leu Leu Asp Thr Ser Pro Val Phe Ala Ala
        2495                2500                2505

Arg Ile Ala Glu Cys Ala Glu Ala Leu Arg Pro Trp Val Asp Trp
        2510                2515                2520

Ser Leu Asp Glu Val Leu Arg Gly Asp Ala Ser Ala Asp Val Leu
        2525                2530                2535

Gly Arg Val Asp Val Val Gln Pro Ala Ser Phe Ala Val Met Val
        2540                2545                2550

Gly Leu Ala Ala Val Trp Glu Ser Ala Gly Val Arg Pro Asp Ala
        2555                2560                2565

Val Leu Gly His Ser Gln Gly Glu Ile Ala Ala Ala Tyr Val Ala
        2570                2575                2580

Gly Ala Leu Ser Leu Thr Asp Ala Ala Lys Ile Val Ala Val Arg
        2585                2590                2595

Ser Arg Leu Ile Ala Ala Arg Leu Ala Gly Arg Gly Gly Met Ala
        2600                2605                2610

Ser Val Ala Leu Ala Pro Asp Glu Ala Ala Ala Lys Leu Gly Arg
        2615                2620                2625

Thr Glu Leu Ala Ala Val Asn Gly Pro Ala Ser Val Val Ile Ala
        2630                2635                2640

Gly Asp Ala Glu Ala Leu Asp Glu Thr Leu Ala Met Leu Glu Gly
        2645                2650                2655

Glu Ala Val Arg Val Arg Arg Val Ala Val Asp Tyr Ala Ser His
        2660                2665                2670

Thr Pro His Val Glu Glu Leu Glu Gln Ser Met Ala Glu Ala Leu
        2675                2680                2685

Ala Asp Val Arg Ser Arg Gln Pro Arg Val Gly Phe Leu Ser Thr
        2690                2695                2700

Val Thr Gly Asp Trp Val Thr Glu Ala Gly Ala Leu Asp Gly Gly
        2705                2710                2715

Tyr Trp Tyr Arg Asn Leu Arg Gln Pro Val Arg Phe Gly Pro Ala
        2720                2725                2730

Val Ala Ser Leu Ala Glu Ala Gly Tyr Thr Val Phe Val Glu Ala
        2735                2740                2745
```

```
Ser Ala His Pro Val Leu Val Gln Pro Val Ala Glu Thr Leu Asp
    2750                2755            2760

Arg Thr Asp Ala Val Val Thr Gly Thr Leu Arg Arg Gln Asp Gly
    2765                2770            2775

Gly Leu Pro Arg Leu Leu Thr Ser Met Ala Glu Leu Phe Val Gly
    2780                2785            2790

Gly Val Pro Val Asn Trp Pro Val Leu Leu Pro Ala Gly Ala Val
    2795                2800            2805

Arg Gly Trp Val Asp Leu Pro Thr Tyr Ala Phe Asp His Gln Arg
    2810                2815            2820

Tyr Trp Leu Glu Asn Arg Val Ala Thr Asp Ala Ala Ala Leu Gly
    2825                2830            2835

Leu Ala Gly Ala Asp His Pro Leu Leu Gly Ala Ile Val Ala Val
    2840                2845            2850

Pro Gln Ser Gly Gly Val Ala Met Thr Ser Arg Leu Ser Pro Arg
    2855                2860            2865

Asn His Pro Trp Leu Ala Glu His Thr Leu Gly Gly Val Pro Thr
    2870                2875            2880

Val Pro Thr Ser Val Leu Val Glu Leu Ala Val Arg Ala Gly Asp
    2885                2890            2895

Glu Val Gly Cys Gly Val Val Glu Glu Leu Thr Val Asp Ala Pro
    2900                2905            2910

Leu Leu Leu Pro Glu Arg Gly Gly Val Arg Val Gln Val Ile Val
    2915                2920            2925

Gly Ala Thr Asp Ala Asn Gly Gln Arg Gly Leu Asp Ile Phe Ser
    2930                2935            2940

Ala Pro Glu Asp Thr Gly Gln Glu Ala Trp Thr Arg His Ala Thr
    2945                2950            2955

Gly Thr Leu Ala Pro Gly Gly Asp Ile Ala Ala Asp Val Asp Leu
    2960                2965            2970

Ser Ala Trp Pro Pro Ala Asn Ala Gln Pro Val Asp Val Thr Asp
    2975                2980            2985

Gly Tyr Asp Leu Leu Glu Arg Ala Gly Tyr Gly Tyr Gly Pro Ala
    2990                2995            3000

Phe Gln Gly Val Arg Ala Ile Trp Arg Arg Gly Glu Glu Leu Phe
    3005                3010            3015

Ala Glu Val Ala Leu Glu Pro Glu Leu Thr Asp Thr Ala Ala Arg
    3020                3025            3030

Phe Gly Leu His Pro Ala Leu Leu Asp Ala Ala Trp His Pro Glu
    3035                3040            3045

Leu Arg Asp Glu Val Ala Glu Thr Ser Pro Asp Gly Arg Arg Trp
    3050                3055            3060

Trp Ser Gln Pro Ser Arg Trp Ala Gly Leu Arg Leu His Thr Ala
    3065                3070            3075

Gly Ala Thr Val Leu Arg Val Arg Leu Ala Pro Val Asp Ala Asp
    3080                3085            3090

Ser Met Ser Leu Gln Ala Ala Asp Glu Thr Gly Asp Pro Val Leu
    3095                3100            3105

Thr Val Asp Ser Leu Ser Leu Cys Ala Val Ser Ala Asp Gln Leu
    3110                3115            3120

Thr Thr Ala Glu Ser Ser Asp Asp Ala Leu Phe Arg Leu Glu Trp
    3125                3130            3135
```

```
Thr Pro Leu Ser Lys Ala Pro Thr Ala Ala Arg Ser Trp Val Pro
    3140            3145            3150

Val Glu Thr Gly Ala Asp Val Ala Ala Leu Asp Gly Gln Ala Val
    3155            3160            3165

Val Asp Ala Val Met Leu Glu Ala Ala Gly Thr Gly Asp Ala Leu
    3170            3175            3180

Glu Leu Thr Cys Arg Val Leu Glu Val Val Gln Ala Trp Leu Thr
    3185            3190            3195

Leu Pro Gly Trp Asp Glu Ser Arg Leu Val Val Val Thr Arg Gly
    3200            3205            3210

Ala Val Gly Ala Val Gly Asp Pro Ala Gly Ser Ala Val Trp Gly
    3215            3220            3225

Leu Val Arg Ala Ala Gln Ala Glu Asn Pro Asp Arg Ile Ala Leu
    3230            3235            3240

Leu Asp Leu Asp Gly Gly Arg Pro Val Glu Pro Leu Leu Ala Glu
    3245            3250            3255

Ser Glu Pro Gln Leu Ala Ile Arg Gly Ala Glu Ala Leu Val Pro
    3260            3265            3270

Arg Leu Ile Arg Ala Ala Ala Ala Thr Asp Ala Pro Ala Leu Phe
    3275            3280            3285

Asp Glu Ser Gln Thr Val Leu Ile Thr Gly Gly Thr Gly Ser Leu
    3290            3295            3300

Gly Gly Leu Leu Ala Arg His Leu Val Gly Arg Tyr Gly Leu Arg
    3305            3310            3315

Arg Leu Val Leu Val Ser Arg Arg Gly Pro Asp Ala Pro Gly Ala
    3320            3325            3330

Tyr Glu Leu Ala Ala Glu Leu Ala Ala His Gly Ala Glu Ala Ala
    3335            3340            3345

Leu Val Ala Cys Asp Leu Thr Asp Arg Asp Ala Val Ala Arg Leu
    3350            3355            3360

Leu Thr Glu His His Pro Thr Ala Val Val His Ala Ala Gly Val
    3365            3370            3375

Ser Asp Asp Gly Val Ile Gly Thr Leu Thr Ser Asp Arg Leu Ala
    3380            3385            3390

Tyr Val Phe Gly Pro Lys Ala Thr Ala Ala Arg His Leu Asp Glu
    3395            3400            3405

Leu Thr Arg Glu Leu Leu Pro Asp Leu Ala Ala Phe Val Thr Tyr
    3410            3415            3420

Ser Ser Ile Ser Ala Val Phe Leu Gly Ala Gly Ser Gly Gly Tyr
    3425            3430            3435

Ala Ala Ala Asn Ala Tyr Leu Asp Gly Leu Met Ala Arg Arg His
    3440            3445            3450

Ala Glu Gly Leu Pro Gly Leu Ser Leu Ala Trp Gly Leu Trp Asp
    3455            3460            3465

Gln Glu Ala Asp Gly Gly Gly Met Ala Ala Gly Leu Gln Asp Ile
    3470            3475            3480

Thr Arg Asn Arg Met Arg Arg Gly Gly Val Leu Ser Phe Thr
    3485            3490            3495

Pro Ala Glu Gly Met Ala Leu Phe Asp Ala Ala Met Ala Thr Asp
    3500            3505            3510

Glu Ala Leu Val Val Pro Val Arg Leu Asp Leu Pro Ala Leu Arg
    3515            3520            3525

Ala Glu Ala Val Ala Glu Gly Arg Ser Ala Pro Val Leu Leu Arg
```

-continued

```
            3530                3535                3540

Gly Leu Val Arg Pro Gly Arg Arg Leu Ala Arg Thr Val Ser Gly
        3545                3550                3555

Gly Thr Gly Val Leu Ala Asp Leu Thr Pro Glu Ala Leu Leu Lys
        3560                3565                3570

Leu Val Arg Gly Arg Ala Ala Ala Val Leu Gly His Val Asp Ala
        3575                3580                3585

Asp Ala Val Pro Val Ala Ala Ala Phe Lys Asp Leu Gly Val Asp
        3590                3595                3600

Ser Leu Thr Ala Val Glu Leu Arg Asn Ser Leu Ala Lys Ala Thr
        3605                3610                3615

Gly Leu Arg Leu Pro Ala Thr Leu Val Phe Asp Tyr Pro Thr Pro
        3620                3625                3630

Thr Val Leu Ala Gly Arg Leu Gly Glu Leu Leu Ala Gly Gly Thr
        3635                3640                3645

Ala Pro Val Arg Ala Ala Val Val Arg Arg Ala Ala Ala Ser Asp
        3650                3655                3660

Glu Pro Leu Ala Ile Val Gly Met Ala Cys Arg Leu Pro Gly Gly
        3665                3670                3675

Val Leu Ser Pro Glu Asp Leu Trp Arg Leu Val Glu Ser Gly Gly
        3680                3685                3690

Asp Ala Ile Ser Gly Phe Pro Val Asp Arg Gly Trp Asp Val Glu
        3695                3700                3705

Asn Leu Phe Asp Pro Asp Pro Asp Ala Ala Gly Arg Thr Tyr Ala
        3710                3715                3720

Val Arg Gly Gly Phe Leu Asp Gly Ala Ala Gly Phe Asp Ala Ser
        3725                3730                3735

Phe Phe Gly Ile Ser Pro Arg Glu Ala Gln Ala Met Asp Pro Gln
        3740                3745                3750

Gln Arg Leu Val Leu Glu Val Ser Trp Glu Ala Phe Glu Arg Ala
        3755                3760                3765

Gly Ile Glu Pro Gly Ser Val Arg Gly Ser Asp Thr Gly Val Phe
        3770                3775                3780

Met Gly Ala Tyr Pro Gly Gly Tyr Gly Met Gly Thr Asp Leu Gly
        3785                3790                3795

Gly Phe Gly Met Thr Ser Val Ala Val Ser Val Leu Ala Gly Arg
        3800                3805                3810

Val Ser Tyr Phe Phe Gly Leu Glu Gly Pro Ala Met Thr Val Asp
        3815                3820                3825

Thr Ala Cys Ser Ser Ser Leu Val Ala Leu His Gln Ala Gly Ser
        3830                3835                3840

Ala Leu Arg Gln Gly Glu Cys Ser Leu Ala Leu Val Gly Gly Val
        3845                3850                3855

Thr Val Met Pro Thr Pro Gln Thr Phe Val Glu Phe Ser Arg Gln
        3860                3865                3870

Arg Gly Leu Ala Ala Asp Gly Arg Cys Lys Ala Phe Ala Asp Ala
        3875                3880                3885

Ala Asp Gly Thr Gly Phe Ser Glu Gly Val Gly Val Leu Leu Val
        3890                3895                3900

Glu Arg Leu Ser Asp Ala Gln Ala Arg Gly His Asn Ile Leu Ala
        3905                3910                3915

Val Val Arg Gly Ser Ala Val Asn Gln Asp Gly Ala Ser Asn Gly
        3920                3925                3930
```

```
Leu Thr Ala Pro Asn Gly Pro Ala Gln Gln Arg Val Ile Gln Ser
    3935            3940            3945

Ala Leu Ala Gly Ala Gly Leu Ala Ser Ala Asp Val Asp Val Val
    3950            3955            3960

Glu Ala His Gly Thr Gly Thr Leu Gly Asp Pro Ile Glu Ala
    3965            3970            3975

Gln Ala Val Ile Ala Thr Tyr Gly Gln Asp Arg Asp Gln Pro Val
    3980            3985            3990

Leu Leu Gly Ser Leu Lys Ser Asn Leu Gly His Thr Gln Ala Ala
    3995            4000            4005

Ala Gly Val Ser Gly Val Ile Lys Met Val Met Ala Leu Gln Asn
    4010            4015            4020

Gly Val Val Pro Arg Thr Leu His Ile Asp Glu Pro Ser Arg His
    4025            4030            4035

Ile Asp Trp Thr Ala Gly Ala Val Glu Leu Val Thr Glu Asn Gln
    4040            4045            4050

Ser Trp Pro Glu Thr Gly Arg Ala Arg Arg Ala Ala Val Ser Ser
    4055            4060            4065

Phe Gly Ile Ser Gly Thr Asn Ala His Val Ile Leu Glu Ser Ala
    4070            4075            4080

Pro Ala Gln Pro Val Pro Leu Val Asp Thr Pro Val Ser Asp Val
    4085            4090            4095

Thr Ala Gly Val Val Pro Leu Pro Ile Ser Ala Arg Thr Val Pro
    4100            4105            4110

Ala Leu Ala Asp Leu Glu Asp Gln Leu Arg Ala Tyr Leu Thr Thr
    4115            4120            4125

Ala Pro Glu Thr Asp Leu Pro Ala Val Ala Ser Thr Leu Ala Met
    4130            4135            4140

Thr Arg Ser Val Phe Glu His Arg Ala Val Leu Leu Gly Glu Glu
    4145            4150            4155

Thr Val Thr Gly Ile Ala Val Ser Asp Pro Arg Val Val Phe Val
    4160            4165            4170

Phe Ser Gly Gln Gly Ser Gln Arg Val Gly Met Gly Glu Glu Leu
    4175            4180            4185

Ala Ala Ala Phe Pro Leu Phe Ala Arg Leu His Arg Gln Val Trp
    4190            4195            4200

Asp Leu Leu Asp Val Pro Asp Leu Glu Val Asp Thr Gly Tyr
    4205            4210            4215

Val Gln Pro Ala Leu Phe Ala Leu Gln Val Ala Leu Phe Gly Leu
    4220            4225            4230

Leu Glu Ser Trp Gly Val Arg Pro Arg Ala Val Ile Gly His Ser
    4235            4240            4245

Val Gly Glu Val Ala Ala Gly Tyr Val Ala Gly Val Trp Ser Leu
    4250            4255            4260

Glu Asp Ala Cys Thr Leu Val Ser Ala Arg Ala Arg Leu Met Gln
    4265            4270            4275

Ala Leu Pro Ala Gly Gly Ala Met Val Ala Val Pro Val Ser Glu
    4280            4285            4290

Glu Arg Ala Arg Ala Val Leu Val Asp Gly Val Glu Ile Ala Ala
    4295            4300            4305

Val Asn Gly Pro Ala Ser Val Val Leu Ser Gly Asp Glu Ser Ala
    4310            4315            4320
```

| | | | | | | | | | | | |
|---|---|---|---|---|---|---|---|---|---|---|---|
| Val | Leu | Arg | Val | Ala | Glu | Gly | Leu | Gly | Arg | Trp | Thr | Arg | Leu | Ser |
| 4325 | | | | | 4330 | | | | | 4335 | | | | |
| Ala | Ser | His | Ala | Phe | His | Ser | Val | Arg | Met | Glu | Pro | Met | Leu | Glu |
| 4340 | | | | | 4345 | | | | | 4350 | | | | |
| Glu | Phe | Arg | Gln | Val | Ala | Ser | Glu | Leu | Thr | Tyr | Arg | Glu | Pro | Arg |
| 4355 | | | | | 4360 | | | | | 4365 | | | | |
| Ile | Val | Met | Ala | Ala | Gly | Glu | Gln | Val | Thr | Thr | Pro | Glu | Tyr | Trp |
| 4370 | | | | | 4375 | | | | | 4380 | | | | |
| Val | Arg | Gln | Val | Arg | Asp | Thr | Val | Arg | Phe | Gly | Asp | Gln | Val | Ala |
| 4385 | | | | | 4390 | | | | | 4395 | | | | |
| Ala | Phe | Gly | Asp | Ala | Val | Phe | Leu | Glu | Ile | Gly | Pro | Asp | Arg | Thr |
| 4400 | | | | | 4405 | | | | | 4410 | | | | |
| Leu | Ser | Arg | Leu | Ile | Asp | Gly | Ile | Ala | Met | Leu | Asp | Gly | Asp | Asp |
| 4415 | | | | | 4420 | | | | | 4425 | | | | |
| Glu | Val | Arg | Ala | Ala | Val | Ala | Ala | Leu | Ala | Met | Met | His | Val | Gln |
| 4430 | | | | | 4435 | | | | | 4440 | | | | |
| Gly | Val | Gly | Val | Asp | Trp | Pro | Ala | Val | Leu | Gly | Thr | Thr | Thr | Gly |
| 4445 | | | | | 4450 | | | | | 4455 | | | | |
| Arg | Val | Leu | Asp | Leu | Pro | Thr | Tyr | Ala | Phe | Gln | His | Glu | Arg | Tyr |
| 4460 | | | | | 4465 | | | | | 4470 | | | | |
| Trp | Met | Val | Ser | Thr | Gly | Arg | Pro | Gly | Glu | Gly | His | Pro | Leu |
| 4475 | | | | | 4480 | | | | | 4485 | | | | |
| Leu | Gly | Trp | Gly | Val | Pro | Val | Ala | Glu | Ala | Asp | Gly | Arg | Leu | Tyr |
| 4490 | | | | | 4495 | | | | | 4500 | | | | |
| Thr | Gly | Arg | Val | Ala | Arg | Gln | Asp | Gly | Pro | Val | Leu | Pro | Val | Ala |
| 4505 | | | | | 4510 | | | | | 4515 | | | | |
| Ala | Phe | Val | Glu | Met | Ala | Phe | Ala | Ala | Ala | Gly | Gly | Arg | Pro | Ile |
| 4520 | | | | | 4525 | | | | | 4530 | | | | |
| Arg | Glu | Leu | Ser | Val | Asp | Ala | Leu | Leu | Tyr | Ile | Pro | Asp | Asp | Gly |
| 4535 | | | | | 4540 | | | | | 4545 | | | | |
| Thr | Ala | Glu | Leu | Gln | Thr | Trp | Val | Ser | Glu | His | Arg | Leu | Thr | Ile |
| 4550 | | | | | 4555 | | | | | 4560 | | | | |
| His | Ala | Arg | Tyr | Arg | Asp | Thr | Glu | Pro | Trp | Thr | Arg | Leu | Ala | Thr |
| 4565 | | | | | 4570 | | | | | 4575 | | | | |
| Ala | Thr | Leu | Asp | Thr | Thr | Glu | Pro | Ala | Thr | Thr | His | Thr | Pro | His |
| 4580 | | | | | 4585 | | | | | 4590 | | | | |
| Pro | Gly | Leu | Ile | Thr | Thr | Ala | Leu | Thr | Leu | Thr | Gly | Asp | Glu | Ala |
| 4595 | | | | | 4600 | | | | | 4605 | | | | |
| Pro | Ala | Ile | Trp | His | Asp | Leu | Thr | Leu | His | Thr | Ser | Asn | Ala | Thr |
| 4610 | | | | | 4615 | | | | | 4620 | | | | |
| Glu | Leu | His | Thr | His | Ile | Thr | Pro | Gly | Asp | Asp | Gly | Thr | Leu | Thr |
| 4625 | | | | | 4630 | | | | | 4635 | | | | |
| Ile | Thr | Ala | Thr | Asp | Ala | Thr | Gly | Gln | Pro | Val | Leu | Thr | Ala | His |
| 4640 | | | | | 4645 | | | | | 4650 | | | | |
| Ala | Ala | Thr | Pro | Thr | Thr | Ile | Pro | Val | His | Thr | Pro | Thr | Thr | Pro |
| 4655 | | | | | 4660 | | | | | 4665 | | | | |
| Ala | Asp | Asp | Leu | Leu | Thr | Leu | Thr | Trp | Thr | Gln | Ile | Pro | Thr | Pro |
| 4670 | | | | | 4675 | | | | | 4680 | | | | |
| Gly | Pro | Gly | Asp | Gly | Ala | Asp | Ile | Ala | Val | Cys | Thr | Ala | Leu | Pro |
| 4685 | | | | | 4690 | | | | | 4695 | | | | |
| Asp | Pro | Asp | Ser | Asp | Pro | Leu | Ala | Gln | Thr | Arg | Thr | Leu | Thr | Ala |
| 4700 | | | | | 4705 | | | | | 4710 | | | | |
| Gln | Val | Leu | His | Ser | Ile | Gln | Ala | Ser | Leu | Thr | Gly | Glu | Asp | Arg |

-continued

```
            4715                4720                4725

Pro Leu Val Val His Thr Gly Thr Gly Leu Ala Ser Ala Ala Val
    4730                4735                4740

Ser Gly Leu Val Arg Ser Ala Gln Ser Glu His Pro Asp Arg Phe
    4745                4750                4755

Ile Leu Val Glu Ser Asp Glu Thr Leu Thr Pro Asp Gln Leu Ala
    4760                4765                4770

Ala Val Ala Gly Leu Asp Glu Pro Trp Leu Arg Ile Thr Asp Gly
    4775                4780                4785

Arg Tyr Glu Val Pro Arg Leu Thr Lys Thr Thr Thr Ala Thr
    4790                4795                4800

Ala Thr Ala Val Ser Glu Pro Val Trp Asp Pro Asp Gly Thr Val
    4805                4810                4815

Leu Ile Thr Gly Gly Ser Gly Ala Leu Ala Gly Ile Leu Ala Arg
    4820                4825                4830

His Leu Val Thr Glu Arg Gly Val Arg His Leu Leu Leu Val Ser
    4835                4840                4845

Arg Ser Thr Pro Ser Thr Thr Leu Ile Asp Glu Leu Arg Glu Leu
    4850                4855                4860

Gly Ala His Val Asp Val Ala Cys Asp Val Ser Asp Arg Ala
    4865                4870                4875

Ala Leu Ala Arg Val Leu Asp Gly Val Asp Leu Thr Ala Val Phe
    4880                4885                4890

His Thr Ala Gly Ala Leu Asp Asp Gly Val Val Glu Ser Leu Thr
    4895                4900                4905

Pro Gln Arg Val Asp Ala Val Leu Arg Pro Lys Ala Asp Gly Ala
    4910                4915                4920

Trp His Leu His Glu Leu Thr Arg Asp Arg Asp Leu Thr Ala Phe
    4925                4930                4935

Val Met Tyr Ser Ser Ala Ala Gly Val Met Gly Ala Ala Gly Gln
    4940                4945                4950

Gly Asn Tyr Ala Ala Ala Asn Ala Phe Leu Asp Ala Leu Ala Glu
    4955                4960                4965

His Arg Arg Ala Asp Gly Leu Pro Ala Leu Ser Leu Ala Trp Gly
    4970                4975                4980

Met Trp Asp Asp Ala Asp Gly Met Thr Ala Ser Leu Ser Gly Thr
    4985                4990                4995

Asp His Arg Arg Ile Arg Arg Ser Gly Gln Arg Ala Ile Thr Ala
    5000                5005                5010

Glu His Gly Met Arg Leu Leu Asp Lys Ala Ser Gly Arg Ser Glu
    5015                5020                5025

Pro Val Leu Val Ala Thr Ala Met Asn Pro Ile Pro Asp Thr Asp
    5030                5035                5040

Leu Pro Ala Leu Leu Arg Ser Leu Tyr Pro Lys Thr Ala Arg Lys
    5045                5050                5055

Ser Gln Pro Ile Gln Glu Leu Ser Pro Glu Ala Leu Leu Lys Ile
    5060                5065                5070

Val Arg Asp Ser Ala Ala Met Val Leu Gly His Ala Asn Ala Asp
    5075                5080                5085

Thr Val Pro Thr Ala Thr Ala Leu Gln Glu Leu Gly Leu Asp Ser
    5090                5095                5100

Leu Thr Ala Val Glu Leu Arg Asn Ser Leu Thr Lys Ala Thr Gly
    5105                5110                5115
```

```
Leu Arg Leu Pro Ala Thr Met Ala Phe Asp Tyr Pro Thr Pro Ala
    5120            5125                5130

Ala Leu Ala Gly Arg Leu Gly Glu Leu Leu Ala Gly Asp Thr Thr
    5135            5140                5145

Pro Ala Thr Ala Ala Val Val Arg Arg Ala Thr Ala Ser Asp Glu
    5150            5155                5160

Pro Leu Ala Ile Val Gly Met Ala Cys Arg Leu Pro Gly Gly Val
    5165            5170                5175

Ser Thr Pro Glu Asp Leu Trp Arg Leu Val Glu Ser Gly Thr Asp
    5180            5185                5190

Ala Ile Thr Asp Phe Pro Thr Asp Arg Gly Trp Asp Thr Asp Asp
    5195            5200                5205

Leu Phe Asp Pro Asp Pro Asp Thr Pro Gly Lys Thr Tyr Thr Val
    5210            5215                5220

His Gly Gly Phe Leu Asp Asp Val Ala Gly Phe Asp Ala Ser Phe
    5225            5230                5235

Phe Gly Ile Ser Pro Arg Glu Ala Leu Ala Met Asp Ser Gln Gln
    5240            5245                5250

Arg Leu Val Leu Glu Ala Ala Trp Glu Ala Phe Glu Arg Ala Gly
    5255            5260                5265

Ile Glu Pro Gly Ser Val Arg Gly Ser Asp Thr Gly Val Phe Met
    5270            5275                5280

Gly Ala Tyr Pro Asp Gly Tyr Gly Ile Gly Ala Asp Leu Gly Gly
    5285            5290                5295

Phe Gly Ala Thr Ala Gly Ala Gly Ser Val Leu Ser Gly Arg Leu
    5300            5305                5310

Ser Tyr Phe Phe Gly Leu Glu Gly Pro Ala Met Thr Val Asp Thr
    5315            5320                5325

Ala Cys Ser Ser Ser Leu Val Ala Leu His Gln Ala Gly Ser Ala
    5330            5335                5340

Leu Arg Gln Gly Glu Cys Ser Leu Ala Leu Val Gly Gly Val Thr
    5345            5350                5355

Val Ile Ala Asn Pro Gln Ile Phe Val Glu Phe Ser Arg Gln Arg
    5360            5365                5370

Gly Leu Ala Ala Asp Gly Arg Cys Lys Ala Phe Ala Asp Asn Ala
    5375            5380                5385

Asp Gly Thr Gly Phe Ser Glu Gly Val Gly Val Leu Leu Val Glu
    5390            5395                5400

Arg Leu Ser Asp Ala Gln Ala Lys Gly His Asn Ile Leu Ala Leu
    5405            5410                5415

Val Arg Ser Ser Ala Val Asn Gln Asp Gly Ala Ser Asn Gly Leu
    5420            5425                5430

Thr Ala Pro Asn Gly Pro Ser Gln Gln Arg Val Ile Arg Gln Ala
    5435            5440                5445

Leu Ala Asn Ala Gly Leu Thr Gly Ala Glu Val Asp Val Val Glu
    5450            5455                5460

Ala His Gly Thr Gly Thr Thr Leu Gly Asp Pro Ile Glu Ala Gln
    5465            5470                5475

Ala Val Leu Ala Thr Tyr Gly Gln Asp Arg Asp Gln Pro Val Leu
    5480            5485                5490

Leu Gly Ser Leu Lys Ser Asn Leu Gly His Thr Gln Ala Ala Ala
    5495            5500                5505
```

-continued

| | | | | | | | | | | | |
|---|---|---|---|---|---|---|---|---|---|---|---|
| Gly | Val | Ser | Gly | Val | Ile | Lys | Met | Val | Met | Ala | Leu | Arg | His | Asp |
| | | 5510 | | | | 5515 | | | | 5520 | | | | |
| Thr | Val | Pro | Ala | Thr | Leu | His | Ile | Asp | Glu | Pro | Ser | Arg | His | Ile |
| | | 5525 | | | | 5530 | | | | 5535 | | | | |
| Asp | Trp | Thr | Ala | Gly | Ala | Val | Glu | Leu | Val | Thr | Glu | Asn | Gln | Pro |
| | | 5540 | | | | 5545 | | | | 5550 | | | | |
| Trp | Pro | Val | Leu | Gly | Arg | Pro | Arg | Ala | Ala | Val | Ser | Ala | Phe |
| | | 5555 | | | | 5560 | | | | 5565 | | | | |
| Gly | Val | Ser | Gly | Thr | Asn | Ala | His | Val | Ile | Leu | Glu | Ser | Ala | Pro |
| | | 5570 | | | | 5575 | | | | 5580 | | | | |
| Asp | Gln | Pro | Pro | Ala | Pro | Ala | Thr | Asp | Thr | Pro | Ala | Pro | Ala | Ala |
| | | 5585 | | | | 5590 | | | | 5595 | | | | |
| Thr | Ala | Gly | Val | Val | Pro | Leu | Pro | Ile | Ser | Ala | Lys | Thr | Val | Pro |
| | | 5600 | | | | 5605 | | | | 5610 | | | | |
| Ala | Leu | Ala | Asp | Leu | Glu | Asp | Arg | Leu | Arg | Thr | Tyr | Leu | Thr | Thr |
| | | 5615 | | | | 5620 | | | | 5625 | | | | |
| Thr | Pro | Glu | Thr | Asp | Leu | Pro | Ala | Val | Ala | Ser | Thr | Leu | Ala | Thr |
| | | 5630 | | | | 5635 | | | | 5640 | | | | |
| Thr | Arg | Ser | Leu | Phe | Glu | His | Arg | Ala | Val | Leu | Leu | Gly | Glu | Asp |
| | | 5645 | | | | 5650 | | | | 5655 | | | | |
| Thr | Val | Thr | Gly | Thr | Thr | Ile | Pro | Asp | Pro | Arg | Ile | Val | Phe | Val |
| | | 5660 | | | | 5665 | | | | 5670 | | | | |
| Phe | Pro | Gly | Gln | Gly | Trp | Gln | Trp | Gln | Gly | Met | Gly | Ser | Ala | Leu |
| | | 5675 | | | | 5680 | | | | 5685 | | | | |
| Leu | Thr | Ser | Ser | Thr | Val | Phe | Ala | Glu | Arg | Met | Ala | Glu | Cys | Ala |
| | | 5690 | | | | 5695 | | | | 5700 | | | | |
| Ala | Ala | Leu | Ser | Glu | Phe | Val | Asp | Trp | Asp | Leu | Leu | Thr | Val | Leu |
| | | 5705 | | | | 5710 | | | | 5715 | | | | |
| Asp | Asp | Pro | Ser | Ile | Val | Asp | Arg | Val | Asp | Val | Val | Gln | Pro | Ala |
| | | 5720 | | | | 5725 | | | | 5730 | | | | |
| Cys | Trp | Ala | Val | Met | Ile | Ser | Leu | Ala | Ala | Val | Trp | Gln | Ala | Ala |
| | | 5735 | | | | 5740 | | | | 5745 | | | | |
| Gly | Ile | His | Pro | Asp | Ile | Val | Leu | Gly | His | Ser | Gln | Gly | Glu | Ile |
| | | 5750 | | | | 5755 | | | | 5760 | | | | |
| Ala | Ala | Ala | Cys | Leu | Ala | Gly | Ala | Ile | Ser | Leu | Pro | Asp | Ala | Ala |
| | | 5765 | | | | 5770 | | | | 5775 | | | | |
| Arg | Ile | Val | Ala | Gln | Arg | Ser | Gln | Leu | Ile | Ala | His | Gln | Leu | Thr |
| | | 5780 | | | | 5785 | | | | 5790 | | | | |
| Gly | His | Gly | Ala | Met | Ala | Ser | Ile | Ser | Leu | Pro | Ala | Asp | Asp | Ile |
| | | 5795 | | | | 5800 | | | | 5805 | | | | |
| Pro | Thr | Thr | Asp | Lys | Val | Trp | Ile | Ala | Ala | His | Asn | Gly | Thr | Ser |
| | | 5810 | | | | 5815 | | | | 5820 | | | | |
| Thr | Val | Ile | Ala | Gly | Asp | Pro | Gln | Ala | Leu | Asp | Thr | Val | Leu | Ala |
| | | 5825 | | | | 5830 | | | | 5835 | | | | |
| Thr | Cys | Glu | Thr | His | Gly | Ala | Arg | Val | Arg | Lys | Ile | Asn | Val | Asp |
| | | 5840 | | | | 5845 | | | | 5850 | | | | |
| Tyr | Ala | Ser | His | Thr | Pro | His | Val | Glu | Gln | Ile | Arg | Thr | Glu | Leu |
| | | 5855 | | | | 5860 | | | | 5865 | | | | |
| Leu | Asp | Ile | Thr | Thr | Asp | Ile | Glu | Ala | His | Thr | Pro | Thr | Val | Pro |
| | | 5870 | | | | 5875 | | | | 5880 | | | | |
| Trp | Leu | Ser | Thr | Thr | Asp | Asn | Thr | Trp | Ile | Asp | Gln | Pro | Leu | Asp |
| | | 5885 | | | | 5890 | | | | 5895 | | | | |
| Pro | Thr | Tyr | Trp | Tyr | Arg | Asn | Leu | Arg | Glu | Pro | Val | Arg | Phe | Gly |

-continued

```
            5900                5905                5910

Pro Ala Ile Asp Leu Leu Gln Thr Gln Asp Asn Asn Leu Phe Ile
            5915                5920                5925

Glu Ile Ser Ala Ser Pro Val Leu Leu Gln Thr Met Asp Asn Ala
            5930                5935                5940

Thr Thr Val Ala Thr Leu Arg Arg Asp Glu Asp Thr Thr Gln Arg
            5945                5950                5955

Leu Leu Thr Ala Phe Ala Glu Ala His Val His Gly Ala Thr Ile
            5960                5965                5970

Asp Trp Pro Thr Val Leu Asp Thr Thr Thr Thr Pro Val Leu Asp
            5975                5980                5985

Leu Pro Thr Tyr Pro Phe Gln Arg Gln Arg Tyr Trp Ala Thr Ser
            5990                5995                6000

Asn Gly Arg Pro Thr Ser Gln Gly His Pro Leu Leu Glu Thr Val
            6005                6010                6015

Val Ala Leu Pro Gly Thr His Gly Val Ala Leu Thr Gly Arg Ile
            6020                6025                6030

Ser Leu Ala Thr His Pro Trp Leu Thr Asp His Thr Val Arg Gly
            6035                6040                6045

Thr Val Leu Leu Pro Gly Thr Ala Phe Val Glu Leu Val Thr His
            6050                6055                6060

Ala Ala Thr Glu Val Asn Cys Gln Val Ile Asp Glu Leu Ile Ile
            6065                6070                6075

Glu Ala Pro Leu Pro Leu Pro Gln Asn Gly Gly Val Gln Leu Ser
            6080                6085                6090

Val Thr Val Gly Glu Ala Asp Glu Ala Gly His Arg Pro Val Thr
            6095                6100                6105

Val Tyr Ser Gln Thr Asp Glu Ser Asp Asp Trp Val Gln His Val
            6110                6115                6120

Thr Ala Thr Ile Ala Pro Gly Val Ser Ser Glu Ser Ala Ala
            6125                6130                6135

Trp Pro Pro Ala Gln Ala Glu Pro Val Asn Val Thr Gly Leu Tyr
            6140                6145                6150

Asp Asn Leu Ala Ala Ala Gly Tyr Glu Tyr Gly Pro Ala Phe Gln
            6155                6160                6165

Gly Leu Gln Thr Ala Trp Arg Asp Gly Ser Thr Val Tyr Ala Glu
            6170                6175                6180

Val Thr Leu Ala Glu Glu Gln Ala Gln Glu Thr Ala Arg Phe Thr
            6185                6190                6195

Met His Pro Ala Leu Leu Asp Ala Ala Leu His Thr Ile Ala Leu
            6200                6205                6210

His Asp Thr Ala Asp Leu Gln Leu Pro Phe Ser Trp Arg Gln Val
            6215                6220                6225

Gln Phe His Gly Ser Gly Ala Ala Thr Leu Arg Val Ala Val Thr
            6230                6235                6240

Pro Ala Ala Asp Gly Trp Asn Ile Arg Ala Thr Asp Asp Thr Gly
            6245                6250                6255

Gln Thr Val Ala Thr Ile Gly Ser Leu Val Thr Arg Pro Met Ala
            6260                6265                6270

Ala Glu Thr Thr Asn Asp Leu Leu Ala Leu Thr Trp Thr Glu Ile
            6275                6280                6285

Pro Ala Pro Glu Pro Val Asp Pro Ala Asp Val Val Phe Thr
            6290                6295                6300
```

-continued

Ala Leu Pro Glu Pro Gly Ser Asp Pro Leu Ala Gln Thr Arg Ala
    6305              6310             6315

Leu Thr Thr Arg Val Leu His Thr Ile Gln Glu Trp Leu Ala Asp
    6320              6325             6330

Asp Asp Arg Thr Leu Ile Val Arg Thr Gly Thr Asp Leu Ala Ser
    6335              6340             6345

Ala Ala Val Ser Gly Leu Val Arg Ser Ala Gln Ser Glu His Pro
    6350              6355             6360

Gly Arg Phe Ile Leu Val Glu Ser Asp Asp Glu Thr Leu Thr His
    6365              6370             6375

Glu Gln Leu Ala Ala Thr Ala Gly Leu Asp Glu Pro Arg Leu Arg
    6380              6385             6390

Ile Thr Asp Gly Arg Tyr Glu Val Pro Arg Leu Thr Arg Glu Asp
    6395              6400             6405

Thr Ala Leu Ala Val Pro Glu Gly Gly Ala Trp Met Leu Asp Gln
    6410              6415             6420

Pro Ser Arg Ser Gly Thr Leu Gln Asp Leu Arg Leu Val Pro Thr
    6425              6430             6435

Asp Ala Ala Glu Arg Pro Leu Arg Pro Gly Glu Val Arg Val Gly
    6440              6445             6450

Val Arg Ala Ala Gly Leu Asn Phe Arg Asp Val Ala Val Ala Leu
    6455              6460             6465

Gly Met Val Thr Asp Thr Arg Leu Ile Gly Gly Glu Gly Ala Gly
    6470              6475             6480

Val Val Leu Glu Ala Gly Pro Gly Val Glu Asp Leu Arg Pro Gly
    6485              6490             6495

Asp Arg Val Phe Gly Leu Leu Glu Gly Gly Phe Gly Pro Val Ala
    6500              6505             6510

Val Ala Asp Arg Arg Ala Leu Ala Leu Ile Pro Asp Gly Trp Ser
    6515              6520             6525

Phe Thr Thr Ala Ala Ser Val Pro Ile Ala Phe Ala Thr Ala Tyr
    6530              6535             6540

Tyr Gly Leu Leu Asp Leu Ala Gly Leu Arg Ala Gly Glu Ser Val
    6545              6550             6555

Leu Ile His Ala Ala Thr Gly Gly Val Gly Met Ala Ala Thr Gln
    6560              6565             6570

Ile Ala Arg His Leu Gly Ala Asp Val Tyr Ala Thr Ala Ser Thr
    6575              6580             6585

Gly Lys Gln His Val Leu Arg Asp Ala Gly Leu Ser Asp Asp Arg
    6590              6595             6600

Ile Ala Asp Ser Arg Thr Thr Gly Phe Arg Glu Thr Phe Arg Asp
    6605              6610             6615

Ser Thr Asp Gly Arg Gly Val Asp Val Val Leu Asn Ser Leu Lys
    6620              6625             6630

Gly Asp Phe Val Asp Ala Ser Leu Asp Leu Leu Val Asp Gly Gly
    6635              6640             6645

Arg Phe Ile Glu Met Gly Lys Thr Asp Ile Arg Asp Ala Ala Gln
    6650              6655             6660

Ile Pro Asp Ala Thr Tyr Arg Ala Phe Asp Leu Met Asp Ala Gly
    6665              6670             6675

Pro Glu Arg Leu Arg Glu Ile Ile Thr Glu Leu Leu Ala Leu Phe
    6680              6685             6690

```
Glu Gln Gly Val Leu Arg Pro Leu Pro Val His Ala Phe Asp Ile
    6695                6700                6705

Arg Gln Ala Arg Asp Ala Phe Gly Trp Met Ser Arg Ala Arg His
    6710                6715                6720

Ile Gly Lys Leu Val Leu Thr Ile Pro Gln Pro Ile Asp Pro Asp
    6725                6730                6735

Gly Thr Val Leu Ile Thr Gly Gly Ser Gly Val Leu Ala Gly Ile
    6740                6745                6750

Val Ala Arg His Leu Val Ile Ala Glu Gly Leu Arg Asn Leu Leu
    6755                6760                6765

Leu Leu Ser Arg Ser Ala Pro Ser Glu Ala Leu Ile Gly Glu Leu
    6770                6775                6780

Thr Ala Leu Gly Ala Gln Val Glu Thr Ala Ala Cys Asp Ile Ala
    6785                6790                6795

Asp Arg Ala Ala Leu Ala Arg Val Leu Asp Gly Val Pro Leu Thr
    6800                6805                6810

Ala Val Ile His Thr Ala Gly Ala Leu Asp Asp Gly Val Val Glu
    6815                6820                6825

Ser Leu Asp Pro Gln Arg Leu Asp Ser Val Leu Thr Pro Lys Ala
    6830                6835                6840

Asp Gly Ala Trp His Leu His Glu Leu Thr Arg Asp Arg Asp Leu
    6845                6850                6855

Ala Ala Phe Ile Met Tyr Ser Ser Ala Ala Gly Val Leu Gly Ala
    6860                6865                6870

Ala Gly Gln Gly Asn Tyr Ala Ala Ala Asn Ala Phe Val Asp Ala
    6875                6880                6885

Leu Ala Val His Arg Arg Phe Met Gly Leu Pro Ala Leu Ser Leu
    6890                6895                6900

Ala Trp Gly Leu Trp Asp Asp Thr Ser Ala Leu Thr Ala Gly Leu
    6905                6910                6915

Thr Asp Ser Asp His Asp Arg Ile Arg Arg Ser Gly Ala Arg Thr
    6920                6925                6930

Ile Thr Ala Glu His Gly Met Arg Met Phe Asp Ala Ala Thr Arg
    6935                6940                6945

Gln Ser Glu Ala Val Leu Leu Ala Ala Pro Met Gly Pro Ile Arg
    6950                6955                6960

Gly Glu Asp Val Pro Ala Leu Leu Arg Gly Leu Ala Thr Val Arg
    6965                6970                6975

Gln Pro Arg Thr Arg Ala Lys Arg Asp Met Gly Pro Glu Arg Leu
    6980                6985                6990

Arg Asp Arg Leu Asn Gly Arg Thr Ser Val Glu Gln His Arg Ile
    6995                7000                7005

Met Val Glu Leu Val Leu Ala His Ala Thr Ser Val Leu Gly His
    7010                7015                7020

Glu Ser Pro Asp Ala Ile Ala Pro Asp Arg Ala Phe Lys Asp Leu
    7025                7030                7035

Gly Met Asp Ser Leu Thr Ala Ile Glu Leu Arg Asn His Leu Val
    7040                7045                7050

Ala Glu Thr Gly Val Arg Leu Pro Ala Thr Thr Ala Phe Asp His
    7055                7060                7065

Pro Thr Ala Asp Asp Leu Ala Lys Arg Leu Leu Ala Glu Val Gly
    7070                7075                7080

Leu Thr Pro Ala Pro Gln Arg Thr Glu Ala Asp Ile Arg Glu Glu
```

```
                    7085              7090              7095
Val Val Val Arg Glu Pro Ala Gly Asp Asp Ser Trp Thr Ser Glu
    7100              7105              7110
Pro Ile Ala Ile Val Ser Met Ser Cys Arg Ala Pro Gly Gly Val
    7115              7120              7125
Asp Ser Pro Glu Ser Leu Trp Arg Leu Val Glu Ser Gly Thr Asp
    7130              7135              7140
Ala Ile Thr Asp Phe Pro Gly Asp Arg Gly Trp Asp Val Ala Gly
    7145              7150              7155
Leu Tyr Ser Pro Asp Pro Asp Thr Gly Tyr Lys Thr Tyr Cys Val
    7160              7165              7170
Gln Gly Gly Phe Leu Asp Ala Ala Ala Asp Phe Asp Ala Ala Phe
    7175              7180              7185
Phe Gly Ile Ser Pro Arg Glu Ala Leu Gly Met Asp Pro Gln Gln
    7190              7195              7200
Arg Leu Leu Leu Glu Thr Ser Trp Glu Ala Ile Glu Arg Ala Arg
    7205              7210              7215
Ile Asp Pro Arg Ser Leu Arg Gly Arg Asn Val Gly Val Tyr Val
    7220              7225              7230
Gly Gly Ala Ala Gln Gly Tyr Gly Val Gly Ala Ile Asp Gln Gln
    7235              7240              7245
Arg Asp Asn Val Ile Thr Gly Ser Ser Ile Ser Leu Leu Ser Gly
    7250              7255              7260
Arg Leu Ser Tyr Ala Leu Gly Leu Glu Gly Pro Gly Val Thr Val
    7265              7270              7275
Asp Thr Ala Cys Ser Ser Ser Leu Val Ala Leu His Leu Ala Cys
    7280              7285              7290
Gln Ala Leu Arg Gln Arg Glu Cys Ser Met Ala Leu Val Ser Gly
    7295              7300              7305
Val Ser Val Ile Pro Thr Pro Asp Val Phe Val Glu Phe Ser Arg
    7310              7315              7320
Gln Arg Gly Leu Ala Ala Asp Gly Arg Cys Lys Ser Phe Ser Ala
    7325              7330              7335
Ser Ala Asp Gly Thr Ile Trp Ala Glu Gly Val Gly Val Leu Val
    7340              7345              7350
Leu Glu Arg Leu Ser Glu Ala Thr Arg Leu Gly His Arg Val Leu
    7355              7360              7365
Ala Val Val Arg Gly Ser Ala Val Asn Ser Asp Gly Ala Ser Asn
    7370              7375              7380
Gly Leu Thr Ala Pro Asn Gly Val Ser Gln Gln Arg Val Ile Arg
    7385              7390              7395
Gln Ala Leu Thr Gly Ala Gly Leu Thr Ala Ala Asp Val Asp Val
    7400              7405              7410
Val Glu Ala His Gly Thr Gly Thr Lys Leu Gly Asp Pro Ile Glu
    7415              7420              7425
Ala Glu Ala Ile Leu Ala Thr Tyr Gly Gln Asp Arg Ser Thr Pro
    7430              7435              7440
Val Cys Leu Gly Ser Leu Lys Ser Asn Ile Gly His Ala Met Ala
    7445              7450              7455
Ala Ser Gly Val Leu Ala Val Ile Lys Met Val Glu Ala Met Arg
    7460              7465              7470
His Gly Leu Ile Pro Arg Thr Leu His Val Glu Glu Pro Ser Pro
    7475              7480              7485
```

-continued

His Val Asp Trp Ala Ser Gly Asp Val Ala Leu Leu Thr Glu Asn
7490               7495           7500

Gln Pro Trp Pro Asp Asp Ala Lys Leu Arg Arg Ala Gly Val Ser
7505               7510           7515

Ser Phe Gly Leu Ser Gly Thr Asn Ala His Val Val Leu Glu Gln
7520               7525           7530

Tyr Arg Ala Pro Ala Ala Pro Asp Ile Thr Thr Thr Glu His Glu
7535               7540           7545

Pro Leu Ala Trp Thr Leu Ser Ala Arg Asp Pro Lys Ala Leu Arg
7550               7555           7560

Glu Gln Ala Gly Arg Leu His Ala Ala Leu Thr Glu Ser Pro Gln
7565               7570           7575

Trp Arg Pro Leu Asp Ile Gly Tyr Ser Leu Ala Thr Thr Arg Ser
7580               7585           7590

Asn Phe Ala His Arg Ala Val Ala Val Gly Ser Asp Arg Glu Asp
7595               7600           7605

Leu Leu Arg Ala Leu Ser Lys Leu Ala Asp Gly Ser Ala Trp Pro
7610               7615           7620

Ala Leu Val Thr Ala Thr Ala Lys Asp Arg Arg Val Ala Tyr Leu
7625               7630           7635

Phe Asp Gly Gln Gly Ser Gln Arg Pro Asp Met Gly Ser Gly Leu
7640               7645           7650

Tyr Glu Arg Phe Pro Ala Phe Ala Arg Ala Trp Asp Arg Ile Ser
7655               7660           7665

Ala Glu Phe Gly Lys His Leu Asp His Ser Leu Thr Asp Val Tyr
7670               7675           7680

Leu Gly Arg Gly Asp Ala Ala Thr Ala Asp Leu Val Asp Asp Thr
7685               7690           7695

Leu Tyr Ala Gln Ala Gly Leu Phe Thr Met Glu Ile Ala Leu Phe
7700               7705           7710

Glu Leu Leu Ala Glu Trp Gly Val Arg Pro Asp Phe Val Ser Gly
7715               7720           7725

His Ser Ile Gly Glu Thr Ala Ala Ala Tyr Ala Ala Gly Val Leu
7730               7735           7740

Ser Leu Glu Asp Val Thr Thr Leu Ile Val Ala Arg Gly Arg Ala
7745               7750           7755

Leu Arg Gln Val Pro Pro Gly Ala Met Val Ala Leu Arg Ala Gly
7760               7765           7770

Glu Asp Glu Ala Arg Glu Phe Leu Gly Arg Thr Gly Ala Ala Leu
7775               7780           7785

Asp Leu Ala Ala Val Asn Ser Pro Thr Ser Val Val Val Ser Gly
7790               7795           7800

Ala Ser Glu Ala Val Ala Gly Phe Arg Ala Arg Trp Thr Glu Ser
7805               7810           7815

Gly Arg Glu Ala Arg Thr Leu Asn Val Arg His Ala Phe His Ser
7820               7825           7830

Arg His Val Glu Ala Val Leu Gly Glu Phe Arg Glu Val Leu Glu
7835               7840           7845

Ser Leu Thr Phe Arg Thr Pro Ala Leu Pro Val Val Ser Thr Val
7850               7855           7860

Thr Gly Arg Leu Ile Glu Pro Thr Glu Leu Ser Thr Ser Glu Tyr
7865               7870           7875

-continued

```
Trp Leu Arg Gln Val Arg Gln Thr Val Arg Phe His Asp Ala Val
    7880            7885                7890

Arg Glu Leu Ser Gly Gln Gly Val Gly Thr Phe Val Glu Ile Gly
    7895            7900                7905

Pro Ser Gly Ala Leu Ala Ser Ala Gly Leu Glu Cys Leu Gly Asp
    7910            7915                7920

Glu Ala Ser Phe His Ala Val Gln Arg Pro Gly Ser Pro Gly Asp
    7925            7930                7935

Val Cys Leu Met Thr Ala Val Ala Glu Leu His Ala Gly Gly Thr
    7940            7945                7950

Thr Val Asp Trp Ala Thr Val Leu Ala Gly Gly Arg Ala Thr Asp
    7955            7960                7965

Leu Pro Val Tyr Pro Phe Gln His Gly Ser Tyr Trp Leu Ala Pro
    7970            7975                7980

Val Thr Arg Ala Ala Asp Gly Ala Pro Ser Ala Gly Val Pro Ala
    7985            7990                7995

Pro Gly Glu Tyr Ala Arg Pro Ser Ala Pro Glu Glu Pro Arg Thr
    8000            8005                8010

Met Leu Glu Leu Val Arg Leu Glu Ala Ala Ile Ala Leu Ser Ile
    8015            8020                8025

Thr Asp Pro Gly Leu Ile Ala Asp Asp Ser Ser Phe Leu Asp Leu
    8030            8035                8040

Gly Phe Asp Ser Ile Ser Ala Leu Arg Leu Ser Asn Arg Leu Ala
    8045            8050                8055

Ala Val Thr Gly Leu Asp Leu Pro Pro Ser Leu Leu Phe Asp His
    8060            8065                8070

Pro Thr Pro Ala Glu Leu Ala Ala Arg Leu Asp Glu Leu Ser Ala
    8075            8080                8085

Ala Asp Leu Asp Gly Ala Gly Val Tyr Ala Leu Leu Glu Glu Ile
    8090            8095                8100

Asp Glu Leu Asp Asp Glu Asp Leu Asp Met Thr Glu Glu Glu Gln
    8105            8110                8115

Thr Ala Ile Ser Glu Leu Leu Thr Lys Leu Ser Ala Lys Trp Ser
    8120            8125                8130

Arg
```

<210> SEQ ID NO 12
<211> LENGTH: 123
<212> TYPE: DNA
<213> ORGANISM: Streptomyces malaysiensis NRRL B-24313

<400> SEQUENCE: 12
cgcgaccggg acttggccgc gttcgtcatg tactcctccg cggccggtgt gatgggtgct    60
gagggccagg gcaactacgc ggcggccaac gcgttcctcg atgccctggc cgagcaccgc   120
cgc                                                                  123

<210> SEQ ID NO 13
<211> LENGTH: 193
<212> TYPE: DNA
<213> ORGANISM: Streptomyces malaysiensis NRRL B-24313

<400> SEQUENCE: 13
tcatgtactc ctccgcggcc ggtgtgatgg gtgctgcggg ccagggcaac ttcgcggcgg    60
ccaacgcgtt cctcgatgcc ctggccgagc accgccgcgc tgacggcttg cccgcactct   120

```
cctggcatg gggtatgtgg gacgacgcag acggtatgag cggtcagcgg gccatcaccg    180
ccgaacacgg gat                                                     193

<210> SEQ ID NO 14
<211> LENGTH: 120
<212> TYPE: DNA
<213> ORGANISM: Streptomyces malaysiensis DSM4137

<400> SEQUENCE: 14
ggcgtcgacc tgaccgcggt gttccacacc gccggagccc tggacgacgg tgtcgtggaa    60
ctggtcgcca ccgcaatgaa cccggcgggg gagggtgaag tccccgcgct gctgcgtacg   120

<210> SEQ ID NO 15
<211> LENGTH: 123
<212> TYPE: DNA
<213> ORGANISM: Streptomyces malaysiensis DSM4137

<400> SEQUENCE: 15
cgcgaccggg atctggcggc gttcgtcatg tactcctccg ccgcgggcct catgggcagc    60
gagggacagg gcaactacgc ggcagccaac gccttcctgg acgcgctcgc ggtagagcgt   120
cgt                                                                123

<210> SEQ ID NO 16
<211> LENGTH: 193
<212> TYPE: DNA
<213> ORGANISM: Streptomyces malaysiensis DSM4137

<400> SEQUENCE: 16
tcatgtactc ctccgccgcg ggcctcatgg gcagccccgg acagggcaac ttcgcggcag    60
ccaacgcctt cctggacgcg ctcgcggtag agcgtcgtgc ggagggtttg cccgcgctct   120
cgctggcgtg gggtttctgg gaggaaacga ccggcctggg gggattgcag accatcaccg   180
ccgagcgcgg cat                                                     193

<210> SEQ ID NO 17
<211> LENGTH: 120
<212> TYPE: DNA
<213> ORGANISM: Streptomyces malaysiensis NRRL B-24313

<400> SEQUENCE: 17
gtgccgtccc tgacggcggt gatccacacc gcgggagtcc tcgacgacgg ggtgatggaa    60
ttgcttgccg caccgatggc cccggtccgg gacggcgagg ttcccgccct gctgcggtcg   120

<210> SEQ ID NO 18
<211> LENGTH: 123
<212> TYPE: DNA
<213> ORGANISM: Streptomyces malaysiensis NRRL B-24313

<400> SEQUENCE: 18
gcggcggtgt acggccagag cgtccaggaa cgcgttggcc gcagcgtagt taccttgtcc    60
ctcagcgccc aggacgccgg cggcggacga gtacacgatg aatgcggcca agtccctgtc   120
gcg                                                                123

<210> SEQ ID NO 19
<211> LENGTH: 193
<212> TYPE: DNA
<213> ORGANISM: Streptomyces malaysiensis NRRL B-24313

<400> SEQUENCE: 19
```

```
atcccgtacg cggcgctgat ggcacgctgg ccgctcaggc cgctcgcgtc ctcccacagt    60
ccccaggcca gggacaaacc aggcaaaccc tcaaggcggg ggtgtacggc cagagcgtcc   120
aggaacgcgt tggccgcagc gaagttacct tgtccggcag cgcccaggac gccggcggcg   180
gacgagtaca cga                                                     193

<210> SEQ ID NO 20
<211> LENGTH: 120
<212> TYPE: DNA
<213> ORGANISM: Streptomyces malaysiensis DSM4137

<400> SEQUENCE: 20
tgaccgcagg atcgcgggga cgtccccgtc ctggatcggg ctgatcggcg cggcgagcag    60
ttccacgaca ccgtcgtcga gggcgccggc ggtgtggatc accgcggtca ggtcgacgcc   120

<210> SEQ ID NO 21
<211> LENGTH: 123
<212> TYPE: DNA
<213> ORGANISM: Streptomyces malaysiensis DSM4137

<400> SEQUENCE: 21
gtgccgcctg gccatcaggc cgtcgaggta ggcgttcgcg gccgcgtaac cgccggagcc    60
ctcgcccagg aacaccgcgg agatggagga gtaggtgacg aacgccgcca ggtcggggag   120
caa                                                                123

<210> SEQ ID NO 22
<211> LENGTH: 193
<212> TYPE: DNA
<213> ORGANISM: Streptomyces malaysiensis DSM4137

<400> SEQUENCE: 22
atgccctcgg ccggggtgaa cgacagcacg ccgcccatgc cgccaccgtc ggcttcctgg    60
tcccacaggc cccacgccag ggacaggccg ggcagcccctt cggcgtgccg cctggccatc   120
aggccgtcga ggtaggcgtt cgcggccgcg aaaccgccgg agcccgcgcc caggaacacc   180
gcggagatgg agg                                                     193

<210> SEQ ID NO 23
<211> LENGTH: 120
<212> TYPE: DNA
<213> ORGANISM: Streptomyces malaysiensis DSM4137

<400> SEQUENCE: 23
gagcaccacc cgaccgcggt cgtgcatgcg gctggcgtgt ccgacgacgg cgtgatcggc    60
gtggtgccgg tccggctcga cctgcccgcc ctccgcgccg aagcggtcgc cgagggccgc   120

<210> SEQ ID NO 24
<211> LENGTH: 177
<212> TYPE: DNA
<213> ORGANISM: Streptomyces malaysiensis NRRL B-24313

<400> SEQUENCE: 24
gaggcgcggg aagcagacca gttcctggtg caccccgccc tgctggacgc ggcctggcat    60
ccggagctgc gcgacgaagt ggccgagacg agcccggacg ccggcgctg gtggtcgcaa   120 ccgtcgcgat ggaaccagat cgagttccac gcgaccggcg cggcgatact gcgcgtc    177

<210> SEQ ID NO 25
```

```
<211> LENGTH: 135
<212> TYPE: DNA
<213> ORGANISM: Streptomyces violaceusniger S1524

<400> SEQUENCE: 25
gaggcgcggg aagcagacca gttcctggtg caccccgccc tgctgaccac cgccctcacc    60
ctcaccggcg acgaggcacc cgccatctgg aaccagatcg agttccacgc gaccggcgcg   120
gcgatactgc gcgtc                                                    135

<210> SEQ ID NO 26
<211> LENGTH: 177
<212> TYPE: DNA
<213> ORGANISM: Streptomyces malaysiensis DSM4137

<400> SEQUENCE: 26
gtcacggcca cgatcagccc cgccggccct gccgtctcgc tgccggcctt cgcgggtggc    60
gaacccctgc acatcgcgga cggcaccccg gccggcttcc tcctgcatcc ggacgcgaca   120
ccggccgcca ctggaaccca gatcgagttc cacgcgaccg cgcggcgat actgcgc      177

<210> SEQ ID NO 27
<211> LENGTH: 432
<212> TYPE: DNA
<213> ORGANISM: Streptomyces malaysiensis DSM4137

<400> SEQUENCE: 27
ctcggttcgg tgatggcgtt gccgaactcg acggtgtgg tgctgaccgg caggatctcg    60
cgtcaggacg gtccggttct gtccgttgcg gctttcgttg aaatggcgtt cgcggctgct  120
ggtggtcgcc cgatccgtga actgtctgtt gacgcgctgc tgtacatccc ggacgacggc  180
accgcggaac tgcagacctg ggtctctgaa caccgtctga ccatccacgc acgttaccgt  240
gacaccgaac cgtggacccg tctggcgacc gccgctctgg acaccaccgc gcctgcgacg  300
acccacaccc cgcaccctgg tctgatcacc acggcgctga ccctgaccgg tgacgaagca  360
ccggcgatct ggaaccagat cgagttccac gcgaccggcg cggcgatact gcgcgtcgcg  420
gtgacaccgg tg                                                      432

<210> SEQ ID NO 28
<211> LENGTH: 177
<212> TYPE: DNA
<213> ORGANISM: Streptomyces malaysiensis NRRL B-24313

<400> SEQUENCE: 28
cagacgctgg aggcggcccg gtttacggtg catcccgcgc tgctggacgc ggcctggcat    60
ccggagctgc gcgacgaagt ggccgagacg agcccggacg gccggcgctg gtggtcgcaa   120
ccgtcgcgat ggggtcaggt tcagttccat acgaccggcg cggcgacgct gcgggtc      177

<210> SEQ ID NO 29
<211> LENGTH: 135
<212> TYPE: DNA
<213> ORGANISM: Streptomyces violaceusniger S1524

<400> SEQUENCE: 29
cagacgctgg aggcggcccg gtttacggtg catcccgcgc tgctgaccac cgccctcacc    60
ctcaccggcg acgaggcacc cgccatctgg ggtcaggttc agttccatac gaccggcgcg   120
gcgacgctgc gggtc                                                   135
```

```
<210> SEQ ID NO 30
<211> LENGTH: 177
<212> TYPE: DNA
<213> ORGANISM: Streptomyces malaysiensis DSM4137

<400> SEQUENCE: 30
gtcacggcca cgatcagccc gtccggtccg atcgtctcgc cgccggcctt cgcgggtggc    60
gaacccctgc acatcgcgga cggcaccccg gccggcttcc tcctgcatcc ggacgcgaca   120
ccggccgccg actggggtca ggttcagttc catacgaccg gcgcggcgac gctgcgg      177

<210> SEQ ID NO 31
<211> LENGTH: 432
<212> TYPE: DNA
<213> ORGANISM: Streptomyces malaysiensis DSM4137

<400> SEQUENCE: 31
ctggacaccg tcgtggcgtt gccgggcgcg gacggtgtgg tgctgaccgg caggatctcg    60
cgtcaggacg gtccggttct gtccgttgcg gctttcgttg aaatggcgtt cgcggctgct   120
ggtggtcgcc cgatccgtga actgtctgtt gacgcgctgc tgtacatccc ggacgacggc   180
accgcggaac tgcagacctg ggtctctgaa caccgtctga ccatccacgc acgttaccgt   240
gacaccgaac cgtggacccg tctggcgacc gccgctctgg acaccaccgc gcctgcgacg   300
acccacaccc cgcaccctgg tctgatcacc acggcgctga ccctgaccgg tgacgaagca   360
ccggcgatct ggggtcaggt tcagttccat acgaccggcg cggcgacgct gcgggtcgcg   420
gtgacgccgg tg                                                       432

<210> SEQ ID NO 32
<211> LENGTH: 177
<212> TYPE: DNA
<213> ORGANISM: Streptomyces malaysiensis NRRL B-24313

<400> SEQUENCE: 32
cgacccgtag cgtcgccgcg ccggtaccgt ggaactgcac ccgagccatc gcgacggttg    60
cgaccaccag cgccggccgt ccgggctcgt ctcggccact tcgtcgcgca gctccggatg   120
ccaggccgcg tcgagcaggg cgggatgcat ggtgaagcgg ccgtttcct gggcctg       177

<210> SEQ ID NO 33
<211> LENGTH: 135
<212> TYPE: DNA
<213> ORGANISM: Streptomyces malaysiensis DSM4137

<400> SEQUENCE: 33
cgacccgtag cgtcgccgcg ccggtaccgt ggaactgcac ccgagccaga tggcgggtgc    60
ctcgtcgccg gtgagggtga gggcggtggt gagcagggcg ggatgcatgg tgaagcgggc   120
cgtttcctgg gcctg                                                    135

<210> SEQ ID NO 34
<211> LENGTH: 177
<212> TYPE: DNA
<213> ORGANISM: Streptomyces malaysiensis DSM4137

<400> SEQUENCE: 34
ccgtagcgtc gccgcgccgg taccgtggaa ctgcacccga gtccagtcgg cggccggtgt    60
cgcgtccgga tgcaggagga agccggccgg ggtgccgtcc gcgatgtgca ggggttcgcc   120
acccgcgaag gccggcagtg acgcgccggg accgatggtg gcggtgacgt gctggat      177
```

<210> SEQ ID NO 35
<211> LENGTH: 432
<212> TYPE: DNA
<213> ORGANISM: Streptomyces malaysiensis DSM4137

<400> SEQUENCE: 35

```
ctggaaaccg tcgtggcact gcccggcacc gacggggtgg cactgaccgg ccgaatctca    60
cgtcaggacg gtccggttct gtccgttgcg gctttcgttg aaatggcgtt cgcggctgct   120
ggtggtcgcc cgatccgtga actgtctgtt gacgcgctgc tgtacatccc ggacgacggc   180
accgcggaac tgcagacctg ggtctctgaa caccgtctga ccatccacgc acgttaccgt   240
gacaccgaac cgtggacccg tctggcgacc gccgctctgg acaccaccgc gcctgcgacg   300
acccacaccc cgcaccctgg tctgatcacc acggcgctga ccctgaccgg tgacgaagca   360
ccggcgatct ggactcgggt gcagttccac ggtaccggcg cggcgacgct acgggtcgcg   420
gtgaccccgg cg                                                       432
```

<210> SEQ ID NO 36
<211> LENGTH: 177
<212> TYPE: DNA
<213> ORGANISM: Streptomyces malaysiensis DSM4137

<400> SEQUENCE: 36

```
gaacagggcg agcaactcgg tcatgatctc gcggagccgg tcgtggccgg catccatcag    60
ggtgaaggca tggtaggtgg catccgggat ctgagcggcg tcgcggatgt cggtctggcc   120
catctcgatg aaccggccgc cgtcgaccag caggtcgagg aggcgtcga tgaactc       177
```

<210> SEQ ID NO 37
<211> LENGTH: 174
<212> TYPE: DNA
<213> ORGANISM: Streptomyces malaysiensis DSM4137

<400> SEQUENCE: 37

```
gaacagggcg agcaactcgg tcatgatctc gcggagccgg tcgtggccgg catccatcag    60
gtggaaggca tggtaggtgg catccgggat ctgagcggcg tcgcggatgt cggtgcccat   120
ctcgatgaac cggccgccgt cgaccagcag gtcgaggag gcgtcgatga actc           174
```

<210> SEQ ID NO 38
<211> LENGTH: 914
<212> TYPE: PRT
<213> ORGANISM: Streptomyces hygroscopicus

<400> SEQUENCE: 38

```
Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Ala Lys Ser Asp Ala Ile Thr Leu Arg Ala Val Cys
    50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

Leu Pro Gly Glu His Leu Ser Pro Glu Ala Glu Asn Arg Leu Arg Gly
```

```
                100             105                 110
Asp Leu Thr Arg Thr Leu Leu Ala Leu Ala Ala Glu Arg Pro Val Leu
            115                 120             125
Ile Gly Ile Asp Asp Met His His Ala Asp Thr Ala Ser Leu Asn Cys
        130                 135             140
Leu Leu His Leu Ala Arg Arg Val Gly Pro Ala Arg Ile Ala Met Val
145                 150             155                 160
Leu Thr Glu Leu Arg Arg Leu Thr Pro Ala His Ser Gln Phe His Ala
                165                 170             175
Glu Leu Leu Ser Leu Gly His His Arg Glu Ile Ala Leu Arg Pro Leu
            180                 185             190
Gly Pro Lys His Ile Ala Glu Leu Ala Arg Ala Gly Leu Gly Pro Asp
        195                 200             205
Val Asp Glu Asp Val Leu Thr Gly Leu Tyr Arg Ala Thr Gly Gly Asn
210                 215             220
Leu Asn Leu Gly His Gly Leu Ile Lys Asp Val Arg Glu Ala Trp Ala
225                 230             235                 240
Thr Gly Gly Thr Gly Ile Asn Ala Gly Arg Ala Tyr Arg Leu Ala Tyr
                245             250                 255
Leu Gly Ser Leu Tyr Arg Cys Gly Pro Val Pro Leu Arg Val Ala Arg
            260                 265             270
Val Ala Ala Val Leu Gly Gln Ser Ala Asn Thr Thr Leu Val Arg Trp
        275                 280             285
Ile Ser Gly Leu Asn Ala Asp Ala Val Gly Glu Ala Thr Glu Ile Leu
    290                 295             300
Thr Glu Gly Gly Leu Leu His Asp Leu Arg Phe Pro His Pro Ala Ala
305                 310             315                 320
Arg Ser Val Val Leu Asn Asp Leu Ser Ala Arg Glu Arg Arg Arg Leu
                325             330                 335
His Arg Ser Ala Leu Glu Val Leu Asp Asp Val Pro Val Glu Val Val
            340                 345             350
Ala His His Gln Ala Gly Ala Gly Phe Ile His Gly Pro Lys Ala Ala
        355                 360             365
Glu Ile Phe Ala Lys Ala Gly Gln Glu Leu His Val Arg Gly Glu Leu
    370                 375             380
Asp Ala Ala Ser Asp Tyr Leu Gln Leu Ala His Ala Ser Asp Asp
385                 390             395                 400
Ala Val Thr Arg Ala Ala Leu Arg Val Glu Ala Val Ala Ile Glu Arg
                405             410                 415
Arg Arg Asn Pro Leu Ala Ser Ser Arg His Leu Asp Glu Leu Thr Val
            420                 425             430
Ala Ala Arg Ala Gly Leu Leu Ser Leu Glu His Ala Ala Leu Met Ile
        435                 440             445
Arg Trp Leu Ala Leu Gly Gly Arg Ser Gly Glu Ala Ala Glu Val Leu
    450                 455             460
Ala Ala Gln Arg Pro Arg Ala Val Thr Asp Gln Asp Arg Ala His Leu
465                 470             475                 480
Arg Ala Ala Glu Val Ser Leu Ala Leu Val Ser Pro Gly Ala Ser Gly
                485             490                 495
Val Ser Pro Gly Ala Ser Gly Pro Asp Arg Pro Arg Pro Leu Pro
            500                 505             510
Pro Asp Glu Leu Ala Asn Leu Pro Lys Ala Ala Arg Leu Cys Ala Ile
        515                 520             525
```

Ala Asp Asn Ala Val Ile Ser Ala Leu His Gly Arg Pro Glu Leu Ala
            530                 535                 540

Ser Ala Glu Ala Glu Asn Val Leu Lys Gln Ala Asp Ser Ala Ala Asp
545                 550                 555                 560

Gly Ala Thr Ala Leu Ser Ala Leu Thr Ala Leu Leu Tyr Ala Glu Asn
                565                 570                 575

Thr Asp Thr Ala Gln Leu Trp Ala Asp Lys Leu Val Ser Glu Thr Gly
            580                 585                 590

Ala Ser Asn Glu Glu Glu Gly Ala Gly Tyr Ala Gly Pro Arg Ala Glu
        595                 600                 605

Thr Ala Leu Arg Arg Gly Asp Leu Ala Ala Val Glu Ala Gly Ser
    610                 615                 620

Ala Ile Leu Asp His Arg Arg Gly Ser Leu Leu Gly Ile Thr Ala Ala
625                 630                 635                 640

Leu Pro Leu Ser Ser Ala Val Ala Ala Ile Arg Leu Gly Glu Thr
                645                 650                 655

Glu Arg Ala Glu Lys Trp Leu Ala Glu Pro Leu Pro Glu Ala Ile Arg
            660                 665                 670

Asp Ser Leu Phe Gly Leu His Leu Leu Ser Ala Arg Gly Gln Tyr Cys
        675                 680                 685

Leu Ala Thr Gly Arg His Glu Ser Ala Tyr Thr Ala Phe Arg Thr Cys
    690                 695                 700

Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
            740                 745                 750

Arg Ser Arg Ala Leu Thr Leu Arg Val Gln Ala Ala Tyr Ser Pro Gln
        755                 760                 765

Ala Gln Arg Val Asp Leu Leu Glu Glu Ala Ala Asp Leu Leu Leu Ser
    770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
            820                 825                 830

Arg Leu Gly Ala Lys Pro Gly Gly Pro Gly Trp Leu Glu Glu Ser Gly
        835                 840                 845

Leu Pro Gln Arg Ile Lys Ser Leu Thr Asp Ala Glu Arg Arg Val Ala
    850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
            900                 905                 910

Ala Glu

<210> SEQ ID NO 39
<211> LENGTH: 12
<212> TYPE: DNA

```
<213> ORGANISM: Artificial Sequence
<220> FEATURE:
<223> OTHER INFORMATION: Synthetic Construct

<400> SEQUENCE: 39 ctaggggtt gc                                                              12

<210> SEQ ID NO 40
<211> LENGTH: 6
<212> TYPE: DNA
<213> ORGANISM: Artificial Sequence
<220> FEATURE:
<223> OTHER INFORMATION: Synthetic Construct

<400> SEQUENCE: 40 gggggt                                                                    6

<210> SEQ ID NO 41
<211> LENGTH: 2685
<212> TYPE: DNA
<213> ORGANISM: Streptomyces hygroscopicus

<400> SEQUENCE: 41
atgcctgccg tggagtgcta tgaactggac gcccgcgatg acgagctcag aaaactggag        60
gaggttgtga ccgggcgggc caacggccgg ggtgtggtgg tcaccatcac cggaccgatc       120
gcctgcggca agaccgaact gctcgacgca gccgccgcga aggccgacgc catcacgtta       180
cgagcggtct gctccgcgga ggaacaggca ctcccgtacg ccctgatcgg cagctcatc        240 gacaacccgg cgctcgcctc ccacgcgctg agccggcct gccgaccct cccgggcgag        300 cacctgtcgc cggaggccga gaaccggctg cgcagcgacc tcacccgtac cctgctggcg       360
ctcgccgcca acggccggt gctgatcggc atcgacgagt cacacgcgaa cgctttgtgt       420
ctgctccacc tggcccgaag ggtcggctcg gcccggatcg ccatggtcct caccgagttg       480
cgccggctca ccccggccca ctcacagttc caggccgagc tgctcagcct ggggcaccac       540
cgcgagatcg cgctgcgccc gctcagcccg aagcacaccg ccgagctggt ccgcgccggt       600
ctcggtcccg acgtcgacga ggacgtgctc acggggttgt accgggcgac cggcggcaac       660
ctgaacctca cccgcggact gatcaacgat gtgcgggagg cctgggagac gggagggacg       720
ggcatcagcg cgggccgcgc gtaccggctg catacctcg gttccctcta ccgctgcggc        780
ccggtcccgt tgcgggtcgc acgggtggcc gccgtgctgg gccagagcgc caacaccacc       840
ctggtgcgct ggatcagcgg gctcaacgcg gacgcgtgg gcgaggcaac cgagatcctc       900
accgaaggcg gcctgctgca cgacctgcgg ttcccgcacc cggcggcccg ttcggtggta       960
ctcaacgaca tgtccgccca ggaacgacgc cgcctgcacc ggtccgctct ggaagtgctg      1020
gacgacgtgc ccgtggaagt ggtcgcgcac caccaggtcg gcgccggtct cctgcacggc      1080
ccgaaggccg ccgagatatt cgccaaggcc ggccaggagc tgcatgtgcg cggcgagttg      1140
gacaccgcgt ccgactatct gcaactggcc caccaggcct ccgacgacgc cgtcaccggg      1200
atgcgggccg aggccgtggc gatcgagcgc cgccgcaacc cgctggcctc gagccggcac      1260
ctcgacgagc tgaccgtcgt cgcccgtgcc gggctgctct tccccgagca cgcgcgctg      1320 atgatccgct ggctgggcgt cggcgggcgg tccggcgagg cagccgggct gctggcctcg      1380 cagcgcccc gtgcggtcac cgaccaggac agggcccata tgcgggccgc cgaggtatcg      1440
ctcgcgctgg tcagccccgg cacgtccggc ccggaccggc ggccgcgtcc gctcacgccg      1500
gatgagctcg cgaacctgcc gaaggcggcc cggctctgcg cgatcgccga caatgccgtc      1560
```

```
atgtcggccc tgcgcggtcg tcccgagctc gccgcggccg aggcggagaa cgtcctgcag      1620
cacgccgact cggcggcggc cggcaccacc gccctcgccg cgctgaccgc cttgctgtac      1680
gcggagaaca ccgacaccgc tcagctctgg gccgacaagc tggtctccga gaccggggcg      1740
tcgaacgagg aggaggcggg ctacgcgggg ccgcgcgccg aagccgcgtt gcgtcgcggc      1800
gacctggccg cggcggtcga ggcaggcagc accgttctgg accaccggcg gctctcgacg      1860
ctcggcatca ccgccgcgct accgctgagc agcgcggtgg ccgccgccat ccggctgggc      1920
gagaccgagc gggcggagaa gtggctcgcc cagccgctgc gcaggccat  ccaggacggc      1980 ctgttcggcc tgcaccctgct ctcggcgcgc ggccagtaca gcctcgccac gggccagcac     2040
gagtcggcgt acacggcgtt tcgcacctgc ggggaacgta tgcggaactg ggcgttgac      2100 gtgccgggtc tgtccctgtg gcgcgtcgac gccgccgagg cgctgctgca cggccgcgac    2160
cgggacgagg gccgacggct cgtcgacgag caactcaccc gtgcgatggg acccgttcc     2220 cgcgccttga cgctgcgggt gcaggcggcg tacagcccgc cggcgaagcg ggtcgacctg    2280
ctcgatgaag cggccgacct gctgctctcc tgcaacgacc agtacgagcg ggcacgggtg    2340
ctcgccgacc tgagcgagac gttcagcgcg ctccggcacc acagccgggc gcggggactg    2400
cttcggcagg cccggcacct ggccgcccag cgcggcgcga taccgctgct gcgccgactc    2460
ggggccaagc ccgaggccc cggctggctg gaggaatccg gcctgccgca gcggatcaag     2520
tcgctgaccg acgcggagcg gcgggtggcg tcgctggccg ccggcggaca gaccaaccgc    2580
gtgatcgccg accagctctt cgtcacggcc agcacggtgg agcagcacct cacggacgtc    2640
tccactgggt caaggccgcc agcacctgcc gccgaactcg tctag                     2685
```

<210> SEQ ID NO 42  
<211> LENGTH: 2685  
<212> TYPE: DNA  
<213> ORGANISM: Streptomyces hygroscopicus

<400> SEQUENCE: 42

```
atgcctgccg tggagtgcta tgaactggac gcccgcgatg acgagctcag aaaactggag       60
gaggttgtga ccgggcgggc caacggccgg ggtgtggtgg tcaccatcac cggaccgatc      120
gcctgcggca agaccgaact gctcgacgca gccgccgcga aggccgacgc catcacgctg      180
cgagcggtct gctccgcgga ggaacaggca ctcccgtacg ccctgatcgg cagctcatc      240 gacaacccgg cgctcgcctc ccacgcgctg gagccggcct gcccgaccct cccgggcgag    300
cacctgtcgc cggaggccga gaaccggctg cgcagcgacc tcacccgtac cctgctggcg    360
ctcgccgccg aacggccggt gctgatcggc atcgacgagt cacacgcgaa cgctttgtgt    420
ctgctccacc tggcccgaag ggtcggctcg gccggatcg ccatggtcct caccgagttg     480
cgccggctca ccccggccca ctcacagttc caggccgagc tgctcagcct ggggcaccac    540
cgcgagatcg cgctgcgccc gctcagcccg aagcacaccg ccgagctggt ccgcgccggt     600
ctcggtcccg acgtcgacga ggacgtgctc acggggttgt accgggcgac cggcggcaac    660
ctgaacctca cccgcggact gatcaacgat gtgcgggagg cctgggagac gggagggacg     720
ggcatcagcg cgggccgcgc gtaccggctg gcataccctcg gttccctcta ccgctgcggc     780
ccggtcccgt tgcgggtcgc acgggtggcc gccgtgctgg gccagagcgc caacaccacc    840
ctggtgcgct ggatcagcgg gctcaacgcg gacgcggtgg gcgaggcaac cgagatcctc    900
accgaaggcg gcctgctgca cgacctgcgg ttcccgcacc cggcggcccg ttcggtggta    960
```

```
ctcaacgaca tgtccgccca ggaacgacgc cgcctgcacc ggtccgctct ggaagtgctg    1020
gacgacgtgc ccgtggaagt ggtcgcgcac caccaggtcg cgccggtct cctgcacggc    1080 ccgaaggccg ccgagatatt cgccaaggcc ggccaggagc tgcatgtgcg cggcgagttg    1140
gacaccgcgt ccgactatct gcaactggcc caccaggcct ccgacgacgc cgtcaccggg    1200
atgcgggccg aggccgtggc gatcgagcgc cgccgcaacc cgctggcctc gagccggcac    1260
ctcgacgagc tgaccgtcgt cgcccgtgcc gggctgctct ccccgagca cacgcgctg    1320 atgatccgct ggctgggcgt cggcgggcgg tccggcgagg cagccgggct gctggcctcg    1380
cagcgccccc gtgcggtcac cgaccaggac agggcccata tgcgggccgc cgaggtatcg    1440
ctcgcgctgg tcagccccgg cacgtccggc ccggaccggc ggccgcgtcc gctcacgccg    1500
gatgagctcg cgaacctgcc gaaggcggcc cggctctgcg cgatcgccga caatgccgtc    1560
atgtcggccc tgcgcggtcg tcccgagctc gccgcggccg aggcggagaa cgtcctgcag    1620
cacgccgact cggcggcggc cggcaccacc gccctcgccg cgctgaccgc cttgctgtac    1680
gcggagaaca ccgacaccgc tcagctctgg gccgacaagc tggtctccga gaccggggcg    1740
tcgaacgagg aggaggcggg ctacgcgggg ccgcgcgccg aagccgcgtt gcgtcgcggc    1800
gacctggccg cggcggtcga ggcaggcagc accgttctgg accaccggcg gctctcgacg    1860
ctcggcatca ccgccgcgct accgctgagc agcgcggtgg ccgccgccat ccggctgggc    1920
gagaccgagc gggcggagaa gtggctcgcc cagccgctgc cgcaggccat ccaggacggc    1980
ctgttcggcc tgcacctgct ctcggcgcgc ggccagtaca gcctcgccac gggccagcac    2040
gagtcggcgt acacgcgcgtt cgcacctgc ggggaacgta tgcggaactg ggcgttgac    2100 gtgccgggtc tgtccctgtg gcgcgtcgac gccgccgagg cgctgctgca cggccgcgac    2160
cgggacgagg gccgacggct cgtcgacgag caactcaccc gtgcgatggg accccgttcc    2220
cgcgccttga cgctgcgggt gcaggcggcg tacagcccgc cggcgaagcg ggtcgacctg    2280
ctcgatgaag cggccgacct gctgctctcc tgcaacgacc agtacgagcg ggcacgggtg    2340
ctcgccgacc tgagcgagac gttcagcgcg ctccggcacc acagccgggc gcggggactg    2400
cttcggcagg cccggcacct ggccgcccag cgcggcgcga taccgctgct cgccgactc    2460 ggggccaagc ccggaggccc cggctggctg gaggaatccg gcctgccgca gcggatcaag    2520
tcgctgaccg acgcggagcg gcgggtggcg tcgctggccg ccggcggaca gaccaaccgc    2580
gtgatcgccg accagctctt cgtcacggcc agcacggtgg agcagcacct cacggacgtc    2640
tccactgggt caaggccgcc agcacctgcc gccgaactcg tctag               2685
```

<210> SEQ ID NO 43
<211> LENGTH: 2772
<212> TYPE: DNA
<213> ORGANISM: Streptomyces kanamyceticus

<400> SEQUENCE: 43

```
gtggttcctg aagtgcgagc agcccccgac gaactgatcg cccgcgatga cgagctgagc      60
cgcctccaac gggcactcac cagggcgggg agcggaaggg gcggcgtcgt cgccatcacc     120
gggcccatcg ccagcggaaa gacgcgcctg ctcgacgccg gagcggccaa gtccggcttc     180
gtcgcactcc gtgcggtgtg ctcctgggaa gagcgcactc tgccgtacgg gatgctgggc     240
cagctcttcg accatcccga actggccgcc caggcgccgg accttgccca cttcacgget     300 tcgtgcgaga gccctcaggc cggtaccgac aaccgcctgc gggccgagtt cacccgcacc     360
ctgctggcgc tcgccgcgga ctggcccgtc ctgatcggca tcgacgacgt gcaccacgcc     420
```

```
gacgcggaat cactgcgctg tctgctccac ctcgcccgcc gcatcggccc ggcccgcatc      480
gcggtcgtac tgaccgagct gcgcagaccg acgcccgccg actcccgctt ccaggcggaa      540
ctgctgagcc tgcgctccta ccaggagatc gcgctcagac cgctcaccga ggcgcagacc      600
ggcgaactcg tacgtcggca cctcggcgcg agacccacg aggacgtctc cgccgatacg       660
ttccgggcga ccggcgggaa cctgctcctc gggcacggtt tgatcaatga catccgggag      720
gcgcggacag cgggacggcc gggggtcgtc gggggcggg cgtaccggct cgcgtacctc       780
agctcgctct accgctgcgg cccgagcgcg ctgcgtgtcg cccgggcgtc cgccgtgctc      840
ggcgcgagcg ccgaagccgt gctcgtccag cggatgaccg gactgaacaa ggacgcggtc      900
gaacaggtct atgagcagct gaacgaggga cggctgctgc agggcgagcg gtttccgcac      960
ccggcggccc gctccatcgt ccttgacgac ctgtcggccc tggaacgcag aaacctgcac     1020
gagtcggcgc tggagctgct gcgggaccac ggcgtggccg gcaacgtgct cgcccgccac     1080
cagatcggcg ccggccgggt gcacggcgag gaggccgtcg agctgttcac cggggccgca     1140
cgggagcacc acctgcgcgg tgaactggac gacgcggccg gataccggga actcgcccac     1200
cgtgcctccg acgacccgt cacgcgcgcc gcactacgcg tcggcgccgc cgcgatcgag       1260
cgcctctgca atccggtacg ggcaggccgg catctgcccg agctgctcac cgcgtcgcgc     1320 gcggactgc tctccagcga gcacgccgtg tcgctcgccg actggctggc gatgggcggg       1380
cgcccgggcg aggcggccga ggtcctcgcg acgcagcgtc ccgcggccga cagcgagcag     1440
caccgcgcac tcctgcgcag cggcgagttg tccctcgcgc tggtccaccc cggcgcgtgg     1500
gatccgttgc gccggaccga tcggttcgcc gcgggcgggc tcggctcgct tcccggaccc     1560
gcccggcacc gcgcggtcgc cgaccaagcc gtcatcgcgg cgctgcgtgg acgtctcgac     1620
cgggcggacg ccaacgcgga gagcgttctc cagcacaccg acgccacggc ggaccggacc     1680
acggccatca tggcgttgct ggccctgctc tacgcggaga acaccgatgc tgtccagttc     1740
tgggtcgaca aactggccgg tgacgagggc accaggacac cggccgacga ggcggtccac     1800
gcggggttca cgccgagat cgcgctgcgc cgcggcgact tgatgagagc cgtcgagtac       1860
ggcgaggcag cgctcggcca ccggcacctg cccacctggg gaatggccgc cgctctgccg     1920
ctgagcagca ccgtggttgc cgcgatccgg ctcggcgacc tcgacagggc cgagcggtgg     1980
ctcgccgagc cgctgccgca gcagacgccg gagagcctct cgggctgca cctgctctgg      2040 gcccgcgggc agcaccacct cgcgaccggg cggcacgggg cggcgtacac ggcgttcagg     2100
gaatgcggcc agcggatgcg gcggtgggcc gtcgacgtgc cgggcctggc cctgtggcgg     2160
gtcgacgccg ccgaatcgct gctgctgctc ggccgtgacc gtgccgaagg actgcggctc     2220
gtctccgagc agctgtcccg gccgatgcgc cctcgcgcgc gcgtgcagac gttacgggta     2280
caggcggcct acagtccgcc gccccaacgg atcgacctgc tcgaagaggc cgccgacctg     2340
ctggtcacct gcaacgacca gtacgaactg gcaaacgtac tcagcgactt ggcagaggcc     2400
tccagcatgg tccggcagca cagcagggcg cggggtctgc tccgccgggc acggcacctc     2460
gccacccagt gcggcgccgt gccgctcctg cggcggctcg gcgcggaacc ctcggacatc     2520
ggcggagcct gggacgcgac gctgggacag cggatcgcgt cactgacgga gtcggagcgg     2580
cgggtggccg cgctcgccgc ggtcgggcgt acgaacaggg agatcgccga gcagctgttc     2640
gtcacggcca gcacggtgga acagcacctc acgaacgtgt tccgcaaact ggcggtgaag     2700
ggccgccagc agcttccgaa ggaactggcc gacgtcggcg agccggcgga ccgcgaccgc     2760
```
cggtgcgggt ag 2772

<210> SEQ ID NO 44
<211> LENGTH: 2772
<212> TYPE: DNA
<213> ORGANISM: Streptomyces kanamyceticus

<400> SEQUENCE: 44

| | | | | | |
|---|---|---|---|---|---|
| atggttcctg | aagtgcgagc | agcccccgac | gaactgatcg | cccgcgatga | cgagctgagc | 60 |
| cgcctccaac | gggcactcac | cagggcgggg | agcggaaggg | gcggcgtcgt | cgccatcacc | 120 |
| gggcccatcg | ccagcggaaa | gacgcgctg | ctcgacgccg | gagcggccaa | gtccggcttc | 180 |
| gtcgcactcc | gtgcggtgtg | ctcctgggaa | gagcgcactc | tgccgtacgg | gatgctgggc | 240 |
| cagctcttcg | accatcccga | actggccgcc | caggcgccgg | accttgccca | cttcacggct | 300 |
| tcgtgcgaga | gccctcaggc | cggtaccgac | aaccgcctgc | gggccgagtt | cacccgcacc | 360 |
| ctgctggcgc | tcgccgcgga | ctggcccgtc | ctgatcggca | tcgacgacgt | gcaccacgcc | 420 |
| gacgcggaat | cactgcgctg | tctgctccac | ctcgcccgcc | gcatcggccc | ggcccgcatc | 480 |
| gcggtcgtac | tgaccgagct | gcgcagaccg | acgcccgccg | actcccgctt | ccaggcggaa | 540 |
| ctgctgagcc | tgcgctccta | ccaggagatc | gcgctcagac | cgctcaccga | ggcgcagacc | 600 |
| ggcgaactcg | tacgtcggca | cctcggcgcg | gagacccacg | aggacgtctc | cgccgatacg | 660 |
| ttccgggcga | ccgcgcggaa | cctgctcctc | gggcacggtt | tgatcaatga | catccgggag | 720 |
| gcgcggacag | cgggacggcc | gggggtcgtc | gcggggcggg | cgtaccggct | cgcgtacctc | 780 |
| agctcgctct | accgctgcgg | cccgagcgcg | ctgcgtgtcg | cccgggcgtc | cgccgtgctc | 840 |
| ggcgcgagcg | ccgaagccgt | gctcgtccag | cggatgaccg | gactgaacaa | ggacgcggtc | 900 |
| gaacaggtct | atgagcagct | gaacgaggga | cggctgctgc | agggcgagcg | gtttccgcac | 960 |
| ccggcggccc | gctccatcgt | ccttgacgac | ctgtcggccc | tggaacgcag | aaacctgcac | 1020 |
| gagtcggcgc | tggagctgct | gcgggaccac | ggcgtggccg | gcaacgtgct | cgcccgccac | 1080 |
| cagatcggcg | ccggccgggt | gcacggcgag | gaggccgtcg | agctgttcac | cggggccgca | 1140 |
| cgggagcacc | acctgcgcgg | tgaactggac | gacgcggccg | gatacctgga | actcgcccac | 1200 |
| cgtgcctccg | acgacccgt | cacgcgcgcc | gcactacgcg | tcggcgccgc | cgcgatcgag | 1260 |
| cgcctctgca | atccggtacg | ggcaggccgg | catctgcccg | agctgctcac | cgcgtcgcgc | 1320 |
| gcgggactgc | tctccagcga | gcacgccgtg | tcgctcgccg | actggctggc | gatgggcggg | 1380 |
| cgccggggcg | aggcggccga | ggtcctcgcg | acgcagcgtc | ccgcggccga | cagcgagcag | 1440 |
| caccgcgcac | tcctgcgcag | cggcgagttg | tccctcgcgc | tggtccaccc | cggcgcgtgg | 1500 |
| gatccgttgc | gccggaccga | tcggttcgcc | gcgggcgggc | tcggctcgct | tcccggaccc | 1560 |
| gcccggcacc | gcgcggtcgc | cgaccaagcc | gtcatcgcgg | cgctgcgtgg | acgtctcgac | 1620 |
| cgggcggacg | ccaacgcgga | gagcgttctc | cagcacaccg | acgccacggc | ggaccggacc | 1680 |
| acggccatca | tggcgttgct | ggccctgctc | tacgcggaga | acaccgatgc | tgtccagttc | 1740 |
| tgggtcgaca | aactggccgg | tgacgagggc | accaggacac | cggccgacga | ggcggtccac | 1800 |
| gcggggttca | acgccgagat | cgcgctgcgc | gcggcgact | tgatgagagc | cgtcgagtac | 1860 |
| ggcgaggcag | cgctcggcca | ccggcacctg | cccacctggg | aatggccgc | cgctctgccg | 1920 |
| ctgagcagca | ccgtggttgc | cgcgatccgg | ctcggcgacc | tcgacagggc | cgagcggtgg | 1980 |
| ctcgccgagc | cgctgccgca | gcagacgccg | gagagcctct | tcgggctgca | cctgctctgg | 2040 |
| gcccgcgggc | agcaccacct | cgcgaccggg | cggcacgggg | cggcgtacac | ggcgttcagg | 2100 |

```
gaatgcggcg agcggatgcg gcggtgggcc gtcgacgtgc cgggcctggc cctgtggcgg    2160
gtcgacgccg ccgaatcgct gctgctgctc ggccgtgacc gtgccgaagg actgcggctc    2220
gtctccgagc agctgtcccg gccgatgcgc cctcgcgcgc gcgtgcagac gctgcgggta    2280
caggcggcct acagtccgcc gccccaacgg atcgacctgc tcgaagaggc cgccgacctg    2340
ctggtcacct gcaacgacca gtacgaactg gcaaacgtac tcagcgactt ggcagaggcc    2400
tccagcatgg tccggcagca cagcagggcg cggggtctgc tccgccgggc acggcacctc    2460
gccacccagt gcggcgccgt gccgctcctg cggcggctcg gcgcggaacc ctcggacatc    2520
ggcggagcct gggacgcgac gctgggacag cggatcgcgt cactgacgga gtcggagcgg    2580
cgggtggccg cgctcgccgc ggtcgggcgt acgaacaggg agatcgccga gcagctgttc    2640
gtcacggcca gcacggtgga acagcacctc acgaacgtgt ccgcaaaact ggcggtgaag    2700
ggccgccagc agcttccgaa ggaactggcc gacgtcggcg agccggcgga ccgcgaccgc    2760
cggtgcgggt ag                                                        2772

<210> SEQ ID NO 45
<211> LENGTH: 2742
<212> TYPE: DNA
<213> ORGANISM: Streptomyces ascomyceticus

<400> SEQUENCE: 45
gtgatagcgc gcttatctcc cccagacctg atcgcccgcg atgacgagtt cggttccctc      60
caccgggcgc tcacccgagc ggggggcggg cggggcgtcg tcgccgccgt caccgggccg     120
atcgcctgcg gcaagaccga actcctcgac gccgccgcgg ccaaggccgg cttcgtcacc     180
cttcgcgcgg tgtgctccat ggaggagcgg gccctgccgt acggcatgct cggccagctc     240
ctcgaccagc ccgagctggc cgcccggaca ccggagctgg tccggctgac ggcatcgtgc     300
gaaaacctgc cggccgacgt cgacaaccgc ctggggaccg aactcacccg cacggtgctg     360
acgctcgccg cggagcggcc cgtactgatc ggcatcgacg acgtgcacca cgccgacgcg     420
ccgtcgctgc gctgcctgct ccacctcgcg cgccgcatca gccgggcccg tgtcgccatc     480
gtgctgaccg agctgctccg gccgacgccc gcccactccc aattccgggc ggcactgctg     540
agtctgcgcc actaccagga gatcgcgctg cgcccgctca ccgaggcgca gaccaccgaa     600
ctcgtgcgcc ggcacctcgg ccaggacgcg cacgacgacg tggtggccca ggcgttccgg     660
gcgaccggcg gcaacctgct cctcggccac ggcctgatcg acgacatccg ggaggcacgg     720
acacggacct cagggtgcct ggaagtggtc gcggggcggg cgtaccggct cgcctacctc     780
gggtcgctct atcgttgcgg cccggccgcg ctgagcgtcg cccgagcttc cgccgtgctc     840
ggcgagagtg tcgaactcac cctcgtccag cggatgaccg gcctcgacac cgaggcggtc     900
gagcaggccc acgaacagct ggtcgagggg cggctgctgc gggaagggcg gttcccgcac     960
cccgcggccc gctccgtcgt actcgacgac ctctccgccg ccgagcggcg tggcctgcac    1020
gagctggcgc tggaactgct gcgggaccgc ggcgtggcca gcaaggtgct cgcccgccac    1080
cagatgggta ccggccgggt gcacggcgcc gaggtcgccg ggctgttcac cgacgccgcg    1140
cgcgagcacc acctgcgcgg cgagctcgac gaggccgtca cctacctgga gttcgcctac    1200
cgggcctccg acgacccgc cgtccacgcc gcactgcgcg tcgacaccgc cgccatcgag    1260
cggctctgcg atcccgccag atccggccgg catgtgcccg agctgctcac cgcgtcgcgg    1320
gaacggctcc tctccagcga gcacgccgtg tcgctcgcct gctggctggc gatggacggg    1380
```

-continued

| | |
|---|---|
| cggccgggcg aggccgccga ggtcctggcg gcccagcgct ccgccgcccc gagcgagcag | 1440 |
| ggccgggcgc acctgcgcgt cgcggacctg tccctcgcgc tgatctatcc cggcgcggcc | 1500 |
| gatccgccgc gtccggccga tccgccggcc gaggacgagg tcgcctcgtt ttccggagcc | 1560 |
| gtccggcacc gcgccgtcgc cgacaaggcc ctgagcaacg cgctgcgcgg ctggtccgaa | 1620 |
| caggccgagg ccaaagccga gtacgtgctc cagcactccc gggtcacgac ggaccggacc | 1680 |
| acgaccatga tggcgttgct ggccctgctc tacgccgagg acaccgatgc cgtccagtcc | 1740 |
| tgggtcgaca agctggccgg tgacgacaac atgcggaccc cggccgacga ggcggtccac | 1800 |
| gcggggttcc gcgccgaggc cgcgctgcgc gcggcgacc tgaccgccgc cgtcgaatgc | 1860 |
| ggcgaggccg cgctcgcccc ccgggtcgtg ccctcctggg ggatggccgc cgcattgccg | 1920 |
| ctgagcagca ccgtggccgc cgcgatccga ctgggcgacc tggaccgggc ggagcggtgg | 1980 |
| ctcgccgagc cgttgccgga ggagacctcc gacagcctct tcggactgca catggtctgg | 2040 |
| gcccgtgggc aacaccatct cgcggccggg cggtaccggg cggcgtacaa cgcgttccgg | 2100 |
| gactgcgggg agcggatgcg acgctggtcc gtcgacgtgc cgggcctggc cctgtggcgg | 2160 |
| gtcgacgccg ccgaagcgct tctgctgctc ggccgcggcc gtgacgaggg gctgaggctc | 2220 |
| atctccgagc agctgtcccg gccgatgggg tcccgggcgc gggtgatgac gctgcgggtg | 2280 |
| caggcggcct acagtccgcc ggccaagcgg atcgaactgc tcgacgaggc cgccgatctg | 2340 |
| ctcatcatgt gccgcgacca gtacgagctg gcccgcgtcc tcgccgacat gggcgaagcg | 2400 |
| tgcggcatgc tccggcggca cagccgtgcg cggggactgt tccgccgcgc acggcacctc | 2460 |
| gcgacccagt gcggagccgt gccgctcctc cggcggctcg gtggggagtc ctcggacgcg | 2520 |
| gacggcaccc aggacgtgac gccggcgcag cggatcacat cgctgaccga gcggagcgg | 2580 |
| cgggtggcgt cgcacgccgc ggtcgggcgc accaacaagg agatcgccag ccagctgttc | 2640 |
| gtcacctcca gcacggtgga acagcacctc accaacgtgt tccgcaagct gggggtgaag | 2700 |
| ggccgtcagc aactgcccaa ggaactgtcc gacgccggct ga | 2742 |

<210> SEQ ID NO 46
<211> LENGTH: 2742
<212> TYPE: DNA
<213> ORGANISM: Streptomyces ascomyceticus

<400> SEQUENCE: 46

| | |
|---|---|
| atgatagcgc gcctgtctcc cccagacctg atcgcccgcg atgacgagtt cggttccctc | 60 |
| caccgggcgc tcacccgagc gggggcgggg cggggcgtcg tcgccgccgt caccgggccg | 120 |
| atcgcctgcg gcaagaccga actcctcgac gccgccgcgg ccaaggccgg cttcgtcacc | 180 |
| cttcgcgcgg tgtgctccat ggaggagcgg gccctgccgt acggcatgct cggccagctc | 240 |
| ctcgaccagc ccgagctggc cgcccggaca ccggagctgg tccggctgac ggcatcgtgc | 300 |
| gaaaacctgc cggccgacgt cgacaaccgc ctggggaccg aactcacccg cacggtgctg | 360 |
| acgctcgccg cggagcggcc cgtactgatc ggcatcgacg acgtgcacca cgccgacgcg | 420 |
| ccgtcgctgc gctgcctgct ccacctcgcg cgccgcatca gccgggcccg tgtcgccatc | 480 |
| gtgctgaccg agctgctccg gccgacgccc gccactcccc aattccgggc ggcactgctg | 540 |
| agtctgcgcc actaccagga gatcgcgctg cgcccgctca ccgaggcgca gaccaccgaa | 600 |
| ctcgtgcgcg ggcacctcgg ccaggacgcg cacgacgacg tggtggccca ggcgttccgg | 660 |
| gcgaccggcg gcaacctgct cctcggccac ggcctgatcg acgacatccg ggaggcacgg | 720 |
| acacggacct cagggtgcct ggaagtggtc gcggggcggg cgtaccggct cgcctacctc | 780 |

```
gggtcgctct atcgttgcgg cccggccgcg ctgagcgtcg cccgagcttc cgccgtgctc      840
ggcgagagtg tcgaactcac cctcgtccag cggatgaccg gcctcgacac cgaggcggtc      900
gagcaggccc acgaacagct ggtcgagggg cggctgctgc gggaagggcg gttcccgcac      960
cccgcggccc gctccgtcgt actcgacgac ctctccgccg ccgagcggcg tggcctgcac     1020
gagctggcgc tggaactgct gcgggaccgc ggcgtggcca gcaaggtgct cgcccgccac     1080
cagatgggta ccgccgggt gcacggcgcc gaggtcgccg gctgttcac cgacgccgcg       1140 cgcgagcacc acctgcgcgg cgagctcgac gaggccgtca cctacctgga gttcgcctac     1200
cgggcctccg acgaccccgc cgtccacgcc gcactgcgcg tcgacaccgc cgccatcgag     1260
cggctctgcg atcccgccag atccggccgg catgtgcccg agctgctcac cgcgtcgcgg     1320
gaacggctcc tctccagcga gcacgccgtg tcgctcgcct gctggctggc gatggacggg     1380
cggccgggcg aggccgccga ggtcctggcg gcccagcgct ccgccgcccc gagcgagcag     1440
ggccgggcgc acctgcgcgt cgcggacctg tccctcgcgc tgatctatcc cggcgcggcc     1500
gatccgccgc gtccggccga tccgccggcc gaggacgagg tcgcctcgtt ttccggagcc     1560
gtccggcacc gcgccgtcgc cgacaaggcc ctgagcaacg cgctgcgcgg ctggtccgaa     1620
caggccgagg ccaaagccga gtacgtgctc cagcactccc gggtcacgac ggaccggacc     1680
acgaccatga tggcgttgct ggccctgctc tacgccgagg acaccgatgc cgtccagtcc     1740
tgggtcgaca agctggccgg tgacgacaac atgcggaccc cggccgacga ggcggtccac     1800
gcggggttcc gcgccgaggc cgcgctgcgc gcggcgacc tgaccgccgc cgtcgaatgc      1860
ggcgaggccg cgctcgcccc ccgggtcgtg ccctcctggg ggatggccgc cgcattgccg     1920
ctgagcagca ccgtgccgc cgcgatccga ctgggcgacc tggaccgggc ggagcggtgg      1980
ctcgccgagc cgttgccgga ggagacctcc gacagcctct tcggactgca catggtctgg     2040
gcccgtgggc aacaccatct cgcggccggg cggtaccggg cggcgtacaa cgcgttccgg     2100
gactgcgggg agcggatgcg acgctggtcc gtcgacgtgc cgggcctggc cctgtggcgg     2160
gtcgacgccg ccgaagcgct tctgctgctc ggccgcggcc gtgacgaggg gctgaggctc     2220
atctccgagc agctgtcccg gccgatgggg tcccgggcgc gggtgatgac gctgcgggtg     2280
caggcggcct acagtccgcc ggccaagcgg atcgaactgc tcgacgaggc cgccgatctg     2340
ctcatcatgt gccgcgacca gtacgagctg gcccgcgtcc tcgccgacat gggcgaagcg     2400
tgcggcatgc tccggcggca cagccgtgcg cggggactgt ccgccgcgc acggcacctc      2460 gcgacccagt gcggagccgt gccgctcctc cggcggctcg gtggggagtc ctcggacgcg     2520
gacggcaccc aggacgtgac gccggcgcag cggatcacat cgctgaccga gcggagcgg      2580 cgggtggcgt cgcacgccgc ggtcgggcgc accaacaagg agatcgccag ccagctgttc     2640
gtcacctcca gcacggtgga acagcacctc accaacgtgt ccgcaagct ggggtgaag      2700 ggccgtcagc aactgcccaa ggaactgtcc gacgccggct ga                        2742
```

<210> SEQ ID NO 47
<211> LENGTH: 2706
<212> TYPE: DNA
<213> ORGANISM: Micromonospora sp. S92-306401

<400> SEQUENCE: 47

```
gtggagtttt acgacctggt cgcccgcgat gacgagctca gaaggttgga ccaggccctc       60
ggccgcgccg ccggcggacg gggtgtcgtg gtcaccgtca ccggaccggt cggctgcggc      120
```

```
aagaccgaac tgctggacgc ggccgcggcc gaggaggaat tcatcacgtt gcgtgcggtc    180
tgctcggccg aggagcgggc cctgccgtac gccgtgatcg gccaactcct cgaccatccc    240
gtactctccg cacgcgcgcc cgacctggcc tgcgtgacgg ctccgggccg gacgctgccg    300
gccgacaccg agaaccgcct gcgccgcgac ctcacccggg ccctgctggc cctggcctcc    360
gaacgaccgg ttctgatctg catcgacgac gtgcaccagg ccgacaccgc ctcgctgaac    420
tgcctgctgc acctggcccg gcgggtcgcc tcggcccgga tcgccatgat cctcaccgag    480
ttgcgccggc tcaccccggc tcactcccgg ttcgaggcgg aactgctcag cctgcggcac    540
cgccacgaga tcgcgctgcg tcccctcggc cggccgaca ccgccgaact ggcccgcgcc    600
cggctcggcg ccggcgtcac cgccgacgag ctggcccagg tccacgaggc caccagcggg    660
aaccccaacc tggtcggagg cctggtcaac gacgtgcgag aggcctgggc ggccggtggc    720
acgggcattg cggcggggcg ggcgtaccgg ctggcgtacc tcagctccgt gtaccgctgt    780
ggtccggtcc cgttgcggat cgcccaggcg gcggcggtgc tgggtcccag cgccaccgtc    840
acgctggtgc gccggatcag cgggctcgac gccgagacgg tggacgaggc gaccgcgatc    900
ctcaccgagg gcggcctgct ccgggaccac cggttcccgc atccggcggc ccgctcggtc    960
gtactcgacg acatgtccgc gcaggaacgc cgccgcctgc accggtccac gctggacgtg   1020
ctggacggcg tacccgtcga cgtgctcgcg caccaccagg ccggcgccgg tctgctgcac   1080
ggcccgcagg cggccgagat gttcgcccgg gccagccagg agctgcgggt acgcggcgag   1140
ctggacgccg cgaccgagta cctgcaactg gcctaccggg cctccgacga cgccggcgcc   1200
cggggccgcc tgcaggtgga gaccgtggcc ggcgagcgcc gccgcaaccc gctggccgcc   1260
agccggcacc tggacgagct ggccgccgcc gcccgggccg gcctgctgtc ggccgagcac   1320
gccgccctgg tcgtgcactg gctggccgac gccggacgac ccggcgaggc cgccgaggtg   1380
ctggcgctgc agcgggcgct ggccgtcacc gaccacgacc gggcccgcct gcgggcggcc   1440
gaggtgtcgc tcgcgctgtt ccaccccggc gtccccggtt cggacccgcg gcccctcgcg   1500
ccggaggagc tcgcgagcct gtccctgtcg gcccggcacg gtgtgaccgc cgacaacgcg   1560
gtgctggcgg cgctgcgcgg ccgtcccgag tcggccgccg ccgaggcgga gaacgtgctg   1620
cgcaacgccg acgccgccgc gtccggcccg accgccctgg ccgcgctgac ggccctgctc   1680
tacgccgaga acaccgacgc cgcccagctc tgggcggaca gctggccgc gggcatcggg   1740 gcggggagg gggaggccgg ctacgcgggg ccgcggaccg tggccgccct gcgtcgcggc   1800
gacctgacca ccgcggtcca ggcggccggc gcggtcctgg accgcggccg gccgtcgtcg   1860
ctcggcatca ccgccgtgtt gccgttgagc ggcgcggtcg ccgccgcgat ccggctgggc   1920
gagctcgagc gggccgagaa gtggctggcc gagccgctgc ccgaagccgt ccacgacagc   1980
ctgttcggcc tgcacctgct gatggcgcgg ggccgctaca gcctcgcggt gggccggcac   2040
gaggcggcgt acgccgcgtt ccgggactgc ggtgaacgga tgcgccggtg ggacgtcgac   2100 gtgcccggc tggccctgtg gcgggtggac gcggccgagg cgctgctgcc cggcgatgac   2160
cgggcggagg gccggcggct gatcgacgag cagctcaccc ggccgatggg gccccggtca   2220
cgagccctga ccctgcgggt acgagcggcc tacccccgc cggcgaaacg gatcgacctg   2280
ctcgacgaag cggccgacct gctgctctcc agcaacgacc agtacgagcg gcacgggtg   2340 ctggccgacc tgagcgaggc gttcagcgcg ctccggcaga acggccgggc gcgcggcatc   2400
ctgcggcagg cccggcacct ggccgcccag tgcggggcgg tccccctgct cgccggctg   2460 ggcgtcaagg ccggccggtc cggtcggctc ggccggccgc cgcagggaat ccgctcctg   2520
```

```
accgaggccg agcgccgggt ggccacgctg ccgccgccg ggcagaccaa ccgggagatc   2580
gccgaccagc tcttcgtcac cgccagcacg gtcgagcagc acctcaccaa cgtgttccgc   2640
aagctcggcg tgaagggccg ccagcaattg ccggccgagc tggccgacct gcggccgccg   2700
ggctga                                                               2706

<210> SEQ ID NO 48
<211> LENGTH: 2706
<212> TYPE: DNA
<213> ORGANISM: Micromonospora sp. S92-306401

<400> SEQUENCE: 48
atggagtttt cgacctggt cgcccgcgat gacgagctca gaaggttgga ccaggccctc     60
ggccgcgccg ccggcggacg gggtgtcgtg gtcaccgtca ccggaccggt cggctgcggc   120
aagaccgaac tgctggacgc ggccgcggcc gaggaggaat tcatcacgtt gcgtgcggtc   180
tgctcggccg aggagcgggc cctgccgtac gccgtgatcg ccaactcct cgaccatccc   240 gtactctccg cacgcgcgcc cgacctggcc tgcgtgacgg ctccgggccg gacgctgccg   300
gccgacaccg agaaccgcct cgccgcgac ctcacccggg ccctgctggc cctggcctcc   360
gaacgaccgg ttctgatctg catcgacgac gtgcaccagg ccgacaccgc ctcgctgaac   420
tgcctgctgc acctggcccg gcgggtcgcc tcggcccgga tcgccatgat cctcaccgag   480
ttgcgccggc tcaccccggc tcactcccgg ttcgaggcgg aactgctcag cctgcggcac   540
cgccacgaga tcgcgctgcg tcccctcggc cggccgacca ccgccgaact ggcccgcgcc   600
cggctcggcg ccggcgtcac cgccgacgag ctggcccagg tccacgaggc caccagcggg   660
aaccccaacc tggtcggagg cctggtcaac gacgtgcgag aggcctgggc ggccggtggc   720
acgggcattg cggcggggcg ggcgtaccgg ctggcgtacc tcagctccgt gtaccgctgt   780
ggtccggtcc cgttgcggat cgcccaggcg gggcggtgc tggtcccag cgccaccgtc   840 acgctggtgc gccggatcag cgggctcgac gccgagacgg tggacgaggc gaccgcgatc   900
ctcaccgagg gcggcctgct ccgggaccac cggttcccgc atccggcggc ccgctcggtc   960
gtactcgacg acatgtccgc gcaggaacgc cgccgcctgc accggtccac gctggacgtg  1020
ctggacggcg tacccgtcga cgtgctcgcg caccaccagg ccggcgccgg tctgctgcac  1080
ggcccgcagg cggccgagat gttcgcccgg gccagccagg agctgcgggt acgcggcgag  1140
ctggacgccg cgaccgagta cctgcaactg gcctaccggg cctccgacga cgccggcgcc  1200
cgggccgccc tgcaggtgga gaccgtggcc ggcgagcgcc gccgcaaccc gctggccgcc  1260
agccggcacc tggacgagct ggccgccgcc gcccgggccg gctgctgtc ggccgagcac  1320 gccgccctgg tcgtgcactg gctggccgac ccggacgac ccggcgaggc cgccgaggtg  1380
ctggcgctgc agcgggcgct ggccgtcacc gaccacgacc gggcccgcct gcgggcggcc  1440
gaggtgtcgc tcgcgctgtt ccaccccggc gtccccggtt cggacccgcg ccccctcgcg  1500
ccggaggagc tcgcgagcct gtccctgtcg gcccggcacg gtgtgaccgc cgacaacgcg  1560
gtgctggcgg cgctgcgcgg ccgtcccgag tcggccgccg ccgaggcgga gaacgtgctg  1620
cgcaacgccg acgccgccgc gtccggcccg accgcctggc cgcgctgac ggccctgctc  1680 tacgccgaga acaccgacgc cgcccagctc tgggcggaca agctggccgc gggcatcggg  1740
gcggggggag gggaggccgg ctacgcgggg ccgcggaccg tggccgccct gcgtcgcggc  1800
gacctgacca ccgcggtcca ggcggccggc gcggtcctgg accgcggccg gccgtcgtcg  1860
```

```
ctcggcatca ccgccgtgtt gccgttgagc ggcgcggtcg ccgccgcgat ccggctgggc    1920
gagctcgagc gggccgagaa gtggctggcc gagccgctgc ccgaagccgt ccacgacagc    1980
ctgttcggcc tgcacctgct gatggcgcgg ggccgctaca gcctcgcggt gggccggcac    2040
gaggcggcgt acgccgcgtt ccgggactgc ggtgaacgga tgcgccggtg ggacgtcgac    2100
gtgcccgggc tggccctgtg gcgggtggac gcggccgagg cgctgctgcc cggcgatgac    2160 cggcggagg gccggcggct gatcgacgag cagctcaccc ggccgatggg gccccggtca    2220
cgagccctga ccctgcgggt acgagcggcc tacgccccgc cggcgaaacg gatcgacctg    2280
ctcgacgaag cggccgacct gctgctctcc agcaacgacc agtacgagcg ggcacgggtg    2340
ctggccgacc tgagcgaggc gttcagccgc ctccggcaga acggccgggc gcgcggcatc    2400
ctgcggcagg cccggcacct ggccgcccag tgcggggcgg tccccctgct cgcgcggctg    2460
ggcgtcaagg ccggccggtc cggtcggctc ggccggccgc cgcagggaat ccgctccctg    2520
accgaggccg agcgccgggt ggccacgctg ccgccgccg gcagaccaa ccgggagatc    2580 gccgaccagc tcttcgtcac cgccagcacg gtcgagcagc acctcaccaa cgtgttccgc    2640
aagctcggcg tgaagggccg ccagcaattg ccggccgagc tggccgacct gcggccgccg    2700
ggctga                                                               2706

<210> SEQ ID NO 49
<211> LENGTH: 2616
<212> TYPE: DNA
<213> ORGANISM: Streptomyces violaceusniger

<400> SEQUENCE: 49
gtggtcaccg tcaccggccc aatcgcctgc ggcaagacag aactgcttga cgcggctgcc     60
gcgaaggctg aggccatcat tctgcgcgcg gtctgcgcgc cagaagagcg ggctatgccg    120
tacgccatga tcgggcagct catcgacgac ccggcgctcg cgcatcgggc gccggggctg    180
gctgatcgga tagcccaggg cgggcagctg tcgctgaggg ccgagaaccg actgcgcagg    240
gatctcaccc gtgccctgct ggcgcttgcc gtcgaccggc ctgtgctgat cggcgtcgac    300
gatgtgcatc acgccgacac cgcctctttg aactgtctgc tgcatttggc gcgccgggtc    360
cgtccggccc ggatatccat gatcttcacc gagttgcgca gcctcacccc tactcagtca    420
cggttcaagg cggagctgct cagcctgccg taccaccacg agatcgcgct gcgtccgttc    480
ggaccggagc aatcggcgga gctggcccgc gccgccttcg gcccgggcct cgccgaggat    540
gtgctcgtgg ggttgtataa aacgaccagg ggcaatctga gtctcagccg tggactgatc    600
agcgatgtgc gggaggccct ggccaacgga gagagcgcct tcgaggcggg ccgcgcgttc    660
cggctggcgt acctcggctc gctctaccgc tgtggcccgg tcgcgctgcg ggtcgcccga    720
gtggctgccg tgctgggccc gagcgccacc accacgctgg tgccgccgtct aagcgggctc    780 agcgcggaga cgatagaccg ggcaaccaag atcctcaccg agggcgggct gctgctcgac    840
cagcagttcc cgcacccggc cgcccgctcg gtggtgcttg atgacatgtc cgcccaggaa    900
cgacgcggcc tgcacactct cgccctggaa ctgctggacg aggcgccggt tgaagtgctc    960
gcgcaccacc aggtcggcgc cggtctcata cacgggccca aggctgcgga gatgttcgcc   1020
aaggccggca aggctctggt cgtacgcaac gagttgggcg acgcggcaga atacctgcaa   1080
ctggctcacc gggcctccga cgatgtctcc accccggccg ccttacgggt cgaggccgtg   1140
gcgatcgagc gccgccgcaa tccgctgccc tccagtcggc acatggacga gctgagcgcc   1200
gccggccgcg ccggtctgct ttcccccaag catgcggcgc tggccgtctt ctggctggcc   1260
```

-continued

```
gacggcgggc gatccggcga ggcagccgag gtgctggcgt cggaacgccc gctagcgacc    1320
accgatcaga accgggccca cttgcgattt gtcgaggtga ctctcgcgct gttctctccc    1380
ggcgccttcg gatcggaccg gcgcccacct ccgctgacgc cggacgaact cgccagcctg    1440
ccgaaggcgg cctggcaatg cgcggtcgcc gacaacgcgg ccatgaccgc cttgcacggt    1500
catccagaac ttgccaccgc tcaggcggaa acagttctgc ggcaggctga ttcggcagcc    1560
gacgcgatcc ccgccgcgct gatcgccctg ttgtacgcgg agaacaccga gtccgctcat    1620
atctgggccg acaagctggg cagcacgaat ggcggggtat cgaacgaggc ggaagcgggc    1680
tacgccggcc cgtgcgccga gatcgccctg cggcgcggcg acctggccac ggcgttcgag    1740
gctggtagca ccgtcctgga cgaccggtcg ctgccgtcgc tcggcatcac cgccgcattg    1800
ctgttgagca gcaagacggc cgccgctgtc cggctgggcg aactcgagcg tgcggagaag    1860
ctgctcgccg agccgcttcc gaacggcgtc caggacagcc ttttcggtct gcacctgctc    1920
tcggcatacg gccagtacag cctcgcgatg ggccgatatg aatcggctct ccgggcgttt    1980
cacacctgcg gagaacgtat gcgcagctgg gatgttgacg tgcctggtct ggccctgtgg    2040
cgtgtcgacg ccgccgaggc gctgctcagc ctcgaccgga acgagggcca gcggctcatc    2100
gacgaacaac tcacccgtcc gatggggcct cgttcccgcg cgttaacgct gcggatcaag    2160
gcggcatacc tcccgcggac gaagcggatc ccctgctcc atgaggcggc cgagctgctg    2220
ctcccctgcc ccgacccgta cgagcaagcg cgggtgctcg ccgatctggg cgacacgctc    2280
agcgcgctca gacgctatag ccgggcgcgg ggagttctcc ggcaggctcg tcacctggcc    2340
gcccagtgcg gtgctgtccc gctgctgcgc aggctcgggg gcgagcccgg ccggatcgac    2400
gacgccggcc tgccgcagcg gagcacatcg ttgaccgatg cggagcggcg ggtggcggcg    2460
ctggccgcgg ccggacagac caaccgggag atcgccaaac agctgttcgt cacggccagc    2520
acagtggaac agcacctcac aagcgtcttc cgcaaactgg gggtcaaggg tcgcaagcag    2580
ctgccgaccg cgctggccga cgtggaacag acctga                             2616
```

<210> SEQ ID NO 50
<211> LENGTH: 2721
<212> TYPE: DNA
<213> ORGANISM: Streptomyces violaceusniger

<400> SEQUENCE: 50

```
atgtatagcg gtacctgccg tgaaggatac gaactcgtcg cacgcgagga cgaactcggc    60
attctacaga ggtctctgga acaagcgagc agcggccagg gcgtcgtggt caccgtcacc    120
ggcccaatcg cctgcggcaa gacagaactg cttgacgcgg ctgccgcgaa ggctgaggcc    180
atcattctgc gcgcggtctg cgcgccagaa gagcgggcta tgccgtacgc catgatcggg    240
cagctcatcg acgacccggc gctcgcgcat cgggcgccgg ggctggctga tcggatagcc    300
cagggcgggc agctgtcgct gagggccgag aaccgactgc gcaggatctc acccgtgcc    360 ctgctggcgc ttgccgtcga ccggcctgtg ctgatcggcg tcgacgatgt gcatcacgcc    420
gacaccgcct ctttgaactg tctgctgcat ttggcgcgcc gggtccgtcc ggcccggata    480
tccatgatct tcaccgagtt gcgcagcctc accctactc agtcacggtt caaggcggag    540
ctgctcagcc tgccgtacca ccacgagatc gcgctgcgtc cgttcggacc ggagcaatcg    600
gcggagctgg cccgcgccgc cttcggcccg ggctcgccg aggatgtgct cgtggggttg    660
tataaaacga ccaggggcaa tctgagtctc agccgtggac tgatcagcga tgtgcgggag    720
```

```
gccctggcca acggagagag cgccttcgag gcgggccgcg cgttccggct ggcgtacctc    780
ggctcgctct accgctgtgg cccggtcgcg ctgcgggtcg cccgagtggc tgccgtgctg    840
ggcccgagcg ccaccaccac gctggtgcgc cgtctaagcg ggctcagcgc ggagacgata    900
gaccgggcaa ccaagatcct caccgagggc gggctgctgc tcgaccagca gttcccgcac    960
ccggccgccc gctcggtggt gcttgatgac atgtccgccc aggaacgacg cggcctgcac   1020
actctcgccc tggaactgct ggacgaggcg ccggttgaag tgctcgcgca ccaccaggtc   1080
ggcgccggtc tcatacacgg gcccaaggct gcggagatgt tcgccaaggc cggcaaggct   1140
ctggtcgtac gcaacgagtt gggcgacgcg gcagaatacc tgcaactggc tcaccggggcc  1200
tccgacgatg tctccacccg ggccgccctg cgggtcgagg ccgtggcgat cgagcgccgc   1260
cgcaatccgc tggcctccag tcggcacatg gacgagctga gcgccgccgg ccgcgccggt   1320
ctgcttttcc ccaagcatgc ggcgctggcc gtcttctggc tggccgacgg cgggcgatcc   1380
ggcgaggcag ccgaggtgct ggcgtcggaa cgcccgctag cgaccaccga tcagaaccgg   1440
gcccacttgc gatttgtcga ggtgactctc gcgctgttct ctcccggcgc cttcggatcg   1500
gaccggcgcc cacctccgct gacgccggac gaactcgcca gcctgccgaa ggcggcctgg   1560
caatgcgcgg tcgccgacaa cgcggccatg accgccttgc acggtcatcc agaacttgcc   1620
accgctcagg cggaaacagt tctgcggcag gctgattcgg cagccgacgc gatccccgcc   1680
gcgctgatcg ccctgttgta cgcggagaac accgagtccg ctcatatctg ggccgacaag   1740
ctgggcagca cgaatggcgg ggtatcgaac gaggcggaag cgggctacgc cggcccgtgc   1800
gccgagatcg ccctgcggcg cggcgacctg gccacggcgt tcgaggctgg tagcaccgtc   1860
ctggacgacc ggtcgctgcc gtcgctcggc atcaccgccg cattgctgtt gagcagcaag   1920
acggccgcc ctgtccggct gggcgaactc gagcgtgcgg agaagctgct cgccgagccg    1980
cttccgaacg gcgtccagga cagccttttc ggtctgcacc tgctctcggc atacggccag   2040
tacagcctcg cgatgggccg atatgaatcg gctctccggg cgtttcacac ctgcggagaa   2100
cgtatgcgca gctgggatgt tgacgtgcct ggtctggccc tgtggcgtgt cgacgccgcc   2160
gaggcgctgc tcagcctcga ccggaacgag gccagcggc tcatcgacga acaactcacc    2220
cgtccgatgg ggcctcgttc ccgcgcgctg acgctgcgga tcaaggcggc atacctcccg   2280
cggacgaagc ggatccccct gctccatgag gcggccgagc tgctgctccc ctgccccgac   2340
ccgtacgagc aagcgcgggt gctcgccgat ctgggcgaca cgctcagcgc gctcagacgc   2400
tatagccggg cgcggggagt tctccggcag gctcgtcacc tggccgccca gtgcggtgct   2460
gtcccgctgc tgcgcaggct cggggcgag cccgccgga tcgacgacgc cggcctgccg    2520
cagcggagca catcgttgac cgatgcggag cggcgggtgg cggcgctggc cgcggccgga   2580
cagaccaacc gggagatcgc caaacagctg ttcgtcacgg ccagcacagt ggaacagcac   2640
ctcacaagcg tcttccgcaa actgggggtc aagggtcgca agcagctgcc gaccgcgctg   2700
gccgacgtgg aacagacctg a                                            2721
```

<210> SEQ ID NO 51  
<211> LENGTH: 2745  
<212> TYPE: DNA  
<213> ORGANISM: Streptomyces hygroscopicus

<400> SEQUENCE: 51

```
atgcctgccg tggagagcta tgaactggac gcccgcgatg acgagctcag aagactggag     60
gaggcggtag gccaggcggg caacggccgg ggtgtggtgg tcaccatcac cgggccgatc    120
```

```
gcctgcggca agaccgaact gctcgacgcg gccgccgcga agagcgacgc catcacatta    180
cgtgcggtct gctccgagga ggaacgggcc ctcccgtacg ccctgatcgg gcagctcatc    240
gacaacccgg cggtcgcctc ccagctgccg gatccggtct ccatggccct cccgggcgag    300
cacctgtcgc cggaggccga gaaccggctg cgcggcgacc tcacccgtac cctgctggcg    360
ctcgccgccg aacggccggt gctgatcggc atcgacgaca tgcaccacgc cgacaccgcc    420
tctttgaact gcctgctcca cctggccgg agggtcggcc cggcccggat cgccatggtc     480
ctcaccgagc tgcgccggct cacccccggcc cactcccagt tccacgccga gctgctcagc   540
ctggggcacc accgcgagat cgcgctcgcg ccgctcggcc gaagcacat cgccgagctg     600 gcccgcgccg gcctcggtcc cgatgtcgac gaggacgtgc tcacggggtt gtaccgggcg    660 accgcggca acctgaacct cggccacgga ctgatcaagg atgtgcggga ggcctgggcg     720
acgggcggga cgggcatcaa cgcgggccgc gcgtaccggc tggcgtacct cggttccctc    780
taccgctgcg gcccggtccc gttgcgggtc gcacgggtgg ccgccgtgct gggccagagc    840
gccaacacca ccctggtgcg ctggatcagc gggctcaacg cggacgcggt gggcgaggcg    900
accgagatcc tcaccgaggg cggcctgctg cacgacctgc ggttcccgca tccggcggcc    960
cgttcggtcg tactcaacga cctgtccgcc cgggaacgcc gccgactgca ccggtccgct   1020
ctggaagtgc tggatgacgt acccgttgaa gtggtcgcgc accaccaggc cggtgccggt   1080
ttcatccacg gtcccaaggc cgccgagatc ttcgccaagg ccggccagga gctgcatgtg   1140
cgcggcgagc tggacgccgc gtccgactat ctgcaactgg cccaccacgc ctccgacgac   1200
gccgtcaccc gggccgcgct gcgggtcgag ccgtggcga tcgagcgccg ccgcaacccg    1260
ctggcctcca gccgccacct cgacgagctg accgtcgccg cccgtgccgg tctgctctcc   1320
ctcgagcacg ccgcgctgat gatccgctgg ctggctctcg gcgggcggtc cggcgaggcg   1380
gccgaggtgc tggccgcgca gcgcccgcgt gcggtcaccg accaggacag ggcccacctg   1440
cgggccgccg aggtatcgct ggcgctggtc agcccgggcg cgtccggcgt cagcccgggt   1500
gcgtccggcc cggatcggcg gccgcgtccg ctcccgccgg atgagctcgc gaacctgccg   1560
aaggcggccc ggctttgtgc gatcgccgac aacgccgtca tatcgccct gcacggtcgt    1620 cccgagcttg cctcggccga ggcggagaac gtcctgaagc aggctgactc ggcggcggac   1680
ggcgccaccg ccctctccgc gctgacggcc ttgctgtacg cggagaacac cgacaccgct   1740
cagctctggg ccgacaagct cgtctccgag accggggcgt cgaacgagga ggaaggcgcg   1800
ggctacgcgg gccgcgcgc cgagaccgcg ttgccgcg cgacctggc cgcggcggtc       1860 gaggcgggca gcgccattct ggaccaccgg cggggtcgt tgctcggcat caccgccgcg    1920
ctaccgctga gcagcgcgt agccgccgcc atccggctgg gcgagaccga gcgggcgag     1980 aagtggctcg ccgagccgct gccggaggcc attcgggaca gcctgttcgg gctgcacctg    2040
ctctcggcgc gcgccagta ctgcctcgcg acggccggc acgagtcggc gtacacggcg     2100
ttccgcacct gcggggaacg gatgcggaac tgggcgtcg acgtgccggg tctgtccctg    2160
tggcgcgtcg acgccgccga ggcgctgctg cacggccgcg accgggacga gggccgacgg   2220
ctcatcgacg agcagctcac ccatgcgatg gaccccgtt cccgcgcttt gacgctgcgg    2280
gtgcaggcgg cgtacagccc gcaggcgcag cgggtcgacc tgctcgaaga ggcggccgac   2340
ctgctgctct cctgcaacga ccagtacgag cgggcgcggg tgctcgccga tctgagcgag   2400
gcgttcagcg cgctcaggca ccacagccgg gcgcggggac tgctccggca ggcccggcac   2460
```

```
ctggccgccc agtgcggcgc gaccccgctg ctgcgccggc tcggggccaa gcccggaggc    2520
cccggctggc tggaggaatc cggcctgccg cagcggatca agtcgctgac cgacgcggag    2580
cggcgggtgg cgtcgctggc cgccggcggc cagaccaacc gcgtgatcgc cgaccagctc    2640
ttcgtcacgg ccagcacggt ggagcagcac ctcacgaacg tcttccgcaa gctgggcgtc    2700
aagggccgcc agcacctgcc ggccgaactc gccaacgcgg aatag                    2745

<210> SEQ ID NO 52
<211> LENGTH: 2745
<212> TYPE: DNA
<213> ORGANISM: Streptomyces hygroscopicus

<400> SEQUENCE: 52
atgcctgccg tggagagcta tgaactggac gcccgcgatg acgagctcag aagactggag      60
gaggcggtag gccaggcggg caacggccgg ggtgtggtgg tcaccatcac cgggccgatc     120
gcctgcggca agaccgaact gctcgacgcg gccgccgcga agagcgacgc catcacactg     180
cgtgcggtct gctccgagga ggaacgggcc ctcccgtacg ccctgatcgg gcagctcatc     240
gacaacccgg cggtcgcctc ccagctgccg gatccggtct ccatggccct cccgggcgag     300
cacctgtcgc cggaggccga gaaccggctg cgcggcgacc tcacccgtac cctgctggcg     360
ctcgccgccg aacggccggt gctgatcggc atcgacgaca tgcaccacgc cgacaccgcc     420
tctttgaact gcctgctcca cctggccggg agggtcggcc cggcccggat cgccatggtc     480
ctcaccgagc tgcgccggct caccccggcc cactcccagt tccacgccga gctgctcagc     540
ctggggcacc accgcgagat cgcgctgcgc ccgctcggcc gaagcacat cgccgagctg      600 gcccgcgccg gcctcggtcc cgatgtcgac gaggacgtgc tcacggggtt gtaccgggcg     660 accgcggca acctgaacct cggccacgga ctgatcaagg atgtgcggga ggcctgggcg     720
acgggcggga cgggcatcaa cgcgggccgc gcgtaccggc tggcgtacct cggttccctc     780
taccgctgcg gccggtccc gttgcgggtc gcacgggtgg ccgccgtgct gggccagagc     840
gccaacacca ccctggtgcg ctggatcagc gggctcaacg cggacgcggt gggcgaggcg     900
accgagatcc tcaccgaggg cggcctgctg cacgacctgc ggttcccgca tccgcggcc      960 cgttcggtcg tactcaacga cctgtccgcc cgggaacgcc gccgactgca ccggtccgct    1020
ctggaagtgc tggatgacgt acccgttgaa gtggtcgcgc accaccaggc cggtgccggt    1080
ttcatccacg gtcccaaggc cgccgagatc ttcgccaagg ccggccagga gctgcatgtg    1140
cgcggcgagc tggacgccgc gtccgactat ctgcaactgg cccaccacgc ctccgacgac    1200
gccgtcaccc gggccgcgct gcgggtcgag gccgtggcga tcgagcgccg ccgcaacccg    1260
ctggcctcca gccgccacct cgacgagctg accgtcgccg cccgtgccgg tctgctctcc    1320
ctcgagcacg ccgcgctgat gatccgctgg ctggctctcg gcgggcggtc cggcgaggcg    1380
gccgaggtgc tggccgcgca gcgcccgcgt gcggtcaccg accaggacag ggcccacctg    1440
cgggccgccg aggtatcgct ggcgctggtc agcccgggcg cgtccggcgt cagcccgggt    1500
gcgtccggcc cggatcggcg gccgcgtccg ctcccgccgg atgagctcgc gaacctgccg    1560
aaggcggccc ggctttgtgc gatcgccgac aacgccgtca tatcggccct gcacggtcgt    1620
cccgagcttg cctcggccga ggcggagaac gtcctgaagc aggctgactc ggcggcggac    1680
ggcgccaccg ccctctccgc gctgacggcc ttgctgtacg cggagaacac cgacaccgct    1740
cagctctggg ccgacaagct cgtctccgag accggggcgt cgaacgagga ggaaggcgcg    1800
ggctacgcgg ggccgcgcgc cgagaccgcg ttgcgccgcg gcgacctggc cgcggcggtc    1860
```

```
gaggcgggca gcgccattct ggaccaccgg cggggtcgt tgctcggcat caccgccgcg    1920
ctaccgctga gcagcgcggt agccgccgcc atcggctgg gcgagaccga gcgggcggag    1980
aagtggctcg ccgagccgct gccggaggcc attcgggaca gcctgttcgg gctgcacctg    2040
ctctcggcgc gcggccagta ctgcctcgcg acgggccggc acgagtcggc gtacacggcg    2100
ttccgcacct gcggggaacg gatgcggaac tggggcgtcg acgtgccggg tctgtccctg    2160
tggcgcgtcg acgccgccga ggcgctgctg cacggccgcg accgggacga gggccgacgg    2220
ctcatcgacg agcagctcac ccatgcgatg ggaccccgtt ccgcgcttt gacgctgcgg    2280 gtgcaggcgc gtacagcccc gcaggcgcag cgggtcgacc tgctcgaaga ggcggccgac    2340
ctgctgctct cctgcaacga ccagtacgag cgggcgcggg tgctcgccga tctgagcgag    2400
gcgttcagcg cgctcaggca ccacagccgg gcgcggggac tgctccggca ggcccggcac    2460
ctggccgccc agtgcggcgc gaccccgctg ctgcgccggc tcggggccaa gcccggaggc    2520
cccggctggc tggaggaatc cggcctgccg cagcggatca gtcgctgac cgacgcggag    2580 cggcgggtgg cgtcgctggc cgccggcggc cagaccaacc gcgtgatcgc cgaccagctc    2640
ttcgtcacgg ccagcacggt ggagcagcac ctcacgaacg tcttccgcaa gctgggcgtc    2700
aagggccgcc agcacctgcc ggccgaactc gccaacgcgg aatag              2745

<210> SEQ ID NO 53
<211> LENGTH: 2619
<212> TYPE: DNA
<213> ORGANISM: Actinoplanes sp. N01-109

<400> SEQUENCE: 53
gtgaagcgca acgatctggt tgcccgcgat ggcgagctca ggtggatgca agagattctc      60
agtcaggcga gcgagggccg ggggccgtg gtcaccatca cggggcgat cgcctgtggc     120 aagacggtgc tgctggacgc cgcggcagcc agtcaagacg tgatccaact gcgtgcggtc     180
tgctcggcgg aggagcagga gctgccgtac gcgatggtcg acaactact cgacaatccg     240 gtgctcgccg cgcgagtgcc ggccctgggc aacctggctg cggcgggcga gcggctgctg     300
ccgggcaccg agaacaggat ccggcgggag ctcacccgca ccctgctggc tctcgccgac     360
gaacgaccgg tgctgatcgg cgtcgacgac atgcaccatg cggaccccgc ctcgctggac     420
tgcctgctgc acctggcccg gcgggtcggc ccggcccgca tcgcgatcgt tctgaccgag     480
ttgcgccggc tcaccccggc tcactcgcgc ttccagtccg agctgctcag cctgcggtac     540
caccacgaga tcgggttgca gccgctcacc gcggagcaca ccgccgacct ggcccgcgtc     600
ggcctcggtg ccgaggtcga cgacgacgtg ctcaccgagc tctacgaggc gaccggcggc     660
aacccgagtc tgtgctgcgg cctgatcagg gacgtgcggc aggactggga ggccggggtc     720
accggtatcc acgtcggccg ggcgtaccgg ctggcctatc tcagttcgct ctaccgctgc     780
ggccgggcgg cgctgcggac cgcccgcgcg gccgcggtgc tgggcgacag cgccgacgcc     840
tgcctgatcc gccgggtcag cggcctcggt acggaggccg tgggccaggc gatccagcag     900
ctcaccgagg gcggcctgct gcgtgaccag cagttcccgc acccggcggc ccgctcggtc     960
gtgctcgacg acatgtccgc gcaggaacgc acgcgatgt atcgcagcgc ccgggaggca    1020
gccgccgaag gtcaggccga ccccggcacc ccgggcgagc cgcgggcggc tacggcgtac    1080
gccgggtgtg gtgagcaagc cggtgactac ccggagccgg ccgccggc ctgcgtggac    1140 ggtgccggtc cggccgagta ctgcggcgac ccgcacggcg ccgacgacga cccggacgag    1200
```

| | |
|---|---|
| ctggtcgccg cgctgggcgg gctgctgccg agccggctcg tggcgatgaa gatccggcgc | 1260 |
| ctggcggtgg ccgggcgccc cggggcggct gccgagctgc tgacctcgca gcggttgcac | 1320 |
| gcggtgacca gcgaggaccg ggccagcctg cgggccgccg aggtggcgct cgccacgctg | 1380 |
| tggccgggtg cgaccggccc ggaccggcat ccgctcacgg agcaggaggc ggcgagcctg | 1440 |
| ccggagggtc cgcgcctgct cgctgccgcc gacgatgccg tcggggccgc cctgcgcggt | 1500 |
| cgcgccgagt acgccgcggc cgaggcggag aacgtcctgc ggcacgccga tccggcagcc | 1560 |
| ggtggtgacg cctacgccgc catgatcgcc ctgctgtaca cggagcaccc cgagaacgtg | 1620 |
| ctgttctggg ccgacaagct cgacgcgggc cgccccgacg aggagaccag ttatcccggg | 1680 |
| ctgcgggccg agaccgcggt gcggctcggt gacctggaaa cggcgatgga gctgggccgc | 1740 |
| acggtgctgg accagcggcg gctgccgtcc ctgggtgtcg ccgcgggcct gctcctgggc | 1800 |
| ggcgcggtga cggccgccat ccggctcggc gacctcgacc gggcggagaa gtggctcgcc | 1860 |
| gagccgatcc ccgacgccat ccgtaccagc ctctacggcc tgcacgtgct ggccgcgcgg | 1920 |
| ggccggctcg acctggccgc gggccgctac gaggcggcgt acacggcgtt ccggctgtgt | 1980 |
| ggcgagcgga tggcaggctg ggatgccgat gtctccgggc tggcgctgtg gcgcgtcgac | 2040 |
| gccgccgagg ccctgctgtc cgcgggcatc cgcccgacg agggccgcaa gctcatcgac | 2100 |
| gaccagctca cccgtgagat gggggcccgc tcccgggcgc tgacgctgcg ggcgcaagcg | 2160 |
| gcgtacagcc tgccggtgca ccgggtgggc ctgctcgacg aggcggccgg cctgctgctc | 2220 |
| gcctgccatg acgggtacga gcgggcgcgg gtgctcgcgg acctggggga gaccctgcgc | 2280 |
| acgctgcggc acaccgacgc ggcccagcgg gtgctccggc aggccgagca ggcggccgcg | 2340 |
| cggtgcgggt cggtcccgct gctgcggcgg ctcggggccg aacccgtacg catcggcacc | 2400 |
| cggcgtggtg aacccggcct gccgcagcgg atcaggctgc tgaccgatgc cgagcggcgg | 2460 |
| gttgccgcga tggccgccgc cgggcagacc aaccgggaga tcgccggtcg gctcttcgtc | 2520 |
| acggccagca cggtggagca gcacctgacc agcgtcttcc gcaagctggg cgtcaagggc | 2580 |
| cgccggttcc tgccgaccga gctcgcccaa gccgtctga | 2619 |

<210> SEQ ID NO 54
<211> LENGTH: 2628
<212> TYPE: DNA
<213> ORGANISM: Actinoplanes sp. N01-109

<400> SEQUENCE: 54

| | |
|---|---|
| atgcctgccg tgaagcgcaa cgatctggtt gccgcgatg gcgagctcag gtggatgcaa | 60 |
| gagattctca gtcaggcgag cgagggccgg ggggccgtgg tcaccatcac gggggcgatc | 120 |
| gcctgtggca agacggtgct gctggacgcc gggcagcca gtcaagacgt gatccaactg | 180 |
| cgtgcggtct gctcggcgga ggagcaggag ctgccgtacg cgatggtcgg acaactactc | 240 |
| gacaatccgg tgctcgccgc gcgagtgccg gccctgggca acctggctgc ggcgggcgag | 300 |
| cggctgctgc cgggcaccga gaacaggatc cggcgggagc tcacccgcac cctgctggct | 360 |
| ctcgccgacg aacgaccggt gctgatcggc gtcgacgaca tgcaccatgc ggaccccgcc | 420 |
| tcgctggact gcctgctgca cctggccggg cgggtcggcc cggcccgcat cgcgatcgtt | 480 |
| ctgaccgagt tgcgccggct cacccccggct cactcgcgct tccagtccga gctgctcagc | 540 |
| ctgcggtacc accacgagat cgggttgcag ccgctcaccg cggagcacac cgccgacctg | 600 |
| gcccgcgtcg gcctcggtgc cgaggtcgac gacgacgtgc tcaccgagct ctacgaggcg | 660 |
| accggcggca acccgagtct gtgctgcggc ctgatcaggg acgtgcggca ggactgggag | 720 |

-continued

| | |
|---|---|
| gccggggtca ccggtatcca cgtcggccgg gcgtaccggc tggcctatct cagttcgctc | 780 |
| taccgctgcg gcccggcggc gctgcggacc gcccgcgcgg ccgcggtgct gggcgacagc | 840 |
| gccgacgcct gcctgatccg ccgggtcagc ggcctcggta cggaggccgt gggccaggcg | 900 |
| atccagcagc tcaccgaggg cggcctgctg cgtgaccagc agttcccgca cccggcggcc | 960 |
| cgctcggtcg tgctcgacga catgtccgcg caggaacgcc acgcgatgta tcgcagcgcc | 1020 |
| cgggaggcag ccgccgaagg tcaggccgac cccggcaccc cgggcgagcc gcgggcggct | 1080 |
| acggcgtacg ccgggtgtgg tgagcaagcc ggtgactacc ggagccggc cggccgggcc | 1140 |
| tgcgtggacg tgccggtcc ggccgagtac tgccggcgacc cgcacggcgc cgacgacgac | 1200 |
| ccggacgagc tggtcgccgc gctgggcggg ctgctgccga gcggctcgt ggcgatgaag | 1260 |
| atccggcgcc tggcggtggc cgggcgcccc ggggcggctg ccgagctgct gacctcgcag | 1320 |
| cggttgcacg cggtgaccag cgaggaccgg gccagcctgc gggccgccga ggtggcgctc | 1380 |
| gccacgctgt ggccgggtgc gaccggcccg accggcatc cgctcacgga gcaggaggcg | 1440 |
| gcgagcctgc cggagggtcc gcgcctgctc gctgccgccg acgatgccgt cggggccgcc | 1500 |
| ctgcgcggtc gcgccgagta cgccgcgccc gaggcggaga acgtcctgcg gcacgccgat | 1560 |
| ccggcagccg gtggtgacgc ctacgccgcc atgatcgccc tgctgtacac ggagcacccc | 1620 |
| gagaacgtgc tgttctgggc cgacaagctc gacgcgggcc gccccgacga ggagaccagt | 1680 |
| tatcccgggc tgcgggccga gaccgcggtg cggctcggtg acctggaaac ggcgatggag | 1740 |
| ctgggccgca cggtgctgga ccagcggcgg ctgccgtccc tgggtgtcgc cgcgggcctg | 1800 |
| ctcctgggcg gcgcggtgac ggccgccatc cggctcggcg acctcgaccg ggcggagaag | 1860 |
| tggctcgccg agccgatccc cgacgccatc cgtaccagcc tctacggcct gcacgtgctg | 1920 |
| gccgcgcggg gccggctcga cctggccgcg ggccgctacg aggcggcgta cacggcgttc | 1980 |
| cggctgtgtg gcgagcggat ggcaggctgg gatgccgatg tctccgggct ggcgctgtgg | 2040 |
| cgcgtcgacg ccgccgaggc cctgctgtcc gcgggcatcc gcccggacga gggccgcaag | 2100 |
| ctcatcgacg accagctcac ccgtgagatg ggggcccgct cccggcgct gacgctgcgg | 2160 |
| gcgcaagcgg cgtacagcct gccggtgcac cgggtgggcc tgctcgacga ggcggccggc | 2220 |
| ctgctgctcg cctgccatga cgggtacgag cgggcgcggg tgctcgcgga cctgggggag | 2280 |
| accctgcgca cgctgcggca caccgacgcg gcccagcggg tgctccggca ggccgagcag | 2340 |
| gcggccgcgc ggtgcgggtc ggtcccgctg ctgcggcggc tcggggccga acccgtacgc | 2400 |
| atcggcaccc ggcgtggtga accggcctg ccgcagcgga tcaggctgct gaccgatgcc | 2460 |
| gagcggcggg ttgccgcgat ggccgccgcc gggcagacca accgggagat cgccggtcgg | 2520 |
| ctcttcgtca cggccagcac ggtggagcag cacctgacca gcgtcttccg caagctgggc | 2580 |
| gtcaagggcc gccggttcct gccgaccgag ctcgcccaag ccgtctga | 2628 |

<210> SEQ ID NO 55
<211> LENGTH: 2616
<212> TYPE: DNA
<213> ORGANISM: Streptomyces malaysiensis

<400> SEQUENCE: 55

| | |
|---|---|
| gtggtcaccg tcaccggccc aatcgcctgc ggcaagacag aactgcttga cgcggctgcc | 60 |
| gcgaaggctg aggccatcat tctgcgcgcg gtctgcgcgc cagaagagcg ggctatgccg | 120 |
| tacgccatga tcgggcagct catcgacgac ccggcgctcg cgcatcgggc gccggggctg | 180 |

```
gctgatcgga tagcccaggg cgggcagctg tcgctgaggg ccgagaaccg actgcgcagg      240
gatctcaccc gtgccctgct ggcgcttgcc gtggaccggc ctgtgctgat cggcgtcgac      300
gatgtgcatc acgccgacac cgcctctttg aactgtctgc tgcatttggc ccgccgggtc      360
cgtccggccc ggatatccat gatcttcacc gagttgcgca gcctcacccc tactcagtca      420
cggttcaagg cggagctgct cagcctgcca taccaccacg agatcgcgct gcgtccattc      480
ggaccggagc aatcggcgga gctggctcgc gccgccttcg gcccgggcct cgccgaggat      540
gtgctcgcgg ggttgtataa aacgaccagg ggcaatctga gtctcagccg tggactgatc      600
agcgatgtgc gggaggccct ggccaacgga gagagcgctt tcgaggcggg ccgcgcgttc      660
cggctggcgt acctcagctc gctctaccgc tgtggcccgg tcgcgctgcg ggtcgcccga      720
gtggctgccg tgctgggccc aagcgccacc accacgctgg tgcgccggct aagcgggctc      780
agcgcggaga cgatagaccg ggcaaccaag atcctcactg agggcgggct gctgctcgac      840
cagcagttcc cgcacccggc cgcccgctcg gtggtgctcg atgacatgtc cgcccaggaa      900
cgacgcagcc tgcacactct cgccctggaa ctgctggacg aggcgccggt tgaagtgctc      960
gcgcaccacc aggtcggcgc cggtctcata cacgggccca aggctgcgga gatgttcgcc     1020
aaggccggca aggctctggt cgtacgcaac gagttgggcg acgcggccga ataccgtcaa     1080
ctggctcacc gggcctccga cgatgtctcc acccgggccg ccttacgggt cgaggccgtg     1140
gccatcgagc gccgccgcaa tccgctggcc tccagtcggc acatggacga actgagcgcc     1200
gccggccgcg ccggtctgct ttccccaag catgcggcgc tggccgtctt ctggctagcc     1260
gacggcgggc gatccggcga ggcagccgaa gtgctggcgt cggaacgccc gctcgcgacc     1320
accgatcaga accgggccca cctgcgattt gtcgaggtga ctctcgcgct gttctctccc     1380
ggcgccttcg gatcggaccg gcgcccacct ccgctgacgc cggacgaact cgccagcctg     1440
ccgaaggcgg cctggcaatg cgcggtcgcc gacaacgcgg ccatgaccgc cttgcacggc     1500
catccagaac ttgccaccgc tcaggcggaa acagttctgc ggcaggctga ttcggcagcc     1560
gacgcgatcc ccgccgcgct gatcgccctg ttgtacgcgg agaacaccga gtccgctcat     1620
atctgggccg acaagctggg cagcacgaat gccggggtat cgaacgaggc ggaagcgggc     1680
tacgccggcc cgtgcgccga gatcgccctg cggcgcggcg acctggccac ggcgttcgag     1740
gctggtagcg ccgtcctgga cgaccggtcg ctgccgtcgc tcggcatcac cgccgcattg     1800
ctgttgagca gcaagacggc cgccgctgtc cggctgggcg aactcgagcg tgcggagaag     1860
ctgctcgccg agccgcttcc gaacggcgtc caggacagcc ttttcggtct gcacctgctc     1920
tcggcgtacg gccagtacag cctcgcgatg ggccgatatg aatcagctca ccgggcgttt     1980
cgcacctgcg gagaacgtat gcgcagctgg gatgttgacg tgcctggtct ggccctgtgg     2040
cgtgtcgacg ccgccgaggc gctgctcagc ctcgaccgga acgagggcca gcggctcatc     2100
gacgaacaac tcacccgtcc gatgggggcct cgttcccacg cgttaacgct gcggatcaag     2160
gcggcatacc tcccgcggac gaagcggatc cccctgctcc atgaggcggc cgagctgctg     2220 ctccccctgcc ccgacccgta cgagcaagcg cgggtgctcg ccgatctggg cgacacgctc     2280
agcgcgctca gacgctatag ccgggcgcgg ggagttctcc ggcaggctcg tcacctggcc     2340
acccagtgcg gtgctgtccc gctgctgcgc aggctcgggg gcgagcccgg ccggatcgac     2400
gacgccggcc tgccgcagcg gagcacatcg ttgaccgatg cggagcggcg ggtggcggcg     2460
ctggccgcgc ccgacagac caaccgggag atcgccgaac agctgttcgt cacgccagc     2520 acagtggaac agcacctcac aagcgtcttc cgcaagctgg gcgtcaaggg ccgcaagcag     2580
```

```
ctgccgaccg cgctggccga cgtggaacag acctga                              2616
```

<210> SEQ ID NO 56
<211> LENGTH: 2721
<212> TYPE: DNA
<213> ORGANISM: Streptomyces malaysiensis

<400> SEQUENCE: 56

```
atgtatagcg gtacctgccg tgaaggatac gaactcgtcg cacgcgagga cgaactcggt    60
attctacaga ggtctctgga acaagcgagc agcggccagg gcgtcgtggt caccgtcacc   120
ggcccaatcg cctgcggcaa gacagaactg cttgacgcgg ctgccgcgaa ggctgaggcc   180
atcattctgc gcgcggtctg cgcgccagaa gagcgggcta tgccgtacgc catgatcggg   240
cagctcatcg acgacccggc gctcgcgcat cgggcgccgg gctggctga tcggatagcc    300
cagggcgggc agctgtcgct gagggccgag aaccgactgc gcaggatct cacccgtgcc    360
ctgctggcgc ttgccgtgga ccggcctgtg ctgatcggcg tcgacgatgt gcatcacgcc   420
gacaccgcct ctttgaactg tctgctgcat ttggcccgcc gggtccgtcc ggcccggata   480
tccatgatct tcaccgagtt gcgcagcctc acccctactc agtcacggtt caaggcggag   540
ctgctcagcc tgccatacca ccacgagatc gcgctgcgtc cattcggacc ggagcaatcg   600
gcggagctgg ctcgcgccgc cttcggcccg ggcctcgccg aggatgtgct cgcggggttg   660
tataaaacga ccaggggcaa tctgagtctc agccgtggac tgatcagcga tgtgcgggag   720
gccctggcca acggagagag cgcttcgag gcgggccgcg cgttccggct ggcgtacctc    780
agctcgctct accgctgtgg cccggtcgcg ctgcgggtcg cccgagtggc tgccgtgctg   840
ggcccaagcg ccaccaccac gctggtcgcg cggctaagcg ggctcagcgc ggagacgata   900
gaccgggcaa ccaagatcct cactgagggc gggctgctgc tcgaccagca gttcccgcac   960
ccggccgccc gctcggtggt gctcgatgac atgtccgccc aggaacgacg cagcctgcac  1020
actctcgccc tggaactgct ggacgaggcg ccggttgaag tgctcgcgca ccaccaggtc  1080
ggcgccggtc tcatacacgg gcccaaggct gcggagatgt cgccaaggc cggcaaggct  1140
ctggtcgtac gcaacgagtt gggcgacgcg gccgaatacc tgcaactggc tcaccgggcc  1200
tccgacgatg tctccacccg ggccgccctg cgggtcgagg ccgtggccat cgagcgccgc  1260
cgcaatccgc tggcctccag tcggcacatg gacgaactga gcgccgccgg ccgcgccggt  1320
ctgcttttccc ccaagcatgc ggcgctggcc gtcttctggc tagccgacgg cgggcgatcc  1380
ggcgaggcag ccgaagtgct ggcgtcggaa cgcccgctcg cgaccaccga tcagaaccgg  1440
gcccacctgc gatttgtcga ggtgactctc gcgctgttct ctcccggcgc cttcggatcg  1500
gaccggcgcc cacctccgct gacgccggac gaactcgcca gcctgccgaa ggcggcctgg  1560
caatgcgcgg tcgccgacaa cgcggccatg accgccttgc acggccatcc agaacttgcc  1620
accgctcagg cggaaacagt tctgcggcag gctgattcgg cagccgacgc gatccccgcc  1680
gcgctgatcg ccctgttgta cgcggagaac accgagtccg ctcatatctg ggccgacaag  1740
ctgggcagca cgaatgccgg ggtatcgaac gaggcggaag cgggctacgc cggcccgtgc  1800
gccgagatcg ccctgcggcg cggcgacctg gccacgcgcg tcgaggctgg tagcgccgtc  1860
ctggacgacc ggtcgctgcc gtcgctcggc atcaccgccg cattgctgtt gagcagcaag  1920
acggccgccg ctgtccggct gggcgaactc gagcgtgcgg agaagctgct cgccgagccg  1980
cttccgaacg gcgtccagga cagccttttc ggtctgcacc tgctctcggc gtacggccag  2040
```

```
tacagcctcg cgatgggccg atatgaatca gctcaccggg cgtttcgcac ctgcggagaa    2100
cgtatgcgca gctgggatgt tgacgtgcct ggtctggccc tgtggcgtgt cgacgccgcc    2160
gaggcgctgc tcagcctcga ccggaacgag ggccagcggc tcatcgacga caaactcacc    2220
cgtccgatgg ggcctcgttc ccacgcgctg acgctgcgga tcaaggcggc atacctcccg    2280
cggacgaagc ggatccccct gctccatgag gcggccgagc tgctgctccc ctgccccgac    2340
ccgtacgagc aagcgcgggt gctcgccgat ctgggcgaca cgctcagcgc gctcagacgc    2400
tataccgggg cgcggggagt tctccggcag gctcgtcacc tggccaccca gtgcggtgct    2460
gtcccgctgc tgcgcaggct cgggggcgag cccggccgga tcgacgacgc cggcctgccg    2520
cagcggagca catcgttgac cgatgcggag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                              2721

<210> SEQ ID NO 57
<211> LENGTH: 2715
<212> TYPE: DNA
<213> ORGANISM: Streptomyces violaceusniger

<400> SEQUENCE: 57
gtgtatagcg gtacctgccg tgaaggatac gaactcgtcg cccgcgagga cgaactcggc      60
attctgcaga ggtctctgga agaagcaggc agcggccagg gcgccgtggt caccgtcacc     120
ggcccgatcg cctgcggcaa gacagaactg cttgacgcgg ctgccgcgaa ggctgacgcc     180
atcattctgc gcgcggtctg cgcgcccgaa gagcgcgcta tgccgtacgc catgatcggg     240
cagctcatca cgacccggc gctcgcgcat cgggcgccgg agctggctga tcggatagcc     300
cagggcgggc atctgtcgct gagggccgag aaccgactgc gcagggatct cacccgtgcc     360
ctgctggcgc ttgccgtcga ccggcctgtg ctgatcggcg tcgacgatgt gcatcacgcc     420
gacaccgcct ctttgaactg tctgctgcat ttagcccgcc gggtccgtcc ggcccggata     480
tccatgatct tcaccgagtt gcgcagcctc acccctactc agtcacgatt caaggcggag     540
ctgctcagcc tgccgtacca ccacgagatc gcgctgcgtc cactcggacc ggagcaatcg     600
gcggagctgg cccacgccgc cttcggcccg ggctcgccg aggatgtgct cgcggggttg     660
tatgggatga ccaggggcaa cctgagtctc agccgtggac tgatcagcga tgtgcgggag     720
gcccaggcca acggagagag cgcttttcgag gtgggccgcg cgttccggct ggcgtacctc     780
agctcgctct accgctgtgg cccgatcgcg ctgcgggtcg cccgagtggc tgccgtgctg     840
ggcccaagcg ccaccaccac gctggtgcgc cgtctaagcg ggctcagcgc ggagacgata     900
gaccgggcaa ccaagatcct cactgagggc gggctgctgc tcgaccacca gttcccgcac     960
ccggccgccc gctcggtggt gctcgatgac atgtccgccc aggaacgacg cagcctgcac    1020
actctcgccc tggaactgct ggacgaggcg ccggttgaag tgctcgcgca ccaccaggtc    1080
ggcgccggtc tcatacacgg gcccaaggct gcggagatat cgccagggc tggccaggct    1140 ctggttgtac gcaacgagtt gggcgacgcg ccgaatacc tgcaactggc tcaccgagcc    1200
tccgacgatg tctccacccg gccgccttta cgggtcgagg ccgtggcaat cgagcgccgc    1260
cgcaatccgc tggcctccag tcgtcacatg gacgagctga cgccgccgg ccgcgccggt    1320 ctgctttccc ccaagcatgc agcgctggct gtcttctggc tggccgacgg cgggcgatcc    1380
ggcgaggcag ccgaggtgct ggcgtcggaa caccgctcg cgaccaccga tcagaaccga    1440
```

```
gcacacctgc gatttgccga ggtgactctc gcgctgttct gtcccggcgc cttcgggtcg    1500
gaccggcgcc cacctccgct ggcgccggac gagctcgcca gcttgccgaa ggcggcctgg    1560
caatgcgcgg tcgccgacaa cgcggtcatg acagcgttgc atgctcatcc agaacttgcc    1620
accgctcagg cggaaacagt tctgcggcag gctgattcgg cagccgacgc aatccccgcc    1680
gcactgatcg ccctgttgta cgcagagaac accgagtccg ctcagatctg gccgacaag    1740 ctgggcagca ccaatgccgg ggtatcgaac gaggcggaag cgggctacgc cggcccgtgc    1800
gccgagatcg ccctgcggcg cggcgacctg ccacggcgt tcgaggctgg tggcaccgtc    1860
ctggacgacc ggccgctgcc gtcgctcggc atcaccgccg cattgctgtt gagcagcaag    1920
acggcagccg ctgtccgcct gggcgaactc gagcgtgcgg agaagctgct cgctgagccg    1980
cttccgaacg tgtccagga cagccttttc ggtctgcacc tgctctcggc cacggccag    2040 tacagcctcg cgatgggccg atatgaatcg gctcaccggg cgtttcacac ctgcggagaa    2100
cgtatgcgca gctggggtgt tgacgtgcct ggtctagccc tgtggcgtgt cgacgccgcc    2160
gaggcactgc tcagcctcga ccggaacgag ggccagcggc tcatcgacga caactcgcc    2220 cgtccgatgg gacctcgttc ccgcgcatta acgctgcgga tcaaggcggc atacctcccg    2280
cggacgaagc ggatccccct gctccatgag gcagctgagc tgctgctctc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggggcgag cccggccgga tcgacgacgc cggcctgccg    2520
cagcggagca catcgttgac cgatgcggag cggcgggtgt cggccctggc cgcggccgga    2580
cagaccaacc gggagatcgc caaacagcta ttcgtcacgg ccagcaccgt ggaacagcac    2640
ctcacaagcg tcttccgcaa gctgggcgtt aagggccgca ggcagctacc gaccgcgctg    2700
gccgacgtgg aatag                                                    2715
```

<210> SEQ ID NO 58
<211> LENGTH: 2715
<212> TYPE: DNA
<213> ORGANISM: Streptomyces violaceusniger

<400> SEQUENCE: 58

```
atgtatagcg gtacctgccg tgaaggatac gaactcgtcg cccgcgagga cgaactcggc      60
attctgcaga ggtctctgga agaagcaggc agcggccagg cgccgtggt caccgtcacc      120 ggcccgatcg cctgcggcaa gacagaactg cttgacgcgg ctgccgcgaa ggctgacgcc      180
atcattctgc gcgcggtctg cgcgcccgaa gagcgcgcta tgccgtacgc catgatcggg      240
cagctcatcg acgaccccggc gctcgcgcat cgggcgccgg agctggctga tcggatagcc      300
cagggcgggc atctgtcgct gagggccgag aaccgactgc gcaggatct cacccgtgcc      360 ctgctggcgc ttgccgtcga ccggcctgtg ctgatcggcg tcgacgatgt gcatcacgcc      420
gacaccgcct ctttgaactg tctgctgcat ctggcccgcc gggtccgtcc ggcccggata      480
tccatgatct tcaccgagtt gcgcagcctc accctactc agtcacgatt caaggcggag      540
ctgctcagcc tgccgtacca ccacgagatc gcgctgcgtc cactcggacc ggagcaatcg      600
gcggagctgg cccacgccgc cttcggcccg ggcctcgccg aggatgtgct cgcggggttg      660
tatgggatga ccaggggcaa cctgagtctc agccgtggac tgatcagcga tgtgcggag      720 gcccaggcca acggagagag cgctttcgag gtgggccgcg cgttccggct ggcgtacctc      780
```

| | |
|---|---|
| agctcgctct accgctgtgg cccgatcgcg ctgcgggtcg cccgagtggc tgccgtgctg | 840 |
| ggcccaagcg ccaccaccac gctggtgcgc cgtctaagcg ggctcagcgc ggagacgata | 900 |
| gaccgggcaa ccaagatcct cactgagggc gggctgctgc tcgaccacca gttcccgcac | 960 |
| ccggccgccc gctcggtggt gctcgatgac atgtccgccc aggaacgacg cagcctgcac | 1020 |
| actctcgccc tggaactgct ggacgaggcg ccggttgaag tgctcgcgca ccaccaggtc | 1080 |
| ggcgccggtc tcatacacgg gcccaaggct gcggagatat cgccagggc tggccaggct | 1140 |
| ctggttgtac gcaacgagtt gggcgacgcg gccgaatacc tgcaactggc tcaccgagcc | 1200 |
| tccgacgatg tctccacccg ggccgccctg cgggtcgagg ccgtggcaat cgagcgccgc | 1260 |
| cgcaatccgc tggcctccag tcgtcacatg gacgagctga gcgccgccgg ccgcgccggt | 1320 |
| ctgcttcccc ccaagcatgc agcgctggct gtcttctggc tggccgacgg cgggcgatcc | 1380 |
| ggcgaggcag ccgaggtgct ggcgtcggaa cacccgctcg cgaccaccga tcagaaccga | 1440 |
| gcacacctgc gatttgccga ggtgactctc gcgctgttct gtcccggcgc cttcgggtcg | 1500 |
| gaccggcgcc cacctccgct ggcgccggac gagctcgcca gcttgccgaa ggcggcctgg | 1560 |
| caatgcgcgg tcgccgacaa cgcggtcatg acagcgttgc atgctcatcc agaacttgcc | 1620 |
| accgctcagg cggaaacagt tctgcggcag gctgattcgg cagccgacgc aatccccgcc | 1680 |
| gcactgatcg ccctgttgta cgcagagaac accgagtccg ctcagatctg gccgacaag | 1740 |
| ctgggcagca ccaatgccgg ggtatcgaac gaggcggaag cgggctacgc cggcccgtgc | 1800 |
| gccgagatcg ccctgcggcg cggcgacctg ccacggcgt tcgaggctgg tggcaccgtc | 1860 |
| ctggacgacc ggccgctgcc gtcgctcggc atcaccgccg cattgctgtt gagcagcaag | 1920 |
| acggcagccg ctgtccgcct gggcgaactc gagcgtgcgg agaagctgct cgctgagccg | 1980 |
| cttccgaacg tgtccagga cagccttttc ggtctgcacc tgctctcggc gcacggccag | 2040 |
| tacagcctcg cgatgggccg atatgaatcg gctcaccggg cgtttcacac ctgcggagaa | 2100 |
| cgtatgcgca gctggggtgt tgacgtgcct ggtctagccc tgtggcgtgt cgacgccgcc | 2160 |
| gaggcactgc tcagcctcga ccggaacgag ggccagcggc tcatcgacga caactcgcc | 2220 |
| cgtccgatgg gacctcgttc ccgcgcactg acgctgcgga tcaaggcggc atacctcccg | 2280 |
| cggacgaagc ggatccccct gctccatgag gcagctgagc tgctgctctc ctgccccgac | 2340 |
| ccgtacgagc aagcgcgggt gctcgccgat ctgggcgaca cgctcagcgc gctcagacgc | 2400 |
| tatagccggg cgcggggagt tctccggcag gctcgtcacc tggccaccca gtgcggtgct | 2460 |
| gtcccgctgc tgcgccgact cggggcgag cccggccgga tcgacgacgc cggcctgccg | 2520 |
| cagcggagca catcgttgac cgatgcggag cggcgggtgt cggccctggc cgcggccgga | 2580 |
| cagaccaacc gggagatcgc caaacagcta ttcgtcacgg ccagcaccgt ggaacagcac | 2640 |
| ctcacaagcg tcttccgcaa gctgggcgtt aagggccgca ggcagctacc gaccgcgctg | 2700 |
| gccgacgtgg aatag | 2715 |

<210> SEQ ID NO 59
<211> LENGTH: 2721
<212> TYPE: DNA
<213> ORGANISM: Streptomyces Sp. NRRL F-4729

<400> SEQUENCE: 59

| | |
|---|---|
| gtgtatagcg gtacctgccg tgaaggatac gaactcgtcg cacgcgagga cgaactcggc | 60 |
| attctacaga ggtctctgga acaagcgagc agcggccagg gcgtcgtggt caccgtcacc | 120 |
| ggcccaatcg cctgcggcaa gacagaactg cttgacgcgg ctgccgcgaa ggctgaggcc | 180 |

```
atcattctgc gcgcggtctg cgcgcccgaa gagcgggcta tgccgtacgc catgatcggg    240
cagctcatcg acgacccggc gctcgcgcat cgggcgccgg ggctggctga tcggatagcc    300
cagggcgggc agctgtcgct gagggccgag aaccgactgc gcagggatct cacccgtgcc    360
ctgctggcgc ttgccgtgca ccggcctgtg ctgatcggcg tcgatgatgt gcatcacgcc    420
gacaccgcct ctttgaactg tctgctgcat ttggcgcgcc gggtccgtcc ggcccggata    480
tccatgatct tcaccgagtt gcgcagcctc acccctactc agtcacgatt caaggcggag    540
ctgctcagcc tgccgtacca ccacgagatc gcgctgcgtc cattcggacc ggagcaatcg    600
gcggagctgg ctcgcgccgc cttcggcccg ggcctcgccg aggatgtgct cgcggggttg    660
tataaaacga ccaggggcaa tctgagtctc agccgtggac tgatcagcga tgtgcgggag    720
gccctggcca acgagagag cgctttcgag gcgggccgcg cgttccggct ggcgtacctc    780
agctcgctct accgctgtgg cccggtcgcg ctgcgggtcg cccgagtggc tgccgtgctg    840
ggcccaagcg ccaccaccac gctggtgcgc cggctaagcg ggctcagcgc ggagacgata    900
gaccgggcaa ccaagatcct caccgagggc gggctgctgc tcgaccagca gtttccgcac    960
ccggccgccc gctcggtggt gctcgatgac atgtccgccc aggaacgacg cggcctgcac    1020
actctcgccc tggaactgct ggacgaggcg ccggttgaag tgctcgcgca ccaccaggtc    1080
ggcgccggtc tcatacacgg gcccaaggct gcggagatgt cgccaaggc cggcaaggct    1140 ctggtcgtac gcaacgagtt gggcgacgcg gccgaatacc tgcaactggc tcaccgggcc    1200
tccgacgatg tctccacccg ggccgcctta cgggtcgagg ccgtggcgat cgagcgccgc    1260
cgcaatccgc tggcctccag tcggcacatg gacgagctga gcgccgccgg ccgcgccggt    1320
ctgctttccc ccaagcatgc ggcgctggcc gtcttctggc tggccgacgg cgggcgatcc    1380
ggcgaggcag cccaggtgct ggcgtcggaa cgcccgctcg cgaccaccga tcagaaccgg    1440
gcccacctgc gatttgtcga ggtgactctc gcgctgttct ctcccggcgc cttcggatcg    1500
gaccggcgcc cacctccgct gacgccggac gaactcgcca gctgccgaa ggcggcctgg    1560 caatgcgcgg tcgccgacaa cgcggccatg accgccttgc acggccatcc agaacttgcc    1620
accgctcagg cggaaacagt tctgcggcag gctgattcgg cagccgacgc gatccccgcc    1680
gcgctgatcg ccctgttgta cgcggagaac accgagtccg ctcatatctg gccgacaag    1740 ctgggcagca tgaatgccgg ggtatcgaac gaggcggaag cgggctacgc cggcccgtgc    1800
gccgagatcg ccctgcggcg cggcgacctg ccacggcgt tcgaggctgg tagcaccgtc    1860
ctggacgacc ggtcactgcc gtcgctcggc atcaccgccg cattgctgtt gagcagcaag    1920
acggccgccg ctgtccggct gggcgaactc gagcgtgcgg agaagctgct cgccgagccg    1980
cttccgaacg gcgtccagga cagccttttc ggtctgcacc tgctctcggc gtacggccag    2040
tacagcctcg cgatgggccg atatgaatcg gctcaccggg cgtttcgcac ctgcggagaa    2100
cgtatgcgca gctgggatgt tgacgtgcct ggtctggccc tgtggcgtgt cgacgccgcc    2160
gaggcgctgc tcagcctcga ccggaacgag ggccagcggc tcatcgacga caactcacc    2220 cgtccgatgg gacctcgttc ccgcgcgtta acgctgcgga tcaaggcggc atacctcccg    2280
cggacgaagc ggatcccct gctccatgag gcggccgagc tgctgctccc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggggcgag cccggccgga tcgacgacgc cggcctgccg    2520
```

| | |
|---|---|
| cagcggagca catcgttgac cgatgcggag cggcgggtgg cggcgctggc cgcggccgga | 2580 |
| cagaccaacc gggagatcgc cgaacagctg ttcgtcacgg ccagcacagt ggaacagcac | 2640 |
| ctcacaagcg tcttccgcaa gctgggcgtc aagggccgca agcagctgcc gaccgcgctg | 2700 |
| gccgacgtgg aacagacctg a | 2721 |

<210> SEQ ID NO 60
<211> LENGTH: 2721
<212> TYPE: DNA
<213> ORGANISM: Streptomyces Sp. NRRL F-4729

<400> SEQUENCE: 60

| | |
|---|---|
| atgtatagcg gtacctgccg tgaaggatac gaactcgtcg cacgcgagga cgaactcggc | 60 |
| attctacaga ggtctctgga acaagcgagc agcggccagg gcgtcgtggt caccgtcacc | 120 |
| ggcccaatcg cctgcggcaa gacagaactg cttgacgcgg ctgccgcgaa ggctgaggcc | 180 |
| atcattctgc gcgcggtctg cgcgcccgaa gagcgggcta tgccgtacgc catgatcggg | 240 |
| cagctcatcg acgacccggc gctcgcgcat cgggcgccgg ggctggctga tcggatagcc | 300 |
| cagggcgggc agctgtcgct gagggccgag aaccgactgc gcaggatct cacccgtgcc | 360 |
| ctgctggcgc ttgccgtgca ccggcctgtg ctgatcggcg tcgatgatgt gcatcacgcc | 420 |
| gacaccgcct ctttgaactg tctgctgcat ttggcgcgcc gggtccgtcc ggcccggata | 480 |
| tccatgatct tcaccgagtt gcgcagcctc acccctactc agtcacgatt caaggcggag | 540 |
| ctgctcagcc tgccgtacca ccacgagatc gcgctgcgtc cattcggacc ggagcaatcg | 600 |
| gcggagctgg ctcgcgccgc cttcggcccg gcctcgccg aggatgtgct cgcggggttg | 660 |
| tataaaacga ccaggggcaa tctgagtctc agccgtggac tgatcagcga tgtgcgggag | 720 |
| gccctggcca acggagagag cgcttttcgag gcgggccgcg cgttccggct ggcgtacctc | 780 |
| agctcgctct accgctgtgg cccggtcgcg ctgcgggtcg cccgagtggc tgccgtgctg | 840 |
| ggcccaagcg ccaccaccac gctggtgcgc cggctaagcg ggctcagcgc ggagacgata | 900 |
| gaccgggcaa ccaagatcct caccgagggc gggctgctgc tcgaccagca gtttccgcac | 960 |
| ccggccgccc gctcggtggt gctcgatgac atgtccgccc aggaacgacg cggcctgcac | 1020 |
| actctcgccc tggaactgct ggacgaggcg ccggttgaag tgctcgcgca ccaccaggtc | 1080 |
| ggcgccggtc tcatacacgg gcccaaggct cggagatgt cgccaaggc cggcaaggct | 1140 |
| ctggtcgtac gcaacgagtt gggcgacgcg gccgaatacc tgcaactggc tcaccgggcc | 1200 |
| tccgacgatg tctccacccg gccgccctg cgggtcgagg ccgtggcgat cgagcgccgc | 1260 |
| cgcaatccgc tggcctccag tcggcacatg gacgagctga gcgccgccgg ccgcgccggt | 1320 |
| ctgctttccc ccaagcatgc ggcgctggcc gtcttctggc tggccgacgg cgggcgatcc | 1380 |
| ggcgaggcag cccaggtgct ggcgtcggaa cgcccgctcg cgaccaccga tcagaaccgg | 1440 |
| gcccacctgc gatttgtcga ggtgactctc gcgctgttct ctcccggcgc cttcggatcg | 1500 |
| gaccggcgcc cacctccgct gacgccggac gaactcgcca gctgccgaa ggcggcctgg | 1560 |
| caatgcgcgg tcgccgacaa cgcggccatg accgccttgc acggccatcc agaacttgcc | 1620 |
| accgctcagg cggaaacagt tctgcggcag gctgattcgg cagccgacgc gatccccgcc | 1680 |
| gcgctgatcg ccctgttgta cgcggagaac accgagtccg ctcatatctg ggccgacaag | 1740 |
| ctgggcagca tgaatgccgg ggtatcgaac gaggcggaag cgggctacgc cggcccgtgc | 1800 |
| gccgagatcg ccctgcggcg cggcgacctg gccacggcgt tcgaggctgg tagcaccgtc | 1860 |
| ctggacgacc ggtcactgcc gtcgctcggc atcaccgccg cattgctgtt gagcagcaag | 1920 |

```
acggccgccg ctgtccggct gggcgaactc gagcgtgcgg agaagctgct cgccgagccg    1980
cttccgaacg gcgtccagga cagccttttc ggtctgcacc tgctctcggc gtacggccag    2040
tacagcctcg cgatgggccg atatgaatcg gctcaccggg cgtttcgcac ctgcggagaa    2100
cgtatgcgca gctgggatgt tgacgtgcct ggtctggccc tgtggcgtgt cgacgccgcc    2160
gaggcgctgc tcagcctcga ccggaacgag ggccagcggc tcatcgacga caactcacc     2220 cgtccgatgg gacctcgttc ccgcgcgctg acgctgcgga tcaaggcggc atacctcccg    2280
cggacgaagc ggatccccct gctccatgag gcggccgagc tgctgctccc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggggcgag cccggccgga tcgacgacgc cggcctgccg    2520
cagcggagca catcgttgac cgatgcggag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                              2721

<210> SEQ ID NO 61
<211> LENGTH: 2715
<212> TYPE: DNA
<213> ORGANISM: Streptomyces filamentosus

<400> SEQUENCE: 61
gtgcgagcta ttaatgcgtc cgacaccggt cctgaactgg tcgcccgcga agacgaactg      60
ggacgtgtac gaagtgccct gaaccgagcg aacggcggcc aaggtgtcct gatctccatt     120
accggtccga tcgcctgcgg caagaccgaa ctgcttgagg ctgccgcctc ggaagttgac     180
gccatcactc tgcgcgcggt ctgtgccgcc gaggaacggg cgataccctta tgccctgatc     240 gggcagctta tcgacaaccc cgcgctcggc attccggttc cggatccggc cggcctgacc     300
gcccagggcg gacgactgtc atcgagcgcc gagaaccgac tgcgtcgcga cctcacccgt     360
gccctgctga cgctcgccac cgaccggctg gtgctgatct gtgtcgatga cgtgcagcac     420
gccgacaacg cctcgttgag ctgccttctg tatctggccc gacggcttgt cccggctcga     480
atcgctctgg tattcaccga gttgcgagtc ctcacctcgt ctcagttacg gttcaacgcg     540
gagctgctca gcttgcggaa ccactgcgag atcgcgctgc gcccactcgg cccggggcat     600
gcggccgagc tggcccgcgc caccctcggc cccggcctct ccgacgaaac actcacggag     660
ctgtaccggg tgaccggagg caacctgagt ctcagccgcg ggctgatcga cgatgtgcgg     720
gacgcctggg cacgagggga aacgggcgtc caggtgggcc gggcgttccg gctggcctac     780
ctcggttccc tccaccgctg tggtccgctg gcgttgcggg tcgcccgcgt agccgccgta     840
ctgggcccga cgccaccag cgtcctggtg cgccggatca gtgggctcag cgcggaggcc     900
atggcccagg cgaccgatat cctcgctgac ggcggcctcc tgcgcgacca gcggttcaca     960
catccagcgg cccgctcggt ggtgctcgac gacatgtccg ccgaggaacg acgcagcgtg    1020
cacagcctcg ccctggaact gctggacgag gcaccggccg agatgctcgc gcaccaccgg    1080
gtcggcgccg gtctcgtgca cgggccgaag gccgcggaga cattcaccgg ggccggccgg    1140
gcactggccg ttcgcggcat gctgggcgag gcagccgact acctgcaact ggcgtaccgg    1200
gcctccggcg acgccgctac caaggccgcg atacgcgtcg agtccgtggc ggtcgagcgc    1260
```

```
cgacgcaatc cgctggtcgt cagtcgccat tgggacgagc tgagcgtcgc ggcccgcgcc      1320
ggtctgctct cctgcgagca cgtgtccagg acggcccgct ggctgaccgt cggtgggcgg      1380
cccggcgagg cggccagggt gctggcgtcg caacaccgac gggtcgtcac cgatcaggac      1440
cgggcccacc tgcgggtcgc cgagttctcg ctcgcgctgc tgtacccggg tacgtccggc      1500
tcggaccggc gcccgcaccc gctcacgtcg gacgaactcg cggccctacc gactgcgacc      1560
agacactgcg cgatcgccga taacgctgtc atggctgcct tgcgtggtca tccgagcttt     1620
gccaccgccg aggcagaagc cgttctgcag caagccgacg cggcggacgg cgctgctctc      1680
accgcgctga tgggccctgct gtacgcggag agcatcgagg tcgctgaagt ctgggcggac     1740
aagctggcgg cagaggccgg agcatcgaac gggcaggacg cggagtacgc cggtatacgc      1800
gccgaaatcg ccctgcggcg cggcgatctg accgcggccg tcgagaccgc cggcatggtc     1860
ctggacggcc ggccgctgcc gtcgctcgac atcaccgcca cgttgctgtt ggccggcagg     1920
gcgtccgtcg ccgtccggct gggcgaactc gaccacgcgg aggagctgtt cgccgcgccg      1980
ccggaggacg ccttccagga cagcctcttc ggtctgcatc tgctctcggc gcacggccag     2040
tacagcctcg cgacaggccg gcccgagtcg gcataccggg cctttcgtgc ctgcggcgaa     2100
cgtatgcgcg attggggctt cgacgcgccc ggtgtggccc tgtggcgcgt cggcgccgcc     2160
gaggcgctgc tcggcctcga ccggaacgag ggccgacggc tcatcgacga acagctgagc     2220
cggacgatgg ccccccggtc ccacgcgttg acgctgcgga taaaagcggc gtacatgccg     2280
gagccgaagc gggtcgacct gctctacgaa gcggctgagc tgctgctctc ctgccgggac     2340
cagtatgagc gagcgcgggt gctcgccgat ctgggcgagg cgctcagcgc gctcgggaac     2400
taccggcagg cgcgaggtgt gctccggcag gctcggcatc tggccatgcg aaccggcgcg     2460
gacccgctgc tgcgccggct cggaatcagg cccggccggc aggacgaccc cgaccccgcag     2520 ccgcggagca gatcgctgac caacgctgag cggcgtgcgg cgtcgctggc gcgaccgga      2580 ctgaccaacc gggagatcgc cgaccggctc ttcgtcaccg ccagcaccgt ggagcagcac     2640
ctcaccaacg tcttccgcaa gctgggcgtc aagggccgca agcagctgcc ggccgagttg     2700
gacgacatgg aatag                                                      2715

<210> SEQ ID NO 62
<211> LENGTH: 2715
<212> TYPE: DNA
<213> ORGANISM: Streptomyces filamentosus

<400> SEQUENCE: 62
atgcgagcta ttaatgcgtc cgacaccggt cctgaactgg tcgcccgcga agacgaactg        60
ggacgtgtac gaagtgccct gaaccgagcg aacggcggcc aaggtgtcct gatctccatt      120
accggtccga tcgcctgcgg caagaccgaa ctgcttgagg ctgccgcctc ggaagttgac      180
gccatcactc tgcgcgcggt ctgtgccgcc gaggaacggg cgataccttta tgccctgatc      240 gggcagctta tcgacaaccc cgcgctcggc attccggttc cggatccggc cggcctgacc      300
gcccagggcg gacgactgtc atcgagcgcc gagaaccgac tgcgtcgcga cctcacccgt      360
gccctgctga cgctcgccac cgaccggctg gtgctgatct gtgtcgatga cgtgcagcac      420
gccgacaacg cctcgttgag ctgccttctg tatctggccc gacggcttgt cccggctcga     480
atcgctctgg tattcaccga gttcgagtc ctcacctcgt ctcagctgcg gttcaacgcg       540
gagctgctca gcttgcggaa ccactgcgag atcgcgctgc gcccactcgg cccggggcat      600
gcggccgagc tggcccgcgc caccctcggc cccggcctct ccgacgaaac actcacggag      660
```

```
ctgtaccggg tgaccggagg caacctgagt ctcagccgcg ggctgatcga cgatgtgcgg    720
gacgcctggg cacgagggga aacgggcgtc caggtgggcc gggcgttccg gctggcctac    780
ctcggttccc tccaccgctg tggtccgctg gcgttgcggg tcgcccgcgt agccgccgta    840
ctgggcccga cgccaccag cgtcctggtg cgccggatca gtgggctcag cgcggaggcc     900
atggcccagg cgaccgatat cctcgctgac ggcggcctcc tgcgcgacca gcggttcaca    960
catccagcgg cccgctcggt ggtgctcgac gacatgtccg ccgaggaacg acgcagcgtg   1020
cacagcctcg ccctggaact gctggacgag gcaccggccg agatgctcgc gcaccaccgg   1080
gtcggcgccg gtctcgtgca cgggccgaag gccgcggaga cattcaccgg ggccggccgg   1140
gcactggccg ttcgcggcat gctgggcgag gcagccgact acctgcaact ggcgtaccgg   1200
gcctccggcg acgccgctac caaggccgcg atacgcgtcg agtccgtggc ggtcgagcgc   1260
cgacgcaatc cgctggtcgt cagtcgccat gggacgagc tgagcgtcgc ggcccgcgcc    1320
ggtctgctct cctgcgagca cgtgtccagg acggcccgct ggctgaccgt cggtgggcgg   1380
cccggcgagg cggccagggt gctggcgtcg caacaccgac gggtcgtcac cgatcaggac   1440
cgggcccacc tgcgggtcgc cgagttctcg ctcgcgctgc tgtacccggg tacgtccggc   1500
tcggaccggc gcccgcaccc gctcacgtcg gacgaactcg cggccctacc gactgcgacc   1560
agacactgcg cgatcgccga taacgctgtc atggctgcct tgcgtggtca tccggagctt   1620
gccaccgccg aggcagaagc cgttctgcag caagccgacg cggcggacgg cgctgctctc   1680
accgcgctga tggccctgct gtacgcggag agcatcgagg tcgctgaagt ctgggcggac   1740
aagctggcgg cagaggccgg agcatcgaac gggcaggacg cggagtacgc cggtatacgc   1800
gccgaaatcg ccctgcggcg cggcgatctg accgcggccg tcgagaccgc cggcatggtc   1860
ctggacggcc ggccgctgcc gtcgctcgac atcaccgcca cgttgctgtt ggccggcagg   1920
gcgtccgtcg ccgtccggct gggcgaactc gaccacgcgg aggagctgtt cgccgcgccg   1980
ccggaggacg ccttccagga cagcctcttc ggtctgcatc tgctctcggc gcacggccag   2040
tacagcctcg cgacaggccg gcccgagtcg gcataccggg cctttcgtgc ctgcggcgaa   2100
cgtatgcgcg attggggctt cgacgcgccc ggtgtgccc tgtggcgcgt cggcgccgcc    2160
gaggcgctgc tcggcctcga ccggaacgag ggccgacggc tcatcgacga acagctgagc   2220
cggacgatgg cccccccggtc ccacgcgttg acgctgcgga taaaagcggc gtacatgccg   2280
gagccgaagc gggtcgacct gctctacgaa gcggctgagc tgctgctctc ctgccgggac   2340
cagtatgagc gagcgcgggt gctcgccgat ctgggcgagg cgctcagcgc gctcgggaac   2400
taccggcagg cgcgaggtgt gctccggcag gctcggcatc tggccatgcg aaccggcgcg   2460
gacccgctgc tgcgccggct cggaatcagg cccggccggc aggacgaccc cgaccgcag    2520 ccgcggagca gatcgctgac caacgctgag cggcgtgcgg cgtcgctggc cgcgaccgga   2580
ctgaccaacc gggagatcgc cgaccggctc ttcgtcaccg ccagcaccgt ggagcagcac   2640
ctcaccaacg tcttccgcaa gctgggcgtc aagggccgca agcagctgcc ggccgagttg   2700
gacgacatgg aatag                                                    2715
```

<210> SEQ ID NO 63
<211> LENGTH: 894
<212> TYPE: PRT
<213> ORGANISM: Streptomyces hygroscopicus

<400> SEQUENCE: 63

```
Met Pro Ala Val Glu Cys Tyr Glu Leu Asp Ala Arg Asp Glu Leu
  1               5                  10                  15

Arg Lys Leu Glu Glu Val Val Thr Gly Arg Ala Asn Gly Arg Gly Val
             20                  25                  30

Val Val Thr Ile Thr Gly Pro Ile Ala Cys Gly Lys Thr Glu Leu Leu
             35                  40                  45

Asp Ala Ala Ala Ala Lys Ala Asp Ala Ile Thr Leu Arg Ala Val Cys
             50                  55                  60

Ser Ala Glu Glu Gln Ala Leu Pro Tyr Ala Leu Ile Gly Gln Leu Ile
 65                  70                  75                  80

Asp Asn Pro Ala Leu Ala Ser His Ala Leu Glu Pro Ala Cys Pro Thr
                 85                  90                  95

Leu Pro Gly Glu His Leu Ser Pro Glu Ala Glu Asn Arg Leu Arg Ser
                100                 105                 110

Asp Leu Thr Arg Thr Leu Leu Ala Leu Ala Ala Glu Arg Pro Val Leu
                115                 120                 125

Ile Gly Ile Asp Glu Ser His Ala Asn Ala Leu Cys Leu Leu His Leu
                130                 135                 140

Ala Arg Arg Val Gly Ser Ala Arg Ile Ala Met Val Leu Thr Glu Leu
145                 150                 155                 160

Arg Arg Leu Thr Pro Ala His Ser Gln Phe Gln Ala Glu Leu Leu Ser
                165                 170                 175

Leu Gly His His Arg Glu Ile Ala Leu Arg Pro Leu Ser Pro Lys His
                180                 185                 190

Thr Ala Glu Leu Val Arg Ala Gly Leu Gly Pro Asp Val Asp Glu Asp
                195                 200                 205

Val Leu Thr Gly Leu Tyr Arg Ala Thr Gly Gly Asn Leu Asn Leu Thr
                210                 215                 220

Arg Gly Leu Ile Asn Asp Val Arg Glu Ala Trp Glu Thr Gly Gly Thr
225                 230                 235                 240

Gly Ile Ser Ala Gly Arg Ala Tyr Arg Leu Ala Tyr Leu Gly Ser Leu
                245                 250                 255

Tyr Arg Cys Gly Pro Val Pro Leu Arg Val Ala Arg Val Ala Ala Val
                260                 265                 270

Leu Gly Gln Ser Ala Asn Thr Thr Leu Val Arg Trp Ile Ser Gly Leu
                275                 280                 285

Asn Ala Asp Ala Val Gly Glu Ala Thr Glu Ile Leu Thr Glu Gly Gly
                290                 295                 300

Leu Leu His Asp Leu Arg Phe Pro His Pro Ala Ala Arg Ser Val Val
305                 310                 315                 320

Leu Asn Asp Met Ser Ala Gln Glu Arg Arg Leu His Arg Ser Ala
                325                 330                 335

Leu Glu Val Leu Asp Asp Val Pro Val Glu Val Ala His His Gln
                340                 345                 350

Val Gly Ala Gly Leu Leu His Gly Pro Lys Ala Ala Glu Ile Phe Ala
                355                 360                 365

Lys Ala Gly Gln Glu Leu His Val Arg Gly Glu Leu Asp Thr Ala Ser
                370                 375                 380

Asp Tyr Leu Gln Leu Ala His Gln Ala Ser Asp Ala Val Thr Gly
385                 390                 395                 400

Met Arg Ala Glu Ala Val Ala Ile Glu Arg Arg Asn Pro Leu Ala
                405                 410                 415

Ser Ser Arg His Leu Asp Glu Leu Thr Val Val Ala Arg Ala Gly Leu
```

```
                420                 425                 430
Leu Phe Pro Glu His Thr Ala Leu Met Ile Arg Trp Leu Gly Val Gly
            435                 440                 445

Gly Arg Ser Gly Glu Ala Ala Gly Leu Leu Ala Ser Gln Arg Pro Arg
            450                 455                 460

Ala Val Thr Asp Gln Asp Arg Ala His Met Arg Ala Ala Glu Val Ser
465                 470                 475                 480

Leu Ala Leu Val Ser Pro Gly Thr Ser Gly Pro Asp Arg Arg Pro Arg
                485                 490                 495

Pro Leu Thr Pro Asp Glu Leu Ala Asn Leu Pro Lys Ala Ala Arg Leu
            500                 505                 510

Cys Ala Ile Ala Asp Asn Ala Val Met Ser Ala Leu Arg Gly Arg Pro
            515                 520                 525

Glu Leu Ala Ala Ala Glu Ala Glu Asn Val Leu Gln His Ala Asp Ser
            530                 535                 540

Ala Ala Ala Gly Thr Thr Ala Leu Ala Ala Leu Thr Ala Leu Leu Tyr
545                 550                 555                 560

Ala Glu Asn Thr Asp Thr Ala Gln Leu Trp Ala Asp Lys Leu Val Ser
                565                 570                 575

Glu Thr Gly Ala Ser Asn Glu Glu Ala Gly Tyr Ala Gly Pro Arg
                580                 585                 590

Ala Glu Ala Ala Leu Arg Arg Gly Asp Leu Ala Ala Val Glu Ala
            595                 600                 605

Gly Ser Thr Val Leu Asp His Arg Arg Leu Ser Thr Leu Gly Ile Thr
            610                 615                 620

Ala Ala Leu Pro Leu Ser Ser Ala Val Ala Ala Ile Arg Leu Gly
625                 630                 635                 640

Glu Thr Glu Arg Ala Glu Lys Trp Leu Ala Gln Pro Leu Pro Gln Ala
                645                 650                 655

Ile Gln Asp Gly Leu Phe Gly Leu His Leu Leu Ser Ala Arg Gly Gln
                660                 665                 670

Tyr Ser Leu Ala Thr Gly Gln His Glu Ser Ala Tyr Thr Ala Phe Arg
            675                 680                 685

Thr Cys Gly Glu Arg Met Arg Asn Trp Gly Val Asp Val Pro Gly Leu
            690                 695                 700

Ser Leu Trp Arg Val Asp Ala Ala Glu Ala Leu Leu His Gly Arg Asp
705                 710                 715                 720

Arg Asp Glu Gly Arg Arg Leu Val Asp Glu Gln Leu Thr Arg Ala Met
                725                 730                 735

Gly Pro Arg Ser Arg Ala Leu Thr Leu Arg Val Gln Ala Ala Tyr Ser
                740                 745                 750

Pro Pro Ala Lys Arg Val Asp Leu Asp Glu Ala Ala Asp Leu Leu
            755                 760                 765

Leu Ser Cys Asn Asp Gln Tyr Glu Arg Ala Arg Val Leu Ala Asp Leu
            770                 775                 780

Ser Glu Thr Phe Ser Ala Leu Arg His His Ser Arg Ala Arg Gly Leu
785                 790                 795                 800

Leu Arg Gln Ala Arg His Leu Ala Ala Gln Arg Gly Ala Ile Pro Leu
                805                 810                 815

Leu Arg Arg Leu Gly Ala Lys Pro Gly Gly Pro Gly Trp Leu Glu Glu
            820                 825                 830

Ser Gly Leu Pro Gln Arg Ile Lys Ser Leu Thr Asp Ala Glu Arg Arg
            835                 840                 845
```

```
Val Ala Ser Leu Ala Ala Gly Gly Gln Thr Asn Arg Val Ile Ala Asp
            850                 855                 860

Gln Leu Phe Val Thr Ala Ser Thr Val Glu Gln His Leu Thr Asp Val
865                 870                 875                 880

Ser Thr Gly Ser Arg Pro Pro Ala Pro Ala Ala Glu Leu Val
                885                 890

<210> SEQ ID NO 64
<211> LENGTH: 923
<212> TYPE: PRT
<213> ORGANISM: Streptomyces kanamyceticus

<400> SEQUENCE: 64

Met Val Pro Glu Val Arg Ala Ala Pro Asp Glu Leu Ile Ala Arg Asp
1               5                   10                  15

Asp Glu Leu Ser Arg Leu Gln Arg Ala Leu Thr Arg Ala Gly Ser Gly
                20                  25                  30

Arg Gly Gly Val Val Ala Ile Thr Gly Pro Ile Ala Ser Gly Lys Thr
            35                  40                  45

Ala Leu Leu Asp Ala Gly Ala Ala Lys Ser Gly Phe Val Ala Leu Arg
        50                  55                  60

Ala Val Cys Ser Trp Glu Glu Arg Thr Leu Pro Tyr Gly Met Leu Gly
65                  70                  75                  80

Gln Leu Phe Asp His Pro Glu Leu Ala Ala Gln Ala Pro Asp Leu Ala
                85                  90                  95

His Phe Thr Ala Ser Cys Glu Ser Pro Gln Ala Gly Thr Asp Asn Arg
            100                 105                 110

Leu Arg Ala Glu Phe Thr Arg Thr Leu Leu Ala Leu Ala Ala Asp Trp
        115                 120                 125

Pro Val Leu Ile Gly Ile Asp Asp Val His His Ala Asp Ala Glu Ser
130                 135                 140

Leu Arg Cys Leu Leu His Leu Ala Arg Arg Ile Gly Pro Ala Arg Ile
145                 150                 155                 160

Ala Val Val Leu Thr Glu Leu Arg Arg Pro Thr Pro Ala Asp Ser Arg
                165                 170                 175

Phe Gln Ala Glu Leu Leu Ser Leu Arg Ser Tyr Gln Glu Ile Ala Leu
            180                 185                 190

Arg Pro Leu Thr Glu Ala Gln Thr Gly Glu Leu Val Arg Arg His Leu
        195                 200                 205

Gly Ala Glu Thr His Glu Asp Val Ser Ala Asp Thr Phe Arg Ala Thr
    210                 215                 220

Gly Gly Asn Leu Leu Gly His Gly Leu Ile Asn Asp Ile Arg Glu
225                 230                 235                 240

Ala Arg Thr Ala Gly Arg Pro Val Val Ala Gly Arg Ala Tyr Arg
                245                 250                 255

Leu Ala Tyr Leu Ser Ser Leu Tyr Arg Cys Gly Pro Ser Ala Leu Arg
            260                 265                 270

Val Ala Arg Ala Ser Ala Val Leu Gly Ala Ser Ala Glu Ala Val Leu
        275                 280                 285

Val Gln Arg Met Thr Gly Leu Asn Lys Asp Ala Val Glu Gln Val Tyr
    290                 295                 300

Glu Gln Leu Asn Glu Gly Arg Leu Leu Gln Gly Glu Arg Phe Pro His
305                 310                 315                 320

Pro Ala Ala Arg Ser Ile Val Leu Asp Asp Leu Ser Ala Leu Glu Arg
```

-continued

```
            325                 330                 335
Arg Asn Leu His Glu Ser Ala Leu Glu Leu Arg Asp His Gly Val
            340                 345                 350
Ala Gly Asn Val Leu Ala Arg His Gln Ile Gly Ala Gly Arg Val His
            355                 360                 365
Gly Glu Glu Ala Val Glu Leu Phe Thr Gly Ala Ala Arg Glu His His
            370                 375                 380
Leu Arg Gly Glu Leu Asp Asp Ala Ala Gly Tyr Leu Glu Leu Ala His
385                 390                 395                 400
Arg Ala Ser Asp Asp Pro Val Thr Arg Ala Ala Leu Arg Val Gly Ala
                    405                 410                 415
Ala Ala Ile Glu Arg Leu Cys Asn Pro Val Arg Ala Gly Arg His Leu
                    420                 425                 430
Pro Glu Leu Leu Thr Ala Ser Arg Ala Gly Leu Leu Ser Ser Glu His
                    435                 440                 445
Ala Val Ser Leu Ala Asp Trp Leu Ala Met Gly Gly Arg Pro Gly Glu
                    450                 455                 460
Ala Ala Glu Val Leu Ala Thr Gln Arg Pro Ala Ala Asp Ser Glu Gln
465                 470                 475                 480
His Arg Ala Leu Leu Arg Ser Gly Glu Leu Ser Leu Ala Leu Val His
                    485                 490                 495
Pro Gly Ala Trp Asp Pro Leu Arg Arg Thr Asp Arg Phe Ala Ala Gly
                    500                 505                 510
Gly Leu Gly Ser Leu Pro Gly Pro Ala Arg His Arg Ala Val Ala Asp
                    515                 520                 525
Gln Ala Val Ile Ala Ala Leu Arg Gly Arg Leu Asp Arg Ala Asp Ala
                    530                 535                 540
Asn Ala Glu Ser Val Leu Gln His Thr Asp Ala Thr Ala Asp Arg Thr
545                 550                 555                 560
Thr Ala Ile Met Ala Leu Leu Ala Leu Leu Tyr Ala Glu Asn Thr Asp
                    565                 570                 575
Ala Val Gln Phe Trp Val Asp Lys Leu Ala Gly Asp Glu Gly Thr Arg
                    580                 585                 590
Thr Pro Ala Asp Glu Ala Val His Ala Gly Phe Asn Ala Glu Ile Ala
                    595                 600                 605
Leu Arg Arg Gly Asp Leu Met Arg Ala Val Glu Tyr Gly Glu Ala Ala
                    610                 615                 620
Leu Gly His Arg His Leu Pro Thr Trp Gly Met Ala Ala Ala Leu Pro
625                 630                 635                 640
Leu Ser Ser Thr Val Val Ala Ala Ile Arg Leu Gly Asp Leu Asp Arg
                    645                 650                 655
Ala Glu Arg Trp Leu Ala Glu Pro Leu Pro Gln Gln Thr Pro Glu Ser
                    660                 665                 670
Leu Phe Gly Leu His Leu Leu Trp Ala Arg Gly Gln His His Leu Ala
                    675                 680                 685
Thr Gly Arg His Gly Ala Ala Tyr Thr Ala Phe Arg Glu Cys Gly Glu
                    690                 695                 700
Arg Met Arg Arg Trp Ala Val Asp Val Pro Gly Leu Ala Leu Trp Arg
705                 710                 715                 720
Val Asp Ala Ala Glu Ser Leu Leu Leu Gly Arg Asp Arg Ala Glu
                    725                 730                 735
Gly Leu Arg Leu Val Ser Glu Gln Leu Ser Arg Pro Met Arg Pro Arg
                    740                 745                 750
```

Ala Arg Val Gln Thr Leu Arg Val Gln Ala Ala Tyr Ser Pro Pro Pro
        755                 760                 765

Gln Arg Ile Asp Leu Leu Glu Glu Ala Ala Asp Leu Leu Val Thr Cys
    770                 775                 780

Asn Asp Gln Tyr Glu Leu Ala Asn Val Leu Ser Asp Leu Ala Glu Ala
785                 790                 795                 800

Ser Ser Met Val Arg Gln His Ser Arg Ala Arg Gly Leu Leu Arg Arg
            805                 810                 815

Ala Arg His Leu Ala Thr Gln Cys Gly Ala Val Pro Leu Leu Arg Arg
        820                 825                 830

Leu Gly Ala Glu Pro Ser Asp Ile Gly Gly Ala Trp Asp Ala Thr Leu
    835                 840                 845

Gly Gln Arg Ile Ala Ser Leu Thr Glu Ser Glu Arg Arg Val Ala Ala
850                 855                 860

Leu Ala Ala Val Gly Arg Thr Asn Arg Glu Ile Ala Glu Gln Leu Phe
865                 870                 875                 880

Val Thr Ala Ser Thr Val Glu Gln His Leu Thr Asn Val Phe Arg Lys
            885                 890                 895

Leu Ala Val Lys Gly Arg Gln Gln Leu Pro Lys Glu Leu Ala Asp Val
        900                 905                 910

Gly Glu Pro Ala Asp Arg Asp Arg Arg Cys Gly
    915                 920

<210> SEQ ID NO 65
<211> LENGTH: 913
<212> TYPE: PRT
<213> ORGANISM: Streptomyces ascomyceticus

<400> SEQUENCE: 65

Met Ile Ala Arg Leu Ser Pro Pro Asp Leu Ile Ala Arg Asp Asp Glu
1               5                   10                  15

Phe Gly Ser Leu His Arg Ala Leu Thr Arg Ala Gly Gly Arg Gly
            20                  25                  30

Val Val Ala Ala Val Thr Gly Pro Ile Ala Cys Gly Lys Thr Glu Leu
        35                  40                  45

Leu Asp Ala Ala Ala Lys Ala Gly Phe Val Thr Leu Arg Ala Val
    50                  55                  60

Cys Ser Met Glu Glu Arg Ala Leu Pro Tyr Gly Met Leu Gly Gln Leu
65                  70                  75                  80

Leu Asp Gln Pro Glu Leu Ala Ala Arg Thr Pro Glu Leu Val Arg Leu
            85                  90                  95

Thr Ala Ser Cys Glu Asn Leu Pro Ala Asp Val Asp Asn Arg Leu Gly
        100                 105                 110

Thr Glu Leu Thr Arg Thr Val Leu Thr Leu Ala Ala Glu Arg Pro Val
    115                 120                 125

Leu Ile Gly Ile Asp Asp Val His His Ala Asp Ala Pro Ser Leu Arg
130                 135                 140

Cys Leu Leu His Leu Ala Arg Arg Ile Ser Arg Ala Arg Val Ala Ile
145                 150                 155                 160

Val Leu Thr Glu Leu Leu Arg Pro Thr Pro Ala His Ser Gln Phe Arg
            165                 170                 175

Ala Ala Leu Leu Ser Leu Arg His Tyr Gln Glu Ile Ala Leu Arg Pro
        180                 185                 190

Leu Thr Glu Ala Gln Thr Thr Glu Leu Val Arg Arg His Leu Gly Gln

-continued

```
            195                 200                 205
Asp Ala His Asp Asp Val Val Ala Gln Ala Phe Arg Ala Thr Gly Gly
    210                 215                 220
Asn Leu Leu Leu Gly His Gly Leu Ile Asp Asp Ile Arg Glu Ala Arg
225                 230                 235                 240
Thr Arg Thr Ser Gly Cys Leu Glu Val Val Ala Gly Arg Ala Tyr Arg
                245                 250                 255
Leu Ala Tyr Leu Gly Ser Leu Tyr Arg Cys Gly Pro Ala Ala Leu Ser
            260                 265                 270
Val Ala Arg Ala Ser Ala Val Leu Gly Glu Ser Val Glu Leu Thr Leu
        275                 280                 285
Val Gln Arg Met Thr Gly Leu Asp Thr Glu Ala Val Glu Gln Ala His
    290                 295                 300
Glu Gln Leu Val Glu Gly Arg Leu Leu Arg Gly Arg Phe Pro His
305                 310                 315                 320
Pro Ala Ala Arg Ser Val Val Leu Asp Asp Leu Ser Ala Ala Glu Arg
                325                 330                 335
Arg Gly Leu His Glu Leu Ala Leu Glu Leu Leu Arg Asp Arg Gly Val
            340                 345                 350
Ala Ser Lys Val Leu Ala Arg His Gln Met Gly Thr Gly Arg Val His
        355                 360                 365
Gly Ala Glu Val Ala Gly Leu Phe Thr Asp Ala Ala Arg Glu His His
    370                 375                 380
Leu Arg Gly Glu Leu Asp Glu Ala Val Thr Tyr Leu Glu Phe Ala Tyr
385                 390                 395                 400
Arg Ala Ser Asp Asp Pro Ala Val His Ala Ala Leu Arg Val Asp Thr
                405                 410                 415
Ala Ala Ile Glu Arg Leu Cys Asp Pro Ala Arg Ser Arg His Val
            420                 425                 430
Pro Glu Leu Leu Thr Ala Ser Arg Glu Arg Leu Leu Ser Ser Glu His
        435                 440                 445
Ala Val Ser Leu Ala Cys Trp Leu Ala Met Asp Gly Arg Pro Gly Glu
    450                 455                 460
Ala Ala Glu Val Leu Ala Ala Gln Arg Ser Ala Ala Pro Ser Glu Gln
465                 470                 475                 480
Gly Arg Ala His Leu Arg Val Ala Asp Leu Ser Leu Ala Leu Ile Tyr
                485                 490                 495
Pro Gly Ala Ala Asp Pro Pro Arg Pro Ala Asp Pro Ala Glu Asp
            500                 505                 510
Glu Val Ala Ser Phe Ser Gly Ala Val Arg His Arg Ala Val Ala Asp
        515                 520                 525
Lys Ala Leu Ser Asn Ala Leu Arg Gly Trp Ser Gln Ala Glu Ala
    530                 535                 540
Lys Ala Glu Tyr Val Leu Gln His Ser Arg Val Thr Thr Asp Arg Thr
545                 550                 555                 560
Thr Thr Met Met Ala Leu Leu Ala Leu Leu Tyr Ala Glu Asp Thr Asp
                565                 570                 575
Ala Val Gln Ser Trp Val Asp Lys Leu Ala Gly Asp Asp Asn Met Arg
            580                 585                 590
Thr Pro Ala Asp Glu Ala Val His Ala Gly Phe Arg Ala Glu Ala Ala
        595                 600                 605
Leu Arg Arg Gly Asp Leu Thr Ala Ala Val Glu Cys Gly Glu Ala Ala
    610                 615                 620
```

-continued

```
Leu Ala Pro Arg Val Val Pro Ser Trp Gly Met Ala Ala Leu Pro
625                 630                 635                 640

Leu Ser Ser Thr Val Ala Ala Ile Arg Leu Gly Asp Leu Asp Arg
            645                 650                 655

Ala Glu Arg Trp Leu Ala Glu Pro Leu Pro Glu Glu Thr Ser Asp Ser
        660                 665                 670

Leu Phe Gly Leu His Met Val Trp Ala Arg Gly Gln His His Leu Ala
        675                 680                 685

Ala Gly Arg Tyr Arg Ala Ala Tyr Asn Ala Phe Arg Asp Cys Gly Glu
        690                 695                 700

Arg Met Arg Arg Trp Ser Val Asp Val Pro Gly Leu Ala Leu Trp Arg
705                 710                 715                 720

Val Asp Ala Ala Glu Ala Leu Leu Leu Gly Arg Gly Arg Asp Glu
            725                 730                 735

Gly Leu Arg Leu Ile Ser Glu Gln Leu Ser Arg Pro Met Gly Ser Arg
        740                 745                 750

Ala Arg Val Met Thr Leu Arg Val Gln Ala Ala Tyr Ser Pro Pro Ala
        755                 760                 765

Lys Arg Ile Glu Leu Leu Asp Glu Ala Ala Asp Leu Leu Ile Met Cys
770                 775                 780

Arg Asp Gln Tyr Glu Leu Ala Arg Val Leu Ala Asp Met Gly Glu Ala
785                 790                 795                 800

Cys Gly Met Leu Arg Arg His Ser Arg Ala Arg Gly Leu Phe Arg Arg
            805                 810                 815

Ala Arg His Leu Ala Thr Gln Cys Gly Ala Val Pro Leu Arg Arg
        820                 825                 830

Leu Gly Gly Glu Ser Ser Asp Ala Asp Gly Thr Gln Asp Val Thr Pro
        835                 840                 845

Ala Gln Arg Ile Thr Ser Leu Thr Glu Ala Glu Arg Arg Val Ala Ser
        850                 855                 860

His Ala Ala Val Gly Arg Thr Asn Lys Glu Ile Ala Ser Gln Leu Phe
865                 870                 875                 880

Val Thr Ser Ser Thr Val Glu Gln His Leu Thr Asn Val Phe Arg Lys
            885                 890                 895

Leu Gly Val Lys Gly Arg Gln Gln Leu Pro Lys Glu Leu Ser Asp Ala
            900                 905                 910

Gly
```

<210> SEQ ID NO 66
<211> LENGTH: 901
<212> TYPE: PRT
<213> ORGANISM: Micromonospora sp. S92-306401

<400> SEQUENCE: 66

```
Met Glu Phe Tyr Asp Leu Val Ala Arg Asp Glu Leu Arg Arg Leu
1               5                   10                  15

Asp Gln Ala Leu Gly Arg Ala Gly Gly Arg Gly Val Val Val Thr
            20                  25                  30

Val Thr Gly Pro Val Gly Cys Gly Lys Thr Glu Leu Leu Asp Ala Ala
        35                  40                  45

Ala Ala Glu Glu Glu Phe Ile Thr Leu Arg Ala Val Cys Ser Ala Glu
        50                  55                  60

Glu Arg Ala Leu Pro Tyr Ala Val Ile Gly Gln Leu Leu Asp His Pro
65                  70                  75                  80
```

```
Val Leu Ser Ala Arg Ala Pro Asp Leu Ala Cys Val Thr Ala Pro Gly
                85                  90                  95

Arg Thr Leu Pro Ala Asp Thr Glu Asn Arg Leu Arg Arg Asp Leu Thr
            100                 105                 110

Arg Ala Leu Leu Ala Leu Ala Ser Glu Arg Pro Val Leu Ile Cys Ile
            115                 120                 125

Asp Asp Val His Gln Ala Asp Thr Ala Ser Leu Asn Cys Leu Leu His
130                 135                 140

Leu Ala Arg Arg Val Ala Ser Ala Arg Ile Ala Met Ile Leu Thr Glu
145                 150                 155                 160

Leu Arg Arg Leu Thr Pro Ala His Ser Arg Phe Glu Ala Glu Leu Leu
                165                 170                 175

Ser Leu Arg His Arg His Glu Ile Ala Leu Arg Pro Leu Gly Pro Ala
                180                 185                 190

Asp Thr Ala Glu Leu Ala Arg Ala Arg Leu Gly Ala Gly Val Thr Ala
            195                 200                 205

Asp Glu Leu Ala Gln Val His Glu Ala Thr Ser Gly Asn Pro Asn Leu
            210                 215                 220

Val Gly Gly Leu Val Asn Asp Val Arg Glu Ala Trp Ala Ala Gly Gly
225                 230                 235                 240

Thr Gly Ile Ala Ala Gly Arg Ala Tyr Arg Leu Ala Tyr Leu Ser Ser
                245                 250                 255

Val Tyr Arg Cys Gly Pro Val Pro Leu Arg Ile Ala Gln Ala Ala Ala
                260                 265                 270

Val Leu Gly Pro Ser Ala Thr Val Thr Leu Val Arg Arg Ile Ser Gly
                275                 280                 285

Leu Asp Ala Glu Thr Val Asp Glu Ala Thr Ala Ile Leu Thr Glu Gly
            290                 295                 300

Gly Leu Leu Arg Asp His Arg Phe Pro His Pro Ala Ala Arg Ser Val
305                 310                 315                 320

Val Leu Asp Asp Met Ser Ala Gln Glu Arg Arg Leu His Arg Ser
                325                 330                 335

Thr Leu Asp Val Leu Asp Gly Val Pro Val Asp Val Leu Ala His His
            340                 345                 350

Gln Ala Gly Ala Gly Leu Leu His Gly Pro Gln Ala Ala Glu Met Phe
            355                 360                 365

Ala Arg Ala Ser Gln Glu Leu Arg Val Arg Gly Glu Leu Asp Ala Ala
            370                 375                 380

Thr Glu Tyr Leu Gln Leu Ala Tyr Arg Ala Ser Asp Asp Ala Gly Ala
385                 390                 395                 400

Arg Ala Ala Leu Gln Val Glu Thr Val Ala Gly Glu Arg Arg Arg Asn
                405                 410                 415

Pro Leu Ala Ala Ser Arg His Leu Asp Glu Leu Ala Ala Ala Ala Arg
            420                 425                 430

Ala Gly Leu Leu Ser Ala Glu His Ala Ala Leu Val Val His Trp Leu
            435                 440                 445

Ala Asp Ala Gly Arg Pro Gly Glu Ala Ala Glu Val Leu Ala Leu Gln
450                 455                 460

Arg Ala Leu Ala Val Thr Asp His Asp Arg Ala Arg Leu Arg Ala Ala
465                 470                 475                 480

Glu Val Ser Leu Ala Leu Phe His Pro Gly Val Pro Gly Ser Asp Pro
                485                 490                 495
```

```
Arg Pro Leu Ala Pro Glu Glu Leu Ala Ser Leu Ser Leu Ser Ala Arg
            500                 505                 510

His Gly Val Thr Ala Asp Asn Ala Val Leu Ala Leu Arg Gly Arg
            515                 520                 525

Pro Glu Ser Ala Ala Ala Glu Ala Glu Asn Val Leu Arg Asn Ala Asp
            530                 535                 540

Ala Ala Ala Ser Gly Pro Thr Ala Leu Ala Leu Thr Ala Leu Leu
545                 550                 555                 560

Tyr Ala Glu Asn Thr Asp Ala Ala Gln Leu Trp Ala Asp Lys Leu Ala
                565                 570                 575

Ala Gly Ile Gly Ala Gly Glu Gly Ala Gly Tyr Ala Gly Pro Arg
            580                 585                 590

Thr Val Ala Ala Leu Arg Arg Gly Asp Leu Thr Thr Ala Val Gln Ala
            595                 600                 605

Ala Gly Ala Val Leu Asp Arg Gly Arg Pro Ser Ser Leu Gly Ile Thr
            610                 615                 620

Ala Val Leu Pro Leu Ser Gly Ala Val Ala Ala Ile Arg Leu Gly
625                 630                 635                 640

Glu Leu Glu Arg Ala Glu Lys Trp Leu Ala Glu Pro Leu Pro Glu Ala
            645                 650                 655

Val His Asp Ser Leu Phe Gly Leu His Leu Leu Met Ala Arg Gly Arg
            660                 665                 670

Tyr Ser Leu Ala Val Gly Arg His Glu Ala Ala Tyr Ala Ala Phe Arg
            675                 680                 685

Asp Cys Gly Glu Arg Met Arg Arg Trp Asp Val Asp Val Pro Gly Leu
            690                 695                 700

Ala Leu Trp Arg Val Asp Ala Ala Glu Ala Leu Leu Pro Gly Asp Asp
705                 710                 715                 720

Arg Ala Glu Gly Arg Arg Leu Ile Asp Glu Gln Leu Thr Arg Pro Met
            725                 730                 735

Gly Pro Arg Ser Arg Ala Leu Thr Leu Arg Val Arg Ala Ala Tyr Ala
            740                 745                 750

Pro Pro Ala Lys Arg Ile Asp Leu Leu Asp Glu Ala Ala Asp Leu Leu
            755                 760                 765

Leu Ser Ser Asn Asp Gln Tyr Glu Arg Ala Arg Val Leu Ala Asp Leu
            770                 775                 780

Ser Glu Ala Phe Ser Ala Leu Arg Gln Asn Gly Arg Ala Arg Gly Ile
785                 790                 795                 800

Leu Arg Gln Ala Arg His Leu Ala Ala Gln Cys Gly Ala Val Pro Leu
            805                 810                 815

Leu Arg Arg Leu Gly Val Lys Ala Gly Arg Ser Gly Arg Leu Gly Arg
            820                 825                 830

Pro Pro Gln Gly Ile Arg Ser Leu Thr Glu Ala Glu Arg Arg Val Ala
            835                 840                 845

Thr Leu Ala Ala Ala Gly Gln Thr Asn Arg Glu Ile Ala Asp Gln Leu
            850                 855                 860

Phe Val Thr Ala Ser Thr Val Glu Gln His Leu Thr Asn Val Phe Arg
865                 870                 875                 880

Lys Leu Gly Val Lys Gly Arg Gln Gln Leu Pro Ala Glu Leu Ala Asp
                885                 890                 895

Leu Arg Pro Pro Gly
            900
```

<210> SEQ ID NO 67
<211> LENGTH: 906
<212> TYPE: PRT
<213> ORGANISM: Streptomyces violaceusniger

<400> SEQUENCE: 67

```
Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Thr Val Thr Gly Pro Ile Ala Cys Gly Lys Thr
        35                  40                  45

Glu Leu Leu Asp Ala Ala Ala Lys Ala Glu Ala Ile Ile Leu Arg
    50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Gly Leu Ala
                85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Val Asp Arg
    115                 120                 125

Pro Val Leu Ile Gly Val Asp Asp Val His His Ala Asp Thr Ala Ser
130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
        195                 200                 205

Gly Pro Gly Leu Ala Glu Asp Val Leu Val Gly Leu Tyr Lys Thr Thr
    210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
                245                 250                 255

Leu Ala Tyr Leu Gly Ser Leu Tyr Arg Cys Gly Pro Val Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Gly Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
        355                 360                 365

Lys Ala Ala Glu Met Phe Ala Lys Ala Gly Lys Ala Leu Val Val Arg
    370                 375                 380
```

```
Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
            405                 410                 415

Ile Glu Arg Arg Arg Asn Pro Leu Ala Ser Ser Arg His Met Asp Glu
        420                 425                 430

Leu Ser Ala Ala Gly Arg Ala Gly Leu Leu Ser Pro Lys His Ala Ala
        435                 440                 445

Leu Ala Val Phe Trp Leu Ala Asp Gly Arg Ser Gly Glu Ala Ala
        450                 455                 460

Glu Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
            485                 490                 495

Ala Phe Gly Ser Asp Arg Arg Pro Pro Leu Thr Pro Asp Glu Leu
            500                 505                 510

Ala Ser Leu Pro Lys Ala Ala Trp Gln Cys Ala Val Ala Asp Asn Ala
        515                 520                 525

Ala Met Thr Ala Leu His Gly His Pro Glu Leu Ala Thr Ala Gln Ala
        530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
            565                 570                 575

Trp Ala Asp Lys Leu Gly Ser Thr Asn Gly Gly Val Ser Asn Glu Ala
            580                 585                 590

Glu Ala Gly Tyr Ala Gly Pro Cys Ala Glu Ile Ala Leu Arg Arg Gly
        595                 600                 605

Asp Leu Ala Thr Ala Phe Glu Ala Gly Ser Thr Val Leu Asp Asp Arg
        610                 615                 620

Ser Leu Pro Ser Leu Gly Ile Thr Ala Ala Leu Leu Ser Ser Lys
625                 630                 635                 640

Thr Ala Ala Ala Val Arg Leu Gly Glu Leu Glu Arg Ala Glu Lys Leu
            645                 650                 655

Leu Ala Glu Pro Leu Pro Asn Gly Val Gln Asp Ser Leu Phe Gly Leu
            660                 665                 670

His Leu Leu Ser Ala Tyr Gly Gln Tyr Ser Leu Ala Met Gly Arg Tyr
        675                 680                 685

Glu Ser Ala Leu Arg Ala Phe His Thr Cys Gly Glu Arg Met Arg Ser
        690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
            725                 730                 735

Glu Gln Leu Thr Arg Pro Met Gly Pro Arg Ser Arg Ala Leu Thr Leu
        740                 745                 750

Arg Ile Lys Ala Ala Tyr Leu Pro Arg Thr Lys Arg Ile Pro Leu Leu
        755                 760                 765

His Glu Ala Ala Glu Leu Leu Pro Cys Pro Asp Pro Tyr Glu Gln
        770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Ala
```

```
                        805                 810                 815
Gln Cys Gly Ala Val Pro Leu Arg Arg Leu Gly Glu Pro Gly
                820                 825                 830

Arg Ile Asp Asp Ala Gly Leu Pro Gln Arg Ser Thr Ser Leu Thr Asp
            835                 840                 845

Ala Glu Arg Arg Val Ala Ala Leu Ala Ala Ala Gly Gln Thr Asn Arg
        850                 855                 860

Glu Ile Ala Lys Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 68
<211> LENGTH: 914
<212> TYPE: PRT
<213> ORGANISM: Streptomyces hygroscopicus

<400> SEQUENCE: 68

Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Lys Ser Asp Ala Ile Thr Leu Arg Ala Val Cys
    50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

Leu Pro Gly Glu His Leu Ser Pro Glu Ala Glu Asn Arg Leu Arg Gly
            100                 105                 110

Asp Leu Thr Arg Thr Leu Leu Ala Leu Ala Ala Glu Arg Pro Val Leu
        115                 120                 125

Ile Gly Ile Asp Asp Met His His Ala Asp Thr Ala Ser Leu Asn Cys
    130                 135                 140

Leu Leu His Leu Ala Arg Arg Val Gly Pro Ala Arg Ile Ala Met Val
145                 150                 155                 160

Leu Thr Glu Leu Arg Arg Leu Thr Pro Ala His Ser Gln Phe His Ala
                165                 170                 175

Glu Leu Leu Ser Leu Gly His Arg Glu Ile Ala Leu Arg Pro Leu
            180                 185                 190

Gly Pro Lys His Ile Ala Glu Leu Ala Arg Ala Gly Leu Gly Pro Asp
        195                 200                 205

Val Asp Glu Asp Val Leu Thr Gly Leu Tyr Arg Ala Thr Gly Gly Asn
    210                 215                 220

Leu Asn Leu Gly His Gly Leu Ile Lys Asp Val Arg Glu Ala Trp Ala
225                 230                 235                 240

Thr Gly Gly Thr Gly Ile Asn Ala Gly Arg Ala Tyr Arg Leu Ala Tyr
                245                 250                 255

Leu Gly Ser Leu Tyr Arg Cys Gly Pro Val Pro Leu Arg Val Ala Arg
            260                 265                 270
```

```
Val Ala Ala Val Leu Gly Gln Ser Ala Asn Thr Thr Leu Val Arg Trp
            275                 280                 285
Ile Ser Gly Leu Asn Ala Asp Ala Val Gly Glu Ala Thr Glu Ile Leu
        290                 295                 300
Thr Glu Gly Gly Leu Leu His Asp Leu Arg Phe Pro His Pro Ala Ala
305                 310                 315                 320
Arg Ser Val Val Leu Asn Asp Leu Ser Ala Arg Glu Arg Arg Leu
                325                 330                 335
His Arg Ser Ala Leu Glu Val Leu Asp Asp Val Pro Val Glu Val Val
            340                 345                 350
Ala His His Gln Ala Gly Ala Gly Phe Ile His Gly Pro Lys Ala Ala
            355                 360                 365
Glu Ile Phe Ala Lys Ala Gly Gln Glu Leu His Val Arg Gly Glu Leu
        370                 375                 380
Asp Ala Ala Ser Asp Tyr Leu Gln Leu Ala His His Ala Ser Asp Asp
385                 390                 395                 400
Ala Val Thr Arg Ala Ala Leu Arg Val Glu Ala Val Ala Ile Glu Arg
                405                 410                 415
Arg Arg Asn Pro Leu Ala Ser Ser Arg His Leu Asp Glu Leu Thr Val
                420                 425                 430
Ala Ala Arg Ala Gly Leu Leu Ser Leu Glu His Ala Ala Leu Met Ile
            435                 440                 445
Arg Trp Leu Ala Leu Gly Gly Arg Ser Gly Glu Ala Ala Glu Val Leu
        450                 455                 460
Ala Ala Gln Arg Pro Arg Ala Val Thr Asp Gln Asp Arg Ala His Leu
465                 470                 475                 480
Arg Ala Ala Glu Val Ser Leu Ala Leu Val Ser Pro Gly Ala Ser Gly
                485                 490                 495
Val Ser Pro Gly Ala Ser Gly Pro Asp Arg Arg Pro Arg Pro Leu Pro
                500                 505                 510
Pro Asp Glu Leu Ala Asn Leu Pro Lys Ala Ala Arg Leu Cys Ala Ile
            515                 520                 525
Ala Asp Asn Ala Val Ile Ser Ala Leu His Gly Arg Pro Glu Leu Ala
            530                 535                 540
Ser Ala Glu Ala Glu Asn Val Leu Lys Gln Ala Asp Ser Ala Ala Asp
545                 550                 555                 560
Gly Ala Thr Ala Leu Ser Ala Leu Thr Ala Leu Leu Tyr Ala Glu Asn
                565                 570                 575
Thr Asp Thr Ala Gln Leu Trp Ala Asp Lys Leu Val Ser Glu Thr Gly
            580                 585                 590
Ala Ser Asn Glu Glu Glu Gly Ala Gly Tyr Ala Gly Pro Arg Ala Glu
            595                 600                 605
Thr Ala Leu Arg Arg Gly Asp Leu Ala Ala Val Glu Ala Gly Ser
        610                 615                 620
Ala Ile Leu Asp His Arg Arg Gly Ser Leu Leu Gly Ile Thr Ala Ala
625                 630                 635                 640
Leu Pro Leu Ser Ser Ala Val Ala Ala Ile Arg Leu Gly Glu Thr
                645                 650                 655
Glu Arg Ala Glu Lys Trp Leu Ala Pro Leu Pro Glu Ala Ile Arg
            660                 665                 670
Asp Ser Leu Phe Gly Leu His Leu Leu Ser Ala Arg Gly Gln Tyr Cys
            675                 680                 685
Leu Ala Thr Gly Arg His Glu Ser Ala Tyr Thr Ala Phe Arg Thr Cys
```

```
                690                 695                 700
Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
                740                 745                 750

Arg Ser Arg Ala Leu Thr Leu Arg Val Gln Ala Ala Tyr Ser Pro Gln
                755                 760                 765

Ala Gln Arg Val Asp Leu Leu Glu Glu Ala Ala Asp Leu Leu Leu Ser
                770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
                820                 825                 830

Arg Leu Gly Ala Lys Pro Gly Gly Pro Gly Trp Leu Glu Glu Ser Gly
                835                 840                 845

Leu Pro Gln Arg Ile Lys Ser Leu Thr Asp Ala Glu Arg Arg Val Ala
                850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
                900                 905                 910

Ala Glu

<210> SEQ ID NO 69
<211> LENGTH: 875
<212> TYPE: PRT
<213> ORGANISM: Actinoplanes sp. N01-109

<400> SEQUENCE: 69

Met Pro Ala Val Lys Arg Asn Asp Leu Val Ala Arg Asp Gly Glu Leu
1               5                   10                  15

Arg Trp Met Gln Glu Ile Leu Ser Gln Ala Ser Glu Gly Arg Gly Ala
                20                  25                  30

Val Val Thr Ile Thr Gly Ala Ile Ala Cys Gly Lys Thr Val Leu Leu
                35                  40                  45

Asp Ala Ala Ala Ser Gln Asp Val Ile Gln Leu Arg Ala Val Cys
            50                  55                  60

Ser Ala Glu Glu Gln Glu Leu Pro Tyr Ala Met Val Gly Gln Leu Leu
65                  70                  75                  80

Asp Asn Pro Val Leu Ala Ala Arg Val Pro Ala Leu Gly Asn Leu Ala
                85                  90                  95

Ala Ala Gly Glu Arg Leu Leu Pro Gly Thr Glu Asn Arg Ile Arg Arg
                100                 105                 110

Glu Leu Thr Arg Thr Leu Leu Ala Leu Asp Glu Arg Pro Val Leu
            115                 120                 125

Ile Gly Val Asp Asp Met His His Ala Asp Pro Ala Ser Leu Asp Cys
                130                 135                 140

Leu Leu His Leu Ala Arg Arg Val Gly Pro Ala Arg Ile Ala Ile Val
```

```
                145                 150                 155                 160
Leu Thr Glu Leu Arg Arg Leu Thr Pro Ala His Ser Arg Phe Gln Ser
                165                 170                 175
Glu Leu Leu Ser Leu Arg Tyr His His Glu Ile Gly Leu Gln Pro Leu
                180                 185                 190
Thr Ala Glu His Thr Ala Asp Leu Ala Arg Val Gly Leu Gly Ala Glu
                195                 200                 205
Val Asp Asp Asp Val Leu Thr Glu Leu Tyr Glu Ala Thr Gly Gly Asn
210                 215                 220
Pro Ser Leu Cys Cys Gly Leu Ile Arg Asp Val Arg Gln Asp Trp Glu
225                 230                 235                 240
Ala Gly Val Thr Gly Ile His Val Gly Arg Ala Tyr Arg Leu Ala Tyr
                245                 250                 255
Leu Ser Ser Leu Tyr Arg Cys Gly Pro Ala Ala Leu Arg Thr Ala Arg
                260                 265                 270
Ala Ala Ala Val Leu Gly Asp Ser Ala Asp Ala Cys Leu Ile Arg Arg
                275                 280                 285
Val Ser Gly Leu Gly Thr Glu Ala Val Gly Gln Ala Ile Gln Gln Leu
                290                 295                 300
Thr Glu Gly Gly Leu Leu Arg Asp Gln Gln Phe Pro His Pro Ala Ala
305                 310                 315                 320
Arg Ser Val Val Leu Asp Asp Met Ser Ala Gln Glu Arg His Ala Met
                325                 330                 335
Tyr Arg Ser Ala Arg Glu Ala Ala Glu Gly Gln Ala Asp Pro Gly
                340                 345                 350
Thr Pro Gly Glu Pro Arg Ala Ala Thr Ala Tyr Ala Gly Cys Gly Glu
                355                 360                 365
Gln Ala Gly Asp Tyr Pro Glu Pro Ala Gly Arg Ala Cys Val Asp Gly
                370                 375                 380
Ala Gly Pro Ala Glu Tyr Cys Gly Asp Pro His Gly Ala Asp Asp
385                 390                 395                 400
Pro Asp Glu Leu Val Ala Ala Leu Gly Gly Leu Leu Pro Ser Arg Leu
                405                 410                 415
Val Ala Met Lys Ile Arg Arg Leu Ala Val Ala Gly Arg Pro Gly Ala
                420                 425                 430
Ala Ala Glu Leu Leu Thr Ser Gln Arg Leu His Ala Val Thr Ser Glu
                435                 440                 445
Asp Arg Ala Ser Leu Arg Ala Ala Glu Val Ala Leu Ala Thr Leu Trp
450                 455                 460
Pro Gly Ala Thr Gly Pro Asp Arg His Pro Leu Thr Glu Gln Glu Ala
465                 470                 475                 480
Ala Ser Leu Pro Glu Gly Pro Arg Leu Leu Ala Ala Asp Asp Ala
                485                 490                 495
Val Gly Ala Ala Leu Arg Gly Arg Ala Glu Tyr Ala Ala Ala Glu Ala
                500                 505                 510
Glu Asn Val Leu Arg His Ala Asp Pro Ala Ala Gly Gly Asp Ala Tyr
                515                 520                 525
Ala Ala Met Ile Ala Leu Leu Tyr Thr Glu His Pro Glu Asn Val Leu
                530                 535                 540
Phe Trp Ala Asp Lys Leu Asp Ala Gly Arg Pro Asp Glu Glu Thr Ser
545                 550                 555                 560
Tyr Pro Gly Leu Arg Ala Glu Thr Ala Val Arg Leu Gly Asp Leu Glu
                565                 570                 575
```

```
Thr Ala Met Glu Leu Gly Arg Thr Val Leu Asp Gln Arg Arg Leu Pro
            580                 585                 590

Ser Leu Gly Val Ala Ala Gly Leu Leu Gly Gly Ala Val Thr Ala
        595                 600                 605

Ala Ile Arg Leu Gly Asp Leu Asp Arg Ala Glu Lys Trp Leu Ala Glu
        610                 615                 620

Pro Ile Pro Asp Ala Ile Arg Thr Ser Leu Tyr Gly Leu His Val Leu
625                 630                 635                 640

Ala Ala Arg Gly Arg Leu Asp Leu Ala Ala Gly Arg Tyr Glu Ala Ala
                645                 650                 655

Tyr Thr Ala Phe Arg Leu Cys Gly Glu Arg Met Ala Gly Trp Asp Ala
            660                 665                 670

Asp Val Ser Gly Leu Ala Leu Trp Arg Val Asp Ala Ala Glu Ala Leu
        675                 680                 685

Leu Ser Ala Gly Ile Arg Pro Asp Glu Gly Arg Lys Leu Ile Asp Asp
        690                 695                 700

Gln Leu Thr Arg Glu Met Gly Ala Arg Ser Arg Ala Leu Thr Leu Arg
705                 710                 715                 720

Ala Gln Ala Ala Tyr Ser Leu Pro Val His Arg Val Gly Leu Leu Asp
                725                 730                 735

Glu Ala Ala Gly Leu Leu Leu Ala Cys His Asp Gly Tyr Glu Arg Ala
            740                 745                 750

Arg Val Leu Ala Asp Leu Gly Glu Thr Leu Arg Thr Leu Arg His Thr
        755                 760                 765

Asp Ala Ala Gln Arg Val Leu Arg Gln Ala Glu Gln Ala Ala Ala Arg
        770                 775                 780

Cys Gly Ser Val Pro Leu Leu Arg Arg Leu Gly Ala Glu Pro Val Arg
785                 790                 795                 800

Ile Gly Thr Arg Arg Gly Glu Pro Gly Leu Pro Gln Arg Ile Arg Leu
                805                 810                 815

Leu Thr Asp Ala Glu Arg Arg Val Ala Ala Met Ala Ala Ala Gly Gln
            820                 825                 830

Thr Asn Arg Glu Ile Ala Gly Arg Leu Phe Val Thr Ala Ser Thr Val
        835                 840                 845

Glu Gln His Leu Thr Ser Val Phe Arg Lys Leu Gly Val Lys Gly Arg
        850                 855                 860

Arg Phe Leu Pro Thr Glu Leu Ala Gln Ala Val
865                 870                 875

<210> SEQ ID NO 70
<211> LENGTH: 906
<212> TYPE: PRT
<213> ORGANISM: Streptomyces malaysiensis

<400> SEQUENCE: 70

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Val Thr Val Thr Gly Pro Ile Ala Cys Gly Lys Thr
        35                  40                  45

Glu Leu Leu Asp Ala Ala Ala Lys Ala Glu Ala Ile Ile Leu Arg
    50                  55                  60

Ala Val Cys Ala Pro Glu Glu Arg Ala Met Pro Tyr Ala Met Ile Gly
```

```
            65                  70                  75                  80
        Gln Leu Ile Asp Asp Pro Ala Leu Ala His Arg Ala Pro Gly Leu Ala
                        85                  90                  95
        Asp Arg Ile Ala Gln Gly Gly Gln Leu Ser Leu Arg Ala Glu Asn Arg
                        100                 105                 110
        Leu Arg Arg Asp Leu Thr Arg Ala Leu Leu Ala Leu Ala Val Asp Arg
                        115                 120                 125
        Pro Val Leu Ile Gly Val Asp Val His His Ala Asp Thr Ala Ser
            130                 135                 140
        Leu Asn Cys Leu Leu His Leu Ala Arg Arg Val Arg Pro Ala Arg Ile
        145                 150                 155                 160
        Ser Met Ile Phe Thr Glu Leu Arg Ser Leu Thr Pro Thr Gln Ser Arg
                        165                 170                 175
        Phe Lys Ala Glu Leu Leu Ser Leu Pro Tyr His His Glu Ile Ala Leu
                        180                 185                 190
        Arg Pro Phe Gly Pro Glu Gln Ser Ala Glu Leu Ala Arg Ala Ala Phe
                        195                 200                 205
        Gly Pro Gly Leu Ala Glu Asp Val Leu Ala Gly Leu Tyr Lys Thr Thr
                        210                 215                 220
        Arg Gly Asn Leu Ser Leu Ser Arg Gly Leu Ile Ser Asp Val Arg Glu
        225                 230                 235                 240
        Ala Leu Ala Asn Gly Glu Ser Ala Phe Glu Ala Gly Arg Ala Phe Arg
                        245                 250                 255
        Leu Ala Tyr Leu Ser Ser Leu Tyr Arg Cys Gly Pro Val Ala Leu Arg
                        260                 265                 270
        Val Ala Arg Val Ala Ala Val Leu Gly Pro Ser Ala Thr Thr Thr Leu
                        275                 280                 285
        Val Arg Arg Leu Ser Gly Leu Ser Ala Glu Thr Ile Asp Arg Ala Thr
                        290                 295                 300
        Lys Ile Leu Thr Glu Gly Gly Leu Leu Leu Asp Gln Gln Phe Pro His
        305                 310                 315                 320
        Pro Ala Ala Arg Ser Val Val Leu Asp Asp Met Ser Ala Gln Glu Arg
                        325                 330                 335
        Arg Ser Leu His Thr Leu Ala Leu Glu Leu Leu Asp Glu Ala Pro Val
                        340                 345                 350
        Glu Val Leu Ala His His Gln Val Gly Ala Gly Leu Ile His Gly Pro
                        355                 360                 365
        Lys Ala Ala Glu Met Phe Ala Lys Ala Gly Lys Ala Leu Val Val Arg
        370                 375                 380
        Asn Glu Leu Gly Asp Ala Ala Glu Tyr Leu Gln Leu Ala His Arg Ala
        385                 390                 395                 400
        Ser Asp Asp Val Ser Thr Arg Ala Ala Leu Arg Val Glu Ala Val Ala
                        405                 410                 415
        Ile Glu Arg Arg Arg Asn Pro Leu Ala Ser Ser Arg His Met Asp Glu
                        420                 425                 430
        Leu Ser Ala Ala Gly Arg Ala Gly Leu Leu Ser Pro Lys His Ala Ala
                        435                 440                 445
        Leu Ala Val Phe Trp Leu Ala Asp Gly Gly Arg Ser Gly Glu Ala Ala
                        450                 455                 460
        Glu Val Leu Ala Ser Glu Arg Pro Leu Ala Thr Thr Asp Gln Asn Arg
        465                 470                 475                 480
        Ala His Leu Arg Phe Val Glu Val Thr Leu Ala Leu Phe Ser Pro Gly
                        485                 490                 495
```

```
Ala Phe Gly Ser Asp Arg Arg Pro Pro Leu Thr Pro Asp Glu Leu
            500                 505                 510

Ala Ser Leu Pro Lys Ala Ala Trp Gln Cys Ala Val Ala Asp Asn Ala
        515                 520                 525

Ala Met Thr Ala Leu His Gly His Pro Glu Leu Ala Thr Ala Gln Ala
    530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
                565                 570                 575

Trp Ala Asp Lys Leu Gly Ser Thr Asn Ala Gly Val Ser Asn Glu Ala
            580                 585                 590

Glu Ala Gly Tyr Ala Gly Pro Cys Ala Glu Ile Ala Leu Arg Arg Gly
        595                 600                 605

Asp Leu Ala Thr Ala Phe Glu Ala Gly Ser Ala Val Leu Asp Asp Arg
    610                 615                 620

Ser Leu Pro Ser Leu Gly Ile Thr Ala Ala Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala Tyr Gly Gln Tyr Ser Leu Ala Met Gly Arg Tyr
        675                 680                 685

Glu Ser Ala His Arg Ala Phe Arg Thr Cys Gly Glu Arg Met Arg Ser
    690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser His Ala Leu Thr Leu
            740                 745                 750

Arg Ile Lys Ala Ala Tyr Leu Pro Arg Thr Lys Arg Ile Pro Leu Leu
        755                 760                 765

His Glu Ala Ala Glu Leu Leu Leu Pro Cys Pro Asp Pro Tyr Glu Gln
    770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Gly Gln Thr Asn Arg
    850                 855                 860

Glu Ile Ala Glu Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905
```

<210> SEQ ID NO 71
<211> LENGTH: 904
<212> TYPE: PRT
<213> ORGANISM: Streptomyces violaceusniger

<400> SEQUENCE: 71

```
Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Glu Ala Gly Ser Gly
            20                  25                  30

Gln Gly Ala Val Val Thr Val Thr Gly Pro Ile Ala Cys Gly Lys Thr
        35                  40                  45

Glu Leu Leu Asp Ala Ala Ala Lys Ala Asp Ala Ile Ile Leu Arg
    50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Glu Leu Ala
                85                  90                  95

Asp Arg Ile Ala Gln Gly Gly His Leu Ser Leu Arg Ala Glu Asn Arg
            100                 105                 110

Leu Arg Arg Asp Leu Thr Arg Ala Leu Leu Ala Leu Ala Val Asp Arg
        115                 120                 125

Pro Val Leu Ile Gly Val Asp Asp Val His His Ala Asp Thr Ala Ser
    130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Leu Gly Pro Glu Gln Ser Ala Glu Leu Ala His Ala Ala Phe
        195                 200                 205

Gly Pro Gly Leu Ala Glu Asp Val Leu Ala Gly Leu Tyr Gly Met Thr
    210                 215                 220

Arg Gly Asn Leu Ser Leu Ser Arg Gly Leu Ile Ser Asp Val Arg Glu
225                 230                 235                 240

Ala Gln Ala Asn Gly Glu Ser Ala Phe Glu Val Gly Arg Ala Phe Arg
                245                 250                 255

Leu Ala Tyr Leu Ser Ser Leu Tyr Arg Cys Gly Pro Ile Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp His Gln Phe Pro His
305                 310                 315                 320

Pro Ala Ala Arg Ser Val Val Leu Asp Asp Met Ser Ala Gln Glu Arg
                325                 330                 335

Arg Ser Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
        355                 360                 365

Lys Ala Ala Glu Ile Phe Ala Arg Ala Gly Gln Ala Leu Val Val Arg
    370                 375                 380
```

```
Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
            405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
            450                 455                 460

Glu Val Leu Ala Ser Glu His Pro Leu Ala Thr Thr Asp Gln Asn Arg
465                 470                 475                 480

Ala His Leu Arg Phe Ala Glu Val Thr Leu Ala Leu Phe Cys Pro Gly
                485                 490                 495

Ala Phe Gly Ser Asp Arg Arg Pro Pro Leu Ala Pro Asp Glu Leu
            500                 505                 510

Ala Ser Leu Pro Lys Ala Ala Trp Gln Cys Ala Val Ala Asp Asn Ala
            515                 520                 525

Val Met Thr Ala Leu His Ala His Pro Glu Leu Ala Thr Ala Gln Ala
530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala Gln Ile
                565                 570                 575

Trp Ala Asp Lys Leu Gly Ser Thr Asn Ala Gly Val Ser Asn Glu Ala
            580                 585                 590

Glu Ala Gly Tyr Ala Gly Pro Cys Ala Glu Ile Ala Leu Arg Arg Gly
            595                 600                 605

Asp Leu Ala Thr Ala Phe Glu Ala Gly Gly Thr Val Leu Asp Asp Arg
            610                 615                 620

Pro Leu Pro Ser Leu Gly Ile Thr Ala Ala Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala His Gly Gln Tyr Ser Leu Ala Met Gly Arg Tyr
            675                 680                 685

Glu Ser Ala His Arg Ala Phe His Thr Cys Gly Glu Arg Met Arg Ser
            690                 695                 700

Trp Gly Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Ala Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
            755                 760                 765

His Glu Ala Ala Glu Leu Leu Leu Ser Cys Pro Asp Pro Tyr Glu Gln
            770                 775                 780

Ala Arg Val Leu Ala Asp Leu Gly Asp Thr Leu Ser Ala Leu Arg Arg
785                 790                 795                 800
```

```
Tyr Ser Arg Ala Arg Gly Val Leu Arg Gln Ala Arg His Leu Ala Thr
            805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
            835                 840                 845

Ala Glu Arg Arg Val Ser Ala Leu Ala Ala Gly Gln Thr Asn Arg
850                 855                 860

Glu Ile Ala Lys Gln Leu Phe Val Thr Ala Ser Thr Val Glu Gln His
865                 870                 875                 880

Leu Thr Ser Val Phe Arg Lys Leu Gly Val Lys Gly Arg Arg Gln Leu
            885                 890                 895

Pro Thr Ala Leu Ala Asp Val Glu
            900

<210> SEQ ID NO 72
<211> LENGTH: 906
<212> TYPE: PRT
<213> ORGANISM: Streptomyces Sp. NRRL F-4729

<400> SEQUENCE: 72

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Gln Ala Ser Ser Gly
            20                  25                  30

Gln Gly Val Val Val Thr Val Thr Gly Pro Ile Ala Cys Gly Lys Thr
            35                  40                  45

Glu Leu Leu Asp Ala Ala Ala Lys Ala Glu Ala Ile Ile Leu Arg
50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Gly Leu Ala
            85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Ala Val His Arg
            115                 120                 125

Pro Val Leu Ile Gly Val Asp Asp Val His His Ala Asp Thr Ala Ser
            130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
            165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
            195                 200                 205

Gly Pro Gly Leu Ala Glu Asp Val Leu Ala Gly Leu Tyr Lys Thr Thr
            210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
            245                 250                 255

Leu Ala Tyr Leu Ser Ser Leu Tyr Arg Cys Gly Pro Val Ala Leu Arg
            260                 265                 270
```

```
Val Ala Arg Val Ala Ala Val Leu Gly Pro Ser Ala Thr Thr Thr Leu
            275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Gly Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
            355                 360                 365

Lys Ala Ala Glu Met Phe Ala Lys Ala Gly Lys Ala Leu Val Val Arg
370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
            450                 455                 460

Gln Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
                485                 490                 495

Ala Phe Gly Ser Asp Arg Arg Pro Pro Leu Thr Pro Asp Glu Leu
                500                 505                 510

Ala Ser Leu Pro Lys Ala Ala Trp Gln Cys Ala Val Ala Asp Asn Ala
            515                 520                 525

Ala Met Thr Ala Leu His Gly His Pro Glu Leu Ala Thr Ala Gln Ala
            530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
                565                 570                 575

Trp Ala Asp Lys Leu Gly Ser Met Asn Ala Gly Val Ser Asn Glu Ala
                580                 585                 590

Glu Ala Gly Tyr Ala Gly Pro Cys Ala Glu Ile Ala Leu Arg Arg Gly
            595                 600                 605

Asp Leu Ala Thr Ala Phe Glu Ala Gly Ser Thr Val Leu Asp Asp Arg
            610                 615                 620

Ser Leu Pro Ser Leu Gly Ile Thr Ala Ala Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
                660                 665                 670

His Leu Leu Ser Ala Tyr Gly Gln Tyr Ser Leu Ala Met Gly Arg Tyr
            675                 680                 685
```

```
Glu Ser Ala His Arg Ala Phe Arg Thr Cys Gly Glu Arg Met Arg Ser
    690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
        755                 760                 765

His Glu Ala Ala Glu Leu Leu Leu Pro Cys Pro Asp Pro Tyr Glu Gln
    770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Gly Gln Thr Asn Arg
    850                 855                 860

Glu Ile Ala Glu Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 73
<211> LENGTH: 904
<212> TYPE: PRT
<213> ORGANISM: Streptomyces filamentosus

<400> SEQUENCE: 73

Met Arg Ala Ile Asn Ala Ser Asp Thr Gly Pro Glu Leu Val Ala Arg
1               5                   10                  15

Glu Asp Glu Leu Gly Arg Val Arg Ser Ala Leu Asn Arg Ala Asn Gly
                20                  25                  30

Gly Gln Gly Val Leu Ile Ser Ile Thr Gly Pro Ile Ala Cys Gly Lys
            35                  40                  45

Thr Glu Leu Leu Glu Ala Ala Ser Glu Val Asp Ala Ile Thr Leu
50                  55                  60

Arg Ala Val Cys Ala Ala Glu Glu Arg Ala Ile Pro Tyr Ala Leu Ile
65                  70                  75                  80

Gly Gln Leu Ile Asp Asn Pro Ala Leu Gly Ile Pro Val Pro Asp Pro
                85                  90                  95

Ala Gly Leu Thr Ala Gln Gly Gly Arg Leu Ser Ser Ser Ala Glu Asn
            100                 105                 110

Arg Leu Arg Arg Asp Leu Thr Arg Ala Leu Leu Thr Leu Ala Thr Asp
        115                 120                 125

Arg Leu Val Leu Ile Cys Val Asp Asp Val Gln His Ala Asp Asn Ala
    130                 135                 140

Ser Leu Ser Cys Leu Leu Tyr Leu Ala Arg Arg Leu Val Pro Ala Arg
145                 150                 155                 160
```

```
Ile Ala Leu Val Phe Thr Glu Leu Arg Val Leu Thr Ser Ser Gln Leu
                165                 170                 175

Arg Phe Asn Ala Glu Leu Leu Ser Leu Arg Asn His Cys Glu Ile Ala
            180                 185                 190

Leu Arg Pro Leu Gly Pro Gly His Ala Ala Glu Leu Ala Arg Ala Thr
        195                 200                 205

Leu Gly Pro Gly Leu Ser Asp Glu Thr Leu Thr Glu Leu Tyr Arg Val
    210                 215                 220

Thr Gly Gly Asn Leu Ser Leu Ser Arg Gly Leu Ile Asp Asp Val Arg
225                 230                 235                 240

Asp Ala Trp Ala Arg Gly Glu Thr Gly Val Gln Val Gly Arg Ala Phe
            245                 250                 255

Arg Leu Ala Tyr Leu Gly Ser Leu His Arg Cys Gly Pro Leu Ala Leu
        260                 265                 270

Arg Val Ala Arg Val Ala Ala Val Leu Gly Pro Ser Ala Thr Ser Val
    275                 280                 285

Leu Val Arg Arg Ile Ser Gly Leu Ser Ala Glu Ala Met Ala Gln Ala
    290                 295                 300

Thr Asp Ile Leu Ala Asp Gly Gly Leu Leu Arg Asp Gln Arg Phe Thr
305                 310                 315                 320

His Pro Ala Ala Arg Ser Val Val Leu Asp Asp Met Ser Ala Glu Glu
            325                 330                 335

Arg Arg Ser Val His Ser Leu Ala Leu Glu Leu Leu Asp Glu Ala Pro
        340                 345                 350

Ala Glu Met Leu Ala His His Arg Val Gly Ala Gly Leu Val His Gly
    355                 360                 365

Pro Lys Ala Ala Glu Thr Phe Thr Gly Ala Gly Arg Ala Leu Ala Val
    370                 375                 380

Arg Gly Met Leu Gly Glu Ala Ala Asp Tyr Leu Gln Leu Ala Tyr Arg
385                 390                 395                 400

Ala Ser Gly Asp Ala Ala Thr Lys Ala Ala Ile Arg Val Glu Ser Val
            405                 410                 415

Ala Val Glu Arg Arg Asn Pro Leu Val Val Ser Arg His Trp Asp
        420                 425                 430

Glu Leu Ser Val Ala Ala Arg Ala Gly Leu Leu Ser Cys Glu His Val
    435                 440                 445

Ser Arg Thr Ala Arg Trp Leu Thr Val Gly Gly Arg Pro Gly Glu Ala
    450                 455                 460

Ala Arg Val Leu Ala Ser Gln His Arg Arg Val Val Thr Asp Gln Asp
465                 470                 475                 480

Arg Ala His Leu Arg Val Ala Glu Phe Ser Leu Ala Leu Leu Tyr Pro
            485                 490                 495

Gly Thr Ser Gly Ser Asp Arg Arg Pro His Pro Leu Thr Ser Asp Glu
        500                 505                 510

Leu Ala Ala Leu Pro Thr Ala Thr Arg His Cys Ala Ile Ala Asp Asn
    515                 520                 525

Ala Val Met Ala Ala Leu Arg Gly His Pro Glu Leu Ala Thr Ala Glu
    530                 535                 540

Ala Glu Ala Val Leu Gln Gln Ala Asp Ala Ala Asp Gly Ala Ala Leu
545                 550                 555                 560

Thr Ala Leu Met Ala Leu Leu Tyr Ala Glu Ser Ile Glu Val Ala Glu
            565                 570                 575
```

Val Trp Ala Asp Lys Leu Ala Glu Ala Gly Ala Ser Asn Gly Gln
            580                 585                 590

Asp Ala Glu Tyr Ala Gly Ile Arg Ala Glu Ile Ala Leu Arg Arg Gly
        595                 600                 605

Asp Leu Thr Ala Ala Val Glu Thr Ala Gly Met Val Leu Asp Gly Arg
    610                 615                 620

Pro Leu Pro Ser Leu Asp Ile Thr Ala Thr Leu Leu Leu Ala Gly Arg
625                 630                 635                 640

Ala Ser Val Ala Val Arg Leu Gly Glu Leu Asp His Ala Glu Glu Leu
                645                 650                 655

Phe Ala Ala Pro Pro Glu Asp Ala Phe Gln Asp Ser Leu Phe Gly Leu
            660                 665                 670

His Leu Leu Ser Ala His Gly Gln Tyr Ser Leu Ala Thr Gly Arg Pro
        675                 680                 685

Glu Ser Ala Tyr Arg Ala Phe Arg Ala Cys Gly Glu Arg Met Arg Asp
    690                 695                 700

Trp Gly Phe Asp Ala Pro Gly Val Ala Leu Trp Arg Val Gly Ala Ala
705                 710                 715                 720

Glu Ala Leu Leu Gly Leu Asp Arg Asn Glu Gly Arg Arg Leu Ile Asp
                725                 730                 735

Glu Gln Leu Ser Arg Thr Met Ala Pro Arg Ser His Ala Leu Thr Leu
            740                 745                 750

Arg Ile Lys Ala Ala Tyr Met Pro Glu Pro Lys Arg Val Asp Leu Leu
        755                 760                 765

Tyr Glu Ala Ala Glu Leu Leu Leu Ser Cys Arg Asp Gln Tyr Glu Arg
    770                 775                 780

Ala Arg Val Leu Ala Asp Leu Gly Glu Ala Leu Ser Ala Leu Gly Asn
785                 790                 795                 800

Tyr Arg Gln Ala Arg Gly Val Leu Arg Gln Ala Arg His Leu Ala Met
                805                 810                 815

Arg Thr Gly Ala Asp Pro Leu Leu Arg Arg Leu Gly Ile Arg Pro Gly
            820                 825                 830

Arg Gln Asp Asp Pro Asp Pro Gln Pro Arg Ser Arg Ser Leu Thr Asn
        835                 840                 845

Ala Glu Arg Arg Ala Ala Ser Leu Ala Ala Thr Gly Leu Thr Asn Arg
    850                 855                 860

Glu Ile Ala Asp Arg Leu Phe Val Thr Ala Ser Thr Val Glu Gln His
865                 870                 875                 880

Leu Thr Asn Val Phe Arg Lys Leu Gly Val Lys Gly Arg Lys Gln Leu
                885                 890                 895

Pro Ala Glu Leu Asp Asp Met Glu
            900

<210> SEQ ID NO 74
<211> LENGTH: 6
<212> TYPE: DNA
<213> ORGANISM: Artificial Sequence
<220> FEATURE:
<223> OTHER INFORMATION: Synthetic Construct

<400> SEQUENCE: 74 aggggg                                                                    6

<210> SEQ ID NO 75
<211> LENGTH: 256
<212> TYPE: PRT

<213> ORGANISM: Streptomyces rapamycinicus

<400> SEQUENCE: 75

```
Leu Thr Ile Pro Arg Pro Asp Pro Asp Gly Thr Ile Leu Ile Thr
1               5                  10                  15
Gly Gly Ser Gly Val Leu Ala Gly Ile Leu Ala Arg His Leu Ala Ala
            20                  25                  30
Glu His Gly Ala Arg His Leu Leu Leu Ser Arg Thr Thr Pro Asp
        35                  40                  45
Gln Ala Leu Ile Lys Glu Leu Ala Glu Leu Gly Ala His Val Asp Thr
    50                  55                  60
Ala Thr Cys Asp Val Ser Asp Arg Ala Gly Leu Ala Arg Val Leu Ala
65                  70                  75                  80
Gly Val Ser Pro Glu His Pro Leu Thr Ala Val Ile His Thr Ala Gly
                85                  90                  95
Ala Leu Asp Asp Gly Val Val Glu Ser Leu Thr Thr Gln Gln Leu Asp
            100                 105                 110
Thr Val Leu Arg Pro Lys Ala Asp Gly Ala Trp His Leu His Glu Leu
        115                 120                 125
Thr Gln Asn Thr Asp Leu Ala Ala Phe Val Met Tyr Ser Ser Ala Ala
    130                 135                 140
Gly Val Leu Gly Ser Ala Gly Gln Gly Asn Tyr Ala Ala Ala Asn Ala
145                 150                 155                 160
Phe Val Asp Ala Leu Ala Glu Gln Arg Arg Gly Glu Gly Leu Pro Ala
                165                 170                 175
Leu Ala Val Ala Trp Gly Leu Trp Glu Asp Thr Ser Gly Leu Thr Ala
            180                 185                 190
Lys Met Thr Asp Thr Asp Arg Asp Arg Ile Arg Arg Gly Gly Leu Arg
        195                 200                 205
Ala Ile Ser Ala Gly Arg Gly Met Gly Leu Leu Asp Ala Ala Ser Arg
    210                 215                 220
His Gly Glu Pro Val Leu Leu Ala Ala Ser Met Glu Pro Val Arg Asp
225                 230                 235                 240
Val Glu Val Pro Ala Leu Leu Arg Leu Leu His Arg Pro Val Ala Arg
                245                 250                 255
```

<210> SEQ ID NO 76
<211> LENGTH: 249
<212> TYPE: PRT
<213> ORGANISM: Streptomyces rapamycinicus

<400> SEQUENCE: 76

```
Asp Pro Asp Gly Thr Val Leu Ile Thr Gly Gly Ser Gly Val Leu Ala
1               5                  10                  15
Gly Ile Ala Ala Arg His Leu Val Thr Glu Arg Gly Val Arg His Leu
            20                  25                  30
Leu Leu Leu Ser Arg Ser Ala Pro Asp Glu Ala Leu Ile Gly Glu Leu
        35                  40                  45
Gly Glu Leu Gly Ala Arg Val Glu Thr Ala Ala Cys Asp Val Ser Asp
    50                  55                  60
Pro Ala Ala Leu Thr Gln Val Leu Ala Gly Val Ser Pro Glu His Pro
65                  70                  75                  80
Leu Thr Ala Val Ile His Thr Ala Gly Val Asp Asp Gly Val Val
                85                  90                  95
Glu Ser Leu Thr Val Gln Arg Leu Glu Thr Val Leu Arg Pro Lys Ala
```

```
                    100                 105                 110
Asp Gly Ala Trp Asn Leu His Glu Leu Thr Arg Asp Ala Asp Leu Ala
                115                 120                 125

Ala Phe Val Met Tyr Ser Ser Ala Ala Gly Val Leu Gly Ser Ala Gly
            130                 135                 140

Gln Ala Asn Tyr Ala Ala Asn Ala Phe Leu Asp Ala Leu Ala Glu
145                 150                 155                 160

Gln Arg His Ala Glu Gly Leu Pro Ala Leu Ala Val Ala Trp Gly Leu
                165                 170                 175

Trp Glu Asp Ala Ser Gly Leu Thr Ala Gln Leu Thr Asp Thr Asp Arg
            180                 185                 190

Asp Arg Ile Arg Arg Gly Gly Leu Arg Ala Ile Ser Ala Glu His Gly
                195                 200                 205

Met Gly Leu Phe Asp Ser Ala Ser Arg His Ser Glu Pro Val Leu Val
            210                 215                 220

Ala Ala Pro Met Glu Pro Val Arg Asp Ala Glu Val Pro Ala Leu Leu
225                 230                 235                 240

Arg Ser Leu His Arg Pro Ile Ala Arg
                245

<210> SEQ ID NO 77
<211> LENGTH: 256
<212> TYPE: PRT
<213> ORGANISM: Streptomyces rapamycinicus

<400> SEQUENCE: 77

Leu Thr Ile Pro Arg Arg Pro Asp Pro Asp Gly Thr Ile Leu Ile Thr
1               5                   10                  15

Gly Gly Ser Gly Val Leu Ala Gly Ile Leu Ala Arg His Leu Ala Ala
                20                  25                  30

Glu His Gly Ala Arg His Leu Leu Leu Ser Arg Thr Ala Pro Asp
            35                  40                  45

Glu Ala Leu Ile Lys Glu Leu Ala Gly Leu Gly Ala Arg Val Glu Thr
        50                  55                  60

Ala Ala Cys Asp Val Ser Asp Arg Ala Gly Leu Ala Arg Val Leu Ala
65                  70                  75                  80

Gly Val Ser Pro Glu His Pro Leu Thr Ala Val Ile His Thr Ala Gly
                85                  90                  95

Ala Leu Asp Asp Gly Val Val Glu Ser Leu Thr Thr Gln Gln Leu Asp
                100                 105                 110

Thr Val Leu Arg Pro Lys Ala Asp Gly Ala Trp His Leu His Glu Leu
            115                 120                 125

Thr Arg Asp Ala Asp Leu Ala Ala Phe Val Val Tyr Ser Ser Ala Ala
        130                 135                 140

Ala Val Leu Gly Asn Glu Gly Gln Gly Asn Tyr Ala Ala Ala Asn Ala
145                 150                 155                 160

Phe Leu Asp Ala Leu Ala Glu Gln Arg Arg Thr Gln Gly Leu Pro Ala
                165                 170                 175

Leu Ala Leu Ala Trp Gly Pro Trp Glu Tyr Thr Gly Asp Leu Thr Ala
            180                 185                 190

Gln Leu Thr Gly Thr Asp Gln Asp Arg Ile Arg Cys Ser Gly Met Arg
        195                 200                 205

Thr Ile Thr Ala Glu Asp Gly Met Arg Leu Phe Asp Thr Ala Ser His
    210                 215                 220
```

```
His Gly Glu Pro Leu Leu Val Pro Ala Val Leu Asp Pro Thr Arg Asp
225                 230                 235                 240

Gly Glu Val Pro Ala Leu Leu Arg Ser Leu Arg Arg Pro Ile Ala Arg
                245                 250                 255
```

<210> SEQ ID NO 78
<211> LENGTH: 249
<212> TYPE: PRT
<213> ORGANISM: Streptomyces rapamycinicus

<400> SEQUENCE: 78

```
Asp Pro Asp Gly Thr Val Leu Ile Thr Gly Gly Ser Gly Val Leu Ala
1               5                   10                  15

Gly Ile Ala Ala Arg His Leu Val Ala Glu Arg Gly Val Arg His Leu
                20                  25                  30

Leu Leu Leu Ser Arg Ser Ala Pro Asp Glu Ala Leu Ile Asn Gln Leu
            35                  40                  45

Gly Glu Leu Gly Ala Arg Val Glu Thr Ala Ala Cys Asp Val Ser Asp
50                  55                  60

Arg Ala Ala Leu Ala Gln Val Leu Ala Gly Val Ser Pro Glu His Pro
65                  70                  75                  80

Leu Thr Ala Val Ile His Thr Ala Gly Ala Leu Asp Asp Gly Val Val
                85                  90                  95

Glu Ser Leu Thr Ala Gln Arg Leu Asp Ala Val Leu Arg Pro Lys Ala
            100                 105                 110

Asp Gly Ala Trp Asn Leu His Glu Leu Thr Arg Asp Ala Asp Leu Ala
        115                 120                 125

Ala Phe Val Met Tyr Ser Ser Ala Ala Gly Val Leu Gly Ser Ala Gly
130                 135                 140

Gln Ala Asn Tyr Ala Ala Ala Asn Ala Phe Val Asp Ala Leu Ala Glu
145                 150                 155                 160

Gln Arg Arg Ala Glu Gly Leu Pro Ala Leu Ala Val Ala Trp Gly Leu
                165                 170                 175

Trp Glu Asp Ala Ser Gly Leu Thr Ala Asp Leu Thr Asp Thr Asp Arg
            180                 185                 190

Asp Arg Ile Arg Arg Gly Gly Leu Arg Ala Ile Ser Ala Glu Tyr Gly
        195                 200                 205

Met Gly Leu Phe Asp Ser Ala Ser Arg His Ser Glu Pro Val Leu Val
210                 215                 220

Gly Ala Ala Met Glu Pro Val Arg Asp Ala Glu Val Pro Ala Leu Leu
225                 230                 235                 240

Arg Ser Leu His Arg Pro Ile Ala Arg
                245
```

<210> SEQ ID NO 79
<211> LENGTH: 249
<212> TYPE: PRT
<213> ORGANISM: Streptomyces rapamycinicus

<400> SEQUENCE: 79

```
Asp Pro Asp Gly Thr Val Leu Ile Thr Gly Gly Ser Gly Val Leu Ala
1               5                   10                  15

Gly Ile Val Ala Arg His Leu Val Ala Glu Arg Gly Val Arg His Leu
                20                  25                  30

Leu Leu Leu Ser Arg Gly Thr Pro Asp Arg Ala Leu Leu Ser Glu Leu
            35                  40                  45
```

Ala Glu Leu Gly Ala Ala Val Asp Thr Ala Ala Cys Asp Val Ser Asp
 50                  55                  60

Arg Ala Glu Leu Ala Arg Val Leu Ala Arg Val Ser Pro Glu His Pro
 65                  70                  75                  80

Leu Thr Ala Val Ile His Thr Ala Gly Val Val Asp Asp Gly Val Val
                 85                  90                  95

Glu Ser Leu Ser Ala Gln Arg Leu Glu Thr Val Phe Arg Pro Lys Ala
            100                 105                 110

Asp Gly Ala Trp His Leu His Glu Leu Thr Arg Asp Ala Asp Leu Ala
        115                 120                 125

Ala Phe Val Met Tyr Ser Ser Ala Ala Gly Val Met Ala Gly Ala Gly
130                 135                 140

Gln Gly Asn Tyr Ala Ala Ala Asn Ala Phe Leu Asp Ala Leu Ala Glu
145                 150                 155                 160

Glu Arg Arg Ala Glu Gly Leu Pro Ala Leu Ala Val Ala Trp Gly Leu
                165                 170                 175

Trp Glu Asp Ala Ser Gly Leu Thr Ala Gln Leu Thr Asp Thr Asp Arg
            180                 185                 190

Asp Arg Ile Arg Arg Gly Gly Leu Arg Ala Ile Ser Ala Glu His Gly
        195                 200                 205

Met Arg Leu Phe Asp Asn Ala Ser Arg His Ser Glu Pro Val Leu Val
210                 215                 220

Ala Ala Pro Met Glu Pro Val Arg Asp Ala Glu Val Pro Ala Leu Leu
225                 230                 235                 240

Arg Ser Leu His Arg Pro Asn Val Arg
                245

<210> SEQ ID NO 80
<211> LENGTH: 235
<212> TYPE: PRT
<213> ORGANISM: Streptomyces rapamycinicus

<400> SEQUENCE: 80

Asp Pro His Gly Thr Val Leu Ile Thr Gly Gly Ser Gly Val Leu Ala
1               5                   10                  15

Gly Ala Leu Ala Arg His Leu Val Thr Glu Arg Gly Val Arg His Leu
                20                  25                  30

Leu Leu Leu Ser Arg Thr Thr Ala Asp Glu Gly Leu Leu Asn Glu Leu
            35                  40                  45

Gly Glu Leu Gly Ala Arg Val Glu Thr Ala Asp Cys Asp Val Ser Asp
 50                  55                  60

Arg Ala Gly Leu Ala Arg Val Leu Ala Gly Val Ser Pro Glu His Pro
 65                  70                  75                  80

Leu Thr Ala Val Ile Gln Thr Ala Gly Ala Leu Asp Asp Gly Val Leu
                 85                  90                  95

Glu Thr Leu Thr Ala Gln Arg Leu Asp Thr Val Leu Arg Pro Lys Ala
            100                 105                 110

Asp Gly Ala Trp His Leu His Glu Leu Thr Arg Asn Thr Gly Leu Ala
        115                 120                 125

Ala Phe Val Met Tyr Ser Ser Ala Ala Gly Val Met Gly Asn Pro Gly
130                 135                 140

Gln Gly Asn Leu Ala Ala Ala Thr Ala Phe Leu Asp Ala Leu Ala Asp
145                 150                 155                 160

Gln Arg Arg Ala Glu Gly Leu Pro Ala Leu Ala Leu Ala Trp Gly Ser
                165                 170                 175

Ser Glu Glu Thr Ser Asp Leu Ile Gly Leu Arg Thr Ile Ser Ala Glu
            180                 185                 190

Arg Gly Met Arg Leu Phe Asp Ser Ala Ser His Arg Gly Glu Pro Leu
        195                 200                 205

Leu Met Ala Ala Ser Leu Asp Pro Ala Arg Ala Glu Val Pro Ala
210                 215                 220

Leu Leu Arg Ser Leu Arg Arg Pro Val Ala Arg
225                 230                 235

<210> SEQ ID NO 81
<211> LENGTH: 256
<212> TYPE: PRT
<213> ORGANISM: Streptomyces rapamycinicus

<400> SEQUENCE: 81

Leu Thr Val Pro Gln Gln Leu Asp Ala Asn Gly Thr Val Leu Val Thr
1               5                   10                  15

Gly Gly Ser Gly Val Leu Ala Gly Ile Ala Ala Arg His Leu Val Ala
            20                  25                  30

Glu Gln Gly Val Arg His Leu Leu Leu Ser Arg Ser Thr Pro Asp
        35                  40                  45

Asp Ala Leu Ile Asn Glu Leu Gly Glu Leu Gly Ala Arg Val Asp Thr
    50                  55                  60

Ala Ile Cys Asp Val Ser Asp Arg Ala Gly Leu Ala Arg Ile Leu Ala
65                  70                  75                  80

Gly Val Ser Pro Glu His Pro Leu Thr Ala Val Ile His Thr Ala Gly
                85                  90                  95

Ala Leu Asp Asp Gly Val Val Glu Ser Leu Thr Ala Gln Gln Leu Glu
            100                 105                 110

Thr Val Leu Arg Pro Lys Ala Asp Gly Ala Trp His Leu His Glu Leu
        115                 120                 125

Thr Arg Asp Ala Asp Leu Ala Ala Phe Val Met Tyr Ser Ser Ala Ala
    130                 135                 140

Gly Val Leu Gly Ser Gly Gly Gln Gly Asn Tyr Ala Ala Ala Asn Ala
145                 150                 155                 160

Phe Leu Asp Ala Leu Ala Glu Gln Arg Arg Gly Glu Gly Leu Pro Ala
                165                 170                 175

Leu Ala Val Ala Trp Gly Leu Trp Glu Asp Ala Ser Gly Leu Thr Ala
            180                 185                 190

Glu Met Thr Asp Thr Asp Arg Asp Arg Ile Arg Arg Gly Gly Leu Arg
        195                 200                 205

Ala Ile Ser Ala Gly His Gly Met Gly Leu Leu Asp Ala Ala Ser Arg
    210                 215                 220

His Gly Glu Pro Val Leu Leu Ala Ala Ala Met Glu Pro Val Arg Glu
225                 230                 235                 240

Ala Glu Val Pro Ala Leu Leu Arg Leu Leu His Arg Pro Val Ala Arg
                245                 250                 255

<210> SEQ ID NO 82
<211> LENGTH: 249
<212> TYPE: PRT
<213> ORGANISM: Streptomyces rapamycinicus

<400> SEQUENCE: 82

Asp Pro Asp Gly Thr Val Leu Ile Thr Gly Gly Ser Gly Val Leu Ala
1               5                   10                  15

Gly Ile Ala Ala Arg His Leu Val Ala Glu Arg Gly Val Arg His Leu
            20                  25                  30

Leu Leu Leu Ser Arg Ser Ala Pro Asp Gly Ala Leu Ile Ser Glu Leu
        35                  40                  45

Gly Glu Leu Gly Ala Gln Val Ala Thr Ala Val Cys Asp Val Ser Asp
    50                  55                  60

Arg Pro Gly Leu Val Arg Val Leu Ala Asp Val Ser Pro Glu His Pro
65                  70                  75                  80

Leu Thr Ala Val Ile His Thr Ala Gly Val Val Asp Asp Gly Val Val
                85                  90                  95

Glu Ser Leu Thr Ala Gln Arg Leu Asp Thr Val Leu Arg Pro Lys Ala
            100                 105                 110

Asp Gly Ala Trp His Leu His Glu Leu Thr Arg Asp Ala Asp Leu Ala
        115                 120                 125

Ala Phe Val Met Tyr Ser Ser Ala Ala Gly Val Phe Gly Ser Ala Gly
    130                 135                 140

Gln Gly Asn Tyr Ala Val Ala Asn Ala Phe Leu Asp Ala Leu Ala Glu
145                 150                 155                 160

Gln Arg Arg Ala Glu Gly Leu Pro Ala Leu Ala Leu Ala Trp Gly Leu
                165                 170                 175

Trp Glu Gly Thr Ser Gly Leu Thr Ala Asn Leu Thr Asp Thr Asp His
            180                 185                 190

Asp Arg Ile Arg Arg Ser Gly Met Arg Ala Ile Ser Ala Glu His Gly
        195                 200                 205

Met Arg Leu Phe Asp Gly Ala Ser Arg Arg Asp Pro Val Leu Val
    210                 215                 220

Ala Ala Ala Met Glu Pro Val Arg Glu Ala Glu Val Pro Ala Met Leu
225                 230                 235                 240

Arg Ser Leu His Arg Pro Val Ala Arg
                245

<210> SEQ ID NO 83
<211> LENGTH: 249
<212> TYPE: PRT
<213> ORGANISM: Streptomyces rapamycinicus

<400> SEQUENCE: 83

Asp Pro Asp Gly Thr Val Leu Ile Thr Gly Gly Ser Gly Val Leu Ala
1               5                   10                  15

Gly Ile Ala Val Arg His Leu Val Thr Glu Arg Gly Val Arg His Leu
            20                  25                  30

Leu Leu Leu Ser Arg Ser Ala Pro Asp Glu Ala Leu Ile Asn Gln Leu
        35                  40                  45

Gly Glu Leu Gly Ala Arg Val Glu Thr Ala Ala Cys Asp Val Ser Asp
    50                  55                  60

Arg Ala Ala Leu Ala Gln Val Leu Ala Gly Val Ser Pro Glu His Pro
65                  70                  75                  80

Leu Thr Ala Val Ile His Thr Ala Gly Val Leu Asp Asp Gly Val Val
                85                  90                  95

Glu Ser Leu Thr Ala Gln Arg Leu Asp Ala Val Leu Arg Pro Lys Ala
            100                 105                 110

Asp Gly Ala Trp Asn Leu His Glu Leu Thr Arg Asp Ala Asp Leu Ala
        115                 120                 125

Ala Phe Val Met Tyr Ser Ser Ala Ala Gly Val Leu Gly Ser Gly Gly

```
            130                 135                 140
Gln Gly Asn Tyr Ala Ala Asn Ala Phe Leu Asp Ala Leu Ala Glu
145                 150                 155                 160

Gln Arg His Ala Glu Gly Leu Pro Ala Leu Ala Val Ala Trp Gly Leu
                165                 170                 175

Trp Glu Asp Ala Ser Gly Leu Thr Ala Gln Leu Thr Asp Thr Asp Arg
                180                 185                 190

Asp Arg Ile Arg Arg Gly Gly Leu Arg Ala Ile Ser Ala Glu His Gly
                195                 200                 205

Met Gly Leu Phe Asp Ser Ala Ser Arg His Ser Glu Pro Val Leu Val
            210                 215                 220

Ala Ala Pro Met Glu Pro Val Arg Asp Ala Glu Val Pro Ala Leu Leu
225                 230                 235                 240

Arg Ser Leu His Arg Pro Val Ala Arg
                245

<210> SEQ ID NO 84
<211> LENGTH: 250
<212> TYPE: PRT
<213> ORGANISM: Streptomyces rapamycinicus

<400> SEQUENCE: 84

Asp Pro Asp Gly Thr Val Leu Ile Thr Gly Gly Ser Gly Val Leu Ala
1               5                   10                  15

Gly Ile Ala Ala Arg His Leu Val Ala Glu Arg Gly Val Arg His Leu
                20                  25                  30

Leu Leu Leu Ser Arg Ser Ala Pro Asp Glu Ala Leu Ile Ser Glu Leu
            35                  40                  45

Ala Glu Leu Gly Ala Ala Val Val Asp Thr Ala Val Cys Asp Val Ser
        50                  55                  60

Asp Arg Ala Gly Leu Ala Arg Val Leu Ala Gly Val Ser Pro Asp His
65                  70                  75                  80

Pro Leu Thr Ala Val Ile His Thr Ala Gly Val Leu Asp Asp Gly Val
                85                  90                  95

Val Glu Ser Leu Thr Ala Arg Arg Leu Asp Thr Val Leu Arg Pro Lys
            100                 105                 110

Ala Asp Gly Ala Trp Asn Leu His Glu Leu Thr Arg Asp Ile Asp Leu
        115                 120                 125

Ala Ala Phe Val Met Tyr Ser Ser Ala Ala Gly Val Leu Gly Ser Ala
    130                 135                 140

Gly Gln Gly Asn Tyr Ala Val Ala Asn Ala Phe Val Asp Ala Leu Ala
145                 150                 155                 160

Glu Gln Arg Arg Ala Glu Gly Leu Pro Ala Leu Ala Leu Ala Trp Gly
                165                 170                 175

Leu Trp Glu Asp Ala Ser Gly Leu Thr Ala Lys Leu Thr Gly Thr Asp
                180                 185                 190

His Asp Arg Ile Arg Arg Ser Gly Leu Arg Thr Ile Thr Ala Glu Arg
                195                 200                 205

Gly Met Arg Leu Phe Asp Ile Ala Ser Arg Gln Gly Glu Pro Val Leu
            210                 215                 220

Val Ala Thr Pro Met Glu Pro Val Arg Glu Val Glu Val Pro Ala Leu
225                 230                 235                 240

Leu Arg Leu Leu His Arg Pro Val Ala Arg
                245                 250
```

```
<210> SEQ ID NO 85
<211> LENGTH: 249
<212> TYPE: PRT
<213> ORGANISM: Streptomyces rapamycinicus

<400> SEQUENCE: 85

Asp Pro Asp Gly Thr Val Leu Ile Thr Gly Gly Ser Gly Val Leu Ala
1               5                   10                  15

Gly Ile Ala Ala Arg His Leu Val Thr Glu Arg Gly Val Arg His Leu
            20                  25                  30

Leu Leu Leu Ser Arg Ser Ala Pro Asp Glu Ala Leu Ile Gly Glu Leu
        35                  40                  45

Gly Glu Leu Gly Ala Arg Val Glu Thr Ala Ala Cys Asp Val Ser Asp
    50                  55                  60

Pro Ala Ala Leu Thr Gln Val Leu Ala Gly Val Ser Pro Glu His Pro
65                  70                  75                  80

Leu Thr Ala Val Ile His Thr Ala Gly Val Val Asp Asp Gly Val Val
                85                  90                  95

Glu Ser Leu Thr Val Gln Arg Leu Glu Thr Val Leu Arg Pro Lys Ala
            100                 105                 110

Asp Gly Ala Trp Asn Leu His Glu Leu Thr Arg Asp Ala Asp Leu Ala
        115                 120                 125

Ala Phe Val Met Tyr Ser Ser Ala Ala Gly Val Leu Gly Ser Ala Gly
    130                 135                 140

Gln Gly Asn Tyr Ala Ala Ala Asn Ala Phe Leu Asp Ala Leu Ala Glu
145                 150                 155                 160

Gln Arg His Ala Glu Gly Leu Pro Ala Leu Ala Val Ala Trp Gly Leu
                165                 170                 175

Trp Glu Asp Ala Ser Gly Leu Thr Ala Gln Leu Thr Ala Thr Asp Arg
            180                 185                 190

Asp Arg Ile Arg Arg Gly Gly Leu Arg Ala Ile Ser Ala Glu His Gly
        195                 200                 205

Met Gly Leu Phe Asp Ser Ala Ser Arg His Ser Glu Pro Val Leu Val
    210                 215                 220

Ala Ala Pro Met Glu Pro Val Arg Asp Ala Glu Val Pro Ala Leu Leu
225                 230                 235                 240

Arg Ser Leu His Arg Pro Ile Ala Arg
                245

<210> SEQ ID NO 86
<211> LENGTH: 249
<212> TYPE: PRT
<213> ORGANISM: Streptomyces rapamycinicus

<400> SEQUENCE: 86

Asp Pro Asp Gly Thr Val Leu Ile Thr Gly Gly Ser Gly Val Leu Ala
1               5                   10                  15

Gly Ile Ala Ala Arg His Leu Val Ala Glu Arg Gly Val Arg His Leu
            20                  25                  30

Leu Leu Leu Ser Arg Ser Ala Pro Asp Glu Ala Leu Ile Asn Gln Leu
        35                  40                  45

Gly Glu Leu Gly Ala Arg Val Glu Thr Ala Ala Cys Asp Val Ser Asp
    50                  55                  60

Arg Ala Ala Leu Ala Gln Val Leu Ala Gly Val Ser Pro Glu His Pro
65                  70                  75                  80
```

```
Leu Thr Ala Val Ile His Thr Ala Gly Val Leu Asp Asp Gly Val Val
                85                  90                  95

Glu Ser Leu Thr Ala Gln Arg Leu Asp Thr Val Leu Arg Pro Lys Ala
            100                 105                 110

Asp Gly Ala Trp His Leu His Glu Leu Thr Arg Asn Thr Asp Leu Ala
        115                 120                 125

Ala Phe Val Met Tyr Ser Ser Ala Ala Gly Val Met Gly Gly Gly Gly
    130                 135                 140

Gln Gly Asn Tyr Ala Ala Ala Asn Ala Phe Leu Asp Ala Leu Ala Glu
145                 150                 155                 160

Glu Arg Arg Ala Glu Gly Leu Pro Ala Ile Arg Gly Gly Leu Gly Leu
                165                 170                 175

Trp Glu Asp Thr Ser Gly Leu Thr Thr Gln Leu Thr Asp Thr Asp Arg
            180                 185                 190

Asp Arg Ile Arg Arg Gly Gly Leu Arg Thr Ile Thr Ala Glu Tyr Gly
        195                 200                 205

Met Arg Leu Phe Asp Thr Ala Ser Arg His Gly Asn Pro Ile Leu Val
    210                 215                 220

Ala Ala Pro Met Asp Pro Val Trp Asp Ala Glu Val Pro Ala Leu Leu
225                 230                 235                 240

Arg Ser Leu His Arg Pro Val Ala Arg
                245

<210> SEQ ID NO 87
<211> LENGTH: 256
<212> TYPE: PRT
<213> ORGANISM: Streptomyces rapamycinicus

<400> SEQUENCE: 87

Leu Thr Ile Pro Arg Arg Pro Asp Pro Asp Gly Thr Ile Leu Ile Thr
1               5                   10                  15

Gly Gly Ser Gly Val Leu Ala Gly Ile Leu Ala Arg His Leu Ala Ala
            20                  25                  30

Glu His Gly Ala Arg His Leu Leu Leu Leu Ser Arg Thr Thr Pro Asp
        35                  40                  45

Gln Ala Leu Ile Lys Glu Leu Ala Glu Leu Gly Ala His Val Asp Thr
    50                  55                  60

Ala Thr Cys Asp Val Ser Asp Arg Ala Gly Leu Ala Arg Val Leu Ala
65                  70                  75                  80

Gly Val Ser Pro Glu His Pro Leu Thr Ala Val Ile His Thr Ala Gly
                85                  90                  95

Ala Leu Asp Asp Gly Val Val Glu Ser Leu Thr Thr Gln Gln Leu Asp
            100                 105                 110

Thr Val Leu Arg Pro Lys Ala Asp Gly Ala Trp His Leu His Glu Leu
        115                 120                 125

Thr Gln Asn Thr Asp Leu Ala Ala Phe Val Met Tyr Ser Ser Ala Ala
    130                 135                 140

Gly Val Ile Gly Gly Ala Gly Gln Gly Asn Tyr Ala Ala Ala Asn Ala
145                 150                 155                 160

Phe Leu Asp Ala Leu Ala Glu Gln Arg Arg Ala Glu Gly Leu Pro Ala
                165                 170                 175

Leu Ala Leu Ala Trp Gly Leu Trp Asp Asp Thr Ser Gly Leu Thr Ser
            180                 185                 190

Gly Leu Thr Asp Thr Asp His Asp Arg Ile Arg Arg Ser Gly Met Arg
        195                 200                 205
```

Thr Ile Thr Ala Glu His Gly Met Arg Leu Phe Asp Gly Ala Ser Arg
             210                 215                 220

His Gly Glu Pro Val Leu Phe Ala Ala Ala Met Ser Pro Leu Arg Gly
225                 230                 235                 240

Asp Val Glu Val Pro Ala Leu Leu Arg Gly Leu Gln Thr Val Lys Arg
             245                 250                 255

<210> SEQ ID NO 88
<211> LENGTH: 371
<212> TYPE: PRT
<213> ORGANISM: Streptomyces malaysiensis

<400> SEQUENCE: 88

Thr Ala Leu Ala Glu Ala His Ala His Gly Val Ile Val Asp Trp Pro
1               5                   10                  15

Arg Val Phe Gly Ser Thr Thr Arg Val Leu Asp Leu Pro Thr Tyr Ala
             20                  25                  30

Phe Glu His Gln Arg Tyr Trp Ala Val Ser Ala Asp Arg Pro Ser Asp
         35                  40                  45

Ala Gly His Pro Met Val Glu Thr Val Pro Leu Pro Ala Ser Gly
     50                  55                  60

Gly Val Ala Leu Thr Gly Arg Val Ser Leu Ala Thr His Ala Trp Leu
65                  70                  75                  80

Ala Asp His Ala Val Arg Gly Thr Ala Leu Leu Pro Gly Thr Ala Phe
                 85                  90                  95

Val Glu Leu Val Thr Arg Ala Ala Thr Glu Val Asp Cys Pro Val Ile
            100                 105                 110

Asp Glu Leu Val Ile Glu Ala Pro Leu Pro Leu Thr Gln Thr Gly Ala
         115                 120                 125

Val Gln Leu Ser Thr Thr Val Gly Glu Ala Asp Glu Ser Gly Arg Arg
130                 135                 140

Pro Val Thr Val Phe Ser Gln Ala Asp Gly Thr Asp Ala Trp Thr Arg
145                 150                 155                 160

His Val Thr Ala Thr Ile Gly Arg Ala Ala Ser Leu Pro Asp Pro Val
                165                 170                 175

Ala Trp Pro Pro Ala Gln Ala Glu Pro Val Asp Val Thr Gly Phe Tyr
            180                 185                 190

Asp Glu Leu Ala Ala Ala Gly Tyr Glu Tyr Gly Pro Ala Phe Gln Gly
         195                 200                 205

Leu Arg Ala Ala Trp Ser Asp Gly Asp Thr Val Tyr Ala Glu Val Val
210                 215                 220

Leu Ala Glu Glu Gln Ala His Glu Val Asp Arg Tyr Ala Val His Pro
225                 230                 235                 240

Ala Leu Leu Asp Ala Ala Leu Gln Ala Gly Met Val Asn Thr Ala Gly
                245                 250                 255

Thr Gly Gln Gly Val Arg Leu Pro Phe Ser Trp Asn Gly Ile Gln Val
            260                 265                 270

His Ser Thr Gly Ala Thr Thr Leu Arg Val Ala Ala Thr Pro Leu Ala
         275                 280                 285

Asp Gly Trp Ser Val Arg Ala Ala Asp Asn Gly Arg Pro Val Ala
            290                 295                 300

Thr Ile Gly Ser Leu Val Thr Arg Pro Val Thr Thr Asp Met Leu Gly
305                 310                 315                 320

Ser Thr Thr Asp Asp Leu Phe Ala Val Val Trp Thr Glu Ile Thr Ala

```
                        325                 330                 335
Pro Glu Pro Gly Asp Pro Ser Asp Val Gly Val Phe Thr Ala Leu Pro
            340                 345                 350
Glu Ala Gly Gly Asp Pro Leu Thr Gln Thr Arg Ala Leu Thr Ala Gln
            355                 360                 365
Val Leu Gln
        370

<210> SEQ ID NO 89
<211> LENGTH: 285
<212> TYPE: PRT
<213> ORGANISM: Streptomyces malaysiensis
<220> FEATURE:
<221> NAME/KEY: MISC_FEATURE
<222> LOCATION: (46)..(46)
<223> OTHER INFORMATION: Xaa is Val
<220> FEATURE:
<221> NAME/KEY: MISC_FEATURE
<222> LOCATION: (64)..(64)
<223> OTHER INFORMATION: Xaa is Gly
<220> FEATURE:
<221> NAME/KEY: MISC_FEATURE
<222> LOCATION: (81)..(81)
<223> OTHER INFORMATION: Xaa is Ser

<400> SEQUENCE: 89

Ala Leu Ala Glu Leu His Val Gln Gly Val Pro Ile Asp Trp Ser Ser
1               5                   10                  15
Ile Leu Gly Ala Asn Pro Ala Arg Val Leu Asp Leu Pro Thr Tyr Ala
            20                  25                  30
Phe Gln His Glu Arg Tyr Trp Met Val Ser Thr Gly Arg Xaa Gly Gly
        35                  40                  45
Glu Gly His Pro Leu Leu Gly Trp Gly Val Pro Val Ala Glu Ala Xaa
    50                  55                  60
Gly Arg Leu Tyr Thr Gly Arg Val Ala Arg Gln Asp Gly Pro Val Leu
65                  70                  75                  80
Xaa Val Ala Ala Phe Val Glu Met Ala Phe Ala Ala Gly Gly Arg
                85                  90                  95
Pro Ile Arg Glu Leu Ser Val Asp Ala Leu Leu Tyr Ile Pro Asp Asp
            100                 105                 110
Gly Thr Ala Glu Leu Gln Thr Trp Val Ser Glu His Arg Leu Thr Ile
        115                 120                 125
His Ala Arg Tyr Arg Asp Thr Glu Pro Trp Thr Arg Leu Ala Thr Ala
    130                 135                 140
Ala Leu Asp Thr Thr Ala Pro Ala Thr Thr His Thr Pro His Pro Gly
145                 150                 155                 160
Leu Ile Thr Thr Ala Leu Thr Leu Thr Gly Asp Glu Ala Pro Ala Ile
                165                 170                 175
Trp His Asp Leu Thr Leu His Thr Ser Asn Ala Thr Glu Leu His Thr
            180                 185                 190
His Ile Thr Pro Gly Asp Asp Gly Thr Leu Thr Ile Thr Ala Thr Asp
        195                 200                 205
Ala Thr Gly Gln Pro Val Leu Thr Ala His Ala Thr Pro Thr Thr
    210                 215                 220
Ile Pro Val His Thr Pro Thr Pro Ala Asp Asp Leu Leu Thr Leu
225                 230                 235                 240
Thr Trp Thr Gln Ile Pro Thr Pro Gly Pro Gly Asp Pro Thr Asp Ile
                245                 250                 255
```

```
Ala Val Cys Thr Ala Leu Pro Asp Pro Asp Gly Asp Pro Leu Ala Gln
            260                 265                 270

Thr Arg Thr Leu Thr Ala Gln Val Leu Gln Ser Ile Gln
        275                 280                 285

<210> SEQ ID NO 90
<211> LENGTH: 332
<212> TYPE: PRT
<213> ORGANISM: Streptomyces malaysiensis

<400> SEQUENCE: 90

Met His Val Gln Gly Val Gly Val Asp Trp Pro Ala Ile Leu Gly Thr
1               5                   10                  15

Thr Thr Gly Arg Val Leu Asp Leu Pro Thr Tyr Ala Phe Gln His Glu
            20                  25                  30

Arg Tyr Trp Met Ala Asn Ala Asp Glu Gly His Pro Leu Leu Gly Lys
        35                  40                  45

Val Glu His Pro Leu Leu Gly Ser Val Met Ala Leu Pro Asn Ser Asp
    50                  55                  60

Gly Val Val Leu Thr Gly Arg Ile Ser Leu Ala Thr His Ala Trp Leu
65                  70                  75                  80

Ala Asp His Val Val Arg Gly Thr Val Leu Leu Pro Gly Thr Gly Phe
                85                  90                  95

Val Glu Met Val Ala Arg Ala Ala Glu Val Gly Cys Gly Val Ile
            100                 105                 110

Asp Glu Leu Leu Ile Glu Ala Pro Leu Leu Pro Glu His Gly Gly
            115                 120                 125

Val His Leu Ser Val Ser Val Gly Glu Ala Asp Gly Ala Gly Arg Arg
    130                 135                 140

Pro Val Thr Val Phe Ala Gln Ala Asp Ala Glu Val Trp Val Arg
145                 150                 155                 160

Gln Val Thr Ala Thr Ile Ser Pro Ala Gly Pro Ala Val Ser Leu Pro
            165                 170                 175

Glu Leu Glu Val Trp Pro Pro Val Gln Ala Glu Pro Val Asp Val Ser
            180                 185                 190

Thr Phe Tyr Glu Arg Leu Ala Arg Ala Asp Trp Gln Trp Gly Pro Ala
        195                 200                 205

Phe Gln Gly Leu Arg Ala Ala Trp Arg Asp Gly Asp Thr Ile Tyr Ala
    210                 215                 220

Glu Ile Val Leu Ala Asp Glu Glu Ala Arg Glu Ala Asp Gln Phe Leu
225                 230                 235                 240

Val His Pro Ala Leu Leu Asp Ala Ala Leu Gln Thr Ser Val Leu Lys
            245                 250                 255

Thr Pro Asp Leu Arg Leu Pro Phe Ser Trp Asn Gln Ile Glu Phe
            260                 265                 270

His Ala Thr Gly Ala Ala Ile Leu Arg Val Ala Val Thr Pro Val Ala
        275                 280                 285

Asp Arg Trp Ile Val His Ala Ala Asp Ser Thr Gly Arg Pro Val Ala
    290                 295                 300

Thr Ile Gly Ala Leu Val Ser Arg Pro Val Thr Ala Glu Thr Leu Gly
305                 310                 315                 320

Ser Asn Thr Asp Asp Leu Phe Ala Leu Thr Trp Thr
            325                 330

<210> SEQ ID NO 91
```

<211> LENGTH: 332
<212> TYPE: PRT
<213> ORGANISM: Streptomyces malaysiensis

<400> SEQUENCE: 91

```
Ala Leu Ala Glu Leu His Val Gln Gly Val Pro Ile Asp Trp Pro Ala
1               5                   10                  15

Val Leu Gly Thr Thr Thr Gly Arg Val Leu Asp Leu Pro Thr Tyr Ala
            20                  25                  30

Phe Gln His Gln Arg Tyr Trp Ala Ala Ser Thr Asp Arg Pro Ala Gly
        35                  40                  45

Asp Gly His Pro Leu Leu Asp Thr Val Ala Leu Pro Gly Ala Asp
    50                  55                  60

Gly Val Val Leu Thr Gly Arg Ile Ser Leu Ala Thr His Ala Trp Leu
65                  70                  75                  80

Ala Asp His Ala Val Arg Gly Thr Val Leu Leu Pro Gly Thr Gly Phe
                85                  90                  95

Val Glu Met Val Ala Arg Ala Ala Glu Val Gly Cys Ala Val Val
            100                 105                 110

Asp Glu Leu Val Ile Glu Ala Pro Leu Leu Pro Ala Ser Gly Gly
        115                 120                 125

Val Gln Leu Ser Val Ser Val Gly Glu Ala Asp Asp Ala Gly His Arg
    130                 135                 140

Pro Val Thr Val His Ser Gln Ala Asp Glu Thr Gly Ala Trp Val Arg
145                 150                 155                 160

His Val Thr Ala Thr Ile Ser Pro Ser Gly Pro Ile Val Ser Pro Pro
                165                 170                 175

Glu Phe Glu Val Trp Pro Pro Ala Gln Ala Glu Pro Val Glu Val Ala
            180                 185                 190

Arg Phe Tyr Asp Glu Leu Ala Ala Gly Tyr Glu Tyr Gly Ala Ala
        195                 200                 205

Phe Gln Gly Leu Arg Ala Ala Trp Arg Ala Gly Glu Thr Ile Tyr Ala
    210                 215                 220

Glu Val Val Leu Ala Glu Asp Gln Thr Leu Glu Ala Ala Arg Phe Thr
225                 230                 235                 240

Val His Pro Ala Leu Leu Asp Ala Ala Leu Gln Ala Asn Ile Leu Asn
                245                 250                 255

Ala Ser Gly Asp Leu Arg Leu Pro Phe Ser Trp Gly Gln Val Gln Phe
            260                 265                 270

His Thr Thr Gly Ala Ala Thr Leu Arg Val Ala Val Thr Pro Val Ala
        275                 280                 285

Asp Gly Trp Thr Ile Gln Ala Thr Asp Ala Gly Arg Pro Val Ala
    290                 295                 300

Thr Val Gly Ser Val Val Ala Arg Pro Val Ala Gly Leu Gly Ala Thr
305                 310                 315                 320

Ala Glu Asp Leu Phe Ala Leu Thr Trp Asn Glu Ile
                325                 330
```

<210> SEQ ID NO 92
<211> LENGTH: 329
<212> TYPE: PRT
<213> ORGANISM: Streptomyces malaysiensis

<400> SEQUENCE: 92

```
Ala Phe Ala Glu Ala His Val His Gly Ala Thr Ile Asp Trp Pro Thr
1               5                   10                  15
```

Val Leu Asp Thr Thr Thr Pro Val Leu Asp Leu Pro Thr Tyr Pro
             20                  25                  30

Phe Gln Arg Gln Arg Tyr Trp Ala Thr Ser Asn Gly Arg Ser Thr Gly
         35                  40                  45

Gln Gly His Pro Leu Leu Glu Thr Val Val Ala Leu Pro Gly Thr Asp
     50                  55                  60

Gly Val Ala Leu Thr Gly Arg Ile Ser Leu Ala Thr His Pro Trp Leu
 65                  70                  75                  80

Thr Asp His Thr Val Arg Gly Thr Val Leu Leu Pro Gly Thr Ala Phe
                 85                  90                  95

Val Glu Leu Val Thr Arg Ala Ala Thr Glu Val Asn Cys Gln Ile Ile
             100                 105                 110

Asp Glu Leu Ile Ile Glu Ala Pro Leu Pro Leu Pro Gln Thr Asp Gly
         115                 120                 125

Val Gln Leu Ser Val Thr Val Gly Glu Ala Asp Glu Ala Gly His Arg
     130                 135                 140

Pro Val Thr Val Tyr Ser Gln Thr Asp Glu Ser Asp Asp Trp Ile Gln
145                 150                 155                 160

His Val Thr Ala Thr Ile Gly Pro Gly Ala Ser Leu Pro Glu Thr Ala
                 165                 170                 175

Ala Trp Pro Pro Ala His Ala Glu Pro Val Asn Val Thr Gly Leu Tyr
             180                 185                 190

Asp Asn Leu Ala Ala Ala Gly Tyr Glu Tyr Gly Pro Ala Phe Gln Gly
         195                 200                 205

Leu Gln Ala Ala Trp Arg Ala Gly Asp Thr Val Tyr Ala Glu Val Thr
     210                 215                 220

Leu Ala Glu Glu Gln Ala Gln Glu Thr Ala Arg Phe Thr Met His Pro
225                 230                 235                 240

Ala Leu Leu Asp Ala Ala Leu His Thr Ile Ala Leu His Asp Thr Gly
                 245                 250                 255

Asp Leu His Leu Pro Phe Ser Trp Thr Arg Val Gln Phe His Gly Thr
             260                 265                 270

Gly Ala Ala Thr Leu Arg Val Ala Val Thr Pro Ala Ala Asp Gly Trp
         275                 280                 285

Asn Ile Arg Ala Thr Asp Asp Thr Gly Arg Ala Val Ala Thr Ile Gly
     290                 295                 300

Ser Leu Val Thr Arg Pro Met Ala Ala Glu Thr Thr Asp Asp Leu Leu
305                 310                 315                 320

Ala Leu Thr Trp Thr Glu Ile Pro Ala
                 325

<210> SEQ ID NO 93
<211> LENGTH: 324
<212> TYPE: PRT
<213> ORGANISM: Streptomyces malaysiensis

<400> SEQUENCE: 93

Pro Ala Gly Ala Val Arg Gly Trp Val Asp Leu Pro Thr Tyr Ala Phe
1               5                   10                  15

Asp His Gln Arg Tyr Trp Leu Glu Asn Arg Val Ala Thr Asp Ala Ala
             20                  25                  30

Ala Leu Gly Leu Ala Gly Ala Asp His Pro Leu Leu Gly Ala Ile Val
         35                  40                  45

Ala Val Pro Gln Ser Gly Gly Val Ala Met Thr Ser Arg Leu Ser Pro

```
            50                  55                  60
Arg Asn His Pro Trp Leu Ala Glu His Thr Leu Gly Gly Val Pro Thr
 65                  70                  75                  80

Val Pro Thr Ser Val Leu Val Glu Leu Ala Val Arg Ala Gly Asp Glu
                 85                  90                  95

Val Gly Cys Gly Val Val Glu Glu Leu Thr Val Asp Ala Pro Leu Leu
            100                 105                 110

Leu Pro Glu Arg Gly Gly Val Arg Val Gln Val Ile Val Gly Ala Thr
        115                 120                 125

Asp Ala Asn Gly Gln Arg Gly Leu Asp Ile Phe Ser Ala Pro Glu Asp
    130                 135                 140

Thr Gly Gln Glu Ala Trp Thr Arg His Ala Thr Gly Thr Leu Ala Pro
145                 150                 155                 160

Gly Gly Asp Ile Ala Ala Asp Val Asp Leu Ser Ala Trp Pro Pro Ala
                165                 170                 175

Asn Ala Gln Pro Val Asp Val Thr Asp Gly Tyr Asp Leu Leu Glu Arg
            180                 185                 190

Ala Gly Tyr Gly Tyr Gly Pro Ala Phe Gln Gly Val Arg Ala Ile Trp
        195                 200                 205

Arg Arg Gly Glu Glu Leu Phe Ala Glu Val Ala Leu Glu Pro Glu Leu
    210                 215                 220

Thr Asp Thr Ala Ala Arg Phe Gly Leu His Pro Ala Leu Leu Asp Ala
225                 230                 235                 240

Ala Trp His Pro Glu Leu Arg Asp Glu Val Ala Glu Thr Ser Pro Asp
                245                 250                 255

Gly Arg Arg Trp Trp Ser Gln Pro Ser Arg Trp Ala Gly Leu Arg Leu
            260                 265                 270

His Thr Ala Gly Ala Thr Val Leu Arg Val Arg Leu Ala Pro Val Asp
        275                 280                 285

Ala Asp Ser Met Ser Leu Gln Ala Ala Asp Glu Thr Gly Asp Pro Val
    290                 295                 300

Leu Thr Val Asp Ser Leu Ser Leu Cys Ala Val Ser Ala Asp Gln Leu
305                 310                 315                 320

Thr Thr Ala Glu

<210> SEQ ID NO 94
<211> LENGTH: 329
<212> TYPE: PRT
<213> ORGANISM: Streptomyces malaysiensis

<400> SEQUENCE: 94

Ala Phe Ala Glu Ala His Val His Gly Ala Thr Ile Asp Trp Pro Thr
 1               5                  10                  15

Val Leu Asp Thr Thr Thr Pro Val Leu Asp Leu Pro Thr Tyr Pro
                20                  25                  30

Phe Gln Arg Gln Arg Tyr Trp Ala Thr Ser Asn Gly Arg Pro Thr Ser
        35                  40                  45

Gln Gly His Pro Leu Leu Glu Thr Val Ala Leu Pro Gly Thr His
    50                  55                  60

Gly Val Ala Leu Thr Gly Arg Ile Ser Leu Ala Thr His Pro Trp Leu
 65                  70                  75                  80

Thr Asp His Thr Val Arg Gly Thr Val Leu Leu Pro Gly Thr Ala Phe
                 85                  90                  95

Val Glu Leu Val Thr His Ala Ala Thr Glu Val Asn Cys Gln Val Ile
```

-continued

```
                100                 105                 110
Asp Glu Leu Ile Ile Glu Ala Pro Leu Pro Leu Pro Gln Asn Gly Gly
            115                 120                 125

Val Gln Leu Ser Val Thr Val Gly Glu Ala Asp Glu Ala Gly His Arg
130                 135                 140

Pro Val Thr Val Tyr Ser Gln Thr Asp Glu Ser Asp Asp Trp Val Gln
145                 150                 155                 160

His Val Thr Ala Thr Ile Ala Pro Gly Val Ser Ser Glu Ser Ala
            165                 170                 175

Ala Trp Pro Pro Ala Gln Ala Glu Pro Val Asn Val Thr Asp Phe Tyr
            180                 185                 190

Asn Glu Leu Ala Ala Ala Gly Tyr Glu Tyr Gly Pro Ala Phe Gln Gly
            195                 200                 205

Leu Gln Thr Ala Trp Arg Asp Gly Ser Thr Val Tyr Ala Glu Val Thr
            210                 215                 220

Leu Ala Glu Glu Gln Ala Gln Glu Thr Ala Arg Phe Thr Met His Pro
225                 230                 235                 240

Ala Leu Leu Asp Ala Ala Leu His Thr Ile Ala Leu His Asp Thr Ala
            245                 250                 255

Asp Leu Gln Leu Pro Phe Ser Trp Arg Gln Val Gln Phe His Gly Ser
            260                 265                 270

Gly Ala Ala Thr Leu Arg Val Ala Val Thr Pro Ala Ala Asp Gly Trp
            275                 280                 285

Asn Ile Arg Ala Thr Asp Asp Thr Gly Gln Thr Val Ala Thr Ile Gly
            290                 295                 300

Ser Leu Val Thr Arg Pro Met Ala Ala Glu Thr Thr Asn Asp Leu Leu
305                 310                 315                 320

Ala Leu Thr Trp Thr Glu Ile Pro Ala
            325
```

<210> SEQ ID NO 95
<211> LENGTH: 58
<212> TYPE: PRT
<213> ORGANISM: Streptomyces malaysiensis

<400> SEQUENCE: 95

```
Tyr Ala Ala Ala Asn Ala Tyr Leu Asp Gly Leu Met Ala Arg Arg His
1               5                   10                  15

Ala Glu Gly Leu Pro Gly Leu Ser Leu Ala Trp Gly Leu Trp Asp Gln
            20                  25                  30

Glu Ala Asp Gly Gly Met Ala Ala Gly Leu Gln Asp Ile Thr Arg
        35                  40                  45

Asn Arg Met Arg Arg Arg Gly Gly Val Leu
    50                  55
```

<210> SEQ ID NO 96
<211> LENGTH: 40
<212> TYPE: PRT
<213> ORGANISM: Streptomyces violaceusniger

<400> SEQUENCE: 96

```
Phe Ala Ala Ala Thr Ala Phe Leu Asp Ala Leu Ala Glu Gln Arg Arg
1               5                   10                  15

Ala Glu Gly Leu Pro Ala Leu Ala Leu Ala Trp Gly Ser Ser Glu Glu
            20                  25                  30

Thr Gly Gly Leu Thr Gly Leu Arg
```

```
<210> SEQ ID NO 97
<211> LENGTH: 5
<212> TYPE: PRT
<213> ORGANISM: Streptomyces hygroscopicus S303

<400> SEQUENCE: 97

Tyr Ala Ala Ala Asn
1               5

<210> SEQ ID NO 98
<211> LENGTH: 10
<212> TYPE: PRT
<213> ORGANISM: Micromonospora sp. S679
<220> FEATURE:
<221> NAME/KEY: MISC_FEATURE
<222> LOCATION: (2)..(4)
<223> OTHER INFORMATION: Xaa can be any amino acid
<220> FEATURE:
<221> NAME/KEY: MISC_FEATURE
<222> LOCATION: (6)..(9)
<223> OTHER INFORMATION: Xaa can be any amino acid

<400> SEQUENCE: 98

His Xaa Xaa Xaa Gly Xaa Xaa Xaa Xaa Pro
1               5                   10

<210> SEQ ID NO 99
<211> LENGTH: 5
<212> TYPE: PRT
<213> ORGANISM: Streptomyces malaysiensis DSM4137
<220> FEATURE:
<221> NAME/KEY: MISC_FEATURE
<222> LOCATION: (4)..(4)
<223> OTHER INFORMATION: Xaa can be any amino acid

<400> SEQUENCE: 99

Leu Pro Phe Xaa Trp
1               5
```